(12) United States Patent
Bebernitz et al.

(10) Patent No.: US 9,895,389 B2
(45) Date of Patent: *Feb. 20, 2018

(54) GLYCOSIDE DERIVATIVES AND USES THEREOF

(71) Applicant: Novartis AG, Basel (CH)

(72) Inventors: Gregory Raymond Bebernitz, Stow, MA (US); Mark G. Bock, Boston, MA (US); Dumbala Srinivas Reddy, Hyderabad (IN); Atul Kashinath Hajare, Ahmednagar (IN); Vinod Vyavahare, Bangalore (IN); Sandeep Bhausaheb Bhosale, Pune (IN); Suresh Eknath Kurhade, Pune (IN); Videsh Salunkhe, Bangalore (IN); Nadim S. Shaikh, Bangalore (IN); Debnath Bhuniya, Howrah (IN); P. Venkata Palle, Pune (IN); Lili Feng, Pine Brook, NJ (US); Jessica Liang, Annandale, NJ (US)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/134,016

(22) Filed: Apr. 20, 2016

(65) Prior Publication Data

US 2017/0042925 A1   Feb. 16, 2017

Related U.S. Application Data

(63) Continuation of application No. 14/604,173, filed on Jan. 23, 2015, now abandoned, which is a continuation of application No. 14/291,268, filed on May 30, 2014, now abandoned, which is a continuation of application No. 13/614,534, filed on Sep. 13, 2012, now Pat. No. 8,828,951, which is a continuation of application No. 13/425,888, filed on Mar. 21, 2012, now Pat. No. 8,466,114, which is a continuation of application No. 12/906,682, filed on Oct. 18, 2010, now Pat. No. 8,163,704.

(30) Foreign Application Priority Data

Oct. 20, 2009 (IN) .............................. 2173/DEL/09
Dec. 23, 2009 (IN) .......................... 2689/DELNP/09

(51) Int. Cl.
*A61K 31/7048* (2006.01)
*A61K 31/706* (2006.01)
*A61K 31/7052* (2006.01)
*C07D 405/10* (2006.01)
*C07D 407/10* (2006.01)
*C07D 413/10* (2006.01)
*C07H 7/04* (2006.01)

(52) U.S. Cl.
CPC ........ *A61K 31/7052* (2013.01); *A61K 31/706* (2013.01); *A61K 31/7048* (2013.01); *C07D 405/10* (2013.01); *C07D 407/10* (2013.01); *C07D 413/10* (2013.01); *C07H 7/04* (2013.01)

(58) Field of Classification Search
None
See application file for complete search history.

(56) References Cited

U.S. PATENT DOCUMENTS

| | | |
|---|---|---|
| 5,410,031 A | 4/1995 | Wright et al. |
| 6,627,611 B2 | 9/2003 | Tomiyama et al. |
| 6,838,442 B2 | 1/2005 | Bussolari et al. |
| 6,936,590 B2 | 8/2005 | Washburn et al. |
| 7,417,032 B2 | 8/2008 | Eckhardt et al. |
| 8,097,592 B2 | 1/2012 | Imamura et al. |
| 8,163,704 B2 * | 4/2012 | Bebernitz ............ C07D 405/10 514/23 |

(Continued)

FOREIGN PATENT DOCUMENTS

| | | |
|---|---|---|
| EP | 1 444 890 A1 | 8/2004 |
| EP | 1 568 380 A1 | 8/2005 |

(Continued)

OTHER PUBLICATIONS

Adachi et al.; "T-1095, a Renal Na+-Glucose Transporter Inhibitor, Improves Hyperglycemia in Streptozotocin-Induced Diabetic Rats"; Metabolism; 49(8):990-995 (2000).

(Continued)

*Primary Examiner* — Traviss C McIntosh, III
(74) *Attorney, Agent, or Firm* — Jim Lynch

(57) ABSTRACT

This invention relates to compounds represented by formula (I):

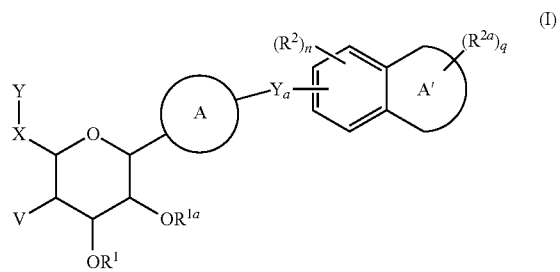

wherein the variables are defined as herein above, which are useful for treating diseases and conditions mediated by the sodium D-glucose co-transporter (SGLT), e.g. diabetes. The invention also provides methods of treating such diseases and conditions, and compositions etc. for their treatment.

4 Claims, 4 Drawing Sheets

(56) References Cited

U.S. PATENT DOCUMENTS

| | | | |
|---|---|---|---|
| 8,466,114 B2 * | 6/2013 | Bebernitz | C07D 405/10 514/23 |
| 8,828,951 B2 * | 9/2014 | Bebernitz | C07D 405/10 514/23 |
| 2007/0275907 A1 | 11/2007 | Chen et al. | |
| 2008/0096802 A1 | 4/2008 | Bussolari et al. | |
| 2010/0099641 A1 | 4/2010 | Himmelsbach et al. | |
| 2014/0274921 A1 | 9/2014 | Bebernitz et al. | |
| 2015/0141354 A1 | 5/2015 | Bebernitz et al. | |

FOREIGN PATENT DOCUMENTS

| | | | |
|---|---|---|---|
| EP | 1 609 785 A1 | 12/2005 | |
| EP | 1 803 721 A1 | 7/2007 | |
| JP | 2001288178 A1 | 10/2001 | |
| WO | 199503300 A1 | 2/1995 | |
| WO | 199831697 A1 | 7/1998 | |
| WO | 2001027128 A1 | 4/2001 | |
| WO | 2002080935 A1 | 10/2002 | |
| WO | 2002080936 A1 | 10/2002 | |
| WO | 2004052902 A1 | 6/2004 | |
| WO | 2004080990 A1 | 9/2004 | |
| WO | 2005012326 A1 | 2/2005 | |
| WO | 2006011502 A1 | 2/2006 | |
| WO | 2006032693 A1 | 3/2006 | |
| WO | 2008013321 A1 | 1/2008 | |
| WO | 2008115574 A1 | 9/2008 | |
| WO | 2008116195 A2 | 9/2008 | |
| WO | 2008131224 A2 | 10/2008 | |
| WO | 2009026389 A2 | 2/2009 | |
| WO | 2009026537 A1 | 2/2009 | |
| WO | 2009091082 A1 | 7/2009 | |
| WO | 2009143010 A1 | 11/2009 | |
| WO | 2009143020 A1 | 11/2009 | |
| WO | 2009143021 A1 | 11/2009 | |
| WO | 2010031813 A1 | 3/2010 | |
| WO | 2010031820 A1 | 3/2010 | |
| WO | 2010043682 A2 | 4/2010 | |
| WO | 2010045656 A2 | 4/2010 | |
| WO | 2010048358 A2 | 4/2010 | |
| WO | 2010074219 A1 | 7/2010 | |
| WO | 2010080976 A1 | 7/2010 | |
| WO | 2010092123 A1 | 8/2010 | |
| WO | 2010092125 A1 | 8/2010 | |
| WO | 2010128152 A1 | 11/2010 | |

OTHER PUBLICATIONS

Balbach et al., International Journal of Pharmaceutics, 275:1-12(2004.

Handlon; "Sodium glucose co-transporter 2 (SGLT2) inhibitors as potential antidiabetic agents"; Expert Opin. Ther. Patents—Review;15(11):1531-1540 (2005).

Hediger et al; "Homology of the human intestinal Na+/glucose and *Escherichia coil* Na+/proline cotransporters"; Proc. Natl. Acad. Sci USA; 86:5748-5752 (1989).

International Search Report for International Application: PCT/EP2010/065747 dated Feb. 9, 2011.

Isaji; "Sodium-glucose cotransporter inhibitors for diabetes"; Current Opinion in Investigational Drugs; 8(4):285-292 (2007).

Kanai et al.; "The Human Kidney Low Affinity Na+/glucose Cotransporter SGLT2"; J. Clin. Invest.; 93:397-404 (1994).

Lostao et al.; "Phenylglucosides and the Na+/Glucose Cotransporter (SGLT1): Analysis of Interactions"; J. Membrane Biol.; 142:161-170 (1994).

Lv et al.; "Conformationally Constrained Spiro C-Aryglycosides as Potent and Selective Renal Sodium-Dependent Glucose Co-transporter 2 (SGLT2) Inhibitors"; ChemMedChem; 5:827-831 (2010).

Nair et al.; "Sodium Glucose Cotransporter 2 Inhibitors as a New Treatment for Diabetes Mellitus"; J. Clin. Endocrinol. Metab.—Special Feature Review; 95(1):1-9 (2010).

Santer et al.; "Familial Renal Glucosuria and SGLT2: From a Mendelian Trait to a Therapeutic Target"; Clin.J. Am. Soc. Nephrol.—In-Depth Review; pp. 1-9 (2009).

Smith et al.; "Appearance of Phloridzin-Sensitive Glucose Transport Is Not Controlled at mRNA Level in Rabbit Jejunal Enterocytes"; Experimental Physiology; 77:525-528 (1992).

Wells et al.; "Cloning of a human kidney cDNA with similarity to the sodium-glocuse cotransporter"; Am. J. Physiol.; 263Renal(32); F459-F465 (1992).

Xu et al.; "Ortho-Substituted C-aryl glucosides as highly potent and selective renal sodium-dependent glucose co-transporter 2 (SGLT2) inhibitors"; Bioorganic & Medicinal Chemistry;18:4422-4432 (2010).

Zhou et al.; "Synthesis and SAR of Benzisothiazole- and Indolizine-.beta.-D-glucopyranoside Inhibitors of SGLT2"; ACS Med. Chem. Lett.; 1:19-23 (2010).

* cited by examiner

GLYCOSIDE DERIVATIVES AND USES THEREOF

BACKGROUND OF THE INVENTION

Diabetes mellitus is a metabolic disorder characterized by recurrent or persistent hyperglycemia (high blood glucose) and other signs, as distinct from a single disease or condition. Glucose level abnormalities can result in serious long-term complications, which include cardiovascular disease, chronic renal failure, retinal damage, nerve damage (of several kinds), microvascular damage and obesity.

Type 1 diabetes, also known as Insulin Dependent Diabetes Mellitus (IDDM), is characterized by loss of the insulin-producing β-cells of the islets of Langerhans of the pancreas leading to a deficiency of insulin. Type-2 diabetes previously known as adult-onset diabetes, maturity-onset diabetes, or Non-Insulin Dependent Diabetes Mellitus (NIDDM)—is due to a combination of increased hepatic glucose output, defective insulin secretion, and insulin resistance or reduced insulin sensitivity (defective responsiveness of tissues to insulin).

Chronic hyperglycemia can also lead to onset or progression of glucose toxicity characterized by decrease in insulin secretion from β-cell, insulin sensitivity; as a result diabetes mellitus is self-exacerbated [*Diabetes Care,* 1990, 13, 610].

Chronic elevation of blood glucose level also leads to damage of blood vessels. In diabetes, the resultant problems are grouped under "microvascular disease" (due to damage of small blood vessels) and "macrovascular disease" (due to damage of the arteries). Examples of microvascular disease include diabetic retinopathy, neuropathy and nephropathy, while examples of macrovascular disease include coronary artery disease, stroke, peripheral vascular disease, and diabetic myonecrosis.

Diabetic retinopathy, characterized by the growth of weakened blood vessels in the retina as well as macular edema (swelling of the macula), can lead to severe vision loss or blindness. Retinal damage (from microangiopathy) makes it the most common cause of blindness among non-elderly adults in the US. Diabetic neuropathy is characterized by compromised nerve function in the lower extremities. When combined with damaged blood vessels, diabetic neuropathy can lead to diabetic foot. Other forms of diabetic neuropathy may present as mononeuritis or autonomic neuropathy. Diabetic nephropathy is characterized by damage to the kidney, which can lead to chronic renal failure, eventually requiring dialysis. Diabetes mellitus is the most common cause of adult kidney failure worldwide. A high glycemic diet (i.e., a diet that consists of meals that give high postprandial blood sugar) is known to be one of the causative factors contributing to the development of obesity.

Type 2 diabetes is characterized by insulin resistance and/or inadequate insulin secretion in response to elevated glucose level. Therapies for type 2 diabetes are targeted towards increasing insulin sensitivity (such as TZDs), hepatic glucose utilization (such as biguanides), directly modifying insulin levels (such as insulin, insulin analogs, and insulin secretagogues), increasing incretin hormone action (such as exenatide and sitagliptin), or inhibiting glucose absorption from the diet (such as alpha glucosidase inhibitors) [*Nature* 2001, 414, 821-827].

Glucose is unable to diffuse across the cell membrane and requires transport proteins. The transport of glucose into epithelial cells is mediated by a secondary active cotransport system, the sodium-D-glucose co-transporter (SGLT), driven by a sodium-gradient generated by the Na+/K+-ATPase. Glucose accumulated in the epithelial cell is further transported into the blood across the membrane by facilitated diffusion through GLUT transporters [*Kidney International* 2007, 72, S27-S35].

SGLT belongs to the sodium/glucose co-transporter family SLCA5. Two different SGLT isoforms, SGLT1 and SGLT2, have been identified to mediate renal tubular glucose reabsorption in humans [*Curr. Opinon in Investigational Drugs* (2007): 8(4), 285-292 and references cited herein]. Both of them are characterized by their different substrate affinity. Although both of them show 59% homology in their amino acid sequence, they are functionally different. SGLT1 transports glucose as well as galactose, and is expressed both in the kidney and in the intestine, while SGLT2 is found exclusively in the S1 and S2 segments of the renal proximal tubule. As a consequence, glucose filtered in the glomerulus is reabsorbed into the renal proximal tubular epithelial cells by SGLT2, a low-affinity/high-capacity system, residing on the surface of epithelial cell lining in S1 and S2 tubular segments. Much smaller amounts of glucose are recovered by SGLT1, as a high-affinity/low-capacity system, on the more distal segment of the proximal tubule. In healthy human, more than 99% of plasma glucose that is filtered in the kidney glomerulus is reabsorbed, resulting in less than 1% of the total filtered glucose being excreted in urine. It is estimated that 90% of total renal glucose absorption is facilitated by SGLT2; remaining 10% is likely mediated by SGLT1 [*J. Parenter. Enteral Nutr.* 2004, 28, 364-371].

SGLT2 was cloned as a candidate sodium glucose co-transporter, and its tissue distribution, substrate specificity, and affinities are reportedly very similar to those of the low-affinity sodium glucose co-transporter in the renal proximal tubule. A drug with a mode of action of SGLT2 inhibition will be a novel and complementary approach to existing classes of medication for diabetes and its associated diseases to meet the patient's needs for both blood glucose control, while preserving insulin secretion. In addition, SGLT2 inhibitors which lead to loss of excess glucose (and thereby excess calories) may have additional potential for the treatment of obesity.

Indeed small molecule SGLT2 inhibitors have been discovered and the anti-diabetic therapeutic potential of such molecules has been reported in literature [T-1095 (Diabetes, 1999, 48, 1794-1800, Dapagliflozin (Diabetes, 2008, 57, 1723-1729)].

Various O-aryl and O-heteroaryl glycosides have been reported as SGLT-2 inhibitors in patent publications such as: WO 01/74834, WO 03/020737, U.S. Ser. No. 04/001,8998, WO 01/68660, WO 01/16147, WO 04/099230, WO 05/011592, U.S. Ser. No. 06/029,3252 and WO 05/021566.

Various glucopyranosyl-substituted aromatic and heteroaromatic compounds have also been reported as SGLT-2 inhibitors in patent publications such as: WO 01/27128, WO 04/080990, U.S. Ser. No. 06/002,5349, WO 05/085265, WO 05/085237, WO 06/054629 and WO 06/011502.

SGLT1 is predominantly found in the intestine and plays a major role in the absorption of D-glucose and D-galactose. Therefore, SGLT1 inhibitors have the potential to act both in the kidney as well as the intestine to reduce calorie intake and hyperglycemia.

WO2004/018491 discloses pyrazole derivatives which are SGLT1 inhibitors.

Glucopyranosyl-substituted aromatic or heteroaromatic compounds where, in general, the sugar moiety has been modified at C4, C5, or C6 positions of pyranose have been published (U.S. Ser. No. 06/000,9400, U.S. Ser. No. 06/001, 9948, U.S. Ser. No. 06/003,5841, U.S. Ser. No. 06/007,4031, U.S. Ser. No. 08/002,7014 and WO 08/016132).

DETAILED DESCRIPTION OF THE INVENTION

Figure 1:
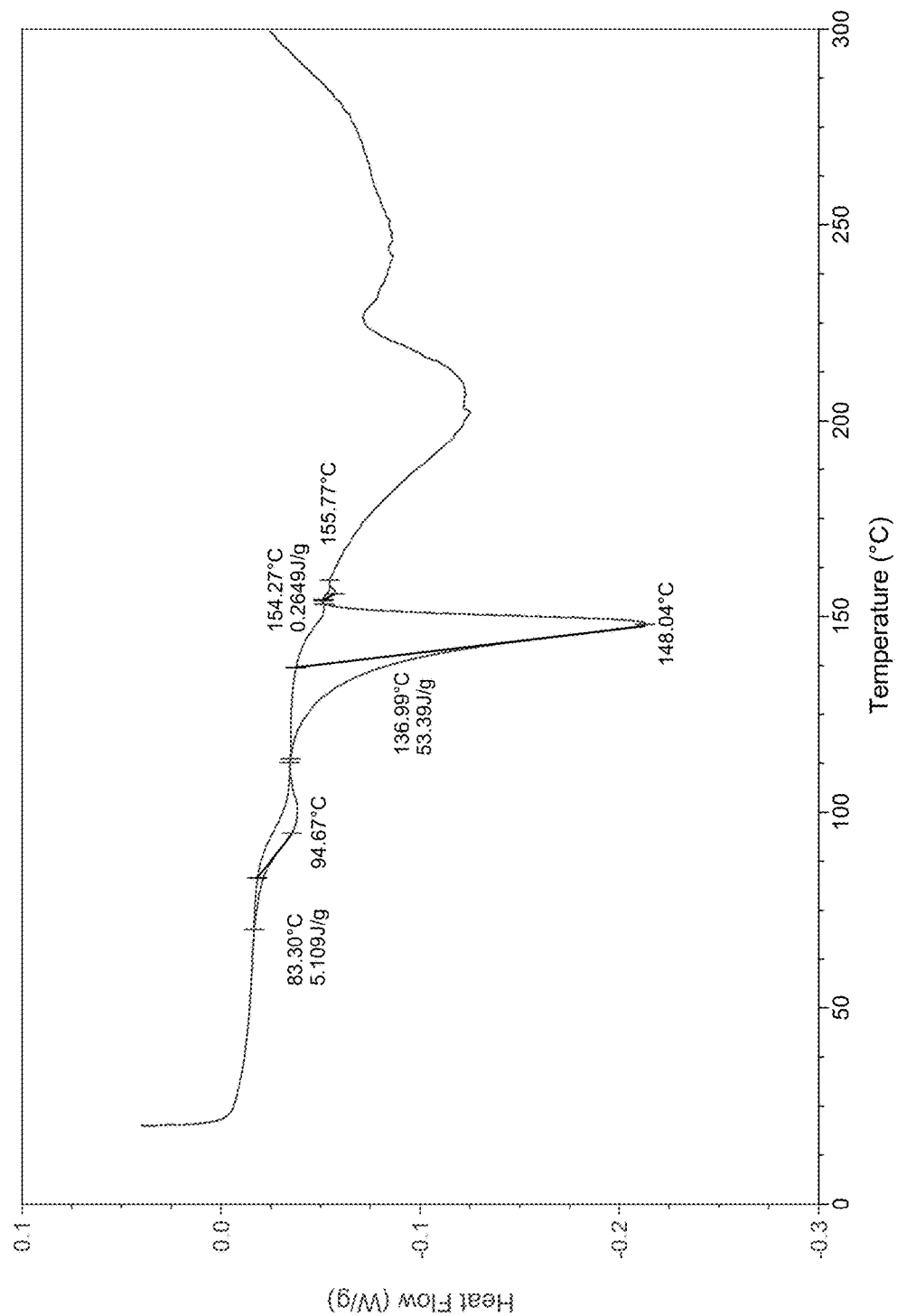
FIG. 1 is a differential scanning calorimetry thermogram of a 1:1 L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol prepared by method 1.

This invention relates to compounds useful for treating diseases and conditions mediated by the sodium D-glucose co-transporter (SGLT), e.g. diabetes. The invention also provides methods of treating such diseases and conditions, and compounds and compositions etc. for their treatment.

The invention provides novel glycoside derivatives, their polymorphs, stereoisomers, pro-drugs, solvates, pharmaceutically acceptable salts and formulations thereof. The invention also relates to processes for the preparation of the compounds of the invention.

The compounds of the invention possess sodium-D-glucose co-transporter (SGLT) inhibition effects, which are beneficial for the prophylaxis, management, treatment, control of progression, or adjunct treatment of diseases and/or medical conditions where the inhibition of SGLT would be beneficial, such as diabetes (including Type-I and Type-II), obesity, dyslipidemia, insulin resistance, and other metabolic syndrome, and/or diabetes-related complications including retinopathy, nephropathy, neuropathy, ischemic heart disease, arteriosclerosis, 1-cell dysfunction, and as therapeutic and/or prophylactic agents for obesity.

The inventors have found compounds of Formula (I) that are useful for inhibiting SGLT.

Accordingly, in a first aspect of the invention, there is provided a compound represented by Formula (I):

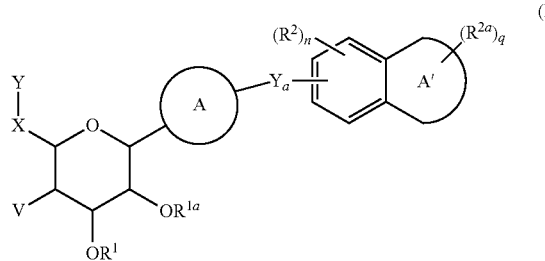

(I)

wherein:
Ring A is an $C_{6-10}$aryl which is optionally substituted with one or more substituents independently selected from the group consisting of halo, hydroxy, cyano, nitro, $C_{1-6}$alkyl, $C_{2-6}$alkenyl, $C_{2-6}$alkynyl, $C_{1-6}$alkoxy, halo$C_{1-6}$alkoxy, $C_{3-7}$cycloalkyl, $C_{3-7}$cycloalkyl $C_{1-4}$alkyl, halo$C_{1-6}$alkyl, $C_{6-10}$aryl, $C_{6-10}$aryl$C_{1-4}$alkyl, —C(O)OR$^3$, —C(O)R$^3$, —C(O)NR$^4$R$^5$, —NR$^4$R$^5$, —CH$_2$NR$^4$R$^5$, $C_{1-6}$alkoxy, $C_{3-7}$ cycloalkoxy, —S(O)$_p$R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy and $C_{1-10}$heterocycloxy; wherein the alkyl, alkenyl, alkynyl, cycloalkyl, aryl, heterocyclyl and heteroaryl groups may be optionally substituted with one or more substituents selected from the group consisting of halo, hydroxy, cyano, nitro, $C_{1-6}$alkyl, —S(O)$_p$R$^3$, —C(O)OR$^3$, —C(O)R$^3$, —C(O)NR$^4$R$^5$, —NR$^4$R$^5$, —CH$_2$NR$^4$R$^5$ and $C_{1-6}$alkoxy;

Ring A' is a 5-, 6- or 7-membered heterocycle, provided that Ring A' is not 1,3-dioxole;

$Y_a$ is a bond or a ($C_1$-$C_6$)alkylene which is optionally substituted with one or more substituents independently selected from halo, hydroxy, $C_{1-4}$alkyl, $C_{1-4}$alkoxy, halo$C_{1-4}$alkyl;

V is hydrogen, halo or —OR$^{1b}$;

n is 0, 1, 2, or 3;

q is 0, 1, 2, or 3;

$R^1$, $R^{1a}$, $R^{1b}$ and $R^{1c}$ are independently selected from hydrogen, $C_{1-6}$ alkyl, $C_{6-10}$aryl-$C_{1-4}$alkyl, —C(O)$C_{6-10}$aryl and —C(O)$C_{1-6}$alkyl;

$R^2$, for each occurrence, is independently selected from the group consisting of halo, hydroxy, cyano, nitro, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —C(O)OR$^3$, —C(O)R$^3$, —C(O)NR$^4$R$^5$, —NR$^4$R$^5$, —CH$_2$NR$^4$R$^5$, $C_{1-6}$alkoxy, $C_{3-7}$ cycloalkoxy, —S(O)R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy and $C_{1-10}$heterocycloxy; wherein when any portion of $R^2$ is an alkyl, cycloalkyl, aryl, heterocyclyl or heteroaryl, for each occurrence, it may be optionally substituted with one or more substituents which are independently selected from halo, hydroxy, $C_{1-4}$alkyl, and $C_{1-4}$alkoxy;

$R^{2a}$, for each occurrence, is independently selected from the group consisting of oxo, halo, hydroxy, cyano, nitro, $C_{1-6}$alkyl, $C_{3-7}$cycloalkyl, $C_{3-7}$cycloalkyl$C_{1-4}$ alkyl, $C_{6-10}$aryl, $C_{6-10}$aryl$C_{1-4}$alkyl, —C(O)OR$^3$, —C(O)R$^3$, —C(O)NR$^4$R$^5$, —NR$^4$R$^5$, —CH$_2$NR$^4$R$^5$, $C_{1-6}$alkoxy, $C_{3-7}$ cycloalkoxy, —S(O)$_p$R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy and $C_{1-10}$heterocycloxy; wherein when any portion of $R^{2a}$ is an alkyl, cycloalkyl, aryl, heterocyclyl or heteroaryl, for each occurrence, it may be optionally substituted with one or more substituents which are independently selected from halo, hydroxy, cyano, nitro, $C_{1-6}$alkyl, —S(O)$_p$R$^3$, —C(O)OR$^3$, —C(O)R$^3$, —C(O)NR$^4$R$^5$, —NR$^4$R$^5$, —CH$_2$NR$^4$R$^5$ and $C_{1-6}$alkoxy; or two R$^{2a}$ on adjacent atoms taken together with the atoms to which they are attached may form a fused C$_{3-7}$cycloalkyl, C$_6$aryl, 3- to 7-membered heterocyclyl, or 5- or 6-membered heteroaryl, wherein the fused cycloalkyl, aryl, heterocyclyl, and heteroaryl may be optionally substituted with one or more substituent independently selected from halo, hydroxy, C$_{1-4}$alkyl, and C$_{1-4}$alkoxy; or two R$^{2a}$ on the same carbon atom taken together may form a spiro 3- to 7-membered heterocyclyl or a spiro C$_{3-7}$cycloalkyl which may be optionally substituted with one or more substituent independently selected from halo, hydroxy, C$_{1-4}$alkyl, and C$_{1-4}$alkoxy; and R$^3$, for each occurrence, is independently selected from hydrogen, C$_{1-6}$ alkyl, C$_{3-7}$ cycloalkyl, C$_{3-7}$ cycloalkylC$_{1-4}$alkyl, C$_{6-10}$aryl, C$_{1-10}$ heteroaryl, and C$_{2-10}$heterocyclyl;

p is 0, 1 or 2;

X is [C(R$^6$)(R$^7$)]$_t$;

Y is H, halo, C$_{1-4}$ alkyl, OR$^{1c}$ or NR$^4$R$^5$;

t is 1, 2, or 3;

R$^6$ and R$^7$, for each occurrence, are independently selected from hydrogen, C$_{1-6}$ alkyl, OR$^{1e}$, and NR$^4$R$^5$;

or when t is 1, R$^6$ and R$^7$ together may form an oxo group, or when R$^6$ and R$^7$ are on the same carbon they can be taken together to form a C$_{3-7}$cycloalkyl or a 3- to 7-membered heterocycle;

R$^{1e}$, for each occurrence, is independently selected from hydrogen, C$_{1-6}$ alkyl, C$_{6-10}$aryl-C$_{1-4}$alkyl, —C(O)C$_{6-10}$aryl and —C(O)C$_{1-6}$alkyl;

R$^4$ and R$^5$, for each occurrence, are independently selected from hydrogen, C$_{1-6}$ alkyl, C$_{3-7}$ cycloalkyl, C$_{3-7}$ cycloalkylC$_{1-4}$alkyl, C$_{6-10}$arylC$_{1-4}$alkyl, C$_{6-10}$aryl, C$_{1-10}$heteroaryl, C$_{1-10}$heteroarylC$_{1-4}$alkyl, C$_{2-10}$heterocyclyl, and C$_{2-10}$heterocyclylC$_{1-4}$alkyl; or R$^4$ and R$^5$ taken together along with the nitrogen to which they are bound may form a monocyclic or a bicyclic heteroaryl or heterocyclyl which may be optionally substituted with one or more halo or C$_{1-4}$alkyl; or a pharmaceutically acceptable salt thereof.

In another aspect of the invention, the compound of Formula (I) is of Formula (I-a):

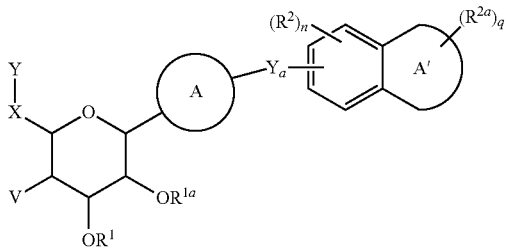

(I-a)

wherein:

Ring A is an C$_{6-10}$aryl which is optionally substituted with one or more substituents independently selected from the group consisting of halo, hydroxy, cyano, C$_{1-6}$alkyl, C$_{2-6}$alkenyl, C$_{2-6}$alkynyl, C$_{1-6}$alkoxy, haloC$_{1-6}$alkoxy, a 5-membered heteroaryl and a 6-membered heteroaryl;

Ring A' is a 5- or 6-membered heterocycle, provided that Ring A' is not 1,3-dioxole;

Y$_a$ is a bond or a (C$_1$-C$_6$)alkylene which is optionally substituted with one or more substituents independently selected from halo, C$_{1-4}$alkyl, haloC$_{1-4}$alkyl;

V is hydrogen, halo or —OR$^{1b}$;

n is 0, 1, 2, or 3;

q is 0, 1, 2, or 3;

R$^1$, R$^{1a}$, R$^{1b}$ and R$^{1c}$ are independently selected from hydrogen, C$_{1-6}$ alkyl, C$_{6-10}$aryl-C$_{1-4}$alkyl, —C(O)C$_{6-10}$aryl and —C(O)C$_{1-6}$alkyl;

R$^2$, for each occurrence, is independently selected from the group consisting of halo, hydroxy, cyano, nitro, C$_{1-6}$alkyl, C$_{3-7}$cycloalkyl, C$_{3-7}$cycloalkylC$_{1-4}$alkyl, C$_{6-10}$aryl, C$_{6-10}$arylC$_{1-4}$alkyl, —C(O)OR$^3$, —C(O)R$^3$, —C(O)NR$^4$R$^5$, —NR$^4$R$^5$, —CH$_2$NR$^4$R$^5$, C$_{1-6}$alkoxy, C$_{3-7}$ cycloalkoxy, —S(O)$_p$R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, C$_{6-10}$aryloxy, C$_{2-10}$heterocyclyl, C$_{2-10}$heterocyclylC$_{1-4}$alkyl, C$_{1-10}$heteroarylC$_{1-4}$alkyl, C$_{1-10}$heteroaryl, C$_{1-10}$heteroaryloxy and C$_{1-10}$heterocycloxy; wherein R$^2$ may, for each occurrence, be optionally substituted with one or more substituents which are independently selected from halo, hydroxy, C$_{1-4}$alkyl, and C$_{1-4}$alkoxy;

R$^{2a}$, for each occurrence, is independently selected from the group consisting of oxo, halo, hydroxy, cyano, nitro, C$_{1-6}$alkyl, C$_{3-7}$cycloalkyl, C$_{3-7}$cycloalkyl C$_{1-4}$alkyl, C$_{6-10}$aryl, C$_{6-10}$arylC$_{1-4}$alkyl, —C(O)OR$^3$, —C(O)R$^3$, —C(O)NR$^4$R$^5$, —NR$^4$R$^5$, —CH$_2$NR$^4$R$^5$, C$_{1-6}$alkoxy, C$_{3-7}$ cycloalkoxy, —S(O)$_p$R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, C$_{6-10}$aryloxy, C$_{2-10}$heterocyclyl, C$_{2-10}$heterocyclylC$_{1-4}$alkyl, C$_{1-10}$heteroarylC$_{1-4}$alkyl, C$_{1-10}$heteroaryl, C$_{1-10}$heteroaryloxy and C$_{1-10}$heterocycloxy; wherein R$^{2a}$ may, for each occurrence, be optionally substituted with one or more substituents which are independently selected from halo, hydroxy, C$_{1-4}$alkyl, and C$_{1-4}$alkoxy; or two R$^{2a}$ on adjacent atoms taken together with the atoms to which they are attached may form a fused C$_{3-7}$cycloalkyl, C$_6$aryl, 3- to 7-membered heterocyclyl, or 5- or 6-membered heteroaryl, wherein the fused cycloalkyl, aryl, heterocyclyl, and heteroaryl may be optionally substituted with one or more substituent independently selected from halo, hydroxy, C$_{1-4}$alkyl, and C$_{1-4}$alkoxy; or two R$^{2a}$ on the same carbon atom taken together may form a spiro 3- to 7-membered heterocyclyl or a spiro C$_{3-7}$cycloalkyl which may be optionally substituted with one or more substituent independently selected from halo, hydroxy, C$_{1-4}$alkyl, and C$_{1-4}$alkoxy; and R$^3$, for each occurrence, is independently selected from hydrogen, C$_{1-6}$ alkyl, C$_{3-7}$ cycloalkyl, C$_{3-7}$ cycloalkylC$_{1-4}$alkyl, C$_{6-10}$aryl, C$_{1-10}$heteroaryl, and C$_{2-10}$heterocyclyl;

p is 0, 1 or 2;

X is [C(R$^6$)(R$^7$)]$_t$;

Y is H, halo, C$_{1-4}$ alkyl, OR$^{1c}$ or NR$^4$R$^5$;

t is 1, 2, or 3;

R$^6$ and R$^7$, for each occurrence, are independently selected from hydrogen, C$_{1-6}$ alkyl, OR$^{1e}$, and NR$^4$R$^5$;

or when t is 1, R$^6$ and R$^7$ together may form an oxo group, or when R$^6$ and R$^7$ are on the same carbon they can be taken together to form a C$_{3-7}$cycloalkyl or a 3- to 7-membered heterocycle;

$R^{1e}$, for each occurrence, is independently selected from hydrogen, $C_{1-6}$ alkyl, $C_{6-10}$aryl-$C_{1-4}$alkyl, —C(O)$C_{1-10}$aryl and —C(O)$C_{1-6}$alkyl;

$R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl; or a pharmaceutically acceptable salt thereof.

In another aspect of the invention, the compound of Formula (I) is of Formula (I-i):

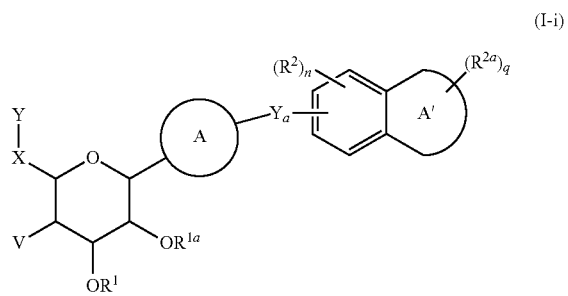

(I-i)

wherein:

Ring A is a $C_{6-10}$aryl which is optionally substituted with one or more substituents independently selected from the group consisting of halo, hydroxy, $C_{1-3}$alkyl, $C_{1-3}$alkoxy, halo$C_{1-3}$alkoxy and 5-membered heteroaryl;

Ring A' is a 5- or 6-membered heterocycle containing at least one O or N heteroatom, provided that Ring A' is not 1,3-dioxole;

$Y_a$ is a bond or a $C_{1-3}$alkylene which is optionally substituted with one or more substituents independently selected from halo, $C_{1-4}$alkyl, and halo$C_{1-4}$alkyl;

V is hydrogen, halo or —$OR^{1b}$;

n is 0, 1 or 2;

q is 0, 1, 2, or 3;

$R^1$, $R^{1a}$, $R^{1b}$ and $R^{1c}$ are independently selected from hydrogen, $C_{1-6}$ alkyl, $C_{6-10}$aryl-$C_{1-4}$alkyl, —C(O)$C_{6-10}$aryl and —C(O)$C_{1-6}$alkyl;

$R^2$, for each occurrence, is independently selected from the group consisting of halo, hydroxy, cyano, nitro, $C_{1-6}$alkyl, $C_{3-7}$cycloalkyl, $C_{6-10}$aryl, $C_{6-10}$aryl$C_{1-4}$alkyl, —C(O)$OR^3$, —C(O)$R^3$, —C(O)$NR^4R^5$, —$NR^4R^5$, —$CH_2NR^4R^5$, $C_{1-6}$alkoxy, $C_{3-7}$cycloalkoxy, —$CH_2C(O)OR^3$, —$CH_2C(O)NR^4R^5$, —$NR^3C(O)NR^4R^5$, —$NR^3C(O)OR^3$, $C_{6-10}$aryloxy, $C_{2-10}$heterocyclyl, $C_{1-10}$heteroaryl, $C_{1-10}$heteroaryloxy and $C_{1-10}$heterocycloxy; wherein $R^2$ may, for each occurrence, be optionally substituted with one or more substituents which are independently selected from halo, hydroxy, $C_{1-4}$alkyl, and $C_{1-4}$alkoxy;

$R^{2a}$, for each occurrence, is independently selected from the group consisting of oxo, hydroxy, $C_{1-6}$alkyl, $C_{3-7}$cycloalkyl$C_{1-4}$alkyl, $C_{6-10}$aryl$C_{1-4}$alkyl, —C(O)$OR^3$, —C(O)$R^3$, —C(O)$NR^4R^5$ and $CH_2C(O)OR^3$; wherein $R^{2a}$ may, for each occurrence, be optionally substituted with one or more substituents which are independently selected from halo, hydroxy, $C_{1-4}$alkyl, and $C_{1-4}$alkoxy; or two $R^{2a}$ on adjacent atoms taken together with the atoms to which they are attached may form a fused $C_{3-7}$cycloalkyl, $C_6$aryl, 3- to 7-membered heterocyclyl, or 5-membered heteroaryl, wherein the fused cycloalkyl, aryl, heterocyclyl, and heteroaryl may be optionally substituted with one or more substituent independently selected from halo, hydroxy, $C_{1-4}$alkyl, and $C_{1-4}$alkoxy; or two $R^{2a}$ on the same carbon atom taken together may form a spiro 3- to 7-membered heterocyclyl or a spiro $C_{3-7}$cycloalkyl which may be optionally substituted with one or more substituent independently selected from halo, hydroxy, $C_{1-4}$alkyl, and $C_{1-4}$alkoxy; and $R^3$, for each occurrence, is independently selected from hydrogen, $C_{1-6}$ alkyl, $C_{3-7}$ cycloalkyl, $C_{3-7}$ cycloalkyl$C_{1-4}$alkyl, $C_{6-10}$aryl, $C_{1-10}$heteroaryl, and $C_{2-10}$heterocyclyl;

X is $[C(R^6)(R^7)]_t$;

Y is H, halo, $C_{1-4}$ alkyl, $OR^{1c}$ or $NR^4R^5$;

t is 1, 2, or 3;

$R^6$ and $R^7$, for each occurrence, are independently selected from hydrogen, $C_{1-6}$ alkyl, $OR^{1e}$, and $NR^4R^5$;

or when t is 1, $R^6$ and $R^7$ together may form an oxo group, or when $R^6$ and $R^7$ are on the same carbon they can be taken together to form a $C_{3-7}$cycloalkyl or a 3- to 7-membered heterocycle;

$R^{1e}$, for each occurrence, is independently selected from hydrogen, $C_{1-6}$ alkyl, $C_{6-10}$aryl-$C_{1-4}$alkyl, —C(O)$C_{6-10}$aryl and —C(O)$C_{1-6}$alkyl;

$R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl; or a pharmaceutically acceptable salt thereof.

In another aspect of the invention, the compound of Formula (I) is of Formula (I-ia):

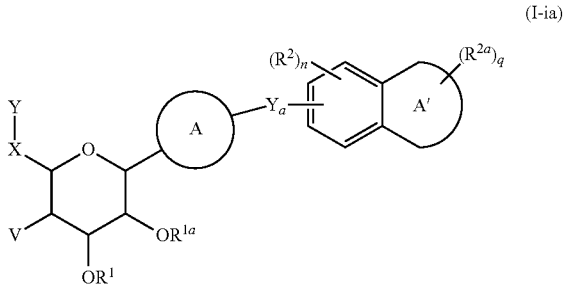

(I-ia)

wherein:

Ring A is an $C_{6-10}$aryl which is optionally substituted with one or more substituents independently selected from the group consisting of halo, hydroxy, cyano, nitro, $C_{1-6}$alkyl, $C_{2-6}$alkenyl, $C_{2-6}$alkynyl, $C_{1-6}$alkoxy, halo$C_{1-6}$alkoxy, $C_{3-7}$cycloalkyl, $C_{3-7}$cycloalkyl$C_{1-4}$alkyl, halo$C_{1-6}$alkyl, $C_{6-10}$aryl, $C_{6-10}$aryl$C_{1-4}$alkyl, —C(O)$OR^3$, —C(O)$R^3$, —C(O)$NR^4R^5$, —$NR^4R^5$, —$CH_2NR^4R^5$, $C_{1-6}$alkoxy, $C_{3-7}$ cycloalkoxy, —$S(O)_pR^3$, —$S(O)_2NR^4R^5$, —$OS(O)_2R^3$, —$CH_2C(O)OR^3$, —$CH_2C(O)NR^4R^5$, —$NR^3C(O)NR^4R^5$, —$NR^3C$ (O)OR$^3$, C$_{6-10}$aryloxy, C$_{2-10}$heterocyclyl, C$_{2-10}$heterocyclylC$_{1-4}$alkyl, C$_{1-10}$heteroarylC$_{1-4}$alkyl, C$_{1-10}$heteroaryl, C$_{1-10}$heteroaryloxy and C$_{1-10}$heterocycloxy; wherein the alkyl, alkenyl, alkynyl, cycloalkyl, aryl, heterocyclyl and heteroaryl groups may be optionally substituted with one or more substituents selected from the group consisting of halo, hydroxy, cyano, nitro, C$_{1-6}$alkyl, —S(O)$_p$R$^3$, —C(O)OR$^3$, —C(O)R$^3$, —C(O)NR$^4$R$^5$, —NR$^4$R$^5$, —CH$_2$NR$^4$R$^5$ and C$_{1-6}$alkoxy;

Ring A' is a 5- or 6-membered heterocycle containing at least one O or N heteroatom, provided that Ring A' is not 1,3-dioxole;

Y$_a$ is a bond or a C$_{1-3}$alkylene which is optionally substituted with one or more substituents independently selected from halo, C$_{1-4}$alkyl, haloC$_{1-4}$alkyl;

V is hydrogen, halo or —OR$^{1b}$;

n is 0, 1 or 2;

q is 0, 1, 2, or 3;

p is 0, 1 or 2;

R$^1$, R$^{1a}$, R$^{1b}$ and R$^{1c}$ are independently selected from hydrogen, C$_{1-6}$ alkyl, C$_{6-10}$aryl-C$_{1-4}$alkyl, —C(O)C$_{6-10}$aryl and —C(O)C$_{1-6}$alkyl;

R$^2$, for each occurrence, is independently selected from the group consisting of halo, hydroxy, cyano, nitro, C$_{1-6}$alkyl, C$_{3-7}$cycloalkyl, C$_{6-10}$aryl, C$_{6-10}$arylC$_{1-4}$alkyl, —C(O)OR$^3$, —C(O)R$^3$, —C(O)NR$^4$R$^5$, —NR$^4$R$^5$, —CH$_2$NR$^4$R$^5$, C$_{1-6}$alkoxy, C$_{3-7}$cycloalkoxy, —CH$_2$C(O)OR$^3$, —CH$_2$C(O)NR$^4$R$^5$, —NR$^3$C(O)NR$^4$R$^5$, —NR$^3$C(O)OR$^3$, C$_{6-10}$aryloxy, C$_{2-10}$heterocyclyl, C$_{1-10}$heteroaryl, C$_{1-10}$heteroaryloxy and C$_{1-10}$heterocycloxy; wherein R$^2$ may, for each occurrence, be optionally substituted with one or more substituents which are independently selected from halo, hydroxy, C$_{1-4}$alkyl, and C$_{1-4}$alkoxy;

R$^{2a}$, for each occurrence, is independently selected from the group consisting of oxo, halo, hydroxy, cyano, nitro, C$_{1-6}$alkyl, C$_{3-7}$cycloalkyl, C$_{3-7}$cycloalkylC$_{1-4}$alkyl, C$_{6-10}$aryl, C$_{6-10}$arylC$_{1-4}$alkyl, —C(O)OR$^3$, —C(O)R$^3$, —C(O)NR$^4$R$^5$, —NR$^4$R$^5$, —CH$_2$NR$^4$R$^5$, C$_{1-6}$alkoxy, C$_{3-7}$cycloalkoxy, —S(O)R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, C$_{6-10}$aryloxy, C$_{2-10}$heterocyclyl, C$_{2-10}$heterocyclylC$_{1-4}$alkyl, C$_{1-10}$heteroarylC$_{1-4}$alkyl, C$_{1-10}$heteroaryl, C$_{1-10}$heteroaryloxy and C$_{1-10}$heterocycloxy; wherein R$^{2a}$ may, for each occurrence, be optionally substituted with one or more substituents which are independently selected from halo, hydroxy, C$_{1-4}$alkyl, and C$_{1-4}$alkoxy; or two R$^{2a}$ on adjacent atoms taken together with the atoms to which they are attached may form a fused C$_{3-7}$cycloalkyl, C$_6$aryl, 3- to 7-membered heterocyclyl, or 5-membered heteroaryl, wherein the fused cycloalkyl, aryl, heterocyclyl, and heteroaryl may be optionally substituted with one or more substituent independently selected from halo, hydroxy, C$_{1-4}$alkyl, and C$_{1-4}$alkoxy; or two R$^{2a}$ on the same carbon atom taken together may form a spiro 3- to 7-membered heterocyclyl or a spiro C$_{3-7}$cycloalkyl which may be optionally substituted with one or more substituent independently selected from halo, C$_{1-4}$alkyl, and C$_{1-4}$alkoxy; and R$^3$, for each occurrence, is independently selected from hydrogen, C$_{1-6}$ alkyl, C$_{3-7}$ cycloalkyl, C$_{3-7}$ cycloalkylC$_{1-4}$alkyl, C$_{6-10}$aryl, C$_{1-10}$heteroaryl, and C$_{2-10}$heterocyclyl;

X is [C(R$^6$)(R$^7$)]$_t$;

Y is H, halo, C$_{1-4}$ alkyl, OR$^{1c}$ or NR$^4$R$^5$;

t is 1, 2, or 3;

R$^6$ and R$^7$, for each occurrence, are independently selected from hydrogen, C$_{1-6}$ alkyl, OR$^{1e}$, and NR$^4$R$^5$; or when t is 1, R$^6$ and R$^7$ together may form an oxo group, or when R$^6$ and R$^7$ are on the same carbon they can be taken together to form a C$_{3-7}$cycloalkyl or a 3- to 7-membered heterocycle;

R$^{1e}$, for each occurrence, is independently selected from hydrogen, C$_{1-6}$ alkyl, C$_{6-10}$aryl-C$_{1-4}$alkyl, —C(O)C$_{6-10}$aryl and —C(O)C$_{1-6}$alkyl;

R$^4$ and R$^5$, for each occurrence, are independently selected from hydrogen, C$_{1-6}$ alkyl, C$_{3-7}$ cycloalkyl, C$_{3-7}$ cycloalkylC$_{1-4}$alkyl, C$_{6-10}$arylC$_{1-4}$alkyl, C$_{6-10}$aryl, C$_{1-10}$heteroaryl, C$_{1-10}$heteroarylC$_{1-4}$alkyl, C$_{2-10}$heterocyclyl, and C$_{2-10}$heterocyclylC$_{1-4}$alkyl; or R$^4$ and R$^5$ taken together along with the nitrogen to which they are bound may form a monocyclic or a bicyclic heteroaryl or heterocyclyl which may be optionally substituted with one or more halo or C$_{1-4}$ alkyl; or a pharmaceutically acceptable salt thereof.

In another aspect of the invention, the compound of Formula (I) is of Formula (I-ii):

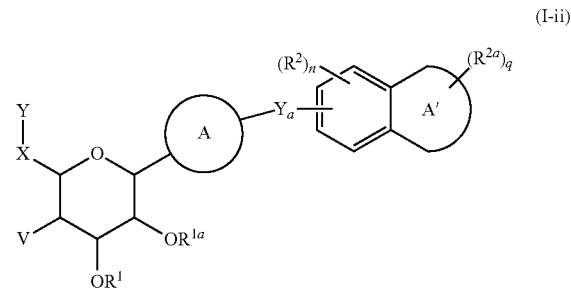

(I-ii)

wherein:

Ring A is a C$_{6-10}$aryl which is optionally substituted with one or more substituents independently selected from the group consisting of halo, hydroxy, C$_{1-3}$alkyl, C$_{1-3}$alkoxy, haloC$_{1-3}$alkoxy and 5-membered heteroaryl;

Ring A' is a 5- or 6-membered heterocycle containing at least one O or N heteroatom, provided that Ring A' is not 1,3-dioxole;

Y$_a$ is a bond or a C$_{1-3}$alkylene which is optionally substituted with one or more substituents independently selected from halo, C$_{1-4}$alkyl, haloC$_{1-4}$alkyl;

V is OH;

n is 0, 1 or 2;

q is 0, 1, 2, or 3;

R$^1$ and R$^{1a}$ are each hydrogen;

R$^2$, for each occurrence, is independently selected from the group consisting of halo, hydroxy, cyano, nitro, C$_{1-6}$alkyl, C$_{3-7}$cycloalkyl, C$_{6-10}$aryl, C$_{6-10}$arylC$_{1-4}$alkyl, —C(O)OR$^3$, —C(O)R$^3$, —C(O)NR$^4$R$^5$, —NR$^4$R$^5$, —CH$_2$NR$^4$R$^5$, C$_{1-6}$alkoxy, C$_{3-7}$cycloalkoxy, —CH$_2$C(O)OR$^3$, —CH$_2$C(O)NR$^4$R$^5$, —NR$^3$C(O)NR$^4$R$^5$, —NR$^3$C(O)OR$^3$, C$_{6-10}$aryloxy, C$_{2-10}$heterocyclyl, C$_{1-10}$heteroaryl, C$_{1-10}$heteroaryloxy and C$_{1-10}$heterocycloxy; wherein R$^2$ may, for each occurrence, be optionally substituted with one or more substituents which are independently selected from halo, hydroxy, C$_{1-4}$alkyl, and C$_{1-4}$alkoxy;

$R^{2a}$, for each occurrence, is independently selected from the group consisting of oxo, hydroxy, $C_{1-6}$alkyl, $C_{3-7}$cycloalkyl$C_{1-4}$alkyl, $C_{6-10}$aryl$C_{1-4}$alkyl, —C(O)OR$^3$, —C(O)R$^3$, —C(O)NR$^4$R$^5$ and CH$_2$C(O)OR$^3$; wherein $R^{2a}$ may, for each occurrence, be optionally substituted with one or more substituents which are independently selected from halo, hydroxy, $C_{1-4}$alkyl, and $C_{1-4}$alkoxy; or two $R^{2a}$ on adjacent atoms taken together with the atoms to which they are attached may form a fused $C_{3-7}$cycloalkyl, $C_6$aryl, 3- to 7-membered heterocyclyl, or 5-membered heteroaryl, wherein the fused cycloalkyl, aryl, heterocyclyl, and heteroaryl may be optionally substituted with one or more substituent independently selected from halo, hydroxy, $C_{1-4}$alkyl, and $C_{1-4}$alkoxy; or two $R^{2a}$ on the same carbon atom taken together may form a spiro 3- to 7-membered heterocyclyl or a spiro $C_{3-7}$cycloalkyl which may be optionally substituted with one or more substituent independently selected from halo, hydroxy, $C_{1-4}$alkyl, and $C_{1-4}$alkoxy; and $R^3$, for each occurrence, is independently selected from hydrogen, $C_{1-6}$ alkyl, $C_{3-7}$ cycloalkyl, $C_{3-7}$ cycloalkyl$C_{1-4}$alkyl, $C_{6-10}$aryl, $C_{1-10}$heteroaryl, and $C_{2-10}$heterocyclyl;

X is [C(R$^6$)(R$^7$)]$_t$;

Y is H or OH;

t is 1;

$R^6$ and $R^7$, for each occurrence, are independently selected from hydrogen and $C_{1-3}$ alkyl;

or when t is 1, $R^6$ and $R^7$ together may form an oxo group;

$R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl; or a pharmaceutically acceptable salt thereof.

In another aspect of the invention, the compound of Formula (I) is of Formula (I-iia):

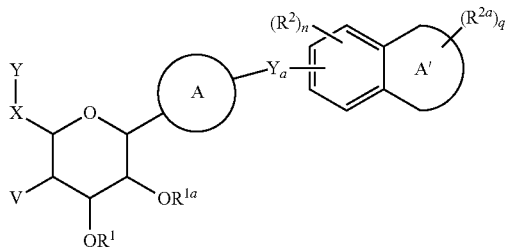

(I-iia)

wherein:

Ring A is an $C_{6-10}$aryl which is optionally substituted with one or more substituents independently selected from the group consisting of halo, hydroxy, cyano, nitro, $C_{1-6}$alkyl, $C_{2-6}$alkenyl, $C_{2-6}$alkynyl, $C_{1-6}$alkoxy, halo$C_{1-6}$alkoxy, $C_{3-7}$cycloalkyl, $C_{3-7}$cycloalkyl$C_{1-4}$alkyl, halo$C_{1-6}$alkyl, $C_{6-10}$aryl, $C_{6-10}$aryl$C_{1-4}$alkyl, —C(O)OR$^3$, —C(O)R$^3$, —C(O)NR$^4$R$^5$, —NR$^4$R$^5$, —CH$_2$NR$^4$R$^5$, $C_{1-6}$alkoxy, $C_{3-7}$ cycloalkoxy, —S(O)$_p$R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy and $C_{1-10}$heterocycloxy; wherein the alkyl, alkenyl, alkynyl, cycloalkyl, aryl, heterocyclyl and heteroaryl groups may be optionally substituted with one or more substituents selected from the group consisting of halo, hydroxy, cyano, nitro, $C_{1-6}$alkyl, —S(O)$_p$R$^3$, —C(O)OR$^3$, —C(O)R$^3$, —C(O)NR$^4$R$^5$, —NR$^4$R$^5$, —CH$_2$NR$^4$R$^5$ and $C_{1-6}$alkoxy;

Ring A' is a 5- or 6-membered heterocycle containing at least one O or N heteroatom, provided that Ring A' is not 1,3-dioxole;

$Y_a$ is a bond or a $C_{1-3}$alkylene which is optionally substituted with one or more substituents independently selected from halo, $C_{1-4}$alkyl, halo$C_{1-4}$alkyl;

V is OH;

n is 0, 1 or 2;

q is 0, 1, 2, or 3;

$R^1$ and $R^{1a}$ are each hydrogen;

$R^2$, for each occurrence, is independently selected from the group consisting of halo, hydroxy, cyano, nitro, $C_{1-6}$alkyl, $C_{3-7}$cycloalkyl, $C_{6-10}$aryl, $C_{6-10}$aryl$C_{1-4}$alkyl, —C(O)OR$^3$, —C(O)R$^3$, —C(O)NR$^4$R$^5$, —NR$^4$R$^5$, —CH$_2$NR$^4$R$^5$, $C_{1-6}$alkoxy, $C_{3-7}$cycloalkoxy, —CH$_2$C(O)OR$^3$, —CH$_2$C(O)NR$^4$R$^5$, —NR$^3$C(O)NR$^4$R$^5$, —NR$^3$C(O)OR$^3$, $C_{6-10}$aryloxy, $C_{2-10}$heterocyclyl, $C_{1-10}$heteroaryl, $C_{1-10}$heteroaryloxy and $C_{1-10}$heterocycloxy; wherein $R^2$ may, for each occurrence, be optionally substituted with one or more substituents which are independently selected from halo, hydroxy, $C_{1-4}$alkyl, and $C_{1-4}$alkoxy; $R^{2a}$, for each occurrence, is independently selected from the group consisting of oxo, halo, hydroxy, cyano, nitro, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —C(O)OR$^3$, —C(O)R$^3$, —C(O)NR$^4$R$^5$, —NR$^4$R$^5$, —CH$_2$NR$^4$R$^5$, $C_{1-6}$alkoxy, $C_{3-7}$ cycloalkoxy, —S(O)$_p$R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy and $C_{1-10}$heterocycloxy; wherein $R^{2a}$ may, for each occurrence, be optionally substituted with one or more substituents which are independently selected from halo, hydroxy, $C_{1-4}$alkyl, and $C_{1-4}$alkoxy; or two $R^{2a}$ on adjacent atoms taken together with the atoms to which they are attached may form a fused $C_{3-7}$cycloalkyl, $C_6$aryl, 3- to 7-membered heterocyclyl, or 5-membered heteroaryl, wherein the fused cycloalkyl, aryl, heterocyclyl, and heteroaryl may be optionally substituted with one or more substituent independently selected from halo, hydroxy, $C_{1-4}$alkyl, and $C_{1-4}$alkoxy; or two $R^{2a}$ on the same carbon atom taken together may form a spiro 3- to 7-membered heterocyclyl or a spiro $C_{3-7}$cycloalkyl which may be optionally substituted with one or more substituent independently selected from halo, hydroxy, $C_{1-4}$alkyl, and $C_{1-4}$alkoxy; and $R^3$, for each occurrence, is independently selected from hydrogen, $C_{1-6}$ alkyl, $C_{3-7}$ cycloalkyl, $C_{3-7}$ cycloalkyl$C_{1-4}$alkyl, $C_{6-10}$aryl, $C_{1-10}$heteroaryl, and $C_{2-10}$heterocyclyl;

p is 0, 1 or 2;
X is [C(R⁶)(R⁷)]ₜ;
Y is H or OH;
t is 1;
R⁶ and R⁷, for each occurrence, are independently selected from hydrogen and $C_{1-3}$ alkyl;
or when t is 1, R⁶ and R⁷ together may form an oxo group;
R⁴ and R⁵, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or
R⁴ and R⁵ taken together along with the nitrogen to which they are bound may form a monocyclic or a bicyclic heteroaryl or heterocyclyl which may be optionally substituted with one or more halo or $C_{1-4}$alkyl; or
a pharmaceutically acceptable salt thereof.

In another aspect of the invention, the compound of Formula (I) is of Formula (I-iii):

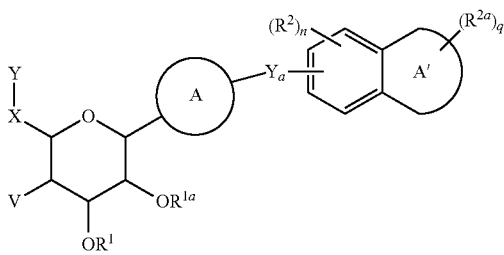

(I-iii)

wherein:
Ring A is a phenyl ring which is optionally substituted with one or more substituents independently selected from the group consisting of chloro, fluoro, hydroxy, methyl, methoxy, ethoxy, trifluoromethoxy and N-pyrazolyl;
the structure represented by the following formula:

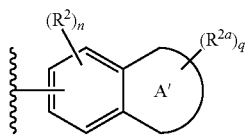

is selected from the group consisting of:

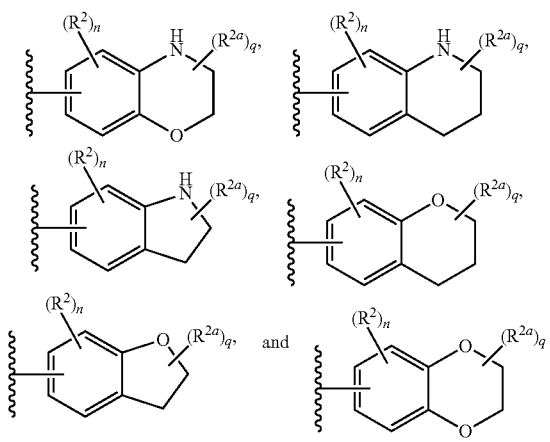

and wherein the hydrogen on each nitrogen may be optionally replaced with $R^{2a}$;
$Y_a$ is CH₂;
V is OH;
n is 0 or 1;
q is 0 or 1;
R¹ and $R^{1a}$ are each hydrogen;
R² is halo; wherein R² may, for each occurrence, be optionally substituted with one or more substituents which are independently selected from halo, hydroxy, $C_{1-4}$alkyl, and $C_{1-4}$alkoxy;
$R^{2a}$, for each occurrence, is independently selected from the group consisting of hydroxy, $C_{1-6}$alkyl, $C_{3-7}$cycloalkyl$C_{1-4}$alkyl; wherein $R^{2a}$ may, for each occurrence, be optionally substituted with one or more substituents which are independently selected from halo, hydroxy, $C_{1-4}$alkyl, and $C_{1-4}$alkoxy; or
two $R^{2a}$ on the same carbon atom taken together may form a spiro $C_{3-7}$cycloalkyl which may be optionally substituted with one or more substituent independently selected from halo, hydroxy, $C_{1-4}$alkyl, and $C_{1-4}$alkoxy;
X is CH₂;
Y is OH; or
a pharmaceutically acceptable salt thereof.

In another aspect of the invention, the compound of Formula (I) is of Formula (I-iiia):

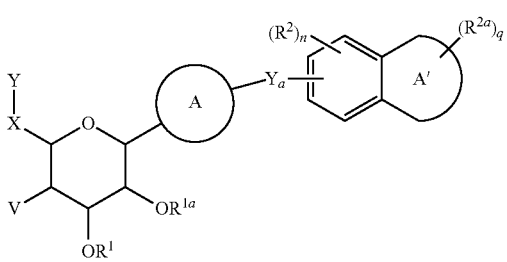

(I-iiia)

wherein:
Ring A is a phenyl ring which is optionally substituted with one or more substituents independently selected from the group consisting of chloro, fluoro, hydroxy, cyano, methyl, ethyl, isopropyl, ethynyl, methoxy, ethoxy, trifluoromethoxy, amino, dimethylamino, methylsulfanyl, methylsulfonyl, carbamoyl, cyclopropyl, cyclobutyl, phenyl, toulyl, phenoxy, oxazolyloxy, and N-pyrazolyl;
the structure represented by the following formula:

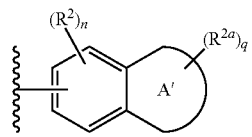

is selected from the group consisting of:

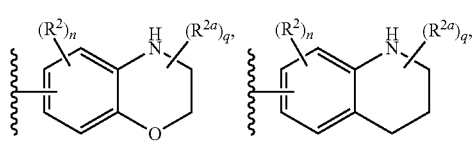

-continued

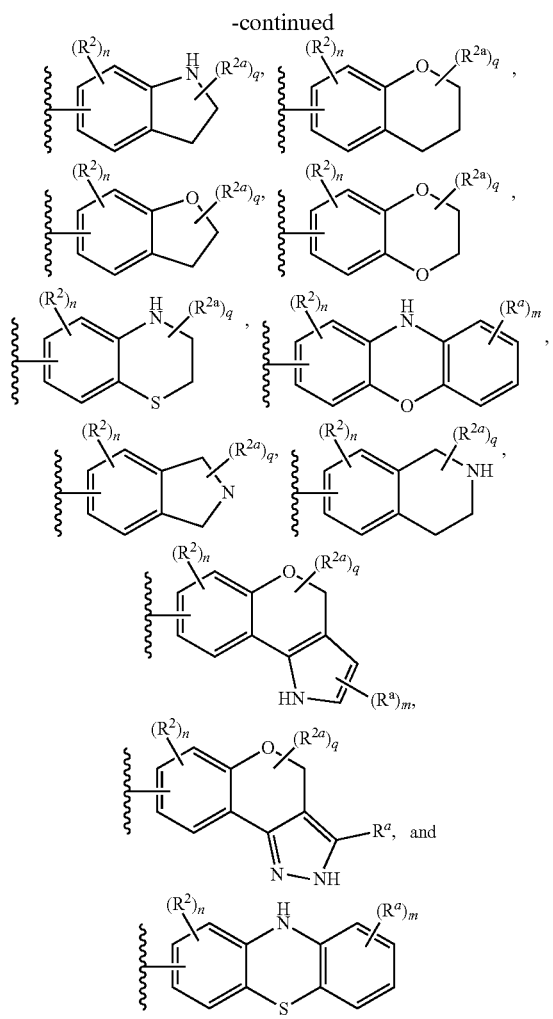

wherein the hydrogen on each nitrogen may be optionally replaced with R$^{2a}$; R$^a$, for each occurrence, is independently selected from halo, hydroxy, cyano, nitro, C$_{1-6}$alkyl, —S(O)$_p$R$^3$, —C(O)OR$^3$, —C(O)R$^3$, —C(O)NR$^4$R$^5$, —NR$^4$R$^5$, —CH$_2$NR$^4$R$^5$ and C$_{1-6}$alkoxy; and m is 0 or an integer from 1-4;
Y$_a$ is CH$_2$;
V is OH;
n is 0 or 1;
q is 0 or 1;
R$^1$ and R$^{1a}$ are each hydrogen;
R$^2$ is halo; wherein R$^2$ may, for each occurrence, be optionally substituted with one or more substituents which are independently selected from halo, hydroxy, C$_{1-4}$alkyl, and C$_{1-4}$alkoxy;
R$^{2a}$, for each occurrence, is independently selected from the group consisting of oxo, halo, hydroxy, cyano, nitro, C$_{1-6}$alkyl, C$_{3-7}$cycloalkyl, C$_{3-7}$cycloalkylC$_{1-4}$alkyl, C$_{6-10}$aryl, C$_{6-10}$arylC$_{1-4}$alkyl, —C(O)OR$^3$, —C(O)R$^3$, —C(O)NR$^4$R$^5$, —NR$^4$R$^5$, —CH$_2$NR$^4$R$^5$, C$_{1-6}$alkoxy, C$_{3-7}$ cycloalkoxy, —S(O)$_p$R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, C$_{6-10}$aryloxy, C$_{2-10}$heterocyclyl, C$_{2-10}$heterocyclylC$_{1-4}$alkyl, C$_{1-10}$heteroarylC$_{1-4}$alkyl, C$_{1-10}$heteroaryl, C$_{1-10}$heteroaryloxy and C$_{1-10}$heterocycloxy; wherein R$^{2a}$ may, for each occurrence, be optionally substituted with one or more substituents which are independently selected from halo, hydroxy, C$_{1-4}$alkyl, and C$_{1-4}$alkoxy; or
two R$^{2a}$ on the same carbon atom taken together may form a spiro C$_{3-7}$cycloalkyl which may be optionally substituted with one or more substituent independently selected from halo, hydroxy, C$_{1-4}$alkyl, and C$_{1-4}$alkoxy;
p is 0, 1 or 2;
X is CH$_2$;
Y is OH; or
a pharmaceutically acceptable salt thereof.

In another aspect of the invention, the compound of Formula (I) is of Formula (I-iv):

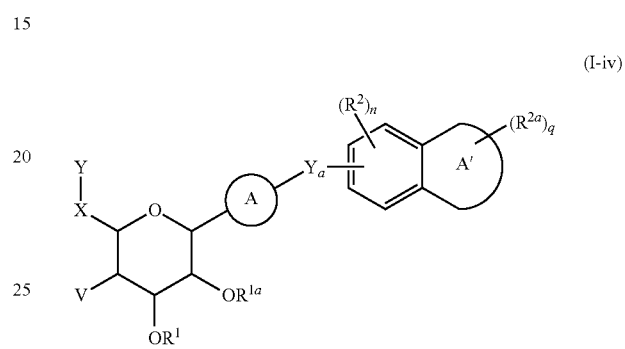

(I-iv)

wherein:
Ring A is a phenyl ring which is optionally substituted with one substituent independently selected from the group consisting of chloro, fluoro, methyl and methoxy; wherein Y$_a$ is situated meta to the tetrahydropyran ring and the one substituent is situated para to the tetrahydropyran ring;
the structure represented by the following formula:

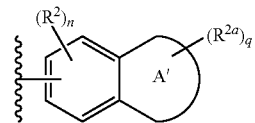

is selected from the group consisting of:

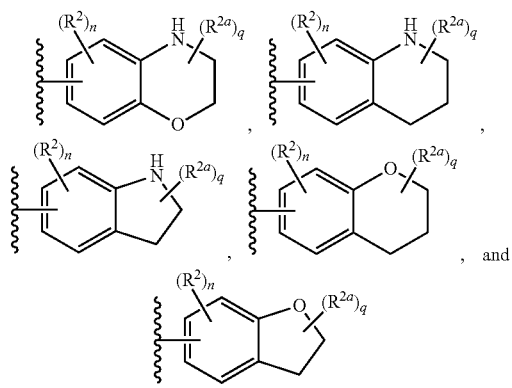

wherein the hydrogen on each nitrogen may be optionally replaced with R$^{2a}$;
Y$_a$ is CH$_2$;
V is OH;

n is 0 or 1;

q is 0 or 1;

$R^1$ and $R^{1a}$ are each hydrogen;

$R^2$ is halo;

$R^{2a}$, for each occurrence, is independently selected from the group consisting of unsubstituted hydroxy and unsubstituted $C_{1-2}$alkyl; and X is $CH_2$;

Y is OH; or a pharmaceutically acceptable salt thereof.

In another aspect of the invention, the compound of Formula (I) is of Formula (I-iva):

(I-iva)

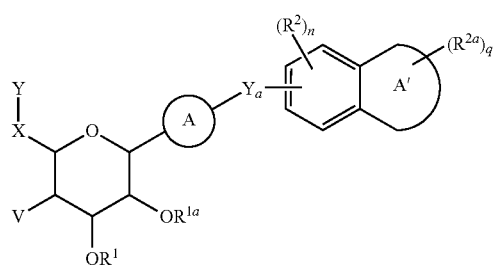

wherein:

Ring A is a phenyl ring which is optionally substituted with one substituent independently selected from the group consisting of chloro, fluoro, hydroxy, cyano, methyl, ethyl, isopropyl, ethynyl, methoxy, ethoxy, trifluoromethoxy, amino, dimethylamino, methylsulfanyl, methylsulfonyl, carbamoyl, cyclopropyl, cyclobutyl, phenyl, toulyl, phenoxy, oxazolyloxy, and N-pyrazolyl; wherein $Y_a$ is situated meta to the tetrahydropyran ring and the one substituent is situated para to the tetrahydropyran ring;

the structure represented by the following formula:

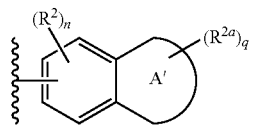

is selected from the group consisting of:

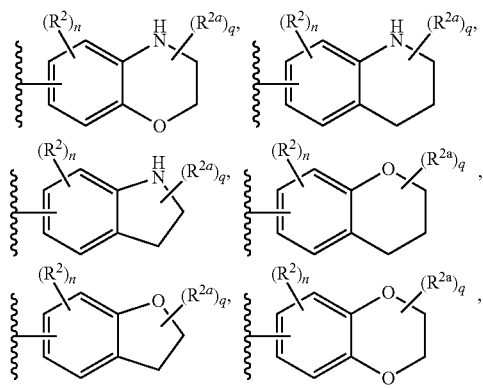

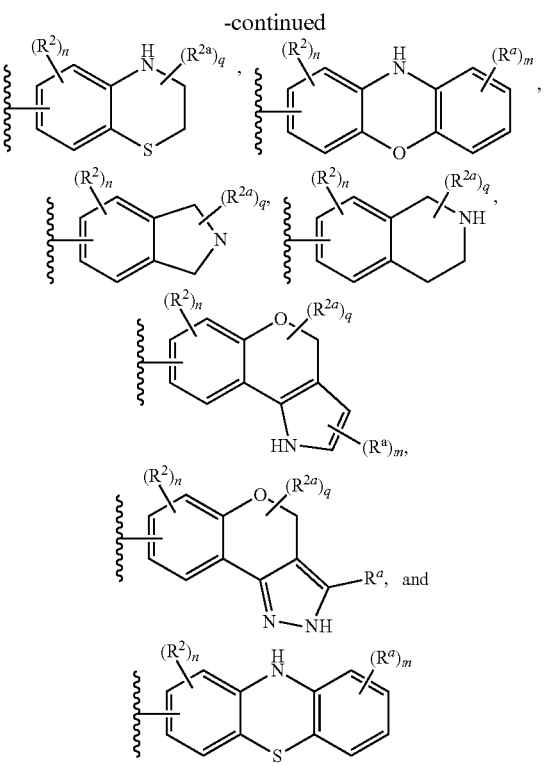

wherein the hydrogen on each nitrogen may be optionally replaced with $R^{2a}$; $R^a$, for each occurrence, is independently selected from halo, hydroxy, cyano, nitro, $C_{1-6}$alkyl, —$S(O)_pR^3$, —$C(O)OR^3$, —$C(O)R^3$, —$C(O)NR^4R^5$, —$NR^4R^5$, —$CH_2NR^4R^5$ and $C_{1-6}$alkoxy; and m is 0 or an integer from 1-4;

p is 0, 1, or 2;

$Y_a$ is $CH_2$;

V is OH;

n is 0 or 1;

q is 0 or 1;

$R^1$ and $R^{1a}$ are each hydrogen;

$R^2$ is halo;

$R^{2a}$, for each occurrence, is independently selected from the group consisting of oxo, halo, hydroxy, cyano, nitro, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —$C(O)OR^3$, —$C(O)R^3$, —$C(O)NR^4R^5$, —$NR^4R^5$, —$CH_2NR^4R^5$, $C_{1-6}$alkoxy, $C_{3-7}$ cycloalkoxy, —$S(O)_pR^3$, —$S(O)_2NR^4R^5$, —$OS(O)_2R^3$, —$CH_2C(O)OR^3$, —$CH_2C(O)NR^4R^5$, —$NR^3C(O)NR^4R^5$, —$NR^3C(O)OR^3$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy and $C_{1-10}$heterocycloxy; wherein $R^{2a}$ may, for each occurrence, be optionally substituted with one or more substituents which are independently selected from halo, hydroxy, cyano, nitro, $C_{1-6}$alkyl, —$S(O)_pR^3$, —$C(O)OR^3$, —$C(O)R^3$, —$C(O)NR^4R^5$, —$NR^4R^5$, —$CH_2NR^4R^5$ and $C_{1-6}$alkoxy;

X is $CH_2$; and

Y is OH; or a pharmaceutically acceptable salt thereof.

In another aspect of the invention, the compound of Formula (I) is of Formula (V):

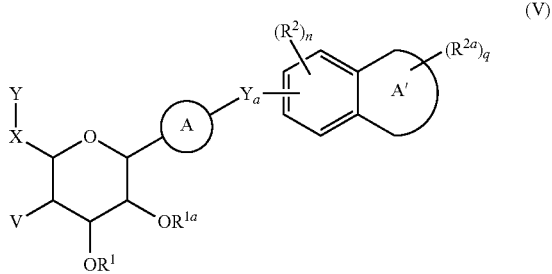

wherein:
ring A is phenyl which is substituted with one substituent selected from halo, $C_{1-4}$alkyl, and $C_{3-7}$cycloalkyl; wherein $Y_a$ is situated meta to the tetrahydropyran ring and the one substituent is situated para to the tetrahydropyran ring;
the structure represented by the following formula:

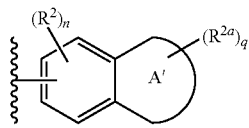

is selected from the group consisting of:

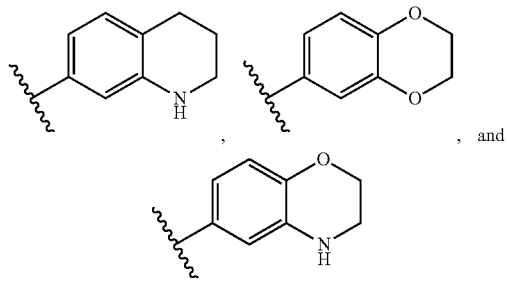

$Y_a$ is $CH_2$;
n is 0;
q is 0;
V is $-OR^{1b}$;
X is $CH_2$;
Y is $OR^{1c}$;
$R^1$, $R^{1a}$, $R^{1b}$ and $R^{1c}$ are hydrogen;
or a pharmaceutically acceptable salt thereof.

Embodiments of the Compounds of Formulae (I), (I-a), (I-i), (I-Ia), (I-ii), (I-Iia), (I-iii), (I-iiia), (I-iv), (I-iva), and (V)

General

Various embodiments of the invention are described herein. It will be recognised that features specified in each embodiment may be combined with other specified features to provide further embodiments. Thus, combinations of the various features are herein implicitly disclosed.

The Tetrahydropyran Ring and its Substituents

In one embodiment, V is $OR^{1b}$. In a further embodiment, V is OH.

In one embodiment, $R^1$ and $R^{1a}$ are independently selected from hydrogen, $C_{1-3}$ alkyl, $C_{6-10}$aryl-$C_{1-4}$alkyl, $-C(O)C_{6-10}$aryl and $-C(O)C_{1-8}$alkyl. In a further embodiment, $R^1$ is H. In a further embodiment, $R^{1a}$ is H. In a further embodiment, $R^1$ and $R^{1a}$ are both H.

In one embodiment, t is 1 or 2. In a further embodiment, t is 1.

In one embodiment, X is $CH_2$.

In one embodiment, Y is H or $OR^{1c}$. In a further embodiment, Y is H or OH. In a further embodiment, Y is OH. In a further embodiment, Y is a halo. In a further embodiment, Y is fluoro.

In one embodiment, the tetrahydropyran ring is a pyranose ring of the structure:

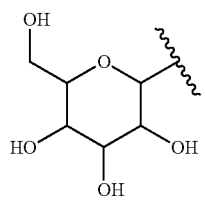 [SMILES: *C1OC(CO)C(O)C(O)C1O]

In a further embodiment, the pyranose ring has the following stereochemistry:

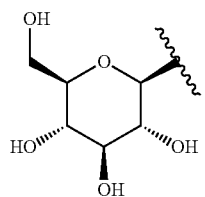 [SMILES: *[C@@H]1O[C@H](CO)[C@@H](O)[C@H](O)[C@H]1O]

In one embodiment, $R^{1b}$ is selected from hydrogen, $C_{1-3}$ alkyl, $C_{6-10}$aryl-$C_{1-4}$alkyl, $-C(O)C_{6-10}$aryl and $-C(O)C_{1-8}$alkyl. In a further embodiment, $R^{1b}$ is H.

In one embodiment, $R^{1c}$ is selected from hydrogen, $C_{1-3}$ alkyl, $C_{6-10}$aryl-$C_{1-4}$alkyl, $-C(O)C_{6-10}$aryl and $-C(O)C_{1-6}$alkyl. In a further embodiment, $R^{1c}$ is H.

In one embodiment, $R^6$ and $R^7$, for each occurrence, are independently selected from hydrogen, $C_{1-3}$ alkyl, $OR^{1e}$, and $NR^4R^5$; or when t is 1, $R^6$ and $R^7$ together may form an oxo group; or when $R^6$ and $R^7$ are on the same carbon they can be taken together to form a $C_{3-7}$cycloalkyl or a 3- to 7-membered heterocycle. In a further embodiment, $R^6$ and $R^7$, for each occurrence, are independently selected from hydrogen and $C_{1-3}$ alkyl.

In one embodiment, $R^{1e}$, for each occurrence, is independently selected from hydrogen, $C_{1-3}$ alkyl, $C_{6-10}$aryl-$C_{1-4}$alkyl, $-C(O)C_{6-10}$aryl and $-C(O)C_{1-6}$alkyl. In a further embodiment, $R^{1e}$, for each occurrence, is independently selected from hydrogen and $C_{1-3}$ alkyl.

Ring a and its Substituents

In one embodiment, Ring A is substituted with one or more substituents independently selected from the group consisting of halo, hydroxy, $C_{1-3}$alkyl, $C_{1-3}$alkoxy, halo$C_{1-3}$alkoxy and 5-membered heteroaryl. In a further embodiment, Ring A is substituted with one or more substituents independently selected from the group consisting of halo, hydroxy, $C_{1-3}$alkyl, $C_{3-7}$cycloalkyl, $C_{1-3}$alkoxy, halo$C_{1-3}$alkoxy and 5-membered heteroaryl. In a further embodiment, Ring A is substituted with one or more substituents independently selected from the group consisting of chloro, fluoro, hydroxy, methyl, methoxy, ethoxy, trifluoromethoxy and N-pyrazolyl. In a further embodiment, Ring A is substituted with one or more substituents independently selected from the group consisting of chloro, fluoro, hydroxy, methyl, ethyl, isopropyl, cyclopropyl, methoxy, ethoxy, trifluoromethoxy and N-pyrazolyl. In a further embodiment, Ring A is substituted with one or more substituents independently selected from the group consisting of chloro, fluoro, methyl and methoxy. In a further embodiment, Ring A is substituted with one or more chloro substituents. In a further embodiment, Ring A is substituted with one or more substituents independently selected from the group consisting of chloro, ethyl, isopropyl, and cyclopropyl. In a further embodiment, Ring A is substituted with one chloro. In a further embodiment, Ring A is substituted with one ethyl. In a further embodiment, Ring A is substituted with one isopropyl. In a further embodiment, Ring A is substituted with one cyclopropyl.

In one embodiment, Ring A is naphthyl which is optionally substituted.

In a one embodiment, Ring A is phenyl which is optionally substituted.

In one embodiment, $Y_a$ is situated meta to the tetrahydropyran ring.

In one embodiment, Ring A has one substituent. In one aspect of this embodiment, Ring A has one substituent which is selected from the group consisting of halo, hydroxy, $C_{1-3}$alkyl, $C_{3-7}$cycloalkyl, $C_{1-3}$alkoxy, halo$C_{1-3}$alkoxy and 5-membered heteroaryl. In another aspect of this embodiment, Ring A has one substituent which is selected from the group consisting of chloro, fluoro, hydroxy, methyl, ethyl, isopropyl, cyclopropyl, methoxy, ethoxy, trifluoromethoxy and N-pyrazolyl. In another aspect of this embodiment, Ring A is substituted with one chloro. In another aspect of this embodiment, Ring A is substituted with one ethyl. In another aspect of this embodiment, Ring A is substituted with one isopropyl. In another aspect of this embodiment, Ring A is substituted with one cyclopropyl.

In a further embodiment, Ring A is unsubstituted.

In one embodiment, Ring A is phenyl with one substituent, $Y_a$ is situated meta to the tetrahydropyran ring and the one substituent is situated para to the tetrahydropyran ring. In one aspect of this embodiment, the substituent on Ring A is selected from the group consisting of halo, hydroxy, $C_{1-3}$alkyl, $C_{3-7}$cycloalkyl, $C_{1-3}$alkoxy, halo$C_{1-3}$alkoxy and 5-membered heteroaryl. In another aspect of this embodiment, the substituent on Ring A is selected from the group consisting of chloro, fluoro, hydroxy, methyl, ethyl, isopropyl, cyclopropyl, methoxy, ethoxy, trifluoromethoxy and N-pyrazolyl. In another aspect of this embodiment, the substituent on Ring A is chloro. In another aspect of this embodiment, the substituent on Ring A is ethyl. In another aspect of this embodiment, the substituent on Ring A is isopropyl. In another aspect of this embodiment, the substituent on Ring A is cyclopropyl.

Linker $Y_a$ In one embodiment, $Y_a$ is a bond or a $C_{1-3}$alkylene.

In one embodiment, $Y_a$ is unsubstituted.
In one embodiment, $Y_a$ is $CH_2$.
The $R^2$ substituent(s)
In one embodiment, $R^2$, for each occurrence, is independently selected from the group consisting of halo, hydroxy, cyano, nitro, $C_{1-6}$alkyl, $C_{3-7}$cycloalkyl, $C_{6-10}$aryl, $C_{6-10}$aryl$C_{1-4}$alkyl, —C(O)OR³, —C(O)R³, —C(O)NR⁴R⁵, —NR⁴R⁵, —CH₂NR⁴R⁵, $C_{1-6}$alkoxy, $C_{3-7}$ cycloalkoxy, —CH₂C(O)OR³, —CH₂C(O)NR⁴R⁵, —NR³C(O)NR⁴R⁵, —NR³C(O)OR³, $C_{6-10}$aryloxy, $C_{2-10}$heterocyclyl, $C_{1-10}$heteroaryl, $C_{1-10}$heteroaryloxy and $C_{1-10}$heterocycloxy.

In a further embodiment, $R^2$, for each occurrence, is independently selected from the group consisting of halo, hydroxy, cyano, nitro, $C_{1-3}$alkyl, $C_{3-7}$cycloalkyl, $C_{6-10}$aryl, $C_{6-10}$aryl$C_{1-3}$alkyl, —C(O)OR³, —C(O)R³, —C(O)NR⁴R⁵, —NR⁴R⁵, —CH₂NR⁴R⁵, $C_{1-3}$alkoxy, $C_{3-7}$ cycloalkoxy, —CH₂C(O)OR³, —CH₂C(O)NR⁴R⁵, —NR³C(O)NR⁴R⁵, —NR³C(O)OR³, $C_{6-10}$aryloxy, $C_{2-6}$heterocyclyl, $C_{5-7}$heteroaryl, $C_{5-7}$heteroaryloxy and $C_{2-6}$heterocycloxy.

In one embodiment, n is 0, 1 or 2. In a further embodiment, n is 0 or 1. In a further embodiment, n is 0.

In one embodiment, $R^2$ is halo and n is 1. In a further embodiment, $R^2$ is fluoro and n is 1.

Ring A' and its Substituents

In one embodiment, Ring A' contains at least one O or N heteroatom. In a further embodiment, Ring A' contains one or two heteroatoms, wherein the heteroatoms are independently O or N.

In one embodiment, Ring A' contains at least one O, S or N heteroatom. In a further embodiment, Ring A' contains one or two heteroatoms, wherein the heteroatoms are independently O, S, or N.

In one embodiment, Ring A' is selected from the group consisting of a morpholine ring, a piperidine ring, a pyrrolidine ring, a tetrahydropyran ring, a tetrahydrofuran ring and a 1,4-dioxane ring.

In one embodiment, Ring A' is selected from the group consisting of a morpholine ring, a piperidine ring, and a 1,4-dioxane ring.

In one embodiment, the structure represented by the following formula:

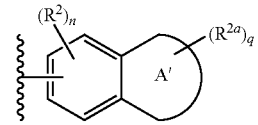

is selected from the group consisting of:

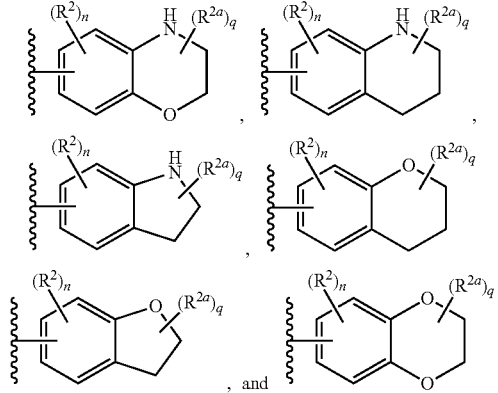

wherein the hydrogen on each nitrogen may be optionally replaced with $R^{2a}$.

In a further embodiment, the structure presented by the following formula:

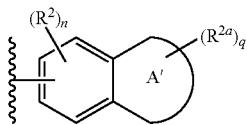

is selected from the group consisting of:

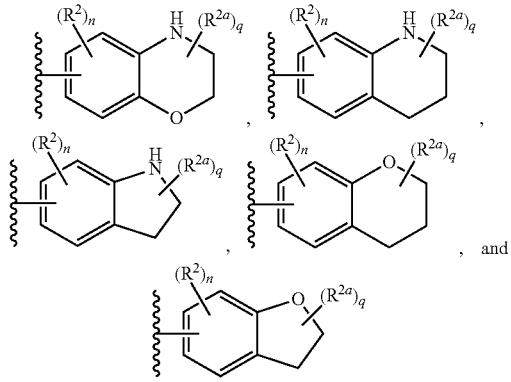

wherein the hydrogen on each nitrogen may be optionally replaced with $R^{2a}$.

In one embodiment, the structure represented by the following formula:

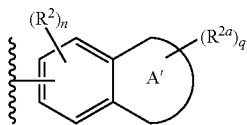

is selected from the group consisting of:

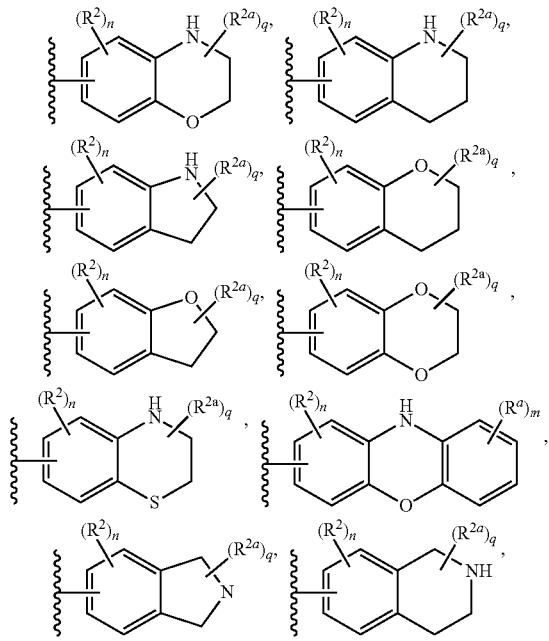

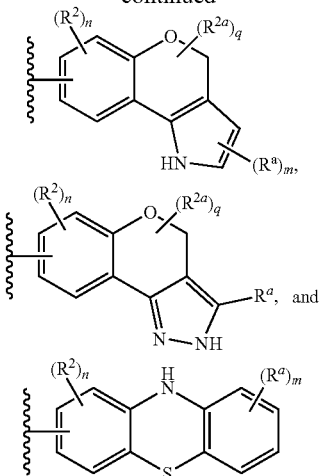

wherein the hydrogen on each nitrogen may be optionally replaced with $R^{2a}$.

In a further embodiment, the structure represented by the following formula:

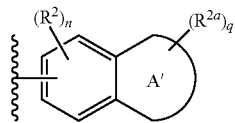

is selected from the group consisting of:

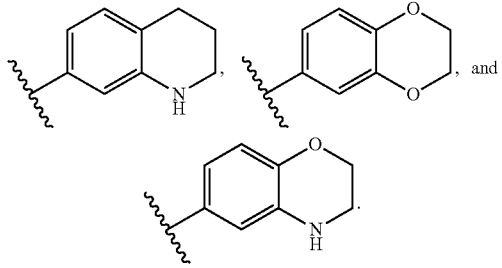

In one embodiment, $R^{2a}$, for each occurrence, is independently selected from the group consisting of oxo, hydroxy, $C_{1-6}$alkyl, $C_{3-7}$cycloalkyl$C_{1-4}$alkyl, $C_{6-10}$aryl$C_{1-4}$alkyl, —C(O)O$R^3$, —C(O)$R^3$, —C(O)N$R^4R^5$ and CH$_2$C(O)O$R^3$; wherein $R^{2a}$ may, for each occurrence, be optionally substituted with one or more substituents which are independently selected from halo, hydroxy, $C_{1-4}$alkyl, and $C_{1-4}$alkoxy; or two $R^{2a}$ on adjacent atoms taken together with the atoms to which they are attached may form a fused $C_{3-7}$cycloalkyl, $C_6$aryl, 3- to 7-membered heterocyclyl, or 5-membered heteroaryl, wherein the fused cycloalkyl, aryl, heterocyclyl, and heteroaryl may be optionally substituted with one or more substituent independently selected from halo, hydroxy, $C_{1-4}$alkyl, and $C_{1-4}$alkoxy; or two $R^{2a}$ on the same carbon atom taken together may form a spiro 3- to 7-membered heterocyclyl or a spiro $C_{3-7}$cycloalkyl which may be optionally substituted with one or more substituent independently selected from halo, hydroxy, $C_{1-4}$alkyl, and $C_{1-4}$alkoxy.

In a further embodiment, $R^{2a}$, for each occurrence, is independently selected from the group consisting of oxo, halo, hydroxy, cyano, nitro, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —C(O)OR$^3$, —C(O)R$^3$, —C(O)NR$^4$R$^5$, —NR$^4$R$^5$, —CH$_2$NR$^4$R$^5$, $C_{1-6}$alkoxy, $C_{3-7}$ cycloalkoxy, —S(O)$_p$R$^3$, —S(O)$_2$NR$^4$R$^5$, —OS(O)$_2$R$^3$, —CH$_2$C(O)OR$^3$, —CH$_2$C(O)NR$^4$R$^5$, —NR$^3$C(O)NR$^4$R$^5$, —NR$^3$C(O)OR$^3$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy and $C_{1-10}$heterocycloxy; wherein $R^{2a}$ may, for each occurrence, be optionally substituted with one or more substituents which are independently selected from halo, hydroxy, cyano, nitro, $C_{1-6}$alkyl, —S(O)$_p$R$^3$, —C(O)OR$^3$, —C(O)R$^3$, —C(O)NR$^4$R$^5$, —NR$^4$R$^5$, —CH$_2$NR$^4$R$^5$ and $C_{1-6}$alkoxy; or two $R^{2a}$ on adjacent atoms taken together with the atoms to which they are attached may form a fused $C_{3-7}$cycloalkyl, $C_6$aryl, 3- to 7-membered heterocyclyl, or 5-membered heteroaryl, wherein the fused cycloalkyl, aryl, heterocyclyl, and heteroaryl may be optionally substituted with one or more substituent independently selected from halo, hydroxy, $C_{1-4}$alkyl, and $C_{1-4}$alkoxy; or two $R^{2a}$ on the same carbon atom taken together may form a spiro 3- to 7-membered heterocyclyl or a spiro $C_{3-7}$cycloalkyl which may be optionally substituted with one or more substituent independently selected from halo, hydroxy, $C_{1-4}$alkyl, and $C_{1-4}$alkoxy.

In a further embodiment, $R^{2a}$, for each occurrence, is independently selected from the group consisting of hydroxy, $C_{1-6}$alkyl, $C_{3-7}$cycloalkyl$C_{1-4}$alkyl; wherein $R^{2a}$ may, for each occurrence, be optionally substituted with one or more substituents which are independently selected from halo, hydroxy, $C_{1-4}$alkyl, and $C_{1-4}$alkoxy; or two $R^{2a}$ on the same carbon atom taken together may form a spiro $C_{3-7}$cycloalkyl which may be optionally substituted with one or more substituent independently selected from halo, hydroxy, $C_{1-4}$alkyl, and $C_{1-4}$alkoxy.

In a further embodiment, $R^{2a}$, for each occurrence, is independently selected from the group consisting of unsubstituted hydroxy and unsubstituted $C_{1-2}$alkyl.

In one embodiment, q is 0, 1 or 2. In a further embodiment, q is 0 or 1. In a further embodiment, q is 0.

Groups $R^3$, $R^4$ and $R^5$

In one embodiment, $R^3$, for each occurrence, is independently selected from hydrogen, $C_{1-3}$ alkyl, $C_{3-7}$ cycloalkyl, $C_{3-7}$ cycloalkyl$C_{1-3}$alkyl, $C_{6-10}$aryl, $C_{1-7}$heteroaryl, and $C_{2-8}$heterocyclyl. In a further embodiment, $R^3$, for each occurrence, is independently selected from hydrogen and $C_{1-3}$ alkyl.

In one embodiment, $R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl (with 5 to 14 members and having 1 to 8 heteroatoms selected from N, O and S) or heterocyclyl (which is a 4 to 7 membered monocyclic ring or a 7 to 12 membered bicyclic ring or a 10 to 15 membered tricyclic ring having at least one heteroatom selected from N, O and S) which may be optionally substituted with one or more halo or $C_{1-4}$alkyl substituent.

In a further embodiment, $R^4$ and $R^5$, for each occurrence, are independently selected from hydrogen, $C_{1-3}$ alkyl, $C_{3-7}$ cycloalkyl, $C_{3-7}$ cycloalkyl$C_{1-3}$alkyl, $C_{6-10}$aryl$C_{1-4}$alkyl, $C_{6-10}$aryl, $C_{1-7}$heteroaryl, $C_{1-7}$heteroaryl$C_{1-3}$alkyl, $C_{2-8}$heterocyclyl, and $C_{2-8}$heterocyclyl$C_{1-3}$alkyl; or $R^4$ and $R^5$ taken together along with the nitrogen to which they are bound may form a monocyclic or a bicyclic heteroaryl or heterocyclyl which may be optionally substituted with one or more halo or $C_{1-3}$alkyl. In a further embodiment, $R^4$ and $R^5$, for each occurrence, are independently selected from hydrogen and $C_{1-3}$ alkyl.

Further Embodiments

In one embodiment, the moiety

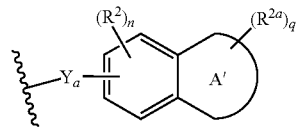

is selected from any one of structures i to xiv below.

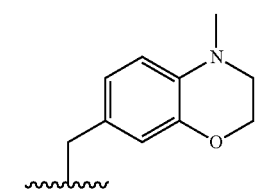

i

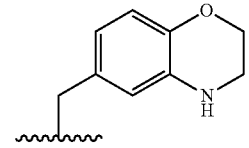

ii

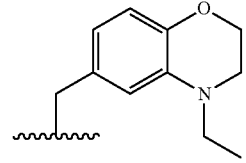

iii

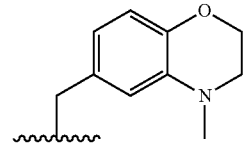

iv

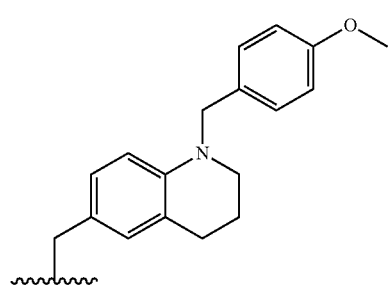

v

27
-continued

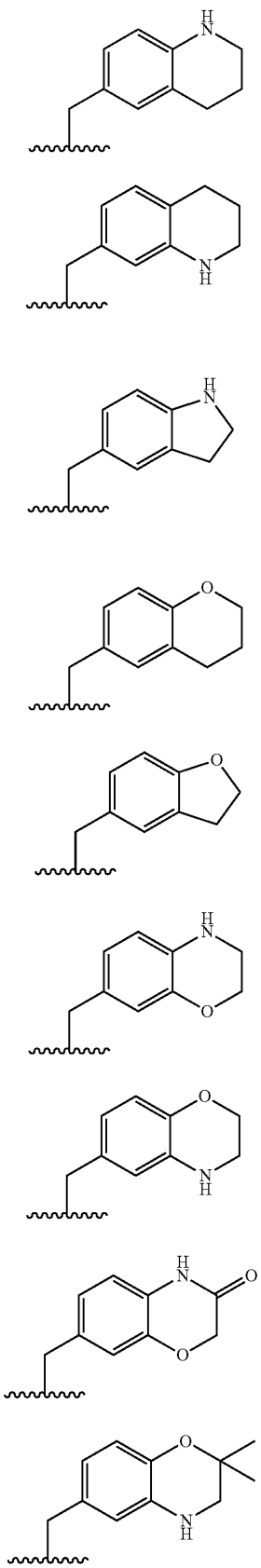

vi vii viii ix x xi xii xiii xiv

28

In one embodiment, the moiety

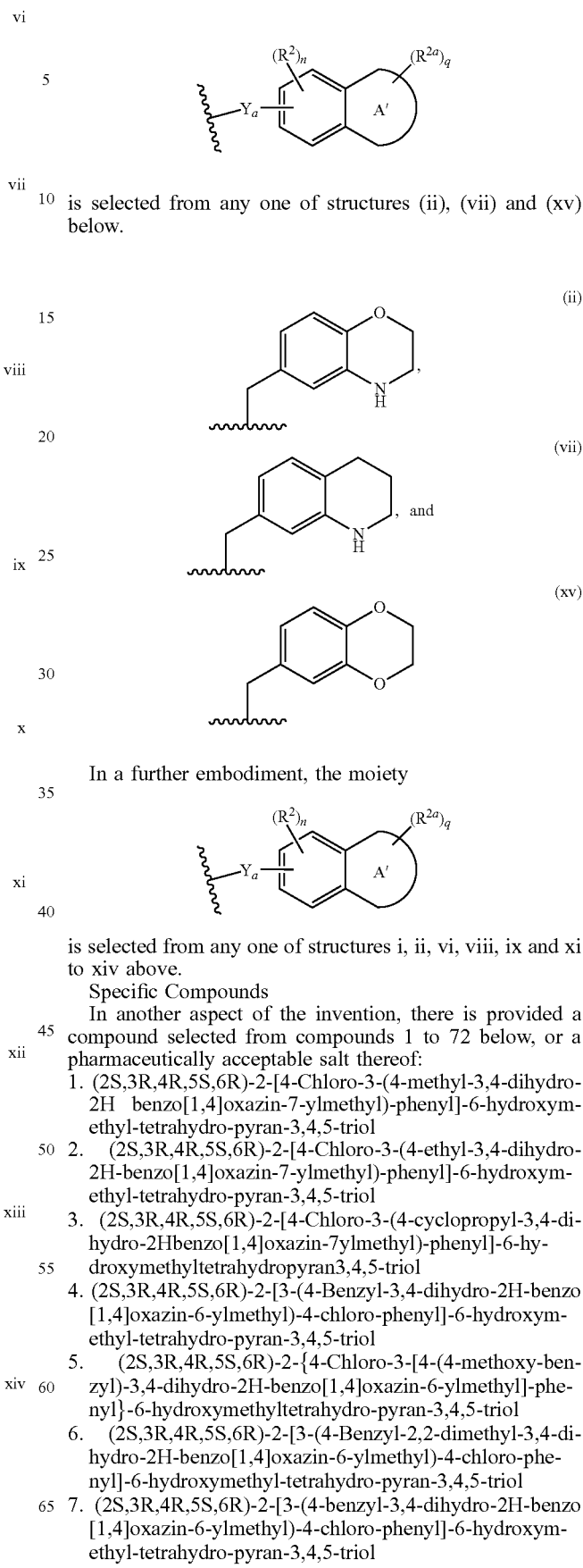

is selected from any one of structures (ii), (vii) and (xv) below.

In a further embodiment, the moiety is selected from any one of structures i, ii, vi, viii, ix and xi to xiv above.

Specific Compounds

In another aspect of the invention, there is provided a compound selected from compounds 1 to 72 below, or a pharmaceutically acceptable salt thereof:

1. (2S,3R,4R,5S,6R)-2-[4-Chloro-3-(4-methyl-3,4-dihydro-2H benzo[1,4]oxazin-7-ylmethyl)-phenyl]-6-hydroxymethyl-tetrahydro-pyran-3,4,5-triol
2. (2S,3R,4R,5S,6R)-2-[4-Chloro-3-(4-ethyl-3,4-dihydro-2H-benzo[1,4]oxazin-7-ylmethyl)-phenyl]-6-hydroxymethyl-tetrahydro-pyran-3,4,5-triol
3. (2S,3R,4R,5S,6R)-2-[4-Chloro-3-(4-cyclopropyl-3,4-dihydro-2Hbenzo[1,4]oxazin-7ylmethyl)-phenyl]-6-hydroxymethyltetrahydropyran3,4,5-triol
4. (2S,3R,4R,5S,6R)-2-[3-(4-Benzyl-3,4-dihydro-2H-benzo[1,4]oxazin-6-ylmethyl)-4-chloro-phenyl]-6-hydroxymethyl-tetrahydro-pyran-3,4,5-triol
5. (2S,3R,4R,5S,6R)-2-{4-Chloro-3-[4-(4-methoxy-benzyl)-3,4-dihydro-2H-benzo[1,4]oxazin-6-ylmethyl]-phenyl}-6-hydroxymethyltetrahydro-pyran-3,4,5-triol
6. (2S,3R,4R,5S,6R)-2-[3-(4-Benzyl-2,2-dimethyl-3,4-dihydro-2H-benzo[1,4]oxazin-6-ylmethyl)-4-chloro-phenyl]-6-hydroxymethyl-tetrahydro-pyran-3,4,5-triol
7. (2S,3R,4R,5S,6R)-2-[3-(4-benzyl-3,4-dihydro-2H-benzo[1,4]oxazin-6-ylmethyl)-4-chloro-phenyl]-6-hydroxymethyl-tetrahydro-pyran-3,4,5-triol 8. (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol
9. (2S,3R,4R,5S,6R)-2-[4-Chloro-3-(4-ethyl-3,4-dihydro-2H-benzo[1,4]oxazin-6-ylmethyl)-phenyl]-6-hydroxymethyl-tetrahydro-pyran-3,4,5-triol
10. (2S,3R,4R,5S,6R)-2-[4-Chloro-3-(4-cyclopropylmethyl-3,4-dihydro-2H-benzo[1,4]oxazin-6-ylmethyl)-phenyl]-6-hydroxymethyl-tetrahydro-pyran-3,4,5-triol
11. (2S,3R,4R,5S,6R)-2-[4-Chloro-3-(4-methyl-3,4-dihydro-2H-benzo[1,4]oxazin-6-ylmethyl)-phenyl]-6-hydroxymethyl-tetrahydro-pyran-3,4,5-triol
12. 6-[2-Chloro-5-((2S,3R,4R,5S,6R)-3,4,5-trihydroxy-6-hydroxymethyl-tetrahydro-pyran-2-yl)-benzyl]-2,3-dihydro-benzo[1,4]oxazine-4-carboxylic acid ethyl ester
13. 1-{6-[2-Chloro-5-((2S,3R,4R,5S,6R)-3,4,5-trihydroxy-6-hydroxymethyl-tetrahydro-pyran-2-yl)-benzyl]-2,3-dihydro-benzo[1,4]oxazin-4-yl}-ethanone
14. (2S,3R,4R,5S,6R)-2-{4-Chloro-3-[1-(4-methoxy-benzyl)-1,2,3,4-tetrahydro-quinolin-6-ylmethyl]-phenyl}-6-hydroxymethyl-tetrahydro-pyran-3,4,5-triol
15. (2S,3R,4R,5S,6R)-2-[4-Chloro-3-(1,2,3,4-tetrahydro-quinolin-6-ylmethyl)-phenyl]-6-hydroxymethyl-tetrahydro-pyran-3,4,5-triol
16. (2S,3R,4R,5S,6R)-2-[4-Chloro-3-(1,2,3,4-tetrahydro-quinolin-7-ylmethyl)-phenyl]-6-hydroxymethyl-tetrahydro-pyran-3,4,5-triol
17. (2S,3R,4R,5S,6R)-2-[4-Chloro-3-(2,3-dihydro-1H-indol-5-ylmethyl)-phenyl]-6-hydroxymethyl-tetrahydro-pyran-3,4,5-triol
18. (2S,3R,4R,5S,6R)-2-[3-(2-Benzyl-1,2,3,4-tetrahydro-isoquinolin-7-ylmethyl)-4-chloro-phenyl]-6-hydroxymethyl-tetrahydro-pyran-3,4,5-triol
19. (2S,3R,4R,5S,6R)-2-[4-Chloro-3-(1,2,3,4-tetrahydro-isoquinolin-7-ylmethyl)-phenyl]-6-hydroxymethyl-tetrahydro-pyran-3,4,5-triol
20. (2S,3R,4R,5S,6R)-2-[4-Chloro-3-(2,2-dimethyl-3,4-dihydro-2H-benzo[1,4]oxazin-6-ylmethyl)-phenyl]-6-hydroxymethyl-tetrahydro-pyran-3,4,5-triol
21. (2S,3R,4R,5S,6R)-2-(4-Chloro-3-chroman-6-ylmethyl-phenyl)-6-hydroxymethyl-tetrahydro-pyran-3,4,5-triol
22. (2S,3R,4R,5S,6R)-2-[4-Chloro-3-(2,3-dihydro-benzofuran-5-ylmethyl)-phenyl]-6-hydroxymethyl-tetrahydro-pyran-3,4,5-triol
23. (2R,3S,4R,5R,6S)-2-Hydroxymethyl-6-[4-methyl-3-(1,2,3,4-tetrahydro-quinolin-7-ylmethyl)-phenyl]-tetrahydro-pyran-3,4,5-triol
24. (2S,3R,4R,5S,6R)-2-[3-(3,4-Dihydro-2H-benzo[1,4]oxazin-6-ylmethyl)-4-fluoro-phenyl]-6-hydroxymethyl-tetrahydro-pyran-3,4,5-triol
25. (2S,3R,4R,5S,6R)-2-[3-(2,3-Dihydro-benzo[1,4]dioxin-6-ylmethyl)-4-methoxy-phenyl]-6-hydroxymethyl-tetrahydro-pyran-3,4,5-triol
26. (2R,3S,4R,5R,6S)-2-Hydroxymethyl-6-[4-methoxy-3-(1,2,3,4-tetrahydro-quinolin-6-ylmethyl)-phenyl]-tetrahydro-pyran-3,4,5-triol
27. (2R,3S,4R,5R,6S)-2-Hydroxymethyl-6-[4-methoxy-3-(1,2,3,4-tetrahydro-quinolin-7-ylmethyl)-phenyl]-tetrahydro-pyran-3,4,5-triol
28. (2S,3R,4R,5S,6R)-2-[4-Chloro-3-(3,4-dihydro-2H-benzo[1,4]oxazin-7-ylmethyl)-phenyl]-6-hydroxymethyl-tetrahydro-pyran-3,4,5-triol
29. (2S,3R,4R,5S,6R)-2-[4-Chloro-3-(4,4-spiro-cyclopropyl-chroman-6-ylmethyl)-phenyl]-6-hydroxymethyl-tetrahydro-pyran-3,4,5-triol
30. 2S,3R,4R,5S,6R)-2-[5-(2,3-Dihydro-benzo[1,4]dioxin-6-ylmethyl)-2-ethoxy-phenyl]-6-hydroxymethyl-tetrahydro-pyran-3,4,5-triol
31. (2S,3R,4R,5S,6R)-2-[3-(3,4-Dihydro-2H-benzo[1,4]oxazin-6-ylmethyl)-4-methoxy-phenyl]-6-hydroxymethyl-tetrahydro-pyran-3,4,5-triol
32. (2S,3R,4R,5S,6R)-2-(3-Chroman-6-ylmethyl-4-methoxy-phenyl)-6-hydroxymethyl-tetrahydro-pyran-3,4,5-triol
33. (2S,3R,4R,5S,6R)-2-(3-Chroman-6-ylmethyl-4-trifluoromethoxy-phenyl)-6-hydroxymethyl-tetrahydro-pyran-3,4,5-triol
34. 6-[2-chloro-5-((2S,3R,4R,5S,6R)-3,4,5-trihydroxy-6-hydroxymethyl-tetrahydro-pyran-2-yl)-benzyl]-chromen-4-one
35. 6-[2-Chloro-5-((2S,3R,4R,5S,6R)-3,4,5-trihydroxy-6-hydroxymethyl-tetrahydro-pyran-2-yl)-benzyl]-chroman-4-one
36. (2S,3R,4R,5S,6R)-2-[4-Chloro-3-(4-hydroxy-chroman-6-ylmethyl)-phenyl]-6-hydroxymethyl-tetrahydro-pyran-3,4,5-triol
37. (2S,3R,4R,5S,6R)-2-[4-Chloro-3-(spiro[chromane-2,1'-cyclopentane]-6-ylmethyl)phenyl]-6-(hydroxymethyl)tetrahydropyran-3,4,5-triol
38. (2S,3R,4R,5S,6R)-2-[4-Chloro-3-(spiro[chromane-2,1'-cyclopentane]-6-ylmethyl)phenyl]-6-(hydroxymethyl)tetrahydropyran-3,4,5-triol
39. 6-[[2-Chloro-5-[(2S,3R,4R,5S,6R)-3,4,5-trihydroxy-6-(hydroxymethyl)tetrahydropyran-2-yl]phenyl]methyl]spiro[chromane-2,4'-piperidine]-4-one
40. 6-(2-Methoxy-5-((2S,3S,4R,5R,6R)-3,4,5-tris(benzyloxy)-6(benzyloxymethyl)tetrahydro-2H-pyran-2-yl)benzyl)spiro[chroman-2,1'-cyclobutane
41. (2S,3R,4R,5S,6R)-2-[4-methoxy-3-(spiro[chromane-2,1'-cyclobutane]-6-ylmethyl)phenyl]-6-(hydroxymethyl)tetrahydropyran-3,4,5-triol
42. 7-[2-Chloro-5-((2S,3R,4R,5S,6R)-3,4,5-trihydroxy-6-hydroxymethyl-tetrahydro-pyran-2-yl)-benzyl]-4H-benzo[1,4]oxazin-3-one
43. 7-[2-Methoxy-5-((2S,3R,4R,5S,6R)-3,4,5-trihydroxy-6-hydroxymethyl-tetrahydro-pyran-2-yl)-benzyl]-4H-benzo[1,4]oxazin-3-one
44. (2S,3R,4R,5S,6R)-2-[4-chloro-3-(spiro[chromane-2,1'-cyclobutane]-6-ylmethyl)phenyl]-6-(hydroxymethyl)tetrahydropyran-3,4,5-triol
45. [(2R,3R,4R,5S,6S)-3,4,5-triacetoxy-6-[4-chloro-3-[(2,2-dimethyl-3-oxo-4H-1,4-benzoxazin-6-yl)methyl]phenyl]tetrahydropyran-2-yl]methyl acetate
46. 6-[2-Chloro-5-((2S,3R,4R,5S,6R)-3,4,5-trihydroxy-6-hydroxymethyl-tetrahydro-pyran-2-yl)-benzyl]-2,2-dimethyl-4H-benzo[1,4]oxazin-3-one
47. 6-(2-chloro-5-((2S,3R,4R,5S,6R)-3,4,5-trihydroxy-6-(hydroxymethyl)tetrahydro-2H-pyran-2-yl)benzyl)-2H-benzo[b][1,4]oxazin-3(4H)-one
48. (2S,3R,4R,5S,6R)-2-[3-[(4-benzylspiro[3H-1,4-benzoxazine-2,1'-cyclopropane]-6-yl)methyl]-4-chloro-phenyl]-6-(hydroxymethyl)tetrahydropyran-3,4,5-triol
49. (2S,3R,4R,5S,6R)-2-[4-Chloro-3-(spiro[3,4-dihydro-1,4-benzoxazine-2,1'-cyclopropane]-6-ylmethyl)phenyl]-6-(hydroxymethyl)tetrahydropyran-3,4,5-triol
50. Acetic acid (2R,3R,4R,5S,6S)-3,4,5-triacetoxy-6-[4-chloro-3-(2-cyano-3,4-dihydro-2H-benzo[1,4]oxazin-6-ylmethyl)-phenyl]-tetrahydro-pyran-2-ylmethyl ester
51. 6-[2-Chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carbonitrile 52. 6-[2-chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carboxylic acid methyl ester
53. 6-[2-Chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carboxylic acid
54. 6-[2-bromo-5-((3S,4R,5R,6R)-3,4,5-tris-benzyloxy-6-benzyloxymethyl-tetrahydro-pyran-2-yl)-benzyl]-chroman
55. 6-[2-cyclopropyl-5-((3S,4R,5R,6R)-3,4,5-tris-benzyloxy-6-benzyloxymethyl-tetrahydro-pyran-2-yl)-benzyl]-chroman
56. (2S,3R,4R,5S,6R)-2-(3-Chroman-6-ylmethyl-4-cyclopropyl-phenyl)-6-hydroxymethyl-tetrahydro-pyran-3,4,5-triol
57. [(2R,3R,4R,5S,6S)-3,4,5-triacetoxy-6-[4-bromo-3-(2,3-dihydro-1,4-benzodioxin-6-ylmethyl)phenyl]tetrahydropyran-2-yl]methyl acetate
58. [(2R,3R,4R,5S,6S)-3,4,5-triacetoxy-6-[4-bromo-3-(2,3-dihydro-1,4-benzodioxin-6-ylmethyl)phenyl]tetrahydropyran-2-yl]methyl acetate
59. Acetic acid (2R,3R,4R,5S)-3,4,5-triacetoxy-6-[4-cyclopropyl-3-(2,3-dihydro-benzo[1,4]dioxin-6-ylmethyl)-phenyl]-tetrahydro-pyran-2-ylmethyl ester
60. (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol
61. Acetic acid (2R,3R,4R,5S)-3,4,5-triacetoxy-6-[3-(2,3-dihydro-benzo[1,4]dioxin-6-ylmethyl)-4-ethyl-phenyl]-tetrahydro-pyran-2-ylmethyl ester
62. (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol
63. 4-Benzyl-6-[2-bromo-5-((2S,3S,4R,5R,6R)-3,4,5-tris-benzyloxy-6-benzyloxymethyl-tetrahydro-pyran-2-yl)-benzyl]-3,4-dihydro-2H-benzo[1,4]oxazine
64. 4-Benzyl-6-[2-cyclopropyl-5-((2S,3S,4R,5R,6R)-3,4,5-tris-benzyloxy-6-benzyloxymethyl-tetrahydro-pyran-2-yl)-benzyl]-3,4-dihydro-2H-benzo[1,4]oxazine
65. (2S,3R,4R,5S,6R)-2-[4-Cyclopropyl-3-(3,4-dihydro-2H-benzo[1,4]oxazin-6-ylmethyl)-phenyl]-6-hydroxymethyl-tetrahydro-pyran-3,4,5-triol
66. (2S,3R,4R,5S,6R)-2-[3-(3,4-Dihydro-2H-benzo[1,4]oxazin-6-ylmethyl)-4-ethyl-phenyl]-6-hydroxymethyl-tetrahydro-pyran-3,4,5-triol
67. (2S,3R,4R,5S,6R)-2-[2-(3,4-Dihydro-2H-benzo[1,4]oxazin-6-ylmethyl)-4'-methyl-biphenyl-4-yl]-6-hydroxymethyl-tetrahydro-pyran-3,4,5-triol
68. (2S,3R,4R,5S,6R)-2-[3-(4-Benzyl-3,4-dihydro-2H-benzo[1,4]oxazin-6-ylmethyl)-4-isopropyl-phenyl]-6-hydroxymethyl-tetrahydro-pyran-3,4,5-triol
69. (2S,3R,4R,5S,6R)-2-[3-(3,4-Dihydro-2H-benzo[1,4]oxazin-6-ylmethyl)-4-isopropyl-phenyl]-6-hydroxymethyl-tetrahydro-pyran-3,4,5-triol
70. (2S,3R,4R,5S,6R)-2-[3-(1-Benzyl-1,2,3,4-tetrahydro-quinolin-7-ylmethyl)-4-isopropyl-phenyl]-6-hydroxymethyl-tetrahydro-pyran-3,4,5-triol
71. (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol
72. (2R,3S,4R,5R,6S)-2-Hydroxymethyl-6-[4-isopropyl-3-(1,2,3,4-tetrahydro-quinolin-6-ylmethyl)-phenyl]-tetrahydro-pyran-3,4,5-triol In another aspect of the invention, there is provided a compound selected from compounds 1 to 72 and compounds 73 to 126 below, or a pharmaceutically acceptable salt thereof:

73 (2S,3R,4R,5S,6R)-2-(3-Chroman-6-ylmethyl-4-methyl-phenyl)-6-hydroxymethyl-tetrahydro-pyran-3,4,5-triol
74 (2S,3R,4R,5S,6R)-2-(3-Chroman-6-ylmethyl-4-hydroxy-phenyl)-6-hydroxymethyl-tetrahydro-pyran-3,4,5-triol
75 (2S,3R,4R,5S,6R)-2-(3-Chroman-6-ylmethyl-4-ethoxy-phenyl)-6-hydroxymethyl-tetrahydro-pyran-3,4,5-triol
76 (2S,3R,4R,5S,6R)-2-(3-Chroman-6-ylmethyl-4-pyrazol-1-yl-phenyl)-6-hydroxymethyl-tetrahydro-pyran-3,4,5-triol
77 (2S,3R,4R,5S,6R)-2-(3-Chroman-6-ylmethyl-2-hydroxy-4-methyl-phenyl)-6-hydroxymethyl-tetrahydro-pyran-3,4,5-triol
78 (2S,3R,4R,5S,6R)-2-[3-(3,4-Dihydro-2H-benzo[1,4]oxazin-6-ylmethyl)-4-hydroxy-phenyl]-6-hydroxymethyl-tetrahydro-pyran-3,4,5-triol
79 (2S,3R,4R,5S,6R)-2-[3-(3,4-Dihydro-2H-benzo[1,4]oxazin-6-ylmethyl)-4-ethoxy-phenyl]-6-hydroxymethyl-tetrahydro-pyran-3,4,5-triol
80 (2S,3R,4R,5S,6R)-2-[3-(3,4-Dihydro-2H-benzo[1,4]oxazin-6-ylmethyl)-4-pyrazol-1-yl-phenyl]-6-hydroxymethyl-tetrahydro-pyran-3,4,5-triol
81 2S,3R,4R,5S,6R)-2-[3-(3,4-Dihydro-2H-benzo[1,4]oxazin-6-ylmethyl)-2-hydroxy-4-methyl-phenyl]-6-hydroxymethyl-tetrahydro-pyran-3,4,5-triol
82 (2S,3R,4R,5S,6R)-2-[3-(3,4-Dihydro-2H-benzo[1,4]oxazin-6-ylmethyl)-2-hydroxy-4-methyl-phenyl]-6-hydroxymethyl-tetrahydro-pyran-3,4,5-triol
83 (2R,3S,4R,5R,6S)-2-(hydroxymethyl)-6-[4-methyl-3-(spiro[chromane-4, 1'-cyclopropane-6-ylmethyl)phenyl]tetrahydropyran-3,4,5-triol
84 (2S,3R,4R,5S,6R)-2-[4-ethoxy-3-(spiro[3,4-dihydro-1,4-benzoxazine-2,1'-cyclopentane]-6-ylmethyl)phenyl]-6-(hydroxymethyl)tetrahydropyran-3,4,5-triol
85 (2S,3R,4R,5S,6R)-2-[4-chloro-3-(spiro[3,4-dihydro-1,4-benzoxazine-2,1'-cyclopropane]-6-ylmethyl)phenyl]-6-(hydroxymethyl)tetrahydropyran-3,4,5-triol
86 (2R,3S,4R,5R,6S)-2-Hydroxymethyl-6-[4-methyl-3-(1-methyl-1,2,3,4-tetrahydro-quinolin-6-ylmethyl)-phenyl]-tetrahydro-pyran-3,4,5-triol
87 6-[2-Chloro-5-((2S,3R,4R,5S,6R)-3,4,5-trihydroxy-6-hydroxymethyl-tetrahydro-pyran-2-yl)-benzyl]-chroman-2-carboxylic acid amide
88 {6-[2-Chloro-5-((2S,3R,4R,5S,6R)-3,4,5-trihydroxy-6-hydroxymethyl-tetrahydro-pyran-2-yl)-benzyl]-2,3-dihydro-benzo[1,4]oxazin-4-yl}-acetic acid
89 (2S,3R,4R,5S,6R)-2-[4-Chloro-3-(1-methyl-1,4-dihydro-chromeno[4,3-b]pyrrol-8-ylmethyl)-phenyl]-6-hydroxymethyl-tetrahydro-pyran-3,4,5-triol
90 (2S,3R,4R,5S,6R)-2-[4-Chloro-3-(1,1a,2,7a-tetrahydro-7-oxa-cyclopropa[b]naphthalen-4-ylmethyl)-phenyl]-6-hydroxymethyl-tetrahydro-pyran-3,4,5-triol
91 (2S,3R,4R,5S,6R)-2-[4-Chloro-3-(8-fluoro-3,4-dihydro-2H-benzo[1,4]oxazin-6-ylmethyl)-phenyl]-6-hydroxymethyl-tetrahydro-pyran-3,4,5-triol
92 (2S,3R,4R,5S,6R)-2-[4-Chloro-3-(8-fluoro-2,3-dihydro-benzo[1,4]dioxin-6-ylmethyl)-phenyl]-6-hydroxymethyl-tetrahydro-pyran-3,4,5-triol
93 6-[2-Chloro-5-((2S,3R,4R,5S,6R)-3,4,5-trihydroxy-6-hydroxymethyl-tetrahydro-pyran-2-yl)-benzyl]-1-methyl-3,4-dihydro-1H-quinolin-2-one 94 (2S,3R,4R,5S,6R)-2-[4-Chloro-3-(2-methyl-2,3-dihydro-1H-isoindol-5-ylmethyl)-phenyl]-6-hydroxymethyl-tetrahydro-pyran-3,4,5-triol
95 (2S,3R,4R,5S,6R)-2-[4-chloro-3-(spiro[cyclopropane-1,4'-isochromane]-7'-ylmethyl)phenyl]-6-(hydroxymethyl)tetrahydropyran-3,4,5-triol
96 (2R,3S,4S,5R,6S)-2-methyl-6-[4-methyl-3-(spiro[chromane-4,1'-cyclopropane]-6-ylmethyl)phenyl]tetrahydropyran-3,4,5-triol
97 (2S,3R,4S,5S,6R)-2-[4-chloro-3-(spiro[chromane-2,3'-pyrrolidine]-6-ylmethyl)phenyl]-6-methyl-tetrahydropyran-3,4,5-triol
98 (2S,3R,4S,5S,6R)-2-[4-chloro-3-(spiro[3,4-dihydro-1,4-benzoxazine-2,1'-cyclopentane]-6-ylmethyl)phenyl]-6-methyl-tetrahydropyran-3,4,5-triol
99 (2S,3R,4R,5S,6S)-2-[4-chloro-3-(spiro[3,4-dihydro-1,4-benzoxazine-2,1'-cyclopentane]-6-ylmethyl)phenyl]-6-(fluoromethyl)tetrahydropyran-3,4,5-triol
100 (2S,3R,4R,5S,6R)-2-[4-chloro-3-(spiro[3,4-dihydro-1,4-benzoxazine-2,1'-cyclopropane]-6-ylmethyl)phenyl]-6-(1-hydroxyethyl)tetrahydropyran-3,4,5-triol
101 (2S,3R,4S,5S,6R)-2-[4-chloro-3-(2,4-dihydrochromeno[4,3-c]pyrazol-8-ylmethyl)phenyl]-6-ethyl-tetrahydropyran-3,4,5-triol
102 (2S,3R,4S,5S,6R)-2-[4-chloro-3-(10H-phenoxazin-2-ylmethyl)phenyl]-6-methyl-tetrahydropyran-3,4,5-triol
103 (2S,3R,4R,5S,6R)-2-[3-(2,3-dihydro-1,4-benzodioxin-6-ylmethyl)-4-isopropyl-phenyl]-6-(hydroxymethyl)tetrahydropyran-3,4,5-triol
104 (2S,3R,4R,5S,6R)-2-[3-(chroman-6-ylmethyl)-4-cyclobutyl-phenyl]-6-(hydroxymethyl)tetrahydropyran-3,4,5-triol
105 (2S,3R,4R,5S,6R)-2-[4-ethyl-3-(1,2,3,4-tetrahydroquinolin-7-ylmethyl)phenyl]-6-(hydroxymethyl)tetrahydropyran-3,4,5-triol
106 (2S,3R,4R,5S,6R)-2-[4-cyclopropyl-3-(1,2,3,4-tetrahydroquinolin-7-ylmethyl)phenyl]-6-(hydroxymethyl)tetrahydropyran-3,4,5-triol
107 (2S,3R,4R,5S,6R)-2-[3-(3,4-dihydro-2H-1,4-benzothiazin-6-ylmethyl)-4-methoxy-phenyl]-6-(hydroxymethyl)tetrahydropyran-3,4,5-triol
108 (2S,3R,4R,5S,6R)-2-[4-chloro-3-(3,4-dihydro-2H-1,4-benzothiazin-6-ylmethyl)phenyl]-6-(hydroxymethyl)tetrahydropyran-3,4,5-triol
109 (2S,3R,4R,5S,6R)-2-[3-(2,3-dihydro-1,4-benzodioxin-6-ylmethyl)-4-ethynyl-phenyl]-6-(hydroxymethyl)tetrahydropyran-3,4,5-triol
110 (2S,3R,4R,5S,6R)-2-[4-ethyl-3-(1,2,3,4-tetrahydroquinolin-6-ylmethyl)phenyl]-6-(hydroxymethyl)tetrahydropyran-3,4,5-triol
111 (2S,3R,4R,5S,6R)-2-[4-ethyl-3-(1,2,3,4-tetrahydroquinolin-6-ylmethyl)phenyl]-6-(hydroxymethyl)tetrahydropyran-3,4,5-triol
112 (2S,3R,4R,5S,6R)-2-[3-(3,4-dihydro-2H-1,4-benzothiazin-6-ylmethyl)-4-methoxy-phenyl]-6-(hydroxymethyl)tetrahydropyran-3,4,5-triol
113 (2S,3R,4R,5S,6R)-2-[4-chloro-3-(3,4-dihydro-2H-1,4-benzothiazin-6-ylmethyl)phenyl]-6-(hydroxymethyl)tetrahydropyran-3,4,5-triol
114 (2S,3R,4R,5S,6R)-2-[3-(chroman-6-ylmethyl)-4-methylsulfanyl-phenyl]-6-(hydroxymethyl)tetrahydropyran-3,4,5-triol
115 (2S,3R,4R,5S,6R)-2-[3-(chroman-6-ylmethyl)-4-methylsulfonyl-phenyl]-6-(hydroxymethyl)tetrahydropyran-3,4,5-triol
116 (2S,3R,4R,5S,6R)-2-[4-cyclopropyl-3-(1,2,3,4-tetrahydroquinolin-6-ylmethyl)phenyl]-6-(hydroxymethyl)tetrahydropyran-3,4,5-triol
117 (2S,3R,4R,5S,6R)-2-[3-(3,4-dihydro-2H-1,4-benzoxazin-6-ylmethyl)-4-dimethylamino-phenyl]-6-(hydroxymethyl)tetrahydropyran-3,4,5-triol
118 (2S,3R,4R,5S,6R)-2-[4-amino-3-(3,4-dihydro-2H-1,4-benzoxazin-6-ylmethyl)phenyl]-6-(hydroxymethyl)tetrahydropyran-3,4,5-triol
119 (2S,3R,4R,5S,6R)-2-[3-(3,4-dihydro-2H-1,4-benzothiazin-6-ylmethyl)-4-methoxy-phenyl]-6-(hydroxymethyl)tetrahydropyran-3,4,5-triol
120 (2S,3R,4R,5S,6R)-2-[3-[(1,1-dioxo-3,4-dihydro-2H-benzo[b][1,4]thiazin-6-yl)methyl]-4-methoxy-phenyl]-6-(hydroxymethyl)tetrahydropyran-3,4,5-triol
121 3-chloro-2-(3,4-dihydro-2H-1,4-benzoxazin-6-ylmethyl)-6-[(2S,3R,4R,5S,6R)-3,4,5-trihydroxy-6-(hydroxymethyl)tetrahydropyran-2-yl]benzamide
122 2-(2,3-dihydro-1,4-benzodioxin-7-ylmethyl)-4-[(2S,3R,4R,5S,6R)-3,4,5-trihydroxy-6-(hydroxymethyl)tetrahydropyran-2-yl]benzonitrile
123 (2S,3R,4R,5S,6R)-2-[3-(2,3-dihydro-1,4-benzodioxin-7-ylmethyl)-4-ethynyl-phenyl]-6-(hydroxymethyl)tetrahydropyran-3,4,5-triol
124 (2S,3R,4R,5S,6R)-2-[3-(3,4-dihydro-2H-1,4-benzoxazin-6-ylmethyl)-4-phenoxy-phenyl]-6-(hydroxymethyl)tetrahydropyran-3,4,5-triol
125 (2S,3R,4R,5S,6R)-2-[3-(3,4-dihydro-2H-1,4-benzoxazin-6-ylmethyl)-4-oxazol-4-yloxy-phenyl]-6-(hydroxymethyl)tetrahydropyran-3,4,5-triol
126 (1R,2R,3S,4S,6R)-4-[3-(9a,10-dihydro-5aH-phenothiazin-3-ylmethyl)-4-chloro-phenyl]-6-(hydroxymethyl)cyclohexane-1,2,3-triol or a pharmaceutically acceptable salt thereof.

Preferably, the compound is compound 40, 39, 30, 16, 14, 1, 7, 15, 13, 27, 20, 8, 10, 21 or 19, or a pharmaceutically acceptable salt thereof.

More preferably, the compound is example 8, or a pharmaceutically acceptable salt thereof.

More preferably, the compound is example 60, or a pharmaceutically acceptable salt thereof.

More preferably, the compound is example 62, or a pharmaceutically acceptable salt thereof.

More preferably, the compound is example 71, or a pharmaceutically acceptable salt thereof.

Compounds of Formula (I), (I-a), (I-i), (I-ia), (I-ii), (I-iia), (I-iii), (I-iiia), (I-iv), (I-iva), and (V) and Derivatives Thereof As used herein, the terms "compound of the invention" and "compound of Formula (I)" etc. include pharmaceutically acceptable derivatives thereof and polymorphs, isomers and isotopically labelled variants thereof. Furthermore, the term "compounds of the invention" and "compound of Formula (I)" etc. include compounds of formulae (I), (I-a), (I-i), (I-ia), (I-ii), (I-iia), (I-iii), (I-iiia), (I-iv), (I-iva), and (V), and the embodiments thereof disclosed herein.

Pharmaceutically Acceptable Derivatives

The term "pharmaceutically acceptable derivative" includes any pharmaceutically acceptable salt, solvate, or hydrate of a compound of Formula (I).

Pharmaceutically Acceptable Salts

The term "pharmaceutically acceptable salt" includes a salt prepared from pharmaceutically acceptable non-toxic acids or bases including inorganic or organic acids and bases.

Compounds of Formula (I) which contain basic, e.g. amino, groups are capable of forming pharmaceutically acceptable salts with acids. In one embodiment, pharmaceutically acceptable acid addition salts of the compounds of Formula (I) include, but are not limited to, those of inorganic acids such as hydrohalic acids (e.g. hydrochloric, hydrobromic and hydroiodic acid), sulfuric acid, nitric acid, and phosphoric acids. In one embodiment, pharmaceutically acceptable acid addition salts of the compounds of Formula (I) include, but are not limited to, those of organic acids such as aliphatic, aromatic, carboxylic and sulfonic classes of organic acids, examples of which include: aliphatic monocarboxylic acids such as formic acid, acetic acid, propionic acid or butyric acid; aliphatic hydroxy acids such as lactic acid, citric acid, tartaric acid or malic acid; dicarboxylic acids such as maleic acid or succinic acid; aromatic carboxylic acids such as benzoic acid, p-chlorobenzoic acid, phenylacetic acid, diphenylacetic acid or triphenylacetic acid; aromatic hydroxyl acids such as o-hydroxybenzoic acid, p-hydroxybenzoic acid, 1-hydroxynaphthalene-2-carboxylic acid or 3-hydroxynaphthalene-2-carboxylic acid; and sulfonic acids such as methanesulfonic acid, ethanesulfonic acid or benzenesulfonic acid. Other pharmaceutically acceptable acid addition salts of the compounds of Formula (I) include, but are not limited to, those of glycolic acid, glucuronic acid, furoic acid, glutamic acid, anthranilic acid, salicylic acid, mandelic acid, embonic (pamoic) acid, pantothenic acid, stearic acid, sulfanilic acid, algenic acid, and galacturonic acid.

Compounds of Formula (I) which contain acidic, e.g. carboxyl, groups are capable of forming pharmaceutically acceptable salts with bases. In one embodiment, pharmaceutically acceptable basic salts of the compounds of Formula (I) include, but are not limited to, metal salts such as alkali metal or alkaline earth metal salts (e.g. sodium, potassium, magnesium or calcium salts) and zinc or aluminium salts. In one embodiment, pharmaceutically acceptable basic salts of the compounds of Formula (I) include, but are not limited to, salts formed with ammonia or pharmaceutically acceptable organic amines or heterocyclic bases such as ethanolamines (e.g. diethanolamine), benzylamines, N-methyl-glucamine, amino acids (e.g. lysine) or pyridine.

Hemisalts of acids and bases may also be formed, e.g. hemisulphate salts.

Pharmaceutically acceptable salts of compounds of Formula (I) may be prepared by methods well-known in the art.

For a review of pharmaceutically acceptable salts, see Stahl and Wermuth, Handbook of Pharmaceutical Salts: Properties, Selection and Use (Wiley-VCH, Weinheim, Germany, 2002).

Solvates & Hydrates

The compounds of the invention may exist in both unsolvated and solvated forms. The term "solvate" includes molecular complexes comprising a compound of the invention and one or more pharmaceutically acceptable solvent molecules such as water or $C_{1-6}$ alcohols, e.g. ethanol. The term "hydrate" means a "solvate" where the solvent is water. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Amorphous & Crystalline Forms

The compounds of the invention may exist in solid states from amorphous through to crystalline forms. All such solid forms are included within the invention.

Co-Crystalline Forms

The compounds of the invention may exist as co-crystals. All such co-crystalline forms are included within the invention. In one embodiment, the compounds of the invention exist as co-crystals with L-proline.

For the avoidance of doubt, the terms "L-proline co-crystal of a compound of the invention", such as an L-proline co-crystal of (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol, an L-proline co-crystal of (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol, an L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol, or an L-proline co-crystal of (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol, refers to all forms of association between L-proline and a compound of the invention, including salt forms. In particular, these terms encompass: (i) a non-ionic association between L-proline and a compound of the invention (i.e. where no proton transfer has occurred between L-proline and a compound of the invention); or (ii) an ionic interaction where proton transfer between L-proline and a compound of the invention has occurred to form an L-proline salt of the compound of the invention, or (iii) mixtures of (i) and (ii) above.

In a particular embodiment of the invention, the L-proline co-crystal comprises is a non-ionic association between a compound of the invention and L-proline (i.e. where no proton transfer has occurred between L-proline and the compound of the invention).

In an alternative embodiment of the invention, the L-proline co-crystal is an L-proline salt of the compound of the invention.

In one embodiment, the invention provides a crystalline form of L-proline co-crystal of (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol. In one aspect, the crystalline form is non-ionic. In another aspect, the crystalline form has differential scanning calorimetry endotherms at about 64° C., about 104° C. and/or about 157° C. In another aspect, the crystalline form has a molar ratio of L-proline to (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol of 1:1. In another aspect, the crystalline form has powder X-ray diffraction peak(s) at about 19.3, about 23.2, about 17.0, and/or about 5.7 degrees 2θ. In one aspect, the crystalline form has powder X-ray diffractions peaks substantially the same as those listed in Table 1A.

In one embodiment, the invention provides a crystalline form of L-proline co-crystal of (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol. In one aspect, the crystalline form is non-ionic. In another aspect, the crystalline form has differential scanning calorimetry endotherms at about 151° C. In another aspect, the crystalline form has a molar ratio of L-proline to (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol of 1:1. In another aspect, the crystalline form has powder X-ray diffraction peak(s) at about 16.7, about 19.9, about 17.6, and/or about 21.9 degrees 2θ. In one aspect, the crystalline form has powder X-ray diffractions peaks substantially the same as those listed in Table 2A.

In one embodiment, the invention provides a crystalline form of L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol. In one aspect, the crystalline form is non-ionic. In another aspect, the crystalline form has differential scanning calorimetry endotherms at about 136° C. In another aspect, the crystalline form has a molar ratio of L-proline to (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol of 1:1. In another aspect, the crystalline form has powder X-ray diffraction peak(s) at about 17.3, about 20.4, about 18.0, about 18.9, and/or about 23.8 degrees 2θ. In one aspect, the crystalline form has powder X-ray diffractions peaks substantially the same as those listed in Table 3A. In another aspect, the crystalline form has a powder X-ray diffraction spectrum substantially the same as the spectrum shown in FIG. 2. In another aspect, the crystalline form has a molar ratio of L-proline to (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol of 2:1. In another aspect, the crystalline form has differential scanning calorimetry endotherms at about 176° C.

In one embodiment, the invention provides a crystalline form of L-proline co-crystal of (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol. In one aspect, the crystalline form is non-ionic. In another aspect, the crystalline form has differential scanning calorimetry endotherms at about 156° C. and/or about 158° C. In another aspect, the crystalline form has a molar ratio of L-proline to (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol of 1:1. In one aspect, the crystalline form has powder X-ray diffractions peaks substantially the same as those listed in Table 4.

In one embodiment, the invention provides a crystalline form of L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol. In one aspect, the crystalline form has a molar ratio of L-proline to (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol of 2:1. In another aspect, the crystalline form is non-ionic. In another aspect, the crystalline form has a differential scanning calorimetry endotherm at about 176° C. In another aspect, the crystalline form has powder X-ray diffraction peak(s) at about 6.1, 9.1, 12.8, 15.2, 16.5, 17.8, 18.9, 20.9, and/or 28.4. In another aspect, the crystalline form has powder X-ray diffraction pattern which is substantially the same as the powder X-ray diffraction pattern shown in FIG. 4.

In the preceding paragraphs defining the molar ratio for a crystalline forms of L-proline and a compound of the invention, the phrase "a molar ratio of about 1:1" is used to indicate that the crystalline form has between 0.9-1.1 moles of a compound of the invention to 1 mole of L-proline. Likewise, the phrase "a molar ratio of about 1:2" is used to indicate that the crystalline form has between 0.9-1.1 moles of a compound of the invention to 2 moles of L-proline.

When it is stated herein that the present invention relates to a crystalline form of an L-proline co-crystal of a compound of the invention such as, (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol, (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol, (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol, or (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol, the degree of crystallinity as determined by X-ray powder diffraction data is conveniently greater than about 60%, more conveniently greater than about 80%, preferably greater than about 90%.

Figure 2:
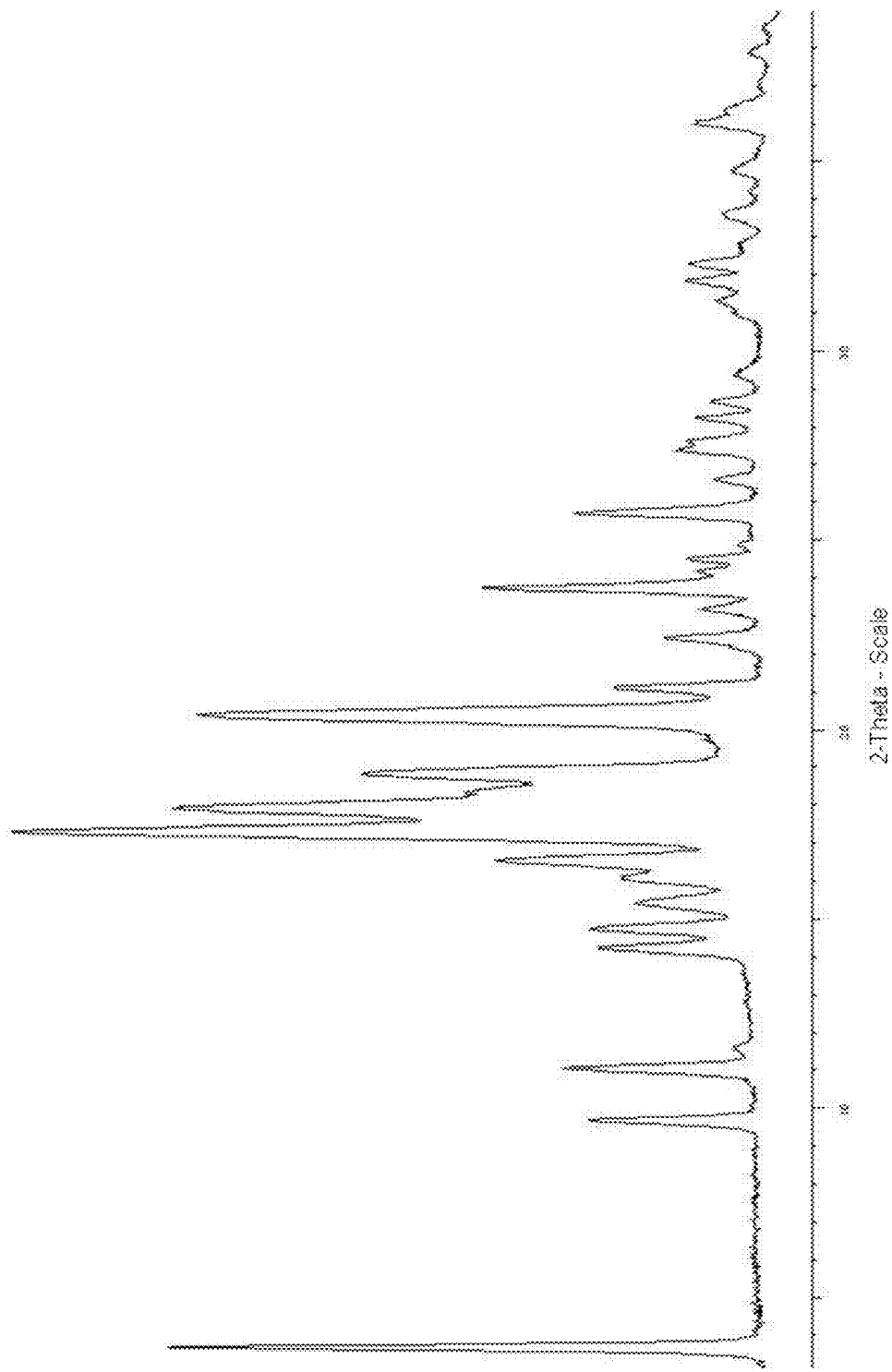
FIG. 2 is a powder X-ray diffraction pattern for a 1:1 L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol prepared by method 1.
Figure 4:
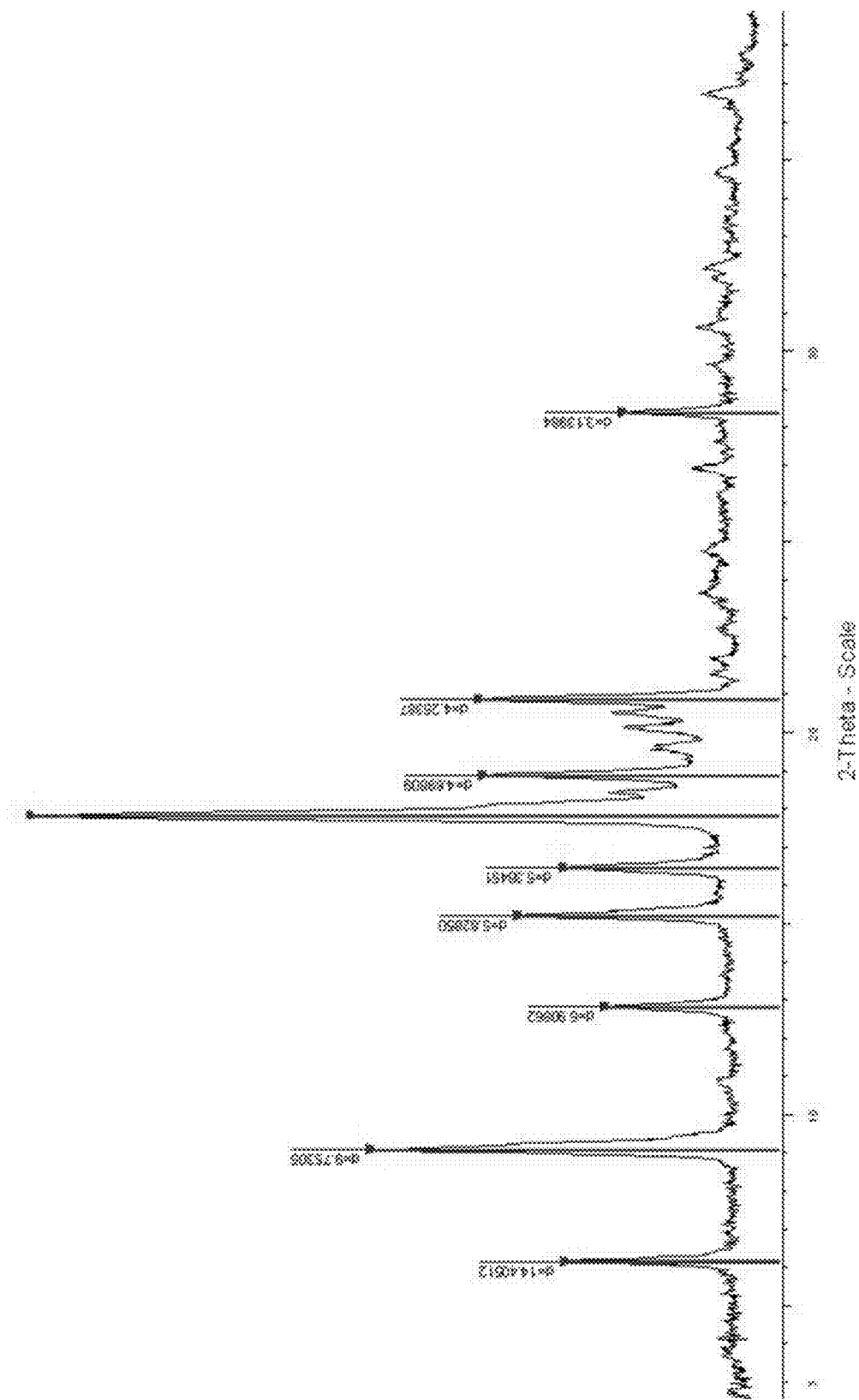
FIG. 4 is a powder X-ray diffraction pattern for a 2:1 L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol prepared by method 3.

In the preceding paragraphs defining the X-ray powder diffraction peaks for a crystalline forms of L-proline and a compound of the invention, the term "at about" is used to indicate that the precise position of peaks (i.e. the recited 2-theta angle values) should not be construed as being absolute values because, as will be appreciated by those skilled in the art, the precise position of the peaks may vary slightly between one machine and another, from one sample to another, or as a result of slight variations in measurement conditions utilized. It is also stated in the preceding paragraphs that a crystalline form of a 1:1 L-proline co-crystal of (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol, a 1:1 L-proline co-crystal of (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol, a 1:1 L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol, a 1:1 L-proline co-crystal of (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol, and a 2:1 L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol have powder X-ray diffraction patterns that have substantially the same most prominent peaks (2-theta angle values) shown in Tables 1A, 2A, 3A, 4, and 5, respectively; and that an L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol which has about a 1:1 molar ratio has substantially the same powder X-ray diffraction spectrum as shown in FIG. 2 and that an L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol which has about a 2:1 molar ratio has substantially the same powder X-ray diffraction spectrum as shown in FIG. 4. It shall be appreciated that the use of the term 'substantially' in this context is also intended to indicate that the 2-theta angle values of the powder X-ray diffraction patterns may vary slightly from one machine to another, from one sample to another, or as a result of slight variations in measurement conditions utilized, so the peak positions shown in the Table or in the specta are again not to be construed as absolute values.

In this regard, it is known in the art that a powder X-ray diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of powder X-ray diffraction will realize that the relative intensity of peaks can be affected by, for example, grains above 30 microns in size and non-unitary aspect ratios, which may affect analysis of samples. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline form of the 1:1 L-proline co-crystal of (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol, the 1:1 L-proline co-crystal of (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol, the 1:1 L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol, the 1:1 L-proline co-crystal of (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol, and the 2:1 L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol of the present invention is not limited to the crystals that provide powder X-ray diffraction patterns having identical peaks as shown in Tables 1A, 2A, 3A, 4, and 5, respectively, and any crystals providing X-ray powder diffraction patterns substantially the same as that shown in Table 1A, 2A, 3A, 4, and 5, respectively, fall within the scope of the present invention. Likewise, it shall be understood that the crystalline form of an L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol of the present invention is not limited to the crystals that provide powder X-ray diffraction spectra having identical peaks as shown in FIG. 2 or 4, respectively, and any crystals providing X-ray powder diffraction spectra substantially the same as that shown in FIG. 2 or 4, fall within the scope of the present invention. A person skilled in the art of powder X-ray diffraction is able to judge the substantial identity of powder X-ray diffraction spectra. Generally, a measurement error of a diffraction angle in a powder X-ray diffractogram is about 2θ=0.5 degrees or less (or, more suitably, about 2θ=0.2 degrees or less) and such degree of a measurement error should be taken into account when interpreting the peak positions referred to the text above and in Tables 1, 1A, 2, 2A, 3, 3A, 4, and 4A and in the spectra shown in FIGS. 2 and 4. Therefore, where it is stated, for example, that the co-crystal has an X-ray powder diffraction pattern with a peak at about 2θ=17.3 degree (or any one of the other angles mentioned above) then this can be interpreted as being 2θ=17.3 degree plus or minus 0.5 degree, or 2θ=17.3 degree plus or minus 0.2 degree.

Isomeric Forms

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. All such isomeric forms are included within the invention. The isomeric forms may be in isomerically pure or enriched form, as well as in mixtures of isomers (e.g. racemic or diastereomeric mixtures).

Accordingly, the invention provides:
stereoisomeric mixtures of compounds of Formula (I);
a diastereomerically enriched or diastereomerically pure isomer of a compound of Formula (I); or
an enantiomerically enriched or enantiomerically pure isomer of a compound of Formula (I).

Where appropriate isomers can be separated from their mixtures by the application or adaptation of known methods (e.g. chromatographic techniques and recrystallisation techniques). Where appropriate isomers can be prepared by the application or adaptation of known methods (e.g. asymmetric synthesis).

Unless otherwise indicated, the present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposeable mirror images of one another.

Isotopic Labeling

The invention includes pharmaceutically acceptable isotopically-labelled compounds of Formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of Formula (I), for example, those incorporating a radioactive isotope, are useful in drug and/or substrate tissue distribution studies. The radioactive isotopes $^3H$ and $^{14}C$ are particularly useful for this purpose in view of their ease of incorporation and ready means of detection.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of Formula (I) can generally be prepared by conventional techniques known to those skilled in the art or by processes analogous to those described herein using an appropriate isotopically-labelled reagent in place of the non-labelled reagent previously employed.

Therapeutic Definitions

As used herein, "treatment" includes curative and prophylactic treatment. As used herein, a "patient" means an animal, preferably a mammal, preferably a human, in need of treatment.

The amount of the compound of the invention administered should be a therapeutically effective amount where the compound or derivative is used for the treatment of a disease or condition and a prophylactically effective amount where the compound or derivative is used for the prevention of a disease or condition.

The term "therapeutically effective amount" used herein refers to the amount of compound needed to treat or ameliorate a targeted disease or condition. The term "prophylactically effective amount" used herein refers to the amount of compound needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, drug combinations, reaction sensitivities and the patient's tolerance or response to therapy. The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day or 1 mg/kg/day to 10 mg/kg/day. Compositions may be administered individually to a patient or may be administered in combination with other agents, drugs or hormones.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. As used herein, the term "disorder" is synonymous with "condition".

Treatment of Diseases and Conditions

Compounds of Formula (I) have been found to be inhibitors of SGLT. As used herein, inhibition of SGLT means inhibition exclusively of SGLT2, inhibition exclusively of SGLT1 or inhibition of both SGLT1 and SGLT2.

The invention provides a compound of Formula (I) for use in therapy. The invention further provides a pharmaceutical composition comprising a compound of Formula (I) in combination with a pharmaceutically acceptable excipient.

The invention further provides a method for the treatment of a disease or condition mediated by the sodium D-glucose co-transporter, comprising the step of administering a therapeutically effective amount of a compound of Formula (I) to a patient. The invention also provides the use of a compound of Formula (I) in the manufacture of a medicament for the treatment of a disease or condition mediated by the sodium D-glucose co-transporter. The invention also provides a compound of Formula (I) for use in treating a disease or condition mediated by the sodium D-glucose co-transporter.

The SGLT inhibitory activity of the compounds of the invention may be demonstrated by the SGLT2 and SGLT1 assays disclosed hereinbelow. Preferred compounds of the invention have an $IC_{50}$ in the SGLT2 assay of <100 nM, in one embodiment <30 nM, in one embodiment <20 nM, in one embodiment <10 nM, in another embodiment <5 nM, and in another embodiment <1 nM, and in another embodiment <0.5 nM. In another embodiment, preferred compounds of the invention have an $IC_{50}$ in the SGLT1 assay of <10,000 nM, in one embodiment <1500 nM, in one embodiment <1000 nM, in one embodiment <700 nM, in another embodiment <500 nM and in another embodiment <200 nM.

The present invention also provides a method of treating diabetes comprising administering a compound of Formula (I) to a subject in need thereof.

In another embodiment, the invention provides a method of treating a disease or condition mediated by the sodium D-glucose co-transporter in a mammal, comprising administering to the mammal in need thereof a therapeutically effective amount of a compound according to claim 1.

The compounds of the present invention are useful as both prophylactic and therapeutic treatments for diseases or conditions related to the inhibition of SGLT-2 and SGLT-1.

Diseases and Conditions Mediated by the Sodium D-Glucose Co-Transporter

The invention is useful for the treatment of a disease or disorder mediated by the sodium D-glucose co-transporter. Diseases and conditions mediated by the sodium D-glucose co-transporter include: metabolic disorders, retinopathy, nephropathy, diabetic foot, ulcers, macroangiopathies, metabolic acidosis or ketosis, reactive hypoglycaemia, hyperinsulinaemia, glucose metabolic disorder, insulin resistance, metabolic syndrome (such as dyslipidemia, obesity, insulin resistance, hypertension, microalbuminemia, hyperuricaemia, and hypercoagulability), dyslipidaemias of different origins, atherosclerosis and related diseases, high blood pressure, chronic heart failure, edema, hyperuricaemia, Syndrome X, diabetes, insulin resistance, decreased glucose tolerance (also known as impaired glucose tolerance, IGT), non-insulin-dependent diabetes mellitus, Type II diabetes, Type I diabetes, diabetic complications, body weight disorders, weight loss, body mass index and leptin related diseases. In one embodiment, the diseases and conditions include metabolic syndrome (such as dyslipidemia, obesity, insulin resistance, hypertension, microalbuminemia, hyperuricaemia, and hypercoagulability), Syndrome X, diabetes, insulin resistance, decreased glucose tolerance (also known as impaired glucose tolerance, IGT), non-insulin-dependent diabetes mellitus, Type II diabetes, Type I diabetes, diabetic complications, body weight disorders, weight loss, body mass index and leptin related diseases. In one embodiment, the disease or disorder is decreased glucose tolerance, Type II diabetes or obesity.

Compounds of formula (I) may be also suitable for preventing beta-cell degeneration such as apoptosis or necrosis of pancreatic beta cells, for improving or restoring the functionality of pancreatic cells, increasing the number and size of pancreatic beta cells, for use as diuretics or antihypertensives and for the prevention and treatment of acute renal failure.

As a further aspect, the invention relates to a method for treating a disorder selected from type I and type II diabetes mellitus, complications of diabetes, comprising administration of an effective amount of a compound of formula (I) or a pharmaceutically acceptable salt thereof.

As used herein a patient is suffering from "obesity" if the patient exhibits at least one of:
 a body mass index (BMI), i.e. the patient's mass (in kg) divided by the square of the patient's height (in m), of 30 or more;
 an absolute waist circumference of >102 cm in men or >88 cm in women;
 a waist-to-hip ratio >0.9 in men or >0.85 in women; or
 a percent body fat >25% in men or >30% in women.

As used herein a patient is suffering from "Type II diabetes" if they meet the World Health Organisation criteria for Diabetes diagnosis (Definition and diagnosis of diabetes mellitus and intermediate hyperglycaemia, WHO, 2006), i.e. the patient exhibits at least one of:
 a fasting plasma glucose >7.0 mmol/l (126 mg/dl); or
 a venous plasma glucose >11.1 mmol/l (200 mg/dl) 2 hours after ingestion of 75 g oral glucose load.

As used herein a patient is suffering from "IGT" if they meet the World Health Organisation criteria for IGT diagnosis (Definition and diagnosis of diabetes mellitus and intermediate hyperglycaemia, WHO, 2006), i.e. the patient exhibits both of:
 a fasting plasma glucose <7.0 mmol/l (126 mg/dl); and
 a venous plasma glucose >7.8 and <11.1 mmol/l (200 mg/dl) 2 hours after ingestion of 75 g oral glucose load.

Administration & Formulation

General

For pharmaceutical use, the compounds of the invention may be administered as a medicament by enteral or parenteral routes, including intravenous, intramuscular, subcutaneous, transdermal, airway (aerosol), oral, intranasal, rectal, vaginal and topical (including buccal and sublingual) administration. The compounds of Formula (I) should be assessed for their biopharmaceutical properties, such as solubility and solution stability (across pH), permeability, etc., in order to select the most appropriate dosage form and route of administration for treatment of the proposed indication.

The compounds of the invention may be administered as crystalline or amorphous products. The compounds of the invention may be administered alone or in combination with one or more other compounds of the invention or in combination with one or more other drugs (or as any combination thereof). Generally, they will be administered as a formulation in association with one or more pharmaceutically acceptable excipients. The term "excipient" includes any ingredient other than the compound(s) of the invention which may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

The present invention provides a pharmaceutical composition comprising a compound according to Formula (I) and a pharmaceutically acceptable excipient.

Typical pharmaceutically acceptable excipients include:
  diluents, e.g. lactose, dextrose, sucrose, mannitol, sorbitol, cellulose and/or glycine;
  lubricants, e.g. silica, talcum, stearic acid, its magnesium or calcium salt and/or polyethyleneglycol;
  binders, e.g. magnesium aluminum silicate, starch paste, gelatin, tragacanth, methylcellulose, sodium carboxymethylcellulose and/or polyvinylpyrrolidone;
  disintegrants, e.g. starches, agar, alginic acid or its sodium salt, or effervescent mixtures; and/or
  absorbants, colorants, flavors and/or sweeteners.

A thorough discussion of pharmaceutically acceptable excipients is available in Gennaro, *Remington: The Science and Practice of Pharmacy* 2000, 20th edition (ISBN: 0683306472).

Accordingly, in one embodiment, the present invention provides a pharmaceutical composition comprising a compound of Formula (I) and a pharmaceutically acceptable excipient.

Oral Administration

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of Formula (I) in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, *Expert Opinion in Therapeutic Patents* 2001, 11(6): 981-986.

The formulation of tablets is discussed in H. Lieberman and L. Lachman, *Pharmaceutical Dosage Forms: Tablets* 1980, vol. 1 (Marcel Dekker, New York).

Parenteral Administration

The compounds of the invention can be administered parenterally.

The compounds of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of Formula (I) used in the preparation of parenteral solutions may be increased by the use of appropriate formulation techniques, such as the incorporation of co-solvents and/or solubility-enhancing agents such as surfactants, micelle structures and cyclodextrins.

Inhalation & Intranasal Administration

The compounds of the invention can be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, for example, PGLA. Modified release formulations include delayed-, sustained-, pulsed-, controlled-, targeted and programmed release.

Transdermal Administration

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Combination Therapy

A compound of formula (I) of the present invention may be usefully combined with another pharmacologically active compound, or with two or more other pharmacologically active compounds, for use in therapy. For example, a compound of the formula (I), or a pharmaceutically acceptable salt thereof, as defined above, may be administered simultaneously, sequentially or separately in combination with one or more agents for the treatment of disorders previously listed.

Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosine-phosphatase 1, substances that affect deregulated glucose production in the liver, such as e.g. inhibitors of glucose-6-phosphatase, orfructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoidi receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-01 13, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

Such combinations may offer significant advantages, including synergistic activity, in therapy.

The present invention thus provides:

The use of an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin in the manufacture of a medicament for the treatment of a disease or condition in a subject mediated by the sodium D-glucose co-transporter, wherein the agent is administered in combination with a compound according to Formula (I);

The use of a compound according to Formula (I) in the manufacture of a medicament for the treatment of a disease or condition in a subject mediated by the sodium D-glucose co-transporter, wherein the compound is administered in combination with an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin, and The use of a compound according to claim 1 in combination with an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin in the manufacture of a medicament for treating a disease or condition in a subject mediated by the sodium D-glucose co-transporter, Wherein the diseases or conditions may be as described herein.

The present invention also provides a pharmaceutical composition comprising a therapeutically effective amount of a compound of Formula (I) in combination with a therapeutically effective amount of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid; or aspirin. In another embodiment, the invention provides a product comprising a compound of Formula (I) and an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin for simultaneous, separate or sequential use in therapy.

Chemical Definitions

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a straight or branched divalent hydrocarbon chain consisting solely of carbon and hydrogen atoms, having from one to twelve carbon atoms, preferably one to 6 carbon atoms, and linking the rest of the molecule to a radical group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the chain.

"Halogen" or "halo" may be fluoro, chloro, bromo or iodo.

The term "alkenyl" refers to a monovalent hydrocarbon having at least one carbon-carbon double bond. The term "$C_2$-$C_6$alkenyl" refers to a monovalent hydrocarbon having two to six carbon atoms and comprising at least one carbon-carbon double bond.

The term "alkynyl" refers to a monovalent hydrocarbon having at least one carbon-carbon triple bond. The term "$C_2$-$C_6$-alkynyl" refers to a monovalent hydrocarbon having two to six carbon atoms and comprising at least one carbon-carbon triple bond.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6, more preferably about 1-4 carbons.

Alkyl, alkenyl, alkynyl, and alkoxy groups, containing the requisite number of carbon atoms, can be unbranched or branched. The requisite number of carbon may be represented as $C_{1-6}$, $C_{1-4}$, etc.

The term "aryl" refers to monocyclic or bicyclic aromatic hydrocarbon groups having 6-10 carbon atoms in the ring portion. Non-limiting examples include phenyl and naphthyl.

The term "aryl" also refers to a group in which a aryl ring is fused to one or more cycloalkyl or heterocyclyl rings, where the radical or point of attachment is on the aryl ring. Nonlimiting examples include 2,3-dihydro-1H-indene, 1,2,3,4-tetrahydronaphthyl and 3,4-dihydro-2H-benzo[b][1,4]oxazinyl.

The term "arylalkyl" refers to an aryl group which is linked to another moiety via an alkyl group which may be branched or unbranched. Examples of arylalkyl groups include benzyl, 2-phenyl-ethyl, 2-(naphth-2-yl)-butan-1-yl, and the like.

The term "aryloxy" refers to an aryl group which is linked to another moiety through an oxygen atom, such as phenoxy.

As used herein, the term "heterocyclyl" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include dihydrofuranyl, [1,3]dioxolane, 1, 4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

As used herein, the term "cycloalkyl" refers to saturated or partially unsaturated (but not aromatic) monocyclic, bicyclic or tricyclic hydrocarbon groups of 3-12 carbon atoms, preferably 3-9, or 3-7 carbon atoms, Exemplary monocyclic hydrocarbon groups include, but are not limited to, cyclopropyl, cyclobutyl, cyclopentyl, cyclopentenyl, cyclohexyl or cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, 6,6-dimethyl-bicyclo[3.1.1]heptyl, 2,6,6-trimethylbicyclo[3.1.1]heptyl, or bicyclo[2.2.2]octyl. Exemplary tricyclic hydrocarbon groups include adamantyl.

The term "heterocycloxy" refers to a heterocyclyl which is linked to another moiety through an oxygen atom, e.g. piperazin-2-yloxy.

As used herein, the term "heteroaryl" refers to a 5-14 membered monocyclic- or bicyclic- or polycyclic-aromatic ring system having 1 to 8 heteroatoms selected from N, O or S. Preferably, the heteroaryl is a 5-10 or 5-7 membered ring system. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. Examples of bicyclic heteroaryl groups include indolyl, benzofuranyl, quinolyl, isoquinolyl indazolyl, indolinyl, isoindolyl, indolizinyl, benzamidazolyl, and quinolinyl.

The term "heteroaryl" also refers to a group in which a heteroaromatic ring is fused to one or more cycloalkyl, or heterocyclyl rings, where the radical or point of attachment is on the heteroaromatic ring. Nonlimiting examples include 5,6,7,8-tetrahydroquinoline and 6,7-dihydro-5H-pyrrolo[3,2-d]pyrimidine.

A heteroaryl group may be mono-, bi-, tri-, or polycyclic, preferably mono-, bi-, or tricyclic, more preferably mono- or bicyclic.

The term "heteroarylalkyl" refers to an heteroaryl group which is linked to another moiety via an alkyl group which may be branched or unbranched. Examples of heteroarylalkyl groups include 2-(pyridin-3-yl)-ethyl, 3-(quinolin-7-yl)-butan-1-yl, and the like.

The term "heteroaryloxy" refers to a heteroaryl group which is linked to another moiety through an oxygen atom, such as pyridin-3-lyoxy.

"Heteroaryl" and "heterocyclyl" is also intended to include oxidized S or N, such as sulfinyl, sulfonyl and N-oxide of tertiary ring nitrogen.

Unless indicated explicitly otherwise, where combinations of groups are referred to herein as one moiety, e.g. arylalkyl, the last mentioned group contains the atom by which the moiety is attached to the rest of the molecule.

An "amino" group as used herein refers to —NH$_2$. The term "N-(alkyl)amino" refers to an amino group in which one hydrogen is replaced by an alkyl group. For example, N—(C$_{1-6}$alkyl)amino refers to an amino group in which one of the hydrogens has been replaced with an alkyl group having from 1 to 6 carbon atoms. The term "N,N-di-(alkyl)amino" refers to an amino group in which both hydrogens have been replaced by an alkyl group which may be the same or different. For example, N,N-di-(C$_{1-6}$alkyl)amino refers to an amino group in which both of the hydrogens have been replaced with an alkyl group which may be the same or different having from 1 to 6 carbon atoms.

A "carbamoyl" group as used herein refers to —C(O)NH$_2$. The term "N-(alkyl)-carbamoyl" refers to a carbamoyl group in which one hydrogen is replaced by an alkyl group. For example, N—(C$_{1-6}$alkyl)-carbamoyl refers to a carbamoyl group in which one of the hydrogens has been replaced with an alkyl group having from 1 to 6 carbon atoms. The term "N,N-di-(alkyl)-carbamoyl" refers to a carbamoyl group in which both hydrogens have been replaced by an alkyl group which may be the same or different. For example, N,N-di-(C$_{1-6}$alkyl)-carbamoyl refers to a carbamoyl group in which both of the hydrogens have been replaced with an alkyl group which may be the same or different having from 1 to 6 carbon atoms.

The term "alkanoyl" refers to a group having the formula —C(O)—R, wherein R is an alkyl group. For example, C1-6alkanoyl refers to an alkanoyl group which has from one to six carbon atoms, such as acetyl, isopropyl-carbonyl, and the like.

General

The term "comprising" encompasses "including" as well as "consisting", e.g. a composition "comprising" X may consist exclusively of X or may include something additional, e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

Whenever appropriate, terms used in the singular will also include the plural and vice versa.

Unless it is explicitly stated that a group is substituted or may optionally be substituted, it is to be understood that the group is unsubstituted.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

Synthesis

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned hereinbefore and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds of Formula (I), (I-i), (I-ii), (I-iii), (I-iv), (IA), (IIIb), (IIc), (IIId), (IIIe), (IIIf), (IIg), (IIh) and (IIi), can be prepared according to the Schemes provided infra.

Method of Preparation

The invention provides, in another aspect, a process for preparing a compound of Formula (I). The schemes, outlined below, show general routes for synthesizing compounds of Formula (I). In the reactions described in the schemes herein below, any reactive group present, such as hydroxyl, amino, carbonyl or imino groups may be protected during the reaction by conventional protecting groups such as trimethylsilyl, tert-butyldimethylsilyl, benzyl, acetal, ketal etc., which are cleaved again after the reaction.

Scheme 1:

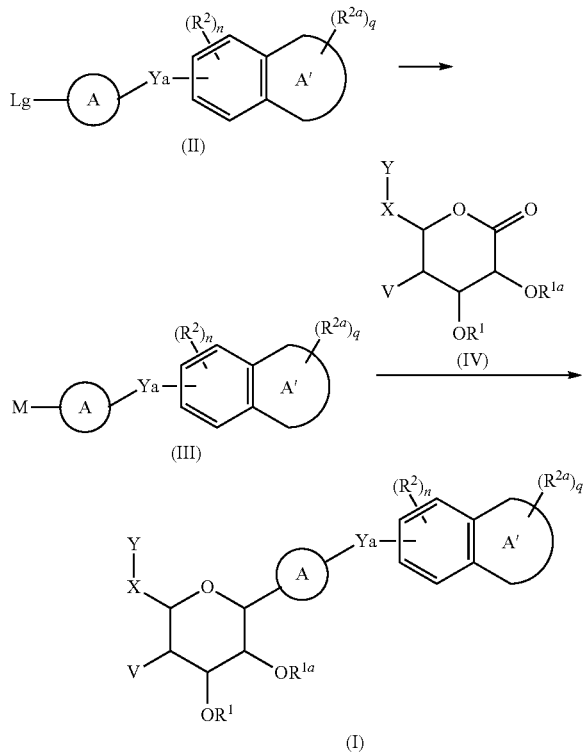

Compounds of formula (II), wherein Lg is a leaving group such as halogen and all other symbols are defined herein above, may be reacted with alkyl lithium or Mg to provide compounds of formula (III) wherein M is selected from Li or Mg-Halogen, and all other symbols are defined herein above. Compounds of formula (III) may be reacted with compounds of formula (IV) wherein all symbols are defined herein above. The resulting intermediate may be dehydroxylated/dealkoxylated using reagent such as triethylsilane BF$_3$-etherate to provide compounds of Formula (I) wherein all symbols are defined herein above.

Scheme 2:

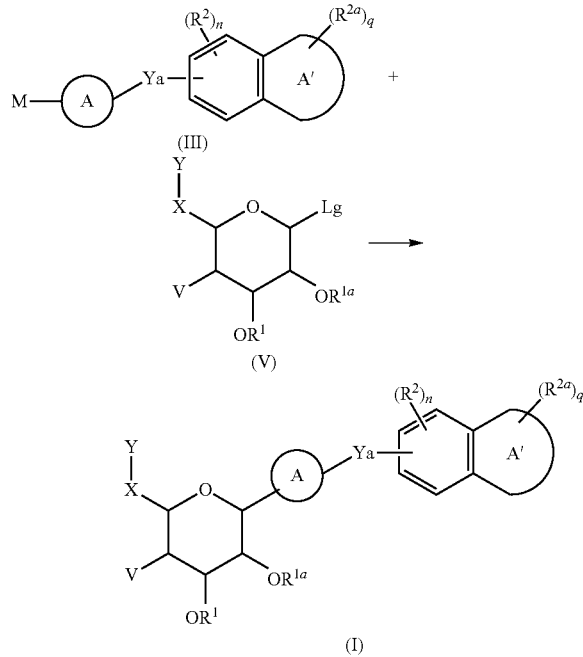

Compounds of formula (III), wherein M is selected from Li or Mg-Halogen and all other symbols are defined herein above, may be reacted with compounds of formula (V) wherein Lg is a leaving group such as halogen, mesylate, tosylate or trifluoromethanesulfonyl and all other symbols are defined herein above, to provide compounds of Formula (I) wherein all symbols are defined herein above.

Scheme 3:

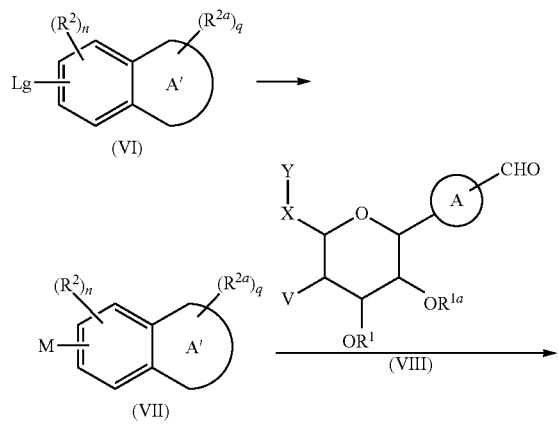

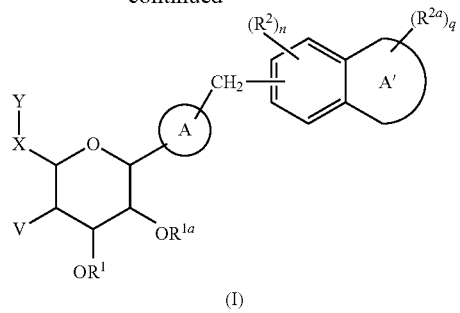

Compounds of formula (VI), wherein Lg is a leaving group such as halogen and all other symbols are defined herein above, may be reacted with alkyl lithium or Mg to provide compounds of formula (VII) wherein M is selected from Li or Mg-Halide and all other symbols are defined herein above. Compounds of formula (VII) may be reacted with compounds of formula (VIII) wherein all symbols are defined herein above. The resulting intermediate may be dehydroxylated using reagent such as triethylsilane BF$_3$-etherate or Pd—C in presence of hydrogen atmosphere to provide compounds of Formula (I) wherein all symbols are defined herein above.

Scheme 4:

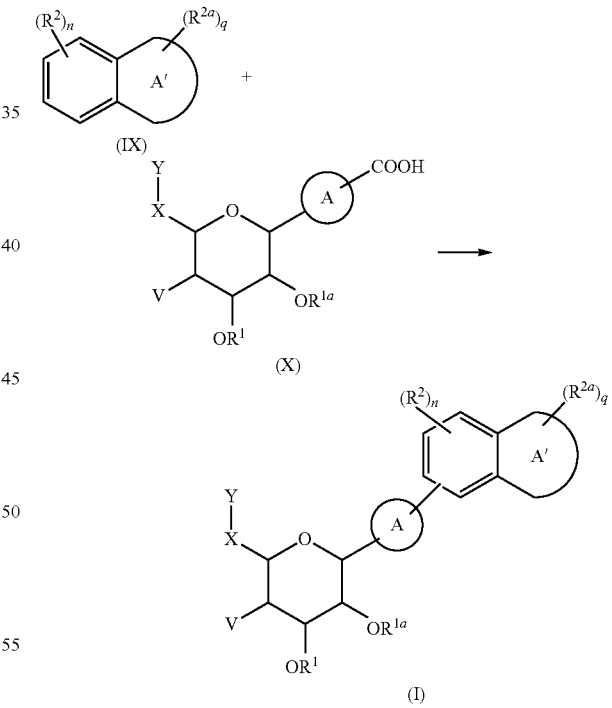

Compounds of formula (IX) wherein all symbols are defined herein above may be reacted with acid of formula (X) or its corresponding acid chloride wherein all symbols are defined herein above. The reaction may be carried out in the presence of a Lewis acid followed by treating the intermediate ketone with triethylsilane BF$_3$-etherate to provide compounds of Formula (I) wherein all symbols are defined herein above.

Scheme 5:

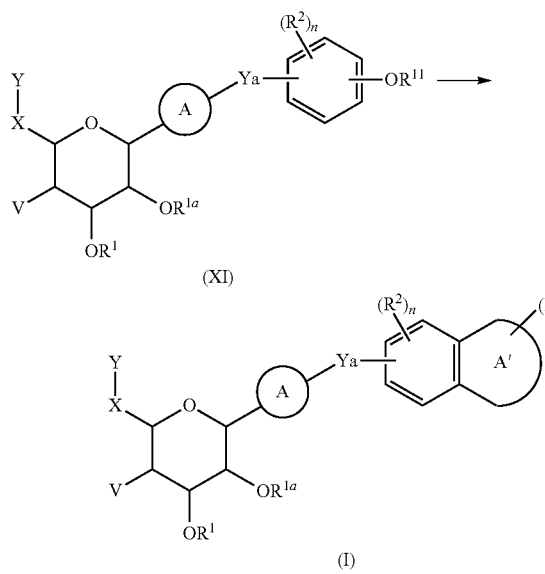

Compounds of formula (XI) wherein $R^{11}$ is selected from hydrogen, alkyl, acyl, trifluoromethanesulfonyl and all symbols are defined herein above may be cyclised using $OR^{11}$ to obtain compounds of Formula (I) wherein ring A' has at least one 'O' atom and all other symbols are defined herein above.

Compounds of Formula (I) may be prepared from other compounds of Formula (I) by methods well known to one skilled in the art.

Scheme 6:

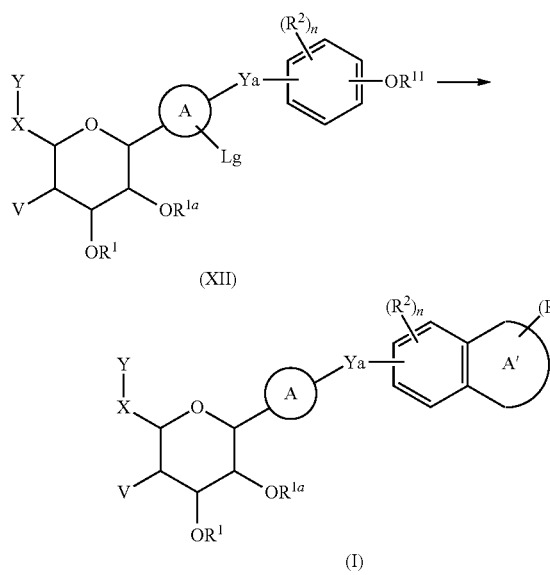

Compounds of formula (XII) wherein Lg is a leaving group such as halogen or triflate and all other symbols are defined herein above may be converted under Suzuki coupling conditions or Buchwald coupling conditions, to obtain compounds of Formula (I) wherein ring A has at least one substituent and all other symbols are defined herein above.

Ring A' may be formed either before or after the Suzuki coupling reaction from $OR^{11}$ as shown in Scheme 5.

Intermediate (II)

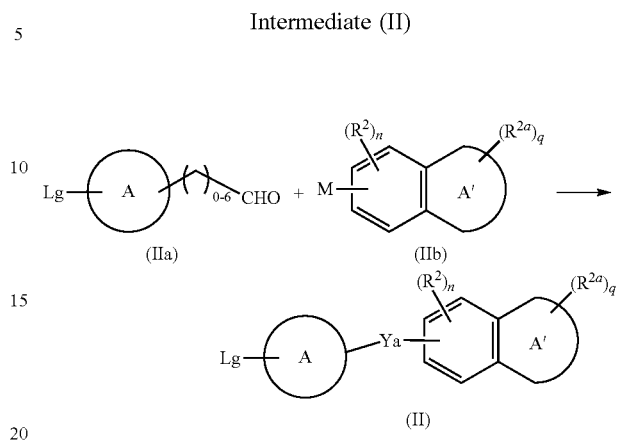

Compounds of formula (IIa), wherein Lg is a leaving group such as halogen and the remaining variables are as defined herein above, may be reacted with compounds of formula (IIb) wherein M is selected from lithium or magnesium halide and all other symbols are defined herein above. The resulting intermediate may be dehyroxylated/dealkoxylated using reagents such as triethylsilane $BF_3$-etherate or under hydrogenation conditions to provide compounds of formula (II) wherein all symbols are defined herein above.

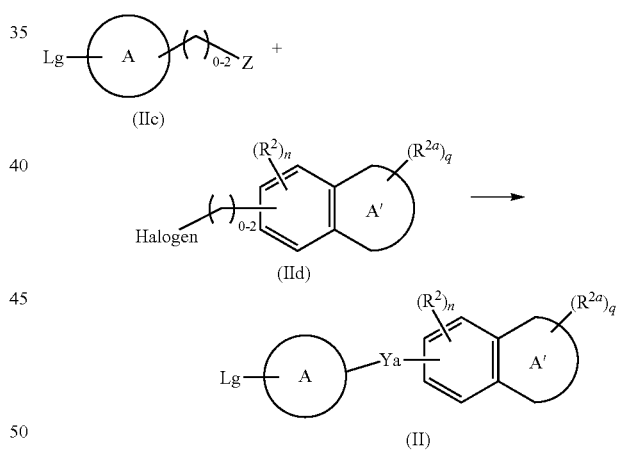

Compounds of formula (IIc), wherein Lg is a leaving group such as halogen, Z is selected from OH, $NH_2$ or SH, and the remaining variables are as defined herein above, may be reacted with compounds of formula (IIId) wherein all symbols are defined herein above to provide intermediate (II) wherein all symbols are defined herein above. The reaction may be carried out in the presence of a base.

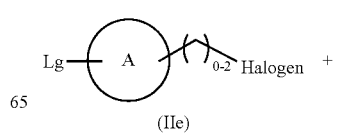

-continued

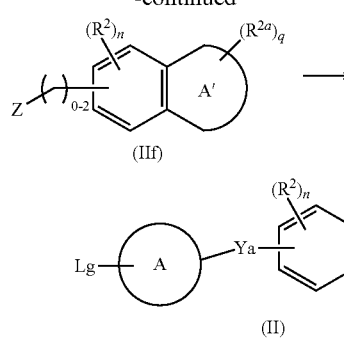

Compounds of formula (IIIe) wherein Lg is a leaving group such as halogen, and the remaining symbols are as defined herein above, may be reacted with compounds of formula (IIf), wherein Z is selected from OH, $NH_2$ or SH and all other symbols are defined herein above to provide intermediate (II) wherein the symbols are defined herein above. The reaction may be carried out in the presence of a base.

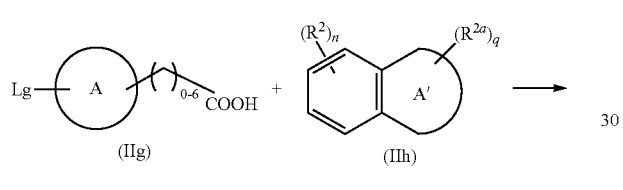

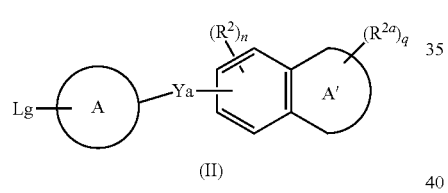

Carboxylic acid of formula (IIg) or corresponding acid halide, wherein Lg is a leaving group such as halogen and ring A is as defined herein above, may be reacted with compounds of formula (IIh), wherein all symbols are defined herein above, to provide intermediate (II) wherein the symbols are defined herein above. The reaction may be carried out in the presence of a Lewis acid followed by reducing the intermediate ketone using reagent such as triethylsilane $BF_3$-etherate or under hydrogenation conditions.

Intermediate (VIII) and (X)

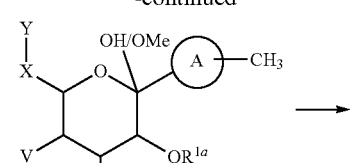

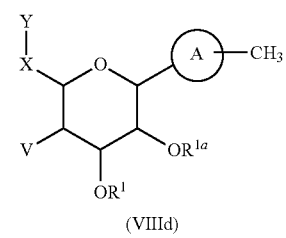

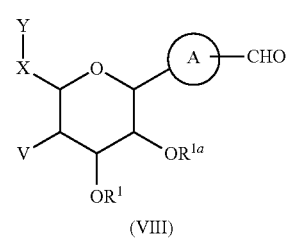

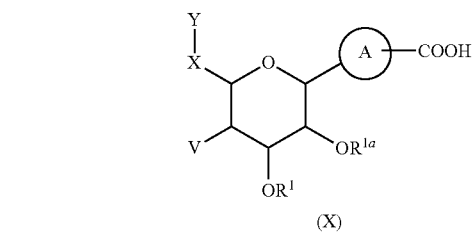

Compounds of formula (VIIIa) wherein the symbols are defined herein above may be reacted with compounds of formula (VIIIb) wherein M is selected from lithium or magnesium halide, to provide intermediate of formula (VIIIc) which may be dehydroxylated/dealkoxylated using reagent such as triethylsilane $BF_3$-etherate or Pd—C in presence of hydrogen atmosphere to provide compounds of formula (VIIId). Compounds of formula (VIIId) may be oxidized to provide aldehyde of formula (VIII) which may be further oxidized to provide acid of formula (X). The oxidations may be carried out with processes known in the literature.

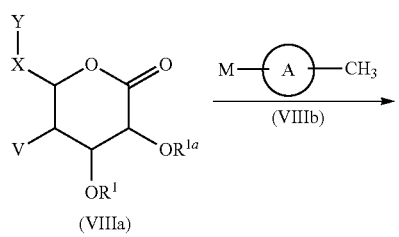

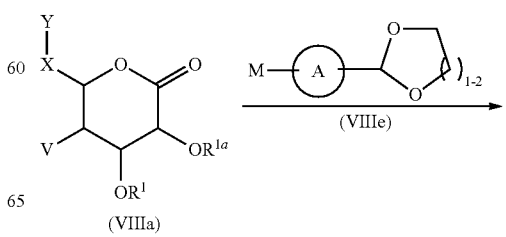

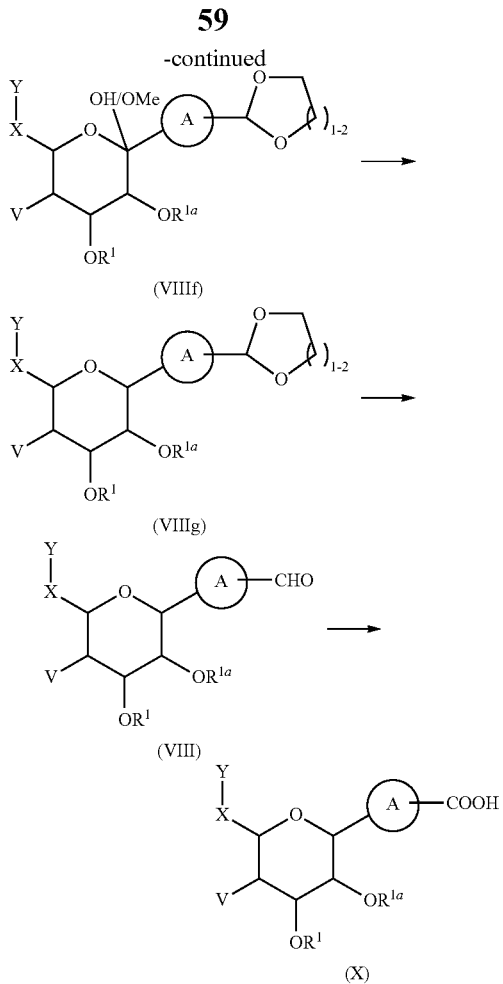

Compounds of formula (VIIIa), wherein all symbols are defined herein above, may be reacted with ketal of formula (VIIIe) wherein M is selected from lithium or magnesium halide, to provide compound of formula (VIIf) which may be dehydroxylated/dealkoxylated using reagent such as triethylsilane BF$_3$-etherate or Pd—C in presence of hydrogen atmosphere to provide compounds of formula (VIIIg). Compounds of formula (VIIIg) may be deprotected to provide aldehyde of formula (VIII) which may be oxidized to provide acid of formula (X). The oxidation may be carried out with processes known in the literature.

It will be understood that the processes detailed above and elsewhere herein are solely for the purpose of illustrating the invention and should not be construed as limiting. A process utilizing similar or analogous reagents and/or conditions known to one skilled in the art may also be used to obtain a compound of the invention.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

The following Examples are intended to illustrate the invention and are not to be construed as being limitations thereon. If not mentioned otherwise, all evaporations are performed under reduced pressure. The structure of final products, intermediates and starting materials have been confirmed by standard analytical methods, e.g., microanalysis, melting point (m.p.) and spectroscopic characteristics, e.g. MS and NMR. Abbreviations used are those conventional in the art.

INTERMEDIATES

Intermediate 1

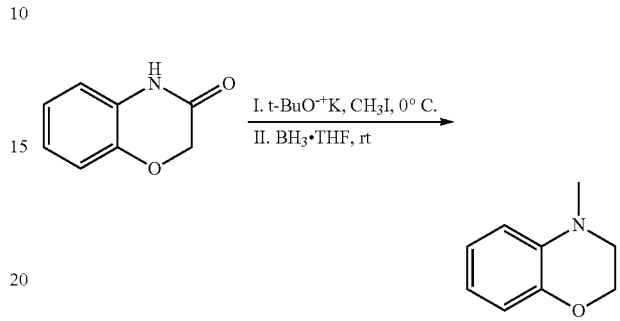

Step I.

To a stirred solution of 4H-Benzo[1,4]oxazin-3-one (2.5 g, 16.77 mmol) in DMF (10 mL) was added potassium tert-butoxide (2.81 g, 25.16 mmol) at 0° C. After stirring for 5 min, methyl iodide (3.54 g, 25.16 mmol) was added and the reaction mixture was stirred for another 3 h. The reaction was quenched by addition of water and extracted with ethyl acetate (30×2 mL). The organic layer was washed with water (20 mL), and evaporated to get a crude product 2.2 g.

Step II.

To a stirred solution of 4-methyl-4H-benzo[1,4]oxazin-3-one (2.18 g, 13.37 mmol) in THF (5 mL) was added borane-tetrahydrofuran complex (4.02 g, 46.8 mmol) at room temperature. After stirring the solution for 2 h, the reaction mixture was refluxed for 4 h. After complete conversion, reaction mixture was quenched by adding MeOH (10 mL) and evaporated the solvents. The residue obtained was extracted with ethyl acetate (30×2 mL) and the organic layer was washed with water (20 mL), brine (20 mL) and evaporation of solvent gave 4-methyl-3,4-dihydro-2H-benzo[1,4]oxazine 2.0 g.

MS (ES) m/z 150.2 (M+1).

Intermediate 2

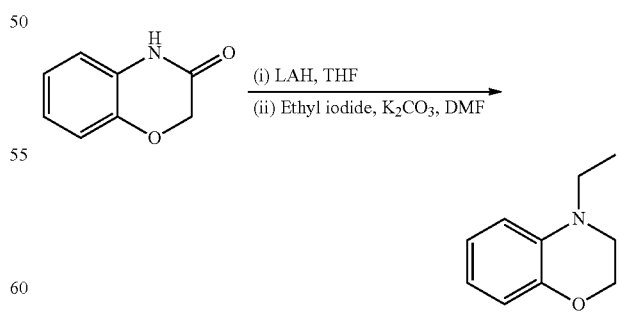

Step I.

To a stirred suspension LiAlH$_4$ (7.6 g, 201 mmol) in THF at 0° C. was added 4H-benzo[1,4]oxazin-3-one (15 g, 100 mmol) in 30 mL of THF and stirred for 4 h at room temperature. After cooling, excess of LiAlH$_4$ was quenched by the addition of EtOAc followed by aq. NH₄Cl solution. The residue was filtered through a celite bed and filtrate was concentrated. The residue was diluted with water and extracted with ethylacetate (200 mL×2), combined organic layer was washed with water (100 mL) and brine (100 mL). Evaporation of the solvent resulted in 3,4-dihydro-2H-benzo[1,4]oxazine (12 g) which was used as such for the next step.

MS (ES) m/z 136 (M+1)

Step II:

To a stirred solution of 3,4-dihydro-2H-benzo[1,4]oxazine (4.0 g, 29.6 mmol) in DMF (20 mL) was added potassium carbonate (10.22 g, 74.0 mmol). After stirring for five min. Iodo-ethane (3.5 mL, 44.4 mmol) was added and heated to 60° C. for overnight. Reaction mixture was cooled to room temperature, quenched by the addition of water (20 mL), extracted with ethyl acetate (3×25 mL). The organic layer was washed with water (30 mL), brine (30 mL), dried over sodium sulfate, concentrated and purified by silica gel column chromatography to furnish 4-ethyl-3,4-dihydro-2H-benzo[1,4]oxazine (2.7 g).

¹H NMR (400 MHz, CD₃OD): δ 1.10 (t, J=6.8 Hz, 3H), 3.26-3.33 (m, 4H), 4.16 (t, J=4.4 Hz, 2H), 4.40 (s, 2H), 6.52-6.58 (m, 1H), 6.60-6.80 (m, 3H).

MS (ES) m/z 163.2 (M+1)

Intermediate 3

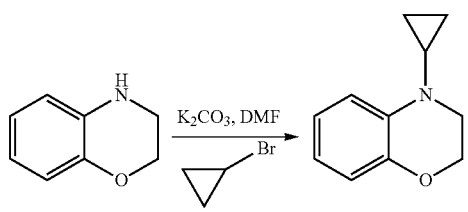

Step I.

To a stirred solution of 3,4-dihydro-2H-benzo[1,4]oxazine (5 g, 37.0 mmol) in DMF (20 mL) was added potassium tert-butoxide (6.22 g, 55.55 mmol) at 0° C. After stirring for 5 min, bromo-cyclopropane (4.44 mL, 55.55 mmol) was added and the reaction mixture was stirred for another 4 h at room temperature. The reaction was quenched by addition of water and extracted with ethyl acetate (50×2 mL). The organic layer was washed with water (20 mL), concentrated and purified by silica gel column chromatography to furnish 4-Cyclopropyl-3,4-dihydro-2H-benzo[1,4]oxazine (4.42 g).

MS (ES) m/z 176 (M+1).

Intermediate 4

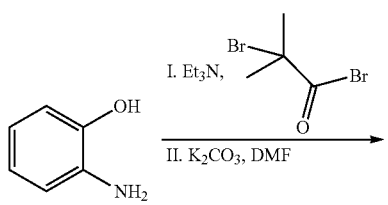

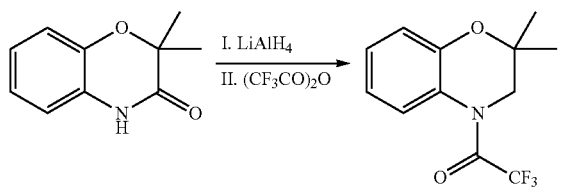

Step I.

To a stirred solution of 2-aminophenol (10 g, 9.2 mmol) in DCM (92 mL) at 0° C. was added 2-bromoisobutyryl bromide (11.4 mL, 9.17 mmol) followed by triethyl amine (12.7 mL, 9.2 mmol) and stirred the reaction mixture at 0° C. for 4 h. Reaction mixture was diluted with DCM 100 mL and then washed with water 100 mL dried over sodium sulfate, concentrated on rotavap to give 2-Bromo-N-(2-hydroxy-phenyl)-2-meth yl-propionamide (21.8 g) brown solid which was used for next reaction without purification Step II.

To a stirred solution of 2-Bromo-N-(2-hydroxy-phenyl)-2-methyl-propionamide (21.8 g, 84.4 mmol) in DMF (85 mL) at 25° C. was added potassium carbonate (23.32 g, 168.99 mmol) and stirred the reaction mixture at 80° C. for 4 h. After TLC reaction mixture was filtered through celite and diluted with ethyl acetate 500 mL and then washed with water (100 mL×3), brine (100 mL), dried over anhydrous sodium sulfate, concentrated to give 2,2-dimethyl-4H-benzo[1,4]oxazin-3-one (12.64 g) as brown solid which was purified by column chromatography to furnish 8.5 g pure compound.

MS (EI) m/z 178.2 (M+1)

Step III.

To a stirred solution of LAH (3.01 g, 79.10 mmol) in THF (80 mL) at 0° C. was added 2,2-dimethyl-4H-benzo[1,4]oxazin-3-one (7.00 g, 39.5 mmol) in portions and stirred the reaction mixture at 25° C. for 1 h and then 50° C. for 3 h. Reaction mixture was quenched by the addition cold saturated sodium sulfate solution and it was filtered through celite and extracted with DCM (100 mL×2), washed with brine (50 mL), dried over sodium sulfate, concentrated to give 2,2-dimethyl-3,4-dihydro-2H-benzo[1,4]oxazine (6.09 g), which was used as such for the next reaction without purification MS (EI) m/z 164.2 (M+1)

Step IV.

To a stirred solution of 2,2-dimethyl-3,4-dihydro-2H-benzo[1,4]oxazine (6 g, 36.8 mmol) in DCM (75 mL) at 0° C. was added trifluoroacetic anhydride (6.2 mL, 44.2 mmol) followed by triethyl amine (6.2 mL, 44.2 mmol) and stirred the reaction mixture at 0° C. for 2 h. Reaction mixture was diluted with DCM (100 mL) and then washed with water (100 mL×2), brine (100 mL), dried over anhydrous sodium sulfate, concentrated on to give 1-(2,2-dimethyl-2,3-dihydro-benzo[1,4]oxazin-4-yl)-2,2,2-trifluoro-ethanone (9.46 g) as brown solid which was purified by column chromatography to furnish 8.7 g pure product.

MS (EI) m/z 260.2 (M+1)

¹H NMR (400 MHz, CDCl₃): δ 1.38 (s, 6H), 3.65 (s, 2H), 6.86-6.96 (m, 2H), 7.12-7.16 (m, 1H), 7.97 (d, 1H).

Intermediate 5

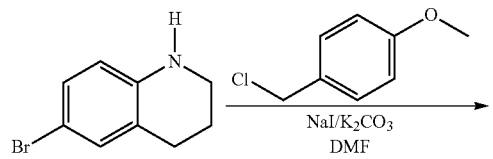

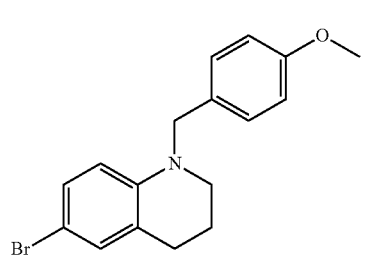

To a stirred solution of 6-bromo-1,2,3,4-tetrahydro-quinoline (3.00 g, 12.1 mmol) in dimethylformamide (25 mL) was added potassium carbonate (3.3 g, 24.1 mmol), sodium iodide (0.905 g, 6.0 mmol) and 4-methoxybenzyl chloride (2.5 mL, 18.1 mmol) and heated at 50° C. After 18 h, reaction mixture was cooled to room temperature and quenched by the addition of water and extracted with ethyl acetate (2×20 mL). The organic layer was washed with water (2×20 mL), brine (20 mL), dried over sodium sulfate, concentrated and purified by the silica gel column chromatography to furnish 6-bromo-1-(4-methoxy-benzyl)-1,2,3,4-tetrahydro-quinoline (2.5 g).

$^1$H NMR (400 MHz, CDCl$_3$): δ 1.96-2.02 (m, 2H), 2.78 (t, J=6.0 Hz, 2H), 3.46 (t, J=5.2 Hz, 2H), 3.80 (s, 3H), 4.40 (s, 2H), 6.38 (d, J=8.4 Hz, 1H), 6.86 (d, J=8.4 Hz, 2H), 7.04 (d, J=8.8 Hz, 1H), 7.07 (s, 1H), 7.15 (d, J=8.4 Hz, 2H).

MS (ES) m/z 332.1, 334.1 (M+1).

EXAMPLES

Example 1: (2S,3R,4R,5S,6R)-2-[4-Chloro-3-(4-methyl-3,4-dihydro-2H benzo[1,4]oxazin-7-ylmethyl)-phenyl]-6-hydroxymethyl-tetrahydro-pyran-3,4,5-triol

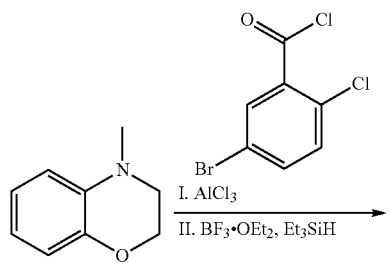

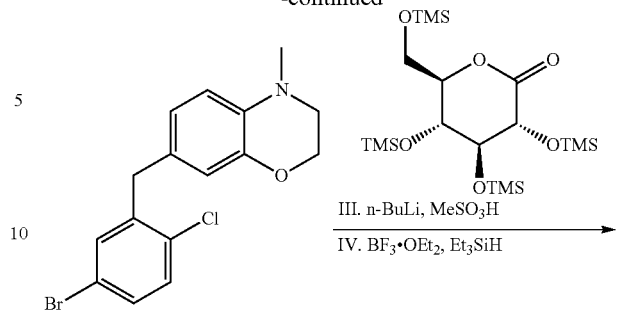

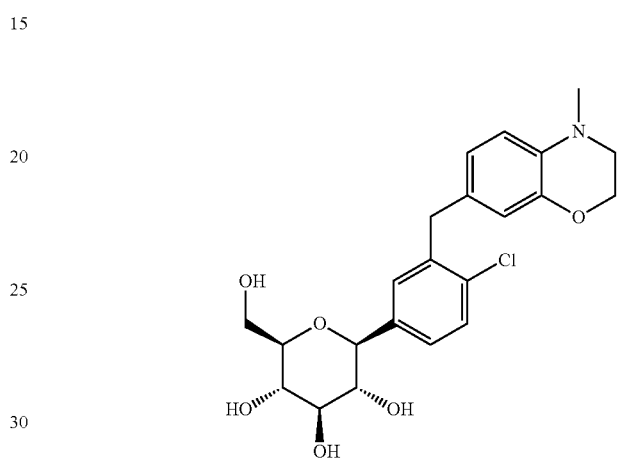

Step I.

To a stirred solution of 4-methyl-3,4-dihydro-2H-benzo[1,4]oxazine (2.00 g, 13.4 mmol) in dichloromethane (30 mL) was added 5-bromo-2-chlorobenzoyl chloride (4.07 g, 16.1 mmol) in dichloromethane (20 mL) at 0° C. followed by addition of AlCl$_3$ (2.14 g, 16.1 mmol). After 2 h, the reaction mixture was brought to room temperature and stirred overnight. The reaction was quenched by pouring over crushed ice and extracted with dichloromethane (30×2 mL). The organic layer was washed with aq. NaHCO$_3$ (20 mL), H$_2$O (20 mL) and to obtain a crude product 3.0 g.

Step II.

To the crude product (0.9 g, 2.45 mmol) in 1:2 mixture of 1,2-dichloroethane/MeCN (12 mL) was added Et$_3$SiH (0.83 mL, 5.16 mmol) and BF3.OEt2 (0.37 mL, 3.19 mmol) simultaneously at 20° C. After stirring overnight, the reaction mixture was heated at 50° C. for 2 h. The reaction was quenched by the addition of aq. NaHCO$_3$ (5 mL). The volatiles were evaporated under reduced pressure; the resulting mixture was extracted with dichloromethane (2×20 mL), washed with brine (5 mL), dried over sodium sulfate, concentrated and purified by silica gel column chromatography to furnish 7-(5-bromo-2-chloro-benzyl)-4-methyl-3,4-dihydro-2H-benzo[1,4]oxazine (0.375 g).

$^1$H NMR (400 MHz, CDCl$_3$): δ 2.89 (s, 3H), 3.27 (s, 2H), 3.93 (s, 2H), 4.32 (t, J=3.6 Hz, 2H), 6.61 (s, 1H), 6.64-6.74 (m, 2H) 7.19-7.32 (m, 3H).

MS (ES) m/z 351.8 (M+1).

Step III:

To a stirred solution of 7-(5-bromo-2-chloro-benzyl)-4-methyl-3,4-dihydro-2H-benzo[1,4]oxazine (0.37 g, 1.06 mmol) in THF–toluene (5 mL of 1:2 mixture) was added 1.6 M solution of n–BuLi in hexanes (0.68 mL, 1.06 mmol) at –78° C. The reaction mixture was stirred for 1 h and then transferred to a stirred solution of 2,3,4,6-tetrakis-O-(trimethylsilyl)-D-glucopyranone (0.49 g, 1.06 mmol) in toluene (5 mL) at –78° C. After stirring for 4 h, 0.6 N methanesulfonic acid in methanol (5 mL) was added and stirred the reaction mixture for 12 h at room temperature. Reaction was quenched by the addition of aq. NaHCO$_3$ solution (5 mL) and extracted with dichloromethane (3×10 mL), dried over sodium sulfate, concentrated and purified by silica gel column chromatography to furnish (2S,3R,4S,5S,6R)-2-[4-chloro-3-(4-methyl-3,4-dihydro-2H-benzo[1,4]oxazin-7-ylmethyl)-phenyl]-6-hydroxymethyl-2-methoxy-tetrahydro-pyran-3,4,5-triol (0.178 g).

$^1$H NMR (400 MHz, CD$_3$OD): δ 2.82 (s, 3H), 3.08 (s, 3H), 3.10 (d, J=10.0 Hz, 1H), 3.18 (t, J=4.0 Hz, 2H), 3.42 (t, J=9.6 Hz, 1H), 3.55-3.62 (m, 1H), 3.75 (t, J=9.2 Hz, 1H), 3.82 (dd, J=12.0, 5.6 Hz, 1H), 3.90 (d, J=14.8 Hz, 1H), 3.94 (d, J=10.4 Hz, 1H), 4.02 (d, J=15.2 Hz, 1H), 4.23 (t, J=4.4 Hz, 2H), 6.51 (s, 1H), 6.60-6.68 (m, 2H), 7.35 (d, J=8.4 Hz, 1H), 7.45 (d, J=8.4 Hz, 1H), 7.53 (s, 1H).

MS (ES) m/z 466.3 (M+1).

Step IV:

To a stirred solution of (2S,3R,4S,5S,6R)-2-[4-chloro-3-(4-methyl-3,4-dihydro-2H-benzo[1,4]oxazin-7-ylmethyl)-phenyl]-6-hydroxymethyl-2-methoxy-tetrahydro-pyran-3,4,5-triol (0.17 g, 0.37 mmol) in acetonitrile-dichloromethane mixture (1:1 mixture, 6 mL) was added boron trifluoride diethyletharate complex (0.09 mL, 0.75 mmol), and triethylsilane (0.24 mL, 1.50 mmol) at –10° C. After stirring for 4 h at the same temperature, the reaction was quenched with aq. NaHCO$_3$ (4 mL). The volatiles were evaporated under reduced pressure; the resulting mixture was extracted with dichloromethane (2×20 mL), washed with brine (3 mL), dried over sodium sulfate, concentrated and purified by preparative HPLC to furnish (2S,3R,4R,5S,6R)-2-[4-chloro-3-(4-methyl-3,4-dihydro-Hbenzo[1,4]oxazin-7-ylmethyl)-phenyl]-6-hydroxymethyl-tetrahydro-pyran-3,4,5-triol (40 mg).

$^1$H NMR (400 MHz, CD$_3$OD): δ 2.80 (s, 3H), 3.15 (t, J=4.4 Hz, 2H), 3.25-3.34 (m, 1H), 3.35-3.48 (m, 3H), 3.68 (dd, J=12.0, 5.6 Hz, 1H), 3.86 (d, J=8.4 Hz, 1H), 3.92 (Abq, J=15.2 Hz, 2H), 4.07 (d, J=9.6 Hz, 1H), 4.21 (t, J=4.4 Hz, 2H), 6.50 (d, J=0.8 Hz, 1H), 6.66 (d, J=8.4 Hz, 1H), 6.64 (dd, J=8.4, 1.2 Hz, 1H), 7.24 (dd, J=8.0, 1.6 Hz, 1H), 7.29 (s, 1H), 7.33 (d, J=8.0, 1H).

MS (ES) m/z 436.0 (M+1).

Following examples were prepared by using the procedures described for example 1.

| Example No. | Structure/IUPAC name | Spectral data |
|---|---|---|
| 2 | 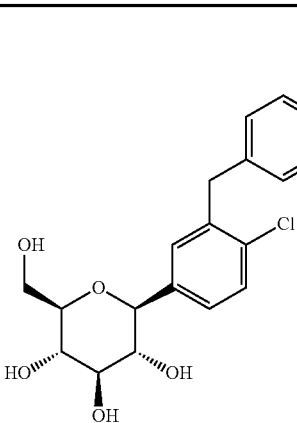<br>(2S,3R,4R,5S,6R)-2-[4-Chloro-3-(4-ethyl-3,4-dihydro-2H-benzo[1,4]oxazin-7-ylmethyl)-phenyl]-6-hydroxymethyl-tetrahydro-pyran-3,4,5-triol | $^1$H NMR (400 MHz, CD$_3$OD): δ 1.08 (t, J = 6.8 Hz, 3H), 3.15-3.48 (m, 8H), 3.66 (d, J = 11.2 Hz, 1H), 3.85 (d, J = 12.0 Hz, 1H), 3.90 (Abq, 15.2 Hz, 2H), 4.06 (d, J = 9.2 Hz, 1H), 4.14 (s, 2H), 6.49 (s, 1H), 6.60 (s, 2H), 7.23 (d, J = 8.0 Hz, 1H), 7.28 (s, 1H), 7.31 (d, J = 8.0 Hz, 1H), . MS (ES) m/z 450.3 (M + 1). |

| Example No. | Structure/IUPAC name | Spectral data |
|---|---|---|
| 3 | 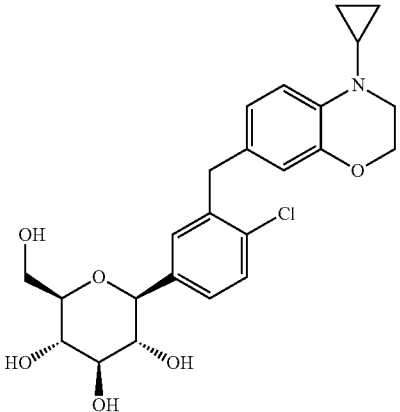 [SMILES: OC[C@H]1O[C@@H](c2ccc(Cl)c(Cc3ccc4c(c3)OCCN4C3CC3)c2)[C@H](O)[C@@H](O)[C@@H]1O]<br>(2S,3R,4R,5S,6R)-2-[4-Chloro-3-(4-cyclopropyl-3,4-dihydro-2Hbenzo[1,4]oxazin-7ylmethyl)-phenyl]-6-hydroxymethyltetrahydropyran3,4,5-triol | $^1$H NMR (400 MHz, CD$_3$OD): δ 0.54 (s, 2H), 0.75 (d, J = 2.0 Hz, 2H), 2.12 (m, 1H), 3.15-3.50 (m, 6H), 3.66 (dd, J = 11.6, 4.0 Hz, 1H), 3.85 (d, J = 10.8 Hz, 1H), 3.91 (Abq, 15.2 Hz, 2H), 4.05 (d, J = 9.2 Hz, 1H), 4.15 (s, 2H), 6.48 (s, 1H), 6.61 (d, J = 8.0 Hz, 1H), 7.05 (d, J = 8.0 Hz, 1H), 7.23 (d, J = 8.0 Hz, 1H), 7.23 (s, 1H), 7.31 (d, J = 8.4 Hz, 1H), . MS (ES) m/z 462.3 (M + 1). |

Example 4: (2S,3R,4R,5S,6R)-2-[3-(4-Benzyl-3,4-dihydro-2H-benzo[1,4]oxazin-6-ylmethyl)-4-chloro-phenyl]-6-hydroxymethyl-tetrahydro-pyran-3,4,5-triol

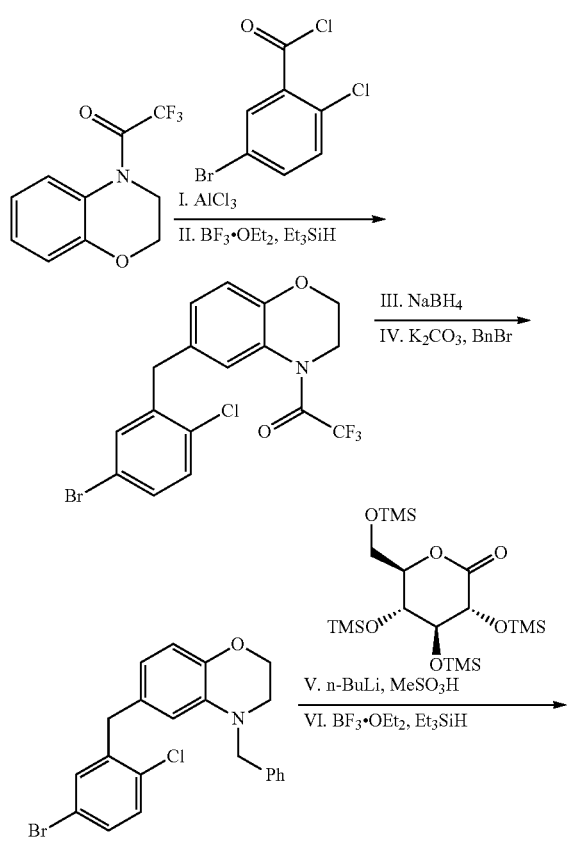

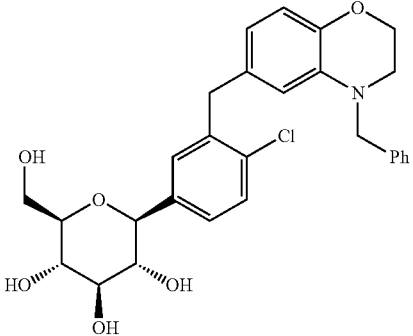

Step I.

To a stirred solution of 1-(2,3-dihydro-benzo[1,4]oxazin-4-yl)-2,2,2-trifluoro-ethanone (6.5 g, 28.1 mmol) in dichloromethane (45 mL) was added 5-bromo-2-chlorobenzoyl chloride (8.54 g, 33.7 mmol) in dichloromethane (35 mL) and AlCl$_3$ (5.61 g, 42.2 mmol) at 0° C. After 2 h, the reaction mixture was brought to room temperature and stirred overnight. The reaction was quenched by pouring over crushed ice and extracted with dichloromethane (2×50 mL). The organic layer was washed with aq. NaHCO$_3$ (30 mL), H$_2$O (20 mL), and the solvent evaporated to get the crude product which was purified by silica gel column chromatography to give 1-[6-(5-bromo-2-chloro-benzoyl)-2,3-dihydro-benzo[1,4]oxazin-4-yl]-2,2,2-trifluoro-ethanone (10.0 g).

$^1$H NMR (400 MHz, CDCl$_3$): 4.03 (t, J=4.0 Hz, 2H), 4.48 (t, J=4.2 Hz, 2H), 7.04 (d, J=8.4 Hz, 1H), 7.34 (d, J=8.4 Hz, 1H), 7.50 (d, J=2.0 Hz, 1H), 7.55 (dd, J=8.4, 2.0 Hz, 1H), 7.68 (d, J=8.4 Hz, 1H) 8.42 (broad s, 1H).

MS (ES) m/z 450 (M+2)

Step II.

To a stirred solution of 1-[6-(5-bromo-2-chloro-benzoyl)-2,3-dihydro-benzo[1,4]oxazin-4-yl]-2,2,2-trifluoro-ethanone (1.0 g, 2.23 mmol) in 1:2 of 1,2-dichloroethane/MeCN (12 mL) was added Et$_3$SiH (0.755 mL, 4.68 mmol) and BF$_3$.OEt$_2$ (0.34 mL, 2.90 mmol) simultaneously at 20° C.

The reaction mixture was heated at 50° C. for 4 h and quenched by the addition of aq. NaHCO₃ (10 mL). The volatiles were evaporated under reduced pressure; the resulting mixture was extracted with dichloromethane (2×20 mL), washed with brine (5 mL), dried over sodium sulfate, concentrated and was purified by silica gel column chromatography to furnish 1-[6-(5-bromo-2-chloro-benzyl)-2,3-dihydro-benzo[1,4]oxazin-4-yl]-2,2,2-trifluoro-ethanone (0.60 g).

¹H NMR (400 MHz, DMSO): δ 3.96 (t, J=4.0 Hz, 2H), 3.99 (s, 2H), 4.37 (t, J=4.4 Hz, 2H), 6.69 (d, J=8.4 Hz, 1H), 7.03 (d, J=7.6 Hz, 1H), 7.40 (d, J=8.4 Hz, 1H), 7.46 (dd, J=8.4, 2.0 Hz, 1H), 7.53 (d, J=2.4 Hz, 1H), 7.82 (broad s, 1H).

Step III:

To a stirred solution of 1-[6-(5-bromo-2-chloro-benzyl)-2,3-dihydro-benzo[1,4]oxazin-4-yl]-2,2,2-trifluoro-ethanone (8.6 g, 19.8 mmol) in ethanol (40 mL) was added NaBH₄ portion wise and the reaction mixture was stirred overnight. The excess of NaBH₄ was quenched by adding aq. HCl. Ethanol was evaporated and the residue was partitioned between dichloromethane and water. Organic layer was washed with brine, water, dried over sodium sulfate followed by evaporation of solvent furnished 6-(5-bromo-2-chloro-benzyl)-3,4-dihydro-2H-benzo[1,4]oxazine (6.1 g).

Step IV:

To a stirred solution of 6-(5-bromo-2-chloro-benzyl)-3,4-dihydro-2H-benzo[1,4]oxazine (8.0 g, 23.66 mmol) in DMF (35 mL) was added potassium carbonate (6.53 g, 36.0 mmol), benzyl bromide (4.33 mL, 35.50 mmol) and heated to 50° C. for 8 h. Reaction mixture was cooled to room temperature, quenched by the addition of water (50 mL), extracted with ethyl acetate (3×20 mL). The organic layer was washed with water (50 mL), brine (50 mL), dried over sodium sulfate, concentrated and purified by silica gel column chromatoghraphy to furnish 4-benzyl-6-(5-bromo-2-chloro-benzyl)-3,4-dihydro-2H-benzo[1,4]oxazine (7.0 g).

¹H NMR (400 MHz, CD₃OD): δ 3.40 (t, J=4.4 Hz, 2H), 3.85 (s, 2H), 4.24 (t, J=4.4 Hz, 2H), 4.40 (s, 2H), 6.40 (dd, J=8.0, 2.0 Hz, 1H), 6.45 (d, J=2.0 Hz, 1H), 6.66 (d, J=8.0, Hz, 1H), 7.20-7.36 (m, 8H).

MS (ES) m/z 429.9 (M+2).

Step V:

To a stirred solution of 4-benzyl-6-(5-bromo-2-chloro-benzyl)-3,4-dihydro-2H-benzo[1,4]oxazine (7.0 g, 16.3 mmol) in THF-toluene (40 mL of 1:2 mixture) was added 1.6 M solution of n-BuLi in hexanes (10.46 mL, 16.35 mmol) at −78° C. The reaction mixture was stirred for 1 h and then transferred to a stirred solution of 2,3,4,6-tetrakis-O-(trimethylsilyl)-D-glucopyranone (7.62 g, 16.35 mmol) in toluene (25 mL) at −78° C. After stirring for 4 h., 0.6 N methanesulfonic acid in methanol (50 mL) was added and stirred for 12 h at room temperature. Reaction was quenched by the addition of aq. saturated sodium bicarbonate solution (25 mL) and extracted with dichloromethane (3×25 mL), dried over sodium sulfate, concentrated and purified by silica gel column chromatography to furnish (2S,3R,4S,5S,6R)-2-[3-(4-benzyl-3,4-dihydro-2H-benzo[1,4]oxazin-6-ylmethyl)-4-chloro-phenyl]-6-hydroxymethyl-2-methoxy-tetrahydro-pyran-3,4,5-triol (5.0 g).

Step VI:

To a stirred solution of (2S,3R,4S,5S,6R)-2-[3-(4-benzyl-3,4-dihydro-2H-benzo[1,4]oxazin-6-ylmethyl)-4-chloro-phenyl]-6-hydroxymethyl-2-methoxy-tetrahydro-pyran-3,4,5-triol (5.0 g, 9.24 mmol) in acetonitrile-dichloromethane mixture (1:1 mixture, 40 mL) was added boron trifluoride diethyletharate complex (2.34 mL, 18.48 mmol), and triethylsilane (5.95 mL, 36.9 mmol) at −10° C. After stirring for 4 h at the same temperature, the reaction was quenched with aq. saturated sodium bicarbonate solution (15 mL). The volatiles were evaporated under reduced pressure; the resulting mixture was extracted with dichloromethane (2×30 mL). The organic layer was washed with brine (10 mL), dried over sodium sulfate, concentrated and purified by preparative HPLC to furnish (2S,3R,4R,5S,6R)-2-[3-(4-benzyl-3,4-dihydro-2H-benzo[1,4]oxazin-6-ylmethyl)-4-chloro-phenyl]-6-hydroxymethyl-tetrahydro-pyran-3,4,5-triol (3.5 g).

¹H NMR (400 MHz, CD₃OD): δ 3.20-3.50 (m, 6H), 3.68 (dd, J=12.0, 4.4 Hz, 1H), 3.75-3.95 (m, 3H), 4.03 (d, J=9.2 Hz, 1H), 4.16 (t, J=3.6 Hz, 2H), 4.35 (s, 2H), 6.37 (d, J=8.0 Hz, 1H), 6.54 (s, 1H), 6.57 (d, J=0.8 Hz, 1H), 7.15-7.62 (m, 8H).

MS (ES) m/z 511.8 (M+1).

Following examples were prepared by using the procedures described for example 4.

| Example No. | Structure/IUPAC name | Spectral data |
| --- | --- | --- |
| 5 | 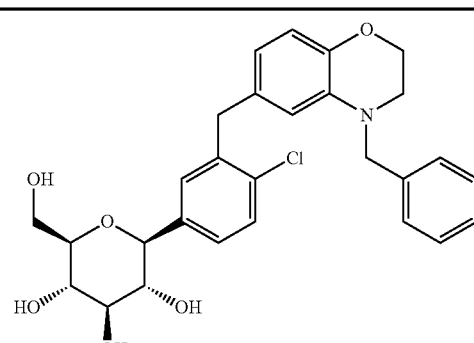<br>(2S,3R,4R,5S,6R)-2-{4-Chloro-3-[4-(4-methoxy-benzyl)-3,4-dihydro-2H-benzo[1,4]oxazin-6-ylmethyl]-phenyl}-6-hydroxymethyltetrahydro-pyran-3,4,5-triol | ¹H NMR (400 MHz, CD₃OD): δ 3.31 (s, 3H), 3.38-3.52 (m, 3H), 3.70 (dd, J = 11.2, 4.0 Hz, 1H), 3.78 (s, 3H), 3.88 (d, 11.6 Hz, 1H), 3.91 (Abq, 14.8 Hz, 2H), 4.08 (d, J = 9.2 Hz, 1H), 4.17 (s, 2H), 4.31 (s, 2H), 6.41 (d, J = 7.6 Hz, 1H), 6.59 (d, J = 7.6 Hz, 2H), 6.86 (d, J = 8.0 Hz, 2H), 7.17 (d, J = 8.0 Hz, 2H), 7.22-7.38 (m, 3H). MS (ES) m/z 541.8 (M + 1). |

| Example No. | Structure/IUPAC name | Spectral data |
|---|---|---|
| 6 | (2S,3R,4R,5S,6R)-2-[3-(4-Benzyl-2,2-dimethyl-3,4-dihydro-2H-benzo[1,4]oxazin-6-ylmethyl)-4-chloro-phenyl]-6-hydroxymethyl-tetrahydro-pyran-3,4,5-triol | $^1$H NMR (400 MHz, CD$_3$OD): δ 1.26 (s, 6H), 3.35-3.46 (m, 2H), 3.64-3.70 (m, 1H), 3.80-3.91 (m, 3H), 4.05 (d, 1H), 4.38 (s, 2H), 4.56 (s, 4H), 6.46-6.52 (m, 1H), 6.54-6.57 (m, 2H), 7.19-7.28 (m, 8H). MS (ES)m/z 540.2 (M + 1) |

Examples 7-8

Step I.

To a stirred suspension LiAlH$_4$ (7.6 g, 201 mmol) in THF (70 mL) at 0° C. was added 4H-benzo[1,4]oxazin-3-one (15 g, 100 mmol) in 30 mL of THF and the mixture was stirred for 4 h at room temperature. After cooling, excess of LiAlH$_4$ was quenched by the addition of ethyl acetate (30 mL) followed by aq. NH$_4$Cl solution. The mixture was filtered through a celite bed and the filtrate was concentrated under reduced pressure and extracted with ethyl acetate (3×30 mL). The combined organic layers were washed with brine (30 mL) and dried over Na₂SO₄. Evaporation of the solvent resulted in benzoxazine (12 g) which was used as such for the next step.

MS (ES) m/z 136 (M+1)

Step II.

To an ice-cold solution of benzoxazine (4.5 g, 33.3 mmol) in dichloromethane (25 mL) was added trifluoroacetic anhydride (6.95 mL, 49.9 mmol) and the reaction mixture was stirred for 2 h then quenched by the addition of aq. NaHCO₃ solution. The mixture was partitioned between dichloromethane and water. The organic layer was separated, and the aqueous layer was extracted with dichloromethane. The combined organic layers were washed with brine, dried over Na₂SO₄, and concentrated to yield 1-(2,3-dihydro-benzo[1,4]oxazin-4-yl)-2,2,2-trifluoro-ethanone (6.5 g).

MS (ES) m/z 232 (M+1).

Step III:

To a stirred solution of 2-bromo-5-chlorobenzoic acid (8 g, 34.0 mmole) in dichloromethane (35 mL) was added DMF (1 mL) and oxalyl chloride (3.54 mL, 37.4 mmol) drop wise at 0° C. After complete addition, the reaction mixture was stirred at room temperature for 3 h. The volatiles were evaporated under reduced pressure to furnish 2-bromo-5-chloro-benzoyl chloride (8.5 g). The crude product was used without further purification.

To an ice cooled solution of 5-bromo-2-chlorobenzoyl chloride in dichloromethane (35 mL) was added 1-(2,3-dihydro-benzo[1,4]oxazin-4-yl)-2,2,2-trifluoro-ethanone (6.5 g, 28.1 mmol) in dichloromethane (45 mL) followed by AlCl₃ (5.61 g, 42.2 mmol) portion wise. After 2 h, the reaction mixture was brought to room temperature and stirred overnight. The reaction was quenched by pouring it over crushed ice. The resulting mixture was extracted with dichloromethane. The organic layer was washed with aq. NaHCO₃ (100 mL) and water (100 mL), and the solvent was evaporated to yield the crude product which was recrystallized from hot ethylacetate to furnish 1-[6-(5-bromo-2-chloro-benzoyl)-2,3-dihydro-benzo[1,4]oxazin-4-yl]-2,2,2-trifluoro-ethanone (10.0 g).

¹H NMR (400 MHz, CDCl₃): 4.03 (t, J=4.0 Hz, 2H), 4.48 (t, J=4.2 Hz, 2H), 7.04 (d, J=8.4 Hz, 1H), 7.34 (d, J=8.4 Hz, 1H), 7.50 (d, J=2.0 Hz, 1H), 7.55 (dd, J=8.4, 2.0 Hz, 1H), 7.68 (d, J=8.4 Hz, 1H) 8.42 (broad s, 1H).

MS (ES) m/z 450 (M+2)

Step IV.

To a stirred solution of 1-[6-(5-bromo-2-chloro-benzoyl)-2,3-dihydro-benzo[1,4]oxazin-4-yl]-2,2,2-trifluoro-ethanone (36 g, 80.35 mmol) in 1,2-dichloroethane:MeCN 1:2 (180 mL) was added BF₃.OEt₂ (13.2 mL, 104 mmol) and Et₃SiH (26.9 mL, 168.7 mmol) at 0° C. The reaction mixture was stirred overnight at room temperature then quenched by the addition of aq. NaHCO₃ (~200 mL). The resulting mixture was extracted with ethyl acetate (3×200 mL), and the combined organic layers were washed with brine (200 mL) and dried over sodium sulfate. Crude product obtained after evaporation of solvent was purified by silica gel column chromatography to furnish 1-[6-(5-bromo-2-chloro-benzyl)-2,3-dihydro-benzo[1,4]oxazin-4-yl]-2,2,2-trifluoro-ethanone (30 g).

¹H NMR (400 MHz, DMSO): δ 3.96 (t, J=4.0 Hz, 2H), 3.99 (s, 2H), 4.37 (t, J=4.4 Hz, 2H), 6.69 (d, J=8.4 Hz, 1H), 7.03 (d, J=7.6 Hz, 1H), 7.40 (d, J=8.4 Hz, 1H), 7.46 (dd, J=8.4, 2.0 Hz, 1H), 7.53 (d, J=2.4 Hz, 1H), 7.82 (br s, 1H).

Step V:

To a stirred solution of 1-[6-(5-bromo-2-chloro-benzyl)-2,3-dihydro-benzo[1,4]oxazin-4-yl]-2,2,2-trifluoro-ethanone (8.6 g, 19.8 mmol) in ethanol (40 mL) was added NaBH₄ (1.5 g, 39.0 mmol) portion wise and the reaction mixture was stirred overnight. Excess of NaBH₄ was quenched by adding aq. NH₄Cl, and ethanol was evaporated. The residue was partitioned between ethyl acetate and water, and the organic layer was separated, washed with brine (40 mL) and dried over sodium sulphate. Crude product obtained after evaporation of solvent was purified by silica gel column chromatography to furnish 6-(5-bromo-2-chloro-benzyl)-3,4-dihydro-2H-benzo[1,4]oxazine (6.1 g).

MS (ES) m/z 340 (M+2).

Step VI:

To a stirred solution of 6-(5-bromo-2-chloro-benzyl)-3,4-dihydro-2H-benzo[1,4]oxazine (8.0 g, 23.66 mmol) in DMF (35 mL) was added potassium carbonate (6.53 g, 47.3 mmol), and benzyl bromide (4.33 mL, 35.50 mmol). The reaction mixture was heated to 60° C. for 8 h, then cooled to room temperature and quenched by the addition of ice-cold water (50 mL). The resulting mixture was extracted with ethyl acetate (3×30 mL), and the combined organic layers were washed with water (50 mL) and brine (50 mL), then dried over sodium sulfate. The sodium sulfate was filtered off and the filtrate was concentrated to crude product which was purified by silica gel column chromatography to furnish 4-benzyl-6-(5-bromo-2-chloro-benzyl)-3,4-dihydro-2H-benzo[1,4]oxazine (7.0 g).

¹H NMR (400 MHz, CD₃OD): δ 3.40 (t, J=4.4 Hz, 2H), 3.85 (s, 2H), 4.24 (t, J=4.4 Hz, 2H), 4.40 (s, 2H), 6.40 (dd, J=8.0, 2.0 Hz, 1H), 6.45 (d, J=2.0 Hz, 1H), 6.66 (d, J=8.0, Hz, 1H), 7.20-7.36 (m, 8H).

MS (ES) m/z 430 (M+2).

Step VII:

To a stirred solution of 4-benzyl-6-(5-bromo-2-chloro-benzyl)-3,4-dihydro-2H-benzo[1,4]oxazine (7.0 g, 16.3 mmol) in THF-toluene 1:2 (40 mL) was added 1.6 M solution of n-BuLi in hexanes (10.46 mL, 16.35 mmol) at −78° C. The reaction mixture was stirred for 1 h and then transferred to a stirred solution of 2,3,4,6-tetrakis-O-(trimethylsilyl)-D-glucopyranone (7.62 g, 16.35 mmol) in toluene (25 mL) at −78° C. After stirring for 1 h, 0.6 N methanesulfonic acid in methanol (70 mL) was added and the reaction mixture was stirred for 12 h at room temperature then quenched by the addition of aq. saturated sodium bicarbonate solution (~25 mL). The resulting mixture was extracted with ethyl acetate (3×100 mL) and the combined organic layers were dried over sodium sulfate, concentrated and purified by silica gel column chromatography to furnish (2S,3R,4S,5S,6R)-2-[3-(4-benzyl-3,4-dihydro-2H-benzo[1,4]oxazin-6-ylmethyl)-4-chloro-phenyl]-6-hydroxymethyl-2-methoxy-tetrahydro-pyran-3,4,5-triol (5.0 g).

Example 7: (2S,3R,4R,5S,6R)-2-[3-(4-benzyl-3,4-dihydro-2H-benzo[1,4]oxazin-6-ylmethyl)-4-chloro-phenyl]-6-hydroxymethyl-tetrahydro-pyran-3,4,5-triol Step VIII:

To a stirred solution of (2S,3R,4S,5S,6R)-2-[3-(4-benzyl-3,4-dihydro-2H-benzo[1,4]oxazin-6-ylmethyl)-4-chloro-phenyl]-6-hydroxymethyl-2-methoxy-tetrahydro-pyran-3,4,5-triol (5.0 g, 9.24 mmol) in acetonitrile-dichloromethane mixture 1:1 (40 mL) was added boron trifluoride diethyletharate complex (2.34 mL, 18.48 mmol), and triethylsilane (5.95 mL, 36.9 mmol) at −5° C. After stirring for 4 h at the same temperature, the reaction was quenched with aq. saturated sodium bicarbonate solution (15 mL). The volatiles were evaporated under reduced pressure, and the resulting mixture was extracted with dichloromethane (2×30 mL). The organic layers were combined and washed with brine (10 mL), dried over sodium sulfate, concentrated and purified by preparative HPLC to furnish (2S,3R,4R,5S,6R)-2-[3-(4-benzyl-3,4-dihydro-2H-benzo[1,4]oxazin-6-ylmethyl)-4-chloro-phenyl]-6-hydroxymethyl-tetrahydro-pyran-3,4,5-triol (3.5 g).

¹H NMR (400 MHz, CD₃OD): δ 3.20-3.50 (m, 6H), 3.68 (dd, J=12.0, 4.4 Hz, 1H), 3.75-3.95 (m, 3H), 4.03 (d, J=9.2 Hz, 1H), 4.16 (t, J=3.6 Hz, 2H), 4.35 (s, 2H), 6.37 (d, J=8.0 Hz, 1H), 6.54 (s, 1H), 6.57 (d, J=0.8 Hz, 1H), 7.15-7.62 (m, 8H).

MS (ES) m/z 511.8 (M+1)

Example 8: (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol Step IX:
To a solution of (2S,3R,4R,5S,6R)-2-[3-(4-benzyl-3,4-dihydro-2H-benzo[1,4]oxazin-6-ylmethyl)-4-chloro-phenyl]-6-hydroxymethyl-tetrahydro-pyran-3,4,5-triol (2.4 g, 4.68 mmol) in methanol (15 mL) was added 10% palladium on charcoal (240 mg) and 0.05 mL conc. HCl. The reaction mixture was stirred under hydrogen atmosphere for 2 h then filtered through celite bed (which was washed with methanol). The resulting filtrate was concentrated to a residue which was purified by preparative HPLC to furnish (2S,3R,4R,5S,6R)-2-[4-chloro-3-(3,4-dihydro-2H-benzo[1,4]oxazin-6-ylmethyl)-phenyl]-6-hydroxymethyl-tetrahydro-pyran-3,4,5-triol (1.6 g).

$^1$H NMR (400 MHz, CD$_3$OD): δ 3.24-3.34 (m, 2H), 3.35-3.49 (m, 4H), 3.69 (dd, J=12.0, 5.6 Hz, 1H), 3.88 (dd, J=11.6, 2.0 Hz, 1H), 3.93 (ABq, J=15.2 Hz, 2H), 4.08 (d, J=9.6 Hz, 1H), 4.15 (t, J=4.4 Hz, 2H), 6.42-6.50 (m, 2H), 6.58 (d, J=8.0 Hz, 1H), 7.26 (dd, J=8.0, 2.4 Hz, 1H), 7.30 (d, J=2.0 Hz, 1H), 7.33 (d, J=8.0 Hz, 1H).

Example 9: (2S,3R,4R,5S,6R)-2-[4-Chloro-3-(4-ethyl-3,4-dihydro-2H-benzo[1,4]oxazin-6-ylmethyl)-phenyl]-6-hydroxymethyl-tetrahydro-pyran-3,4,5-triol

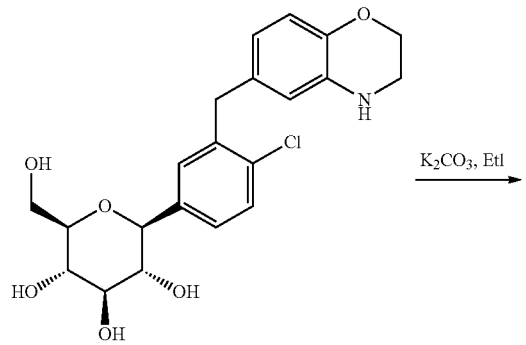

K$_2$CO$_3$, EtI →

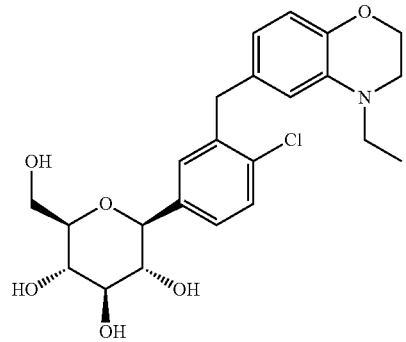

To a stirred solution of (2S,3R,4R,5S,6R)-2-[4-chloro-3-(3,4-dihydro-2H-benzo[1,4]oxazin-6-ylmethyl)-phenyl]-6-hydroxymethyl-tetrahydro-pyran-3,4,5-triol (0.1 g, 0.23 mmol) in DMF (2 mL) was added potassium carbonate (0.065 g, 0.47 mmol), ethyl iodide (0.028 mL, 0.35 mmol) and stirred the solution at 20° C. for 2 h. Reaction mixture was quenched by the addition of water (2 mL), extracted with dichloromethane (3×5 mL). The organic layer was washed with water (5 mL), brine (5 mL), dried over sodium sulfate, concentrated and purified by preparative HPLC to furnish (2S,3R,4R,5S,6R)-2-[4-chloro-3-(4-ethyl-3,4-dihydro-2H-benzo[1,4]oxazin-6-ylmethyl)-phenyl]-6-hydroxymethyl-tetrahydro-pyran-3,4,5-triol (20 mg).

$^1$H NMR (400 MHz, CD$_3$OD): δ 1.17 (t, J=6.8 Hz, 3H), 3.20-3.50 (m, 6H), 3.52-3.62 (m, 2H), 3.63 (dd, J=11.2, 5.6 Hz, 1H), 3.77 (d, J=11.2 Hz, 1H), 3.88 (abq, J=15.2 Hz, 2H), 4.06 (d, J=9.6 Hz, 1H), 4.15 (t, J=3.6 Hz, 2H), 6.43 (d, J=8.8 Hz, 1H), 6.46 (s, 1H), 6.57 (d, J=7.6 Hz, 1H), 7.23 (d, J=8.0 Hz, 1H), 7.27 (s, 1H), 7.34 (d, J=8.4 Hz, 1H). MS (ES) m/z 450 (M+1).

Following examples were prepared using the procedures described for example 9.

| Example No. | Structure/IUPAC name | Spectral data |
|---|---|---|
| 10 | (2S,3R,4R,5S,6R)-2-[4-Chloro-3-(4-cyclopropylmethyl-3,4-dihydro-2H-benzo[1,4]oxazin-6-ylmethyl)-phenyl]-6-hydroxymethyl-tetrahydro-pyran-3,4,5-triol | $^1$H NMR (400 MHz, CD$_3$OD): δ 0.118 (s, 2H), 0.51 (d, J = 6.8 Hz, 2H), 1.00-1.10 (m, 1H), 3.20-3.60 (m, 8H), 3.60-3.75 (m, 1H), 3.82 (d, J = 10.0 Hz, 1H) 3.94 (abq, 15.2 Hz, 2H), 4.07 (d, J = 9.6 Hz, 1H), 4.15 (t, J = 4.0, 2H), 6.43 (d, J = 8.0 Hz, 1H), 6.45 (s, 1H), 6.58 (d, J = 8.0 Hz, 1H), 7.24 (dd, J = 8.0, 1.2 Hz, 1H), 7.25 (s, 1H) 7.34 (d, J = 8.0 Hz, 1H), . MS (ES) m/z 476.3 (M + 1). |

| Example No. | Structure/IUPAC name | Spectral data |
|---|---|---|
| 11 | 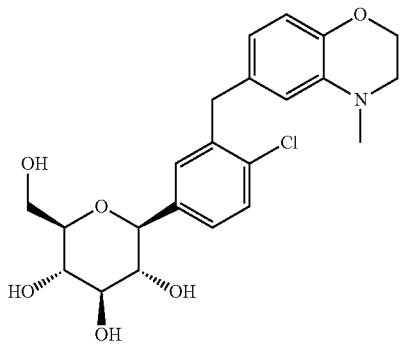 [SMILES: CN1CCOc2ccc(Cc3cc([C@@H]4O[C@H](CO)[C@@H](O)[C@H](O)[C@H]4O)ccc3Cl)cc21]<br>(2S,3R,4R,5S,6R)-2-[4-Chloro-3-(4-methyl-3,4-dihydro-2H-benzo[1,4]oxazin-6-ylmethyl)-phenyl]-6-hydroxymethyl-tetrahydro-pyran-3,4,5-triol | $^1$H NMR (400 MHz, CD$_3$OD): δ 3.20-3.32 (m, 3H), 3.37 (s, 3H), 3.40-3.55 (m, 3H), 3.61 (dd, J = 10.8, 5.2 Hz, 1H), 3.71 (d, J = 10.8 Hz, 1H), 3.93 (abq, 15.2 Hz, 2H), 4.06 (d, J = 9.6 Hz, 1H), 4.15 (t, J = 4.0, 2H), 6.43 (d, J = 8.8 Hz, 1H), 6.45 (s, 1H), 6.57 (d, J = 8.0 Hz, 1H), 7.23 (d, J = 8.4 Hz, 1H), 7.26 (s, 1H) 7.33 (d, J = 8.4 Hz, 1H), . MS (ES) m/z 435 (M + 1). |
| 12 | 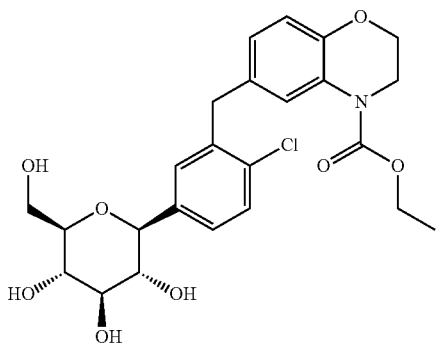 [SMILES: CCOC(=O)N1CCOc2ccc(Cc3cc([C@@H]4O[C@H](CO)[C@@H](O)[C@H](O)[C@H]4O)ccc3Cl)cc21]<br>6-[2-Chloro-5-((2S,3R,4R,5S,6R)-3,4,5-trihydroxy-6-hydroxymethyl-tetrahydro-pyran-2-yl)-benzyl]-2,3-dihydro-benzo[1,4]oxazine-4-carboxylic acid ethyl ester | $^1$H NMR (400 MHz, CD$_3$OD): δ 1.25 (t, J = 6.4 Hz, 3H), 3.30-3.50 (m, 3H), 3.66 (d, J = 11.6 Hz, 1H), 3.84 (d, J = 11.2 Hz, 3H), 3.99 (Abq, J = 15.2 Hz, 2H), 4.07 (d, J = 9.6 Hz, 1H), 4.12-4.26 (m, 3H), 6.58 (s, 2H), 6.72 (d, J = 8.4 Hz, 1H), 6.82 (d, J = 7.6 Hz, 1H), 7.25 (d, J = 7.6 Hz, 1H), 7.32 (d, J = 6.4 Hz, 2H) 7.61 (s, 1H), . MS (ES) m/z 494.3 (M + 1). |
| 13 | 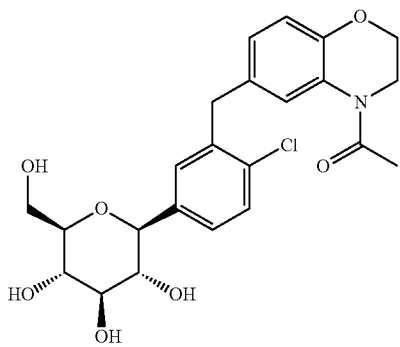 [SMILES: CC(=O)N1CCOc2ccc(Cc3cc([C@@H]4O[C@H](CO)[C@@H](O)[C@H](O)[C@H]4O)ccc3Cl)cc21]<br>1-{6-[2-Chloro-5-((2S,3R,4R,5S,6R)-3,4,5-trihydroxy-6-hydroxymethyl-tetrahydro-pyran-2-yl)-benzyl]-2,3-dihydro-benzo[1,4]oxazin-4-yl}-ethanone | $^1$H NMR (400 MHz, CD$_3$OD): δ 2.25 (s, 3H), 3.25-3.55 (m, 4H), 3.71 (dd, J = 11.6, 4.4 Hz, 1H), 3.88 (d, J = 13.6 Hz, 3H), 4.06 (s, 2H), 4.12 (d, J = 9.6 Hz, 1H), 4.26 (s, 2H), 6.81 (d, J = 8.0 Hz, 2H), 6.98 (br s, 1H), 7.29 (d, J = 8.0 Hz, 1H), 7.36 (d, J = 8.0 Hz, 1H), 7.39 (s, 1H) MS (ES) m/z 464.2 (M + 1). |

79

Example 14: (2S,3R,4R,5S,6R)-2-{4-Chloro-3-[1-(4-methoxy-benzyl)-1,2,3,4-tetrahydro-quinolin-6-ylmethyl]-phenyl}-6-hydroxymethyl-tetrahydro-pyran-3,4,5-triol

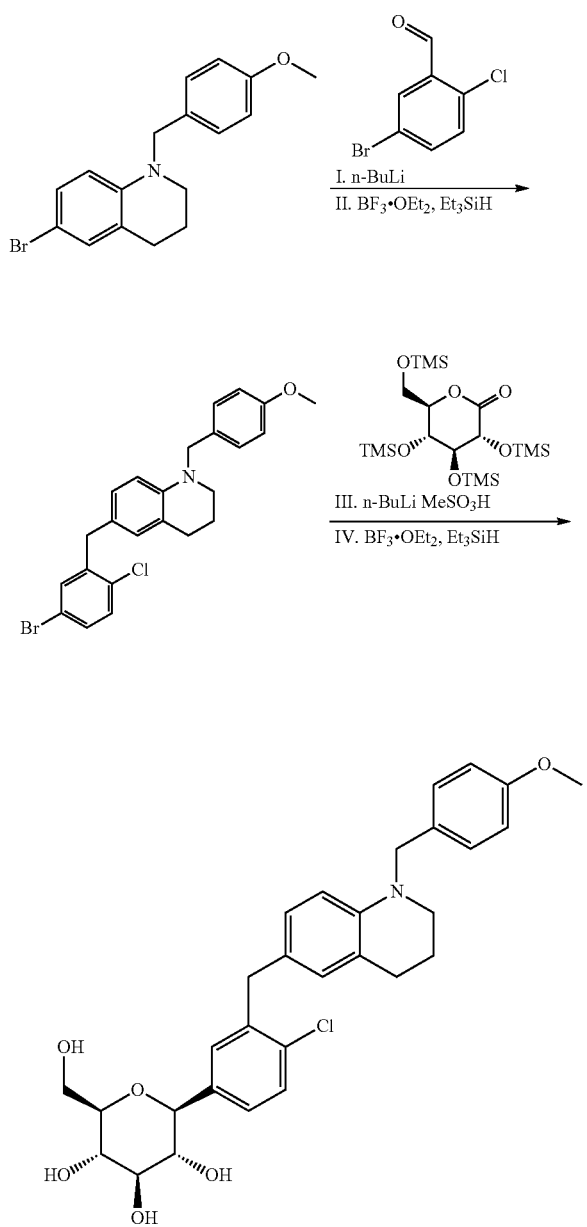

Step I:

To a cooled solution of 6-bromo-1-(4-methoxy-benzyl)-1,2,3,4-tetrahydro-quinoline (2.5 g, 7.5 mmol) in THF (30 mL) was added 1.6 M n-butyl lithium in hexanes (4.7 mL, 7.5 mmol) at −78° C., stirred for 30 min. This was transferred to a stirred solution of 5-bromo-2-chlorobenzaldehyde (1.73 g, 7.9 mmol) in THF (30 mL) at −78° C. After stirring for 30 min, reaction was quenched by the addition of saturated aqueous solution of ammonium chloride and extracted with ethyl acetate (2×50 mL). The ethyl acetate layer was washed with water, brine, dried over sodium sulphate, and concentrated. The resulting residue was purified by silica gel column chromatography to give (5-bromo-2-chloro-phenyl)-[1-(4-methoxy-benzyl)-1,2,3,4-tetrahydro-quinolin-6-yl]-methanol (2.31 g).

$^1$H NMR (400 MHz, CDCl$_3$): δ 1.95-2.10 (m, 3H), 2.77 (t, J=6.4 Hz, 2H), 3.33 (t, J=5.6 Hz, 2H), 3.78 (s, 3H), 4.39 (s, 2H), 5.96 (d, J=3.6 Hz, 1H), 6.46 (d, J=8.0 Hz, 1H), 6.84 (d, J=7.6 Hz, 2H), 6.91-7.91 (m, 7H). MS (ES) m/z 474.1 (M+2).

Step II:

To an ice cold solution of (5-bromo-2-chloro-phenyl)-[1-(4-methoxy-benzyl)-1,2,3,4-tetrahydro-quinolin-6-yl]-methanol (2.2 g, 4.7 mmol) in dichloromethane (50 mL) was added Et$_3$SiH (3.7 mL, 23.3 mmol) followed by BF$_3$.OEt$_2$ (1.5 mL, 11.6 mmol). The reaction mixture was stirred at room temperature overnight. The reaction was quenched by the addition of aq. NaHCO$_3$. The volatiles were evaporated under reduced pressure; the resulting mixture was extracted with dichloromethane (2×50 mL), washed with brine (10 mL), dried over sodium sulfate, concentrated and purified by silica gel column chromatography to give 6-(5-Bromo-2-chloro-benzyl)-1-(4-methoxy-benzyl)-1,2,3,4-tetrahydro-quinoline (1.48 g).

$^1$H NMR (400 MHz, CDCl$_3$): δ 1.96-2.02 (m, 2H), 2.77 (t, J=6.0 Hz, 2H), 3.32 (t, J=5.6 Hz, 2H), 3.79 (s, 3H), 3.89 (s, 2H), 4.39 (s, 2H), 6.47-7.29 (m, 10H). MS (ES) m/z 458.1 (M+2).

Step III:

To a stirred solution of 6-(5-bromo-2-chloro-benzyl)-1-(4-methoxy-benzyl)-1,2,3,4-tetrahydro-quinoline (700 mg, 1.5 mmol) in THF-toluene (15 mL of 1:2 mixture) was added 1.6 M solution of n-BuLi in hexanes (1.0 mL, 1.5 mmol) at −78° C. The reaction mixture was stirred for 30 min., and then transferred to a stirred solution of 2,3,4,6-tetrakis-O-(trimethylsilyl)-D-glucopyranone (715 mg, 1.5 mmol) in toluene (10 mL) at −78° C. After stirring for 40 min., 0.6 N methanesulfonic acid in methanol (30 mL) was added and stirred for 20 h at room temperature. Reaction was quenched by the addition of aq. saturated NaHCO$_3$ (10 mL) and extracted with ethyl acetate (3×20 mL), dried over sodium sulphate, concentrated and purified by silica gel column chromatography to furnish (2S,3R,4S,5S,6R)-2-{4-chloro-3-[1-(4-methoxy-benzyl)-1,2,3,4-tetrahydro-quinolin-6-ylmethyl]-phenyl}-6-hydroxymethyl-2-methoxy-tetrahydro-pyran-3,4,5-triol (330 mg).

MS (ES) m/z 570.2 (M+1).

Step IV:

To a stirred solution of (2S,3R,4S,5S,6R)-2-{4-chloro-3-[1-(4-methoxy-benzyl)-1,2,3,4-tetrahydro-quinolin-6-ylmethyl]-phenyl}-6-hydroxymethyl-2-methoxy-tetrahydro-pyran-3,4,5-triol (325 mg, 0.6 mmol) in acetonitrile-dichloromethane mixture (1:1 mixture, 14 mL) was added triethylsilane (0.4 mL, 2.2 mmol) and boron trifluoride diethyletharate complex (0.15 mL, 1.1 mmol) at −20° C. After stirring for 4 h at 0° C., reaction was quenched with aq. saturated NaHCO$_3$ solution (8 mL). The volatiles were evaporated under reduced pressure; the resulting mixture was extracted with ethyl acetate (3×20 mL). The organic layer was washed with brine (5 mL), dried over sodium sulphate, concentrated and purified by preparative HPLC to furnish (2S,3R,4R,5S,6R)-2-{4-chloro-3-[1-(4-methoxy-benzyl)-1,2,3,4-tetrahydro-quinolin-6-ylmethyl]-phenyl}-6-hydroxymethyl-tetrahydro-pyran-3,4,5-triol (160 mg).

$^1$H NMR (400 MHz, CD$_3$OD): δ 1.91-1.96 (m, J=5.6 Hz, 2H), 2.70 (t, J=6.4 Hz, 2H), 3.25-3.44 (m, 6H), 3.67 (dd, J=12.0, 5.6 Hz, 1H), 3.74 (s, 3H), 3.84-3.95 (m, 3H), 4.06

(d, J=9.6 Hz, 1H), 4.36 (s, 2H), 6.44 (d, J=9.2 Hz, 1H), 6.74 (d, J=7.2 Hz, 2H), 6.83 (d, J=8.8 Hz, 2H), 7.15 (d, J=8.8 Hz, 2H), 7.22-7.28 (m, 2H), 7.31 (d, J=8.0 Hz, 1H).

MS (ES) m/z 540.0 (M+1).

Example 15: (2S,3R,4R,5S,6R)-2-[4-Chloro-3-(1,2,3,4-tetrahydro-quinolin-6-ylmethyl)-phenyl]-6-hydroxymethyl-tetrahydro-pyran-3,4,5-triol

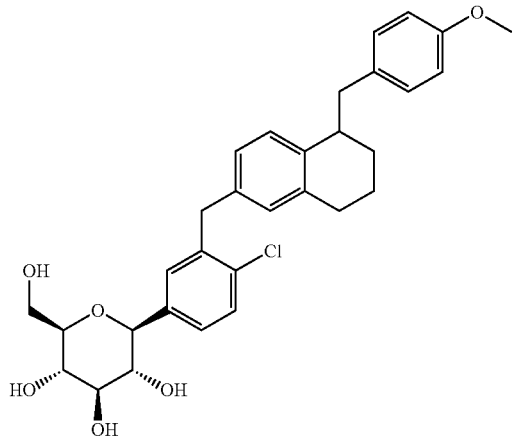

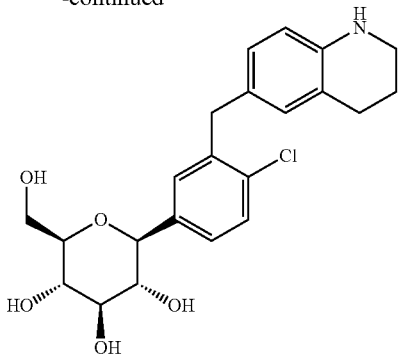

To a solution of (2S,3R,4R,5S,6R)-2-{4-chloro-3-[1-(4-methoxy-benzyl)-1,2,3,4-tetrahydro-quinolin-6-ylmethyl]-phenyl}-6-hydroxymethyl-tetrahydro-pyran-3,4,5-triol (135 mg, 0.25 mmol) in methanol (5 mL) was added 10% palladium on charcoal (60 mg), 0.05 mL conc. HCl and stirred under hydrogen balloon pressure for 18 h. Reaction mixture was filtered through celite bed, washed with methanol and concentrated. The resulting residue was purified by preparative HPLC to furnish (2S,3R,4R,5S,6R)-2-[4-Chloro-3-(1,2,3,4-tetrahydro-quinolin-6-ylmethyl)-phenyl]-6-hydroxymethyl-tetrahydro-pyran-3,4,5-triol (74 mg).

$^1$H NMR (400 MHz, CD$_3$OD): δ 1.84-1.90 (m, 2H), 2.67 (t, J=6.8 Hz, 2H), 3.17-3.20 (m, 2H), 3.25-3.46 (m, 4H), 3.65-3.69 (m, 1H), 3.84-3.96 (m, 3H), 4.06 (d, J=9.2 Hz, 1H), 6.43 (d, J=8.0 Hz, 1H), 6.73-6.76 (m, 2H), 7.23-7.28 (m, 2H), 7.32 (d, J=8.4 Hz, 1H).

MS (ES) m/z 420.0 (M+1).

Following examples were prepared using the procedures described for examples 14 or 15.

| Example No. | Structure/IUPAC name | Spectral data |
|---|---|---|
| 16 | (2S,3R,4R,5S,6R)-2-[4-Chloro-3-(1,2,3,4-tetrahydro-quinolin-7-ylmethyl)-phenyl]-6-hydroxymethyl-tetrahydro-pyran-3,4,5-triol | $^1$H NMR (400 MHz, CD$_3$OD): δ 1.84-1.89 (m, 2H), 2.68 (t, J = 6.4 Hz, 2H), 3.18 (t, J = 5.2 Hz, 2H), 3.26-3.46 (m, 4H), 3.67 (dd, J = 12.0, 4.8, 1H), 3.84-3.97 (m, 3H), 4.06 (d, J = 9.6 Hz, 1H), 6.34 (s, 1H), 6.40 (d, J = 7.6 Hz, 1H), 6.77 (d, J = 7.6 Hz, 1H), 7.24-7.33 (m, 3H). MS (ES) m/z 420.0 (M + 1). |

-continued

| Example No. | Structure/IUPAC name | Spectral data |
|---|---|---|
| 17 | 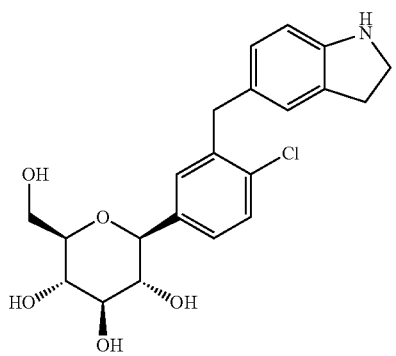 [SMILES: OC[C@H]1O[C@@H](c2ccc(Cl)c(Cc3ccc4c(c3)CCN4)c2)[C@H](O)[C@@H](O)[C@@H]1O]<br>(2S,3R,4R,5S,6R)-2-[4-Chloro-3-(2,3-dihydro-1H-indol-5-ylmethyl)-phenyl]-6-hydroxymethyl-tetrahydro-pyran-3,4,5-triol | $^1$H NMR (400 MHz, CD$_3$OD): δ 2.94 (t, J = 8.0 Hz, 2H), 3.26-3.45 (m, 6H), 3.66-3.70 (m, 1H), 3.86 (d, J = 11.2 Hz, 1H), 3.95 (d, J = 15.2, 1H), 4.01 (d, J = 15.2 Hz, 1H), 4.08 (d, J = 9.6 Hz, 1H), 6.62 (d, J = 8.0 Hz, 1H), 6.85 (d, J = 7.6 Hz, 1H), 6.95 (s, 1H), 7.24-7.34 (m, 3H). MS (ES) m/z 406.0 (M + 1). |
| 18 | 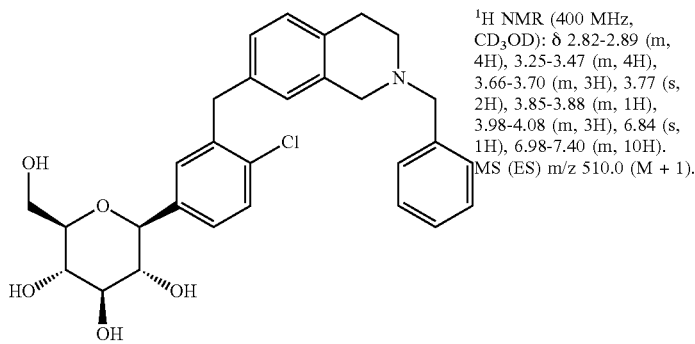<br>(2S,3R,4R,5S,6R)-2-[3-(2-Benzyl-1,2,3,4-tetrahydro-isoquinolin-7-ylmethyl)-4-chloro-phenyl]-6-hydroxymethyl-tetrahydro-pyran-3,4,5-triol | $^1$H NMR (400 MHz, CD$_3$OD): δ 2.82-2.89 (m, 4H), 3.25-3.47 (m, 4H), 3.66-3.70 (m, 3H), 3.77 (s, 2H), 3.85-3.88 (m, 1H), 3.98-4.08 (m, 3H), 6.84 (s, 1H), 6.98-7.40 (m, 10H). MS (ES) m/z 510.0 (M + 1). |
| 19 | 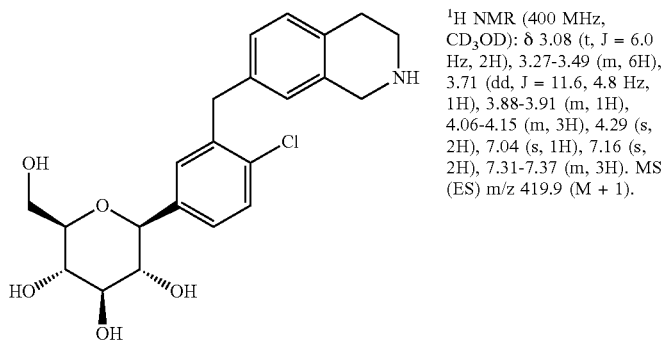<br>(2S,3R,4R,5S,6R)-2-[4-Chloro-3-(1,2,3,4-tetrahydro-isoquinolin-7-ylmethyl)-phenyl]-6-hydroxymethyl-tetrahydro-pyran-3,4,5-triol | $^1$H NMR (400 MHz, CD$_3$OD): δ 3.08 (t, J = 6.0 Hz, 2H), 3.27-3.49 (m, 6H), 3.71 (dd, J = 11.6, 4.8 Hz, 1H), 3.88-3.91 (m, 1H), 4.06-4.15 (m, 3H), 4.29 (s, 2H), 7.04 (s, 1H), 7.16 (s, 2H), 7.31-7.37 (m, 3H). MS (ES) m/z 419.9 (M + 1). |

| Example No. | Structure/IUPAC name | Spectral data |
|---|---|---|
| 20 | 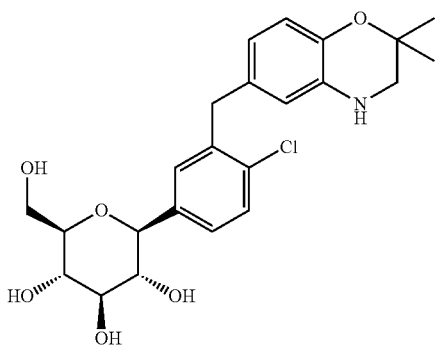 [SMILES: CC1(C)CNc2cc(Cc3cc([C@@H]4O[C@H](CO)[C@@H](O)[C@H](O)[C@H]4O)ccc3Cl)ccc2O1]<br>(2S,3R,4R,5S,6R)-2-[4-Chloro-3-(2,2-dimethyl-3,4-dihydro-2H-benzo[1,4]oxazin-6-ylmethyl)-phenyl]-6-hydroxymethyl-tetrahydro-pyran-3,4,5-triol | $^1$H NMR (400 MHz, CD$_3$OD): δ 1.26 (s, 6H), 2.98 (s, 2H), 3.37-3.44 (m, 4H), 3.65-3.70 (m, 1H), 3.85-3.98 (m, 3H), 4.08 (d, J = 9.48 Hz, 1H), 6.43 (d, J = 8.16 Hz, 1H), 6.46 (s, 1H), 6.54 (d, J = 7.94 Hz, 1H), 7.25 (d, J = 8.16 Hz, 1H), 7.30-7.34 (m, 2H).<br>MS (ES) m/z 450.0 (M + 1) |
| 21 | 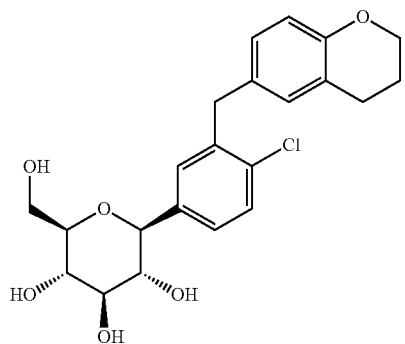 [SMILES: OC[C@H]1O[C@@H](c2ccc(Cl)c(Cc3ccc4c(c3)CCCO4)c2)[C@H](O)[C@@H](O)[C@@H]1O]<br>(2S,3R,4R,5S,6R)-2-(4-Chloro-3-chroman-6-ylmethyl-phenyl)-6-hydroxymethyl-tetrahydro-pyran-3,4,5-triol | $^1$H NMR (400 MHz, CD$_3$OD): δ 1.93-1.96 (m, 2H), 2.71 (t, J = 6.40 Hz, 2H), 3.26-3.44 (m, 4H), 3.66-3.70 (m, 1H), 3.87 (d, J = 11.20 Hz, 1H), 3.90 (d, J = 15.2 Hz, 1H), 3.99 (d, J = 14.8 Hz, 1H), 4.06-4.12 (m, 3H), 6.60 (d, J = 8.16 Hz, 1H), 6.84-6.87 (m, 2H), 7.26 (dd, J = 8.16 Hz, 1.98 Hz 1H), 7.30 (d, J = 1.98 Hz, 1H), 7.33 (d, J = 8.16 Hz, 1H).<br>MS (ES) m/z 420.9 (M + 1), 4437.9 (M + 18) |
| 22 | 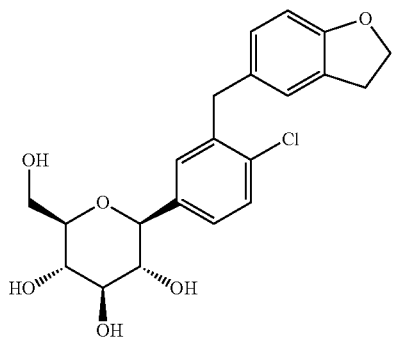 [SMILES: OC[C@H]1O[C@@H](c2ccc(Cl)c(Cc3ccc4c(c3)CCO4)c2)[C@H](O)[C@@H](O)[C@@H]1O]<br>(2S,3R,4R,5S,6R)-2-[4-Chloro-3-(2,3-dihydro-benzofuran-5-ylmethyl)-phenyl]-6-hydroxymethyl-tetrahydro-pyran-3,4,5-triol | $^1$H NMR (400 MHz, CD$_3$OD): δ 3.17 (t, J = 8.56 Hz, 2H), 3.30-3.46 (m, 4H), 3.66-3.70 (m, 1H), 3.85-3.88 (m, 1H), 3.98 (d, J = 15.2 Hz, 1H), 4.02 (d, J = 14.8 Hz, 1H), 4.07 (d, J = 9.2 Hz, 1H), 4.48 (t, J = 8.56 Hz, 2H), 6.60 (d, J = 8.3 Hz, 1H), 6.91 (d, J = 8.1 Hz, 1H), 7.02 (s, 1H), 7.26 (dd, J = 8.1 Hz, 2.0 Hz 1H), 7.31 (d, J = 1.7 Hz, 1H), 7.34 (d, J = 8.1 Hz, 1H).<br>MS (ES) m/z 424.0 (M + 18) |

| Example No. | Structure/IUPAC name | Spectral data |
|---|---|---|
| 23 | 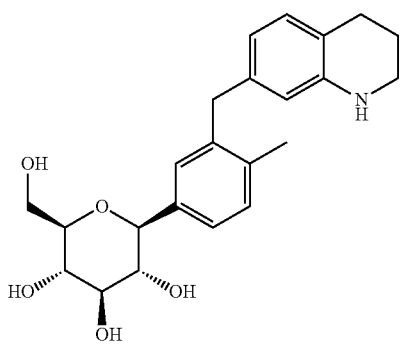 [SMILES: Cc1ccc([C@@H]2O[C@H](CO)[C@@H](O)[C@H](O)[C@H]2O)cc1Cc1ccc2c(c1)NCCC2]<br>(2R,3S,4R,5R,6S)-2-Hydroxymethyl-6-[4-methyl-3-(1,2,3,4-tetrahydroquinolin-7-ylmethyl)-phenyl]-tetrahydro-pyran-3,4,5-triol | $^1$H NMR (400 MHz, CD$_3$OD): δ 1.84-1.90 (m, 2H), 2.18 (s, 3H), 2.67 (t, J = 6.0 Hz, 2H), 3.16-3.19 (m, 2H), 3.35-3.48 (m, 4H), 3.68 (dd, J = 12.0, 5.2, 1H), 3.78-3.88 (m, 3H), 4.06 (d, 8.8 Hz, 1H), 6.27 (d, J = 1.6 Hz, 1H), 6.36 (dd, J = 7.6, 1.6 Hz, 1H), 6.76 (d, J = 7.6 Hz, 1H), 7.00 (d, J = 7.2 Hz, 1H), 7.15-7.18 (m, 2H). MS (ES) m/z 400.3 (M + 1). |
| 24 | 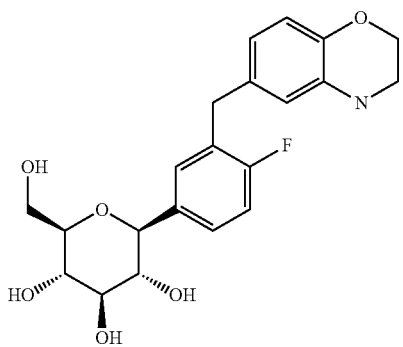 [SMILES: OC[C@H]1O[C@@H](c2ccc(F)c(Cc3ccc4c(c3)NCCO4)c2)[C@H](O)[C@@H](O)[C@@H]1O]<br>(2S,3R,4R,5S,6R)-2-[3-(3,4-Dihydro-2H-benzo[1,4]oxazin-6-ylmethyl)-4-fluoro-phenyl]-6-hydroxymethyl-tetrahydro-pyran-3,4,5-triol | $^1$H NMR (400 MHz, CD$_3$OD): δ 3.29-3.48 (m, 6H), 3.71 (dd, J = 12.0, 5.2 Hz, 1H), 3.79-3.91 (m, 3H), 4.10 (d, J = 9.2, 1H), 4.17 (t, J = 4.4 Hz, 2H), 6.46-6.52 (m, 2H), 6.59 (d, J = 8.0 Hz, 1H), 7.01-7.31 (m, 3H). MS (ES) m/z 406.3 (M + 1). |
| 25 | 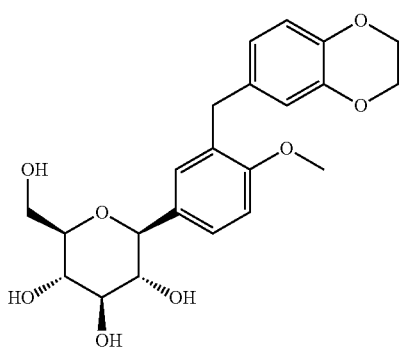 [SMILES: COc1ccc([C@@H]2O[C@H](CO)[C@@H](O)[C@H](O)[C@H]2O)cc1Cc1ccc2c(c1)OCCO2]<br>(2S,3R,4R,5S,6R)-2-[3-(2,3-Dihydro-benzo[1,4]dioxin-6-ylmethyl)-4-methoxy-phenyl]-6-hydroxymethyl-tetrahydro-pyran-3,4,5-triol | $^1$H NMR (400 MHz, CD$_3$OD): δ 3.27-3.45 (m, 4H), 3.66-3.70 (dd, J = 12.0, 5.6 Hz, 1H), 3.76-3.89 (m, 6H), 4.05 (d, J = 9.6, 1H), 4.18 (s, 4H), 6.64-6.67 (m, 3H), 6.92 (d, J = 8.4 Hz, 1H), 7.17 (d, J = 2.0 Hz, 1H), 7.25 (dd, J = 8.0, 2.0 Hz, 1H). MS (ES) m/z 436.0 (M + 18). |

| Example No. | Structure/IUPAC name | Spectral data |
|---|---|---|
| 26 | 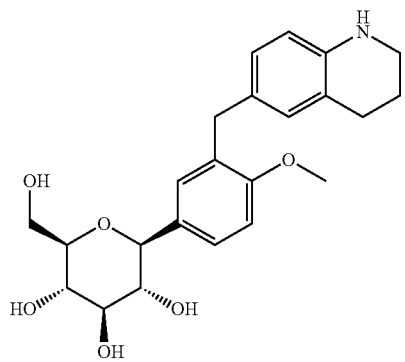 [SMILES: COc1ccc([C@@H]2O[C@H](CO)[C@@H](O)[C@H](O)[C@H]2O)cc1Cc1ccc2c(c1)CCCN2]<br>(2R,3S,4R,5R,6S)-2-Hydroxymethyl-6-[4-methoxy-3-(1,2,3,4-tetrahydro-quinolin-6-ylmethyl)-phenyl]-tetrahydro-pyran-3,4,5-triol | $^1$H NMR (400 MHz, CD$_3$OD): δ 1.84-1.88 (m, 2H), 2.67 (d, J = 6.4 Hz, 2H), 3.17 (t, J = 6.4 Hz, 2H), 3.25-3.44 (m, 4H), 3.65 (dd, J = 12.0, 4.8, 1H), 3.74-3.86 (m, 6H), 4.01 (d, J = 9.2 Hz, 1H), 6.41 (d, J = 8.0 Hz, 1H), 6.73-6.75 (m, 2H) 6.89 (d, J = 8.8 Hz, 1H), 7.12 (d, J = 1.6 Hz, 1H), 7.21 (dd, J = 8.4, 2.0 Hz, 1H). MS (ES) m/z 416.0 (M + 1). |
| 27 | 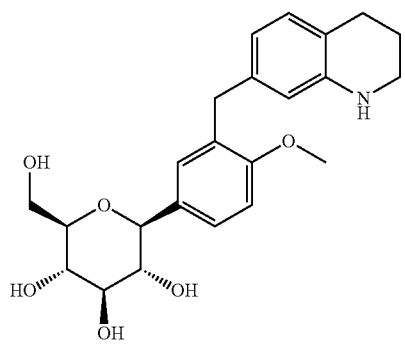 [SMILES: COc1ccc([C@@H]2O[C@H](CO)[C@@H](O)[C@H](O)[C@H]2O)cc1Cc1ccc2c(c1)NCCC2]<br>(2R,3S,4R,5R,6S)-2-Hydroxymethyl-6-[4-methoxy-3-(1,2,3,4-tetrahydro-quinolin-7-ylmethyl)-phenyl]-tetrahydro-pyran-3,4,5-triol | $^1$H NMR (400 MHz, CD$_3$OD): δ 1.84-1.88 (m, 2H), 2.66 (d, J = 6.4 Hz, 2H), 3.17 (t, J = 6.4 Hz, 2H), 3.25-3.43 (m, 4H), 3.65 (dd, J = 12.0, 5.2, 1H), 3.72-3.86 (m, 6H), 4.01 (d, J = 9.2 Hz, 1H), 6.36-6.42 (m, 2H), 6.73 (d, J = 7.6 Hz, 1H) 6.89 (d, J = 8.8 Hz, 1H), 7.14 (d, J = 2.0 Hz, 1H), 7.21 (dd, J = 8.4, 2.0 Hz, 1H). MS (ES) m/z 416.1 (M + 1). |
| 28 | 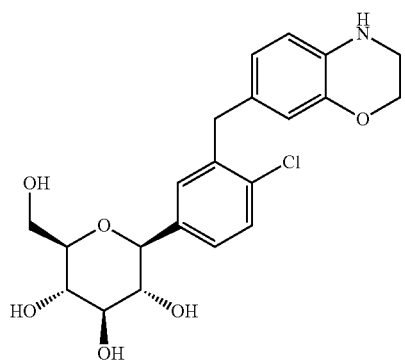 [SMILES: OC[C@H]1O[C@@H](c2ccc(Cl)c(Cc3ccc4c(c3)OCCN4)c2)[C@H](O)[C@@H](O)[C@@H]1O]<br>(2S,3R,4R,5S,6R)-2-[4-Chloro-3-(3,4-dihydro-2H-benzo[1,4]oxazin-7-ylmethyl)-phenyl]-6-hydroxymethyl-tetrahydro-pyran-3,4,5-triol | $^1$H NMR (400 MHz, CD$_3$OD): δ 3.26-3.47 (m, 6H), 3.66-3.70 (m, 1H), 3.85-3.96 (m, 3H), 4.07 (d, J = 9.5 Hz, 1H), 4.15 (t, J = 4.4 Hz, 2H), 6.40-6.45 (m, 2H), 6.56 (d, J = 8.0 Hz, 1H), 7.24-7.30 (m, 2H), 7.32 (d, J = 8.4 Hz, 1H),. MS (ES) m/z 421.9 (M + 1). |

-continued

| Example No. | Structure/IUPAC name | Spectral data |
|---|---|---|
| 29 | 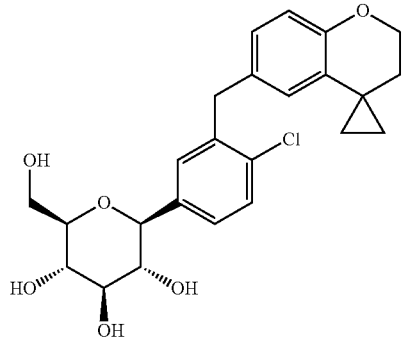 [SMILES: OC[C@H]1O[C@@H](c2ccc(Cl)c(Cc3ccc4c(c3)C3(CCO4)CC3)c2)[C@H](O)[C@@H](O)[C@@H]1O]<br>(2S,3R,4R,5S,6R)-2-[4-Chloro-3-(4,4-spiro-cyclopropyl-chroman-6-ylmethyl)-phenyl]-6-hydroxymethyl-tetrahydro-pyran-3,4,5-triol | $^1$H NMR (400 MHz, CD$_3$OD): δ 0.80-0.83 (m, 2H), 0.96-0.99 (m, 2H), 1.82 (t, J = 5.1 Hz, 2H), 3.27-3.45 (m, 4H), 3.66-3.70 (m, 1H), 3.87 (d, J = 11.7 Hz, 1H), 3.92 (d, J = 15.2 Hz, 1H), 3.97 (d, J = 15.2 Hz, 1H), 4.07 (d, J = 9.2 Hz, 1H), 4.20 (t, J = 5.1 Hz, 2H), 6.55 (d, J = 2.2 Hz, 1H), 6.61 (d, J = 8.3 Hz, 1H), 6.81 (dd, J = 8.3 Hz, J = 2.2 Hz, 1H), 7.25-7.27 (m, 2H), 7.33 (d, J = 8.1 Hz, 1H).<br>MS (ES) m/z 447.2 (M + 1). |
| 30 | 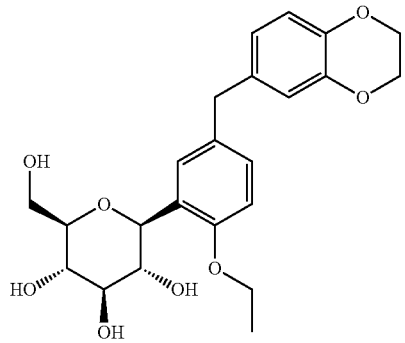 [SMILES: CCOc1ccc(Cc2ccc3c(c2)OCCO3)cc1[C@@H]1O[C@H](CO)[C@@H](O)[C@H](O)[C@H]1O]<br>2S,3R,4R,5S,6R)-2-[5-(2,3-Dihydro-benzo[1,4]dioxin-6-ylmethyl)-2-ethoxy-phenyl]-6-hydroxymethyl-tetrahydro-pyran-3,4,5-triol | $^1$H NMR (400 MHz, CD$_3$OD): δ 1.38 (t, J = 6.8 Hz, 3H), 3.25-3.28 (m, 1H), 3.36-3.47 (m, 2H), 3.56-3.67 (m, 3H), 3.76 (s, 2H), 3.84 (d, J = 11.6 Hz, 1H), 4.01-4.05 (m, 2H), 4.17 (s, 3H), 4.65 (d, J = 8.4 Hz, 1H), 6.62 (d, J = 6.4 Hz, 2H), 6.69 (d, J = 8.8 Hz, 1H), 6.86 (d, J = 2.1 Hz, 1H), 7.04 (d, J = 8.4 Hz, 1H), 7.24 (s, 1H). MS (ES) m/z 449.9 (M + 18). |
| 31 | 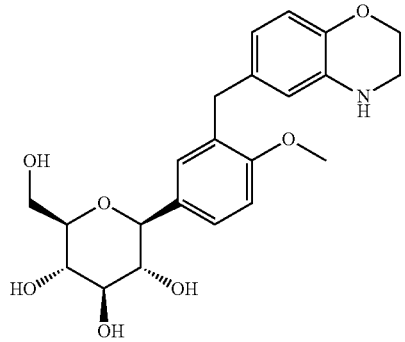 [SMILES: COc1ccc([C@@H]2O[C@H](CO)[C@@H](O)[C@H](O)[C@H]2O)cc1Cc1ccc2c(c1)NCCO2]<br>(2S,3R,4R,5S,6R)-2-[3-(3,4-Dihydro-2H-benzo[1,4]oxazin-6-ylmethyl)-4-methoxy-phenyl]-6-hydroxymethyl-tetrahydro-pyran-3,4,5-triol | $^1$H NMR (400 MHz, CD$_3$OD): δ 3.25-3.28 (m, 1H), 3.3-3.88 (m, 3H), 3.67-3.75 (m, 2H), 3.76 (d, J = 10.8 Hz, 1H), 3.79 (s, 3H), 3.80-3.88 (m, 2H), 4.02 (d, J = 9.2 Hz, 1H), 4.13 (t, J = 4.4 Hz, 2H), 6.43 (dd, J = 8.0 & 1.6 Hz, 2H), 6.46 (s, 1H), 6.53 (d, J = 8.0 Hz, 1H), 6.90 (d, J = 4.8 Hz, 1H), 7.14 (d, J = 2.0 Hz, 1H), 7.22 (dd, J = 8.4 & 2.0 Hz, 1H). MS (ES) m/z 418.0 (M + 1). |

| Example No. | Structure/IUPAC name | Spectral data |
|---|---|---|
| 32 | 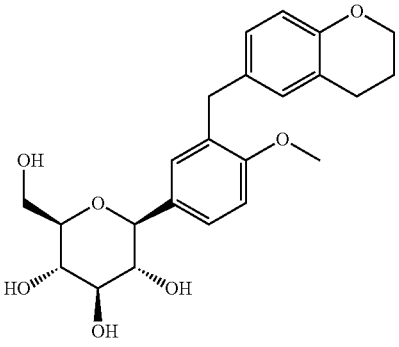 [SMILES: COc1ccc([C@@H]2O[C@H](CO)[C@@H](O)[C@H](O)[C@H]2O)cc1Cc1ccc2c(c1)CCCO2]<br>(2S,3R,4R,5S,6R)-2-(3-Chroman-6-ylmethyl-4-methoxy-phenyl)-6-hydroxymethyl-tetrahydro-pyran-3,4,5-triol | $^1$H NMR (400 MHz, CD$_3$OD): δ 1.94-1.97 (m, 2H), 2.71 (t, J = 6.4 Hz, 2H), 3.27-3.28 (m, 1H), 3.31-3.44 (m, 3H), 3.66-3.70 (m, 1H), 3.75 (d, J = 6.4 Hz, 1H), 3.81 (s, 3H), 3.83-3.89 (m, 3H), 4.04 (d, J = 9.2 Hz, 1H), 4.11 (t, J = 5.2 Hz, 1H), 6.58 (d, J = 8.0 Hz, 1H), 6.85-6.89 (m, 2H), 6.92 (d, J = 8.4 Hz, 1H), 7.16 (d, J = 2.0 Hz, 1H), 7.25 (dd, J = 8.4 & 2.4 Hz, 1H).<br>MS (ES) m/z 434.1 (M + 18). |
| 33 | 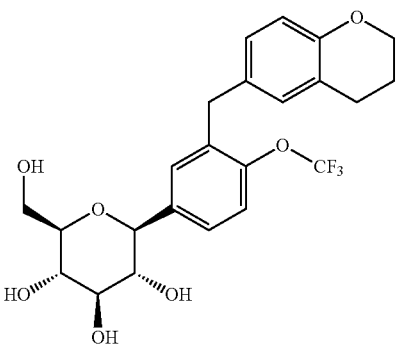 [SMILES: OC[C@H]1O[C@@H](c2ccc(OC(F)(F)F)c(Cc3ccc4c(c3)CCCO4)c2)[C@H](O)[C@@H](O)[C@@H]1O]<br>(2S,3R,4R,5S,6R)-2-(3-Chroman-6-ylmethyl-4-trifluoromethoxy-phenyl)-6-hydroxymethyl-tetrahydro-pyran-3,4,5-triol | $^1$H NMR (400 MHz, CD$_3$OD): δ 1.91-1.97 (m, 2H), 2.71 (t, J = 6.8 Hz, 2H), 3.20-3.28 (m, 1H), 3.35-3.44 (m, 3H), 3.66-3.70 (m, 1H), 3.84-3.94 (m, 3H), 4.09-4.11 (m, 3H), 6.60 (d, J = 8.0 Hz, 1H), 6.84 (d, J = 8.3 Hz, 2H), 7.23 (dd, J = 8.4 & 1.2 Hz, 1H), 7.33 (d, J = 6.0 Hz, 1H), 7.36 (dd, J = 2.0 & 8.4 Hz, 1H).<br>MS (ES) m/z 471.0 (M + 1). |

Examples 34-35

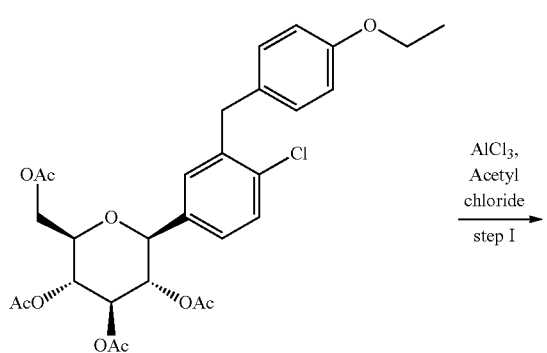

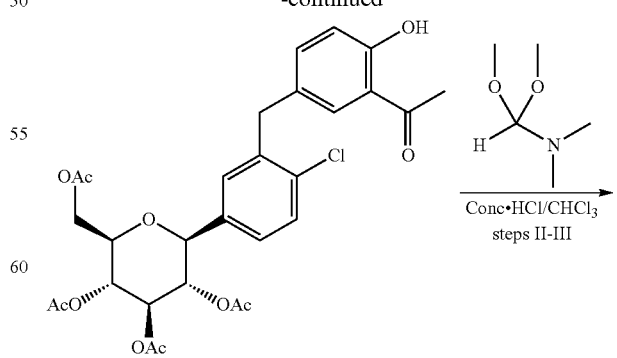

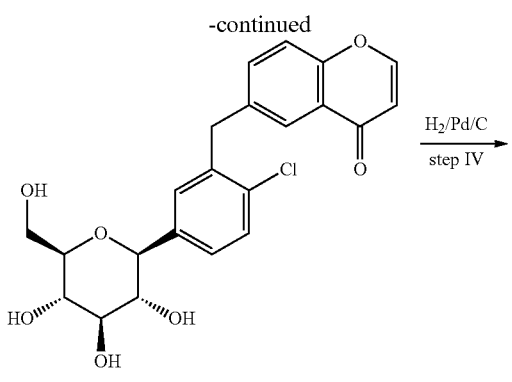

Ex. 34

Ex. 35

Step I:

To a stirred solution of acetic acid (2R,3R,4R,5S,6S)-3,4,5-triacetoxy-6-[4-chloro-3-(4-ethoxy-benzyl)-phenyl]-tetrahydro-pyran-2-ylmethyl ester (13.00 g, 22.56 mmol) prepared using the procedures described in J. Med. Chem. 2008, 51(5), 1145-49, in 1,2-dichloroethane (130 mL) was added acetyl chloride at 0° C. Subsequently, AlCl₃ (9.03 g, 67.68 mmol) was added over 30 min at a rate to ensure that the temperature did not exceed 4° C. After 1 h, the reaction mixture was taken to room temperature and stirred at 50° C. overnight. The reaction was quenched by pouring over ice and the resulting suspension was diluted with water (100 mL) and extracted with dichloromethane (100×2 mL). The organic layer was washed with water (50 mL), brine (50 mL) and dried over anhydrous sodium sulfate. Solvent was removed under reduced pressure to get a crude product (12 g).

¹H NMR (400 MHz, CD₃OD): δ 1.70 (s, 3H), 1.97 (s, 3H), 2.0 (s, 6H), 2.61 (s, 3H), 3.96-4.0 (m, 1H), 4.07-4.17 (m, 3H), 4.31 (dd, J=12.4 Hz, 4.9 Hz, 1H), 4.54 (d, J=9.8 Hz, 1H), 5.03 (t, J=9.8 Hz, 1H), 5.16 (t, J=9.5 Hz, 1H), 5.37 (t, J=9.5 Hz, 1H), 6.88 (d, J=8.5 Hz, 1H), 7.26 (dd, J=8.3 Hz, 1.95 Hz, 1H), 7.32-7.39 (m, 2H), 7.40 (d, J=8.3 Hz, 1H), 7.68 (d, J=2.2 Hz, 1H).

MS (ES) m/z 590.9 (M+1)

Step II:

To acetic acid (2R,3R,4R,5S,6S)-3,4,5-triacetoxy-6-[3-(3-acetyl-4-hydroxy-benzyl)-4-chloro-phenyl]-tetrahydro-pyran-2-ylmethylester (12.00 g, 20.32 mmol) was added N,N-dimethyl formamide dimethyl acetal (3.0 mL, 22.35 mmol). The reaction mixture was stirred at 90° C. overnight. The reaction was quenched by the addition of water (30 mL) and extracted with ethyl acetate (150 mL×3), solvent was removed under reduced pressure to get a crude product (8.12 g). The crude product was used for next reaction without any purification.

MS (ES) m/z 477.9 (M+1)

Example 34: 6-[2-chloro-5-((2S,3R,4R,5S,6R)-3,4,5-trihydroxy-6-hydroxymethyl-tetrahydro-pyran-2-yl)-benzyl]-chromen-4-one Step III:

To (E)-1-{5-[2-Chloro-5-((2S,3R,4R,5S,6R)-3,4,5-trihydroxy-6-hydroxymethyl-tetrahydro-pyran-2-yl)-benzyl]-2-hydroxy-phenyl}-3-dimethylamino-propenone (8.00 g, 16.77 mmol) in chloroform (80 mL) was added conc. HCl (3 mL). The reaction mixture was refluxed overnight. The reaction was quenched by the addition of water (50 mL) and extracted with ethyl acetate (150 mL×3), solvent was removed under reduced pressure to get a crude product (4.0 g).

¹H NMR (400 MHz, CD₃OD): δ 3.28-3.47 (m, 5H), 3.70 (dd, J=12.0 Hz, 7.5 Hz, 1H), 3.90 (d, J=11.5 Hz, 1H), 4.14 (d, J=9.5 Hz, 1H), 4.26 (d, J=3.9 Hz, 1H), 6.35 (d, J=5.8 Hz, 1H), 7.34-7.41 (m, 2H), 7.45 (d, J=2.0 Hz, 1H), 7.53 (d, J=8.8 Hz, 1H), 7.65 (dd, J=8.8 Hz, 2.2 Hz, 1H), 7.93 (d, J=2.2 Hz, 1H), 8.16 (d, J=5.8 Hz, 1H).

MS (ES) m/z 432.8 (M+1)

Example 35: 6-[2-Chloro-5-((2S,3R,4R,5S,6R)-3,4,5-trihydroxy-6-hydroxymethyl-tetrahydro-pyran-2-yl)-benzyl]-chroman-4-one Step IV:

To a stirred solution of 6-[2-chloro-5-((2S,3R,4R,5S,6R)-3,4,5-trihydroxy-6-hydroxymethyl-tetrahydro-pyran-2-yl)-benzyl]-chromen-4-one (0.10 g, 0.2315 mmol) in ethyl acetate (2.5 mL) was added 10% Palladium on C (20 mg, 20% w/w) followed by methanol (2.5 mL). After stirring for 18 h under hydrogen atmosphere, the reaction mixture was filtered through celite and concentrated to furnish the crude product, which was further purified by Preparative HPLC to yield the title compound (41 mg)

¹H NMR (400 MHz, CD₃OD): δ 2.78 (t, J=6.6 Hz, 2H), 3.27-3.49 (m, 4H), 3.71 (dd, J=12.0 Hz, 7.5 Hz, 1H), 3.90 (d, J=11.5 Hz, 1H), 4.04-4.13 (m, 3H), 4.51 (t, J=7.0 Hz, 2H), 6.92 (d, J=8.5 Hz, 1H), 7.30-7.41 (m, 4H), 7.65 (d, J=2.2 Hz, 1H).

MS (ES) m/z 434.9 (M+1)

Example 36: (2S,3R,4R,5S,6R)-2-[4-Chloro-3-(4-hydroxy-chroman-6-ylmethyl)-phenyl]-6-hydroxymethyl-tetrahydro-pyran-3,4,5-triol

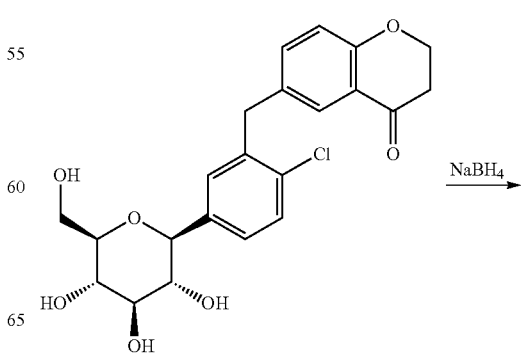

97

-continued

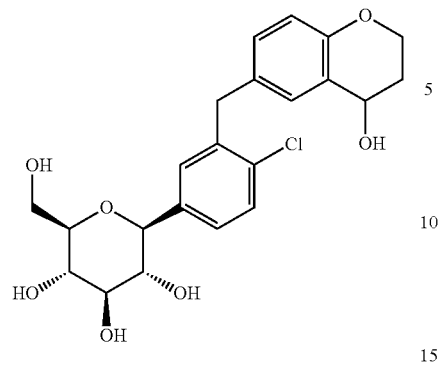

To a solution of 6-[2-chloro-5-((2S,3R,4R,5S,6R)-3,4,5-trihydroxy-6-hydroxymethyl-tetrahydro-pyran-2-yl)-benzyl]-chroman-4-one (0.1 g, 0.23 mmol) in methanol (3 mL) was added sodium borohydride (0.017 g, 0.46 mmol). The reaction mixture was stirred for 2 h and quenched by the addition of water (10 mL) and extracted with ethyl acetate (150 mL×3), solvent was removed under reduced pressure to get crude (2S,3R,4R,5S,6R)-2-[4-chloro-3-(4-hydroxy-chroman-6-ylmethyl)-phenyl]-6-hydroxymethyl-tetrahydro-pyran-3,4,5-triol which was further purified by preparative HPLC (Yield=30 mg).

$^1$H NMR (400 MHz, CD$_3$OD): δ 1.95-2.06 (m, 2H), 3.26-3.46 (m, 5H), 3.68 (dd, J=11.9 Hz, 5.1 Hz, 1H), 3.87 (d, J=11.5 Hz, 1H), 3.97-4.02 (m, 1H), 4.08 (d, J=9.2 Hz, 1H), 4.15-4.20 (m, 2H), 4.65 (t, J=4.4 Hz, 1H), 6.66 (d, J=8.3 Hz, 1H), 7.00 (d, J=8.8 Hz, 1H), 7.15 (s, 1H), 7.23-7.32 (m, 2H), 7.33 (d, J=8.3 Hz, 1H).

MS (ES) m/z 453.9 (M+18)

Example 37: (2S,3R,4R,5S,6R)-2-[4-Chloro-3-(spiro[chromane-2,1'-cyclopentane]-6-ylmethyl)phenyl]-6-(hydroxymethyl)tetrahydropyran-3,4,5-triol

98

-continued

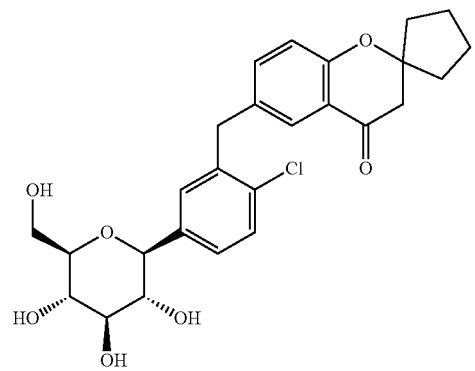

Step I:

To the acetic acid (2R,3R,4R,5S,6S)-3,4,5-triacetoxy-6-[3-(3-acetyl-4-hydroxy-benzyl)-4-chloro-phenyl]-tetrahydro-pyran-2-ylmethylester (0.1 g, 0.17 mmol) was added cyclopentanone (0.015 mL, 0.17 mmol) followed by pyrrolidine (0.056 mL, 0.34 mmol). The reaction mixture was subjected to microwave irradiation for 4 min. Reaction mixture was quenched with water (3 mL), extracted with ethyl acetate (5 mL×3), and solvent was removed under reduced pressure to get a crude product (0.1 g) which was used for next reaction as such.

Step II:

To a stirred solution of the crude product obtained in step 1 in THF:MeOH (3:2, 5 mL) was added lithium hydroxide (0.02 g, 0.52 mmol) in water (1 mL). The reaction mixture was stirred for 3 h at room temperature, diluted with water (3 mL), extracted with ethyl acetate (5 mL×3), solvent was removed under reduced pressure to get a crude product, which was purified by column chromatography to yield the title compound (20 mg).

$^1$H NMR (400 MHz, CD$_3$OD): δ 1.64-1.86 (m, 6H), 2.00-2.04 (m, 2H), 2.81 (s, 2H), 3.26-3.47 (m, 4H), 3.69 (dd, J=11.7 Hz, 4.9 Hz, 1H), 3.87 (d, J=11.9 Hz, 1H), 4.02-4.12 (m, 3H), 6.85 (d, J=8.3 Hz, 1H), 7.29-7.39 (m, 4H), 7.60 (d, J=2.0 Hz, 1H).

MS (ES) m/z 489.4 (M+1)

Example 38: (2S,3R,4R,5S,6R)-2-[4-Chloro-3-(spiro[chromane-2,1'-cyclopentane]-6-ylmethyl)phenyl]-6-(hydroxymethyl)tetrahydropyran-3,4,5-triol

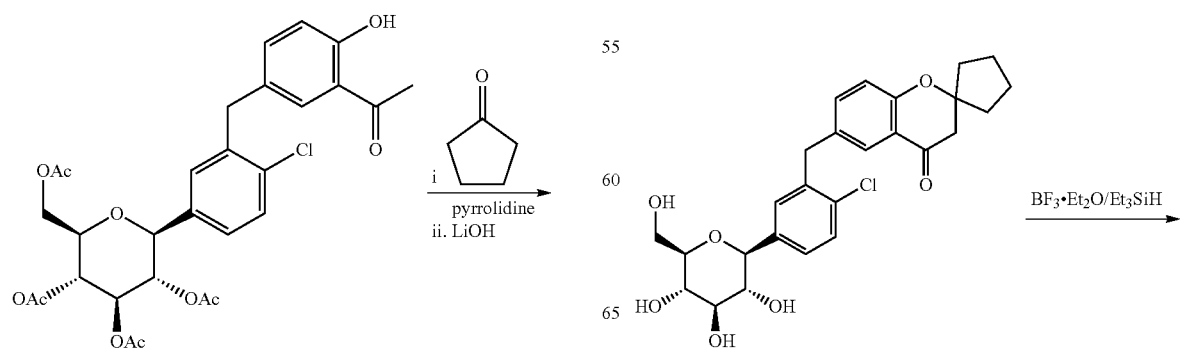

Example 40-41

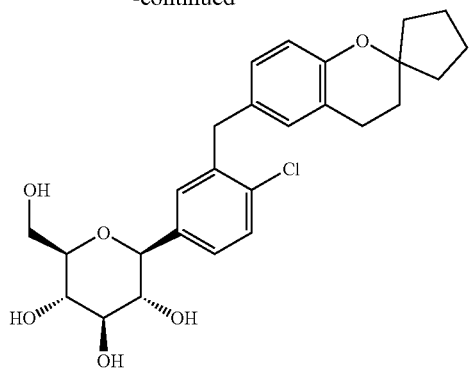

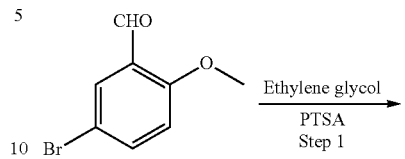
Step 1

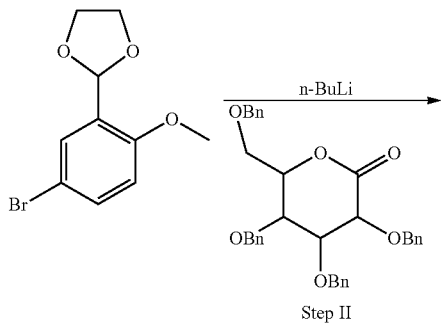
Step II

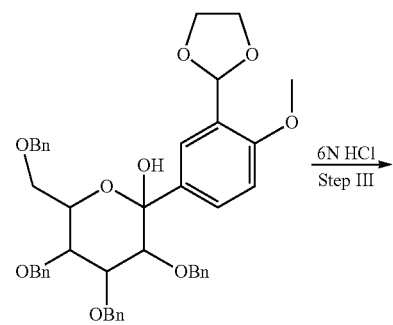
Step III

To 6-[2-chloro-5-((2S,3R,4R,5S,6R)-3,4,5-trihydroxy-6-hydroxymethyl-tetrahydro-pyran-2-yl)-benzyl]-2,2-spirocyclopentyl-chroman-4-one (0.125 g, 0.26 mmol) in acetonitrile/1,2-dichloroethane (1:1 mixture, 2 mL) was added triethylsilane (0.15 mL, 1 mmol) followed by borontrifluoride diethyletherate (0.06 mL, 0.5 mmol) at 0° C. The reaction mixture was stirred at room temperature for 18 h and then heated to 60° C. for 2 h, quenched with saturated NaHCO₃ (5 mL) extracted with dichloromethane (10 mL×3), solvent was removed under reduced pressure to get the crude product which was further purified by preparative HPLC to yield the title compound (Yield=5 mg).

¹H NMR (400 MHz, CD₃OD): δ 1.61-1.70 (m, 6H), 1.86-1.89 (m, 6H), 2.75 (t, J=6.6 Hz, 2H), 3.27-3.46 (m, 2H), 3.68-3.71 (m, 1H), 3.88 (d, J=11.4 Hz, 1H), 3.99 (q, J=15.1 Hz, 2H), 4.11 (d, J=9.3 Hz, 1H), 6.59 (d, J=8.8 Hz, 1H), 6.88-6.90 (m, 2H), 7.28 (d, J=7.8 Hz, 1H), 7.33-7.36 (m, 2H).

MS (ES) m/z 475.0 (M+1)

Following example was prepared by using the analogous procedures described for example 38.

| Example No. | Structure/IUPAC name | Spectral data |
|---|---|---|
| 39 | 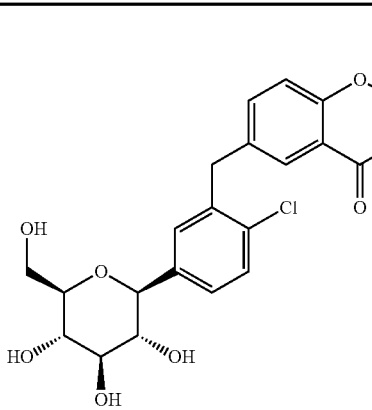

6-[[2-Chloro-5-[(2S,3R,4R,5S,6R)-3,4,5-trihydroxy-6-(hydroxymethyl)tetrahydropyran-2-yl]phenyl]methyl]spiro[chromane-2,4'-piperidine]-4-one | ¹H NMR (400 MHz, CD₃OD): δ 1.85-1.95 (m, 2H), 2.25 (d, J = 14 Hz, 2H), 2.82 (s, 2H), 3.25-3.47 (m, 9H), 3.69 (dd, J = 11.7 & 4.6 Hz, 1H), 3.87 (d, J = 11.5 Hz, 1H), 4.03-4.12 (m, 2H), 7.03 (d, J = 8.5 Hz, 1H), 7.29-7.47 (m, 3H), 7.45 (d, J = 8.5 Hz, 1H), 7.64 (s, 1H).
MS (ES) m/z 503.9 (M + 1) |

-continued

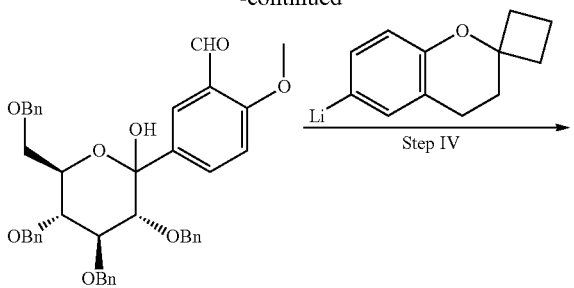

Step IV →

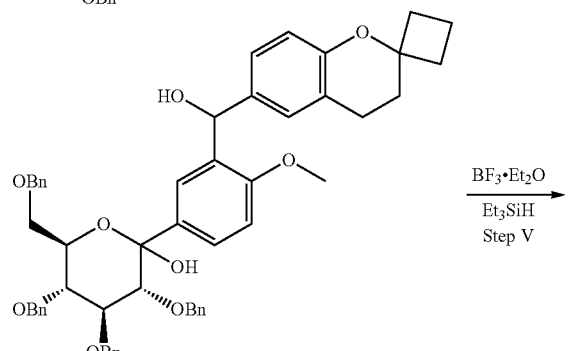

BF₃·Et₂O
Et₃SiH
Step V →

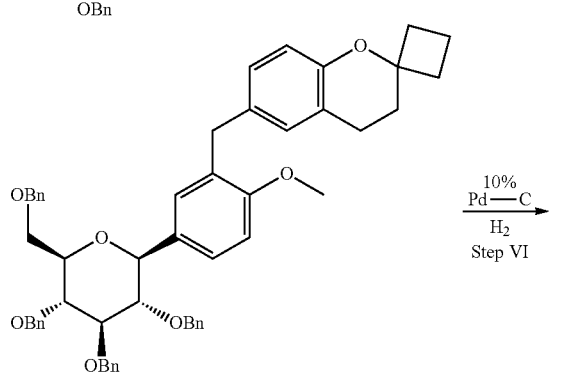

10% Pd—C
H₂
Step VI →

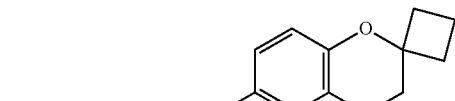

Ex. 40

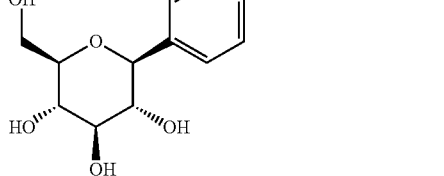

Ex. 41

Step I:

To a stirred solution of 5-bromo-2-methoxybenzaldehyde (5.0 g, 23.25 mmol) in toluene (50 mL) was added ethylene glycol (2.6 mL, 46.5 mmol) and p-toluenesulfonic acid monohydrate (0.45 g, 2.32 mmol) and the reaction mixture was azeotroped for 2 h, quenched with sat. NaHCO₃ (50 mL). Reaction mixture was concentrated under reduced pressure, extracted with ethyl acetate (2×100 mL), washed with water, brine, dried over sodium sulfate, concentrated and purified by silica gel column chromatography to furnish 2-(5-bromo-2-methoxy-phenyl)-[1,3]dioxolane (3.75 g).

Step II:

To a stirred solution of compound prepared in step I (3.50 g, 13.51 mmol) in THF (20 mL) was added n-butyl lithium (8.5 mL, 13.51 mmol) at −78° C. and stirred for 1 h. Ttetra-OBn-glucaranolactone (7.25 g, 13.51 mmol) in toluene (20 mL) was cooled to −78° C. and lthium salt prepared above was added to this at −78° C. and stirred for 1 h, quenched with sat. NH₄Cl soln. (10 mL) and extracted with ethyl acetate (2×70 mL). The ethyl acetate layer was washed with water, brine, dried over sodium sulphate, concentrated and purified by silica gel column chromatography to furnish (3R,4S,5R,6R)-3,4,5-Tris-benzyloxy-6-benzyloxymethyl-2-(3-[1,3]dioxolan-2-yl-4-methoxy-phenyl)-tetrahydro-pyran-2-ol (4.8 g).

Step III:

To a stirred solution of compound prepared in step II (4.80 g, 6.68 mmol) in THF (20 mL) was added 6N HCl (10 mL) and stirred for 16 h. This reaction mixture was concentrated under reduced pressure, diluted with ethyl acetate (100 mL) washed with sat. NH₄Cl (20 mL), dried over sodium sulfate, concentrated and purified by silica gel column chromatography to furnish 2-Methoxy-5-((3R,4S,5R,6R)-3,4,5-tris-benzyloxy-6-benzyloxymethyl-2-hydroxy-tetrahydro-pyran-2-yl)-benzaldehyde (3.2 g).

Step IV:

To a stirred solution of 6-bromospiro[chromane-2,1′-cyclobutane] (0.563 g, 2.23 mmol) in THF (3 mL) at −78° C. was added n-butyl lithium (1.45 mL, 2.23 mmol) and stirred for 1 h. Compound obtained in step III (0.3 g, 0.45 mmol) in toluene (3 mL) was cooled to −78° C. and lthium salt prepared above was added to this at −78° C. This reaction mixture was stirred for 1 h, quenched with sat. NH₄Cl (10 mL) and extracted with ethyl acetate (2×20 mL). The ethyl acetate layer was washed with water, brine, dried over sodium sulphate, concentrated and purified by silica gel column chromatography to furnish [2-methoxy-5-[(3R,4S,5R,6R)-3,4,5-tribenzoyloxy-6-(benzyloxymethyl)-2-hydroxytetrahydropyran-2-yl]phenyl]-spiro[chromane-2,1′-cyclobutane]-6-yl-methanone (0.250 g).

Example 40: 6-(2-Methoxy-5-((2S,3S,4R,5R,6R)-3,4,5-tris(benzyloxy)-6(benzyloxymethyl)tetrahydro-2H-pyran-2-yl)benzyl)spiro[chroman-2,1′-cyclobutane Step V:

To a stirred solution of compound obtained in step IV (0.250 g, 0.29 mmol) in DCE (2 mL) and acetonitrile (2 mL) at −30° C. was added triethylsilane (0.28 g, 1.03 mmol) followed by borntrifluoride.diethyletherate (0.13 g, 1.76 mmol) and stirred at −30° C. for 5 h and then at 25° C. for 16 h. Reaction was quenched with sat. NaHCO₃ (20 mL), the volatiles were evaporated under reduced pressure; the resulting mixture was extracted with dichloromethane (2×20 mL), washed with brine (5 mL), dried over sodium sulfate, concentrated and purified by silica gel column chromatography to furnish the titled compound (Yield=0.21 g,).

Example 41: (2S,3R,4R,5S,6R)-2-[4-methoxy-3-(spiro[chromane-2,1′-cyclobutane]-6-ylmethyl)phenyl]-6-(hydroxymethyl)tetrahydropyran-3,4,5-triol Step VI:

To a stirred solution of (0.21 g, 0.25 mmol) in ethyl acetate (5 mL) was added Palladium on C 10% w/w (50 mg) followed by a drop of conc.HCl was added. The reaction was stirred for 18 h under hydrogen atmosphere. Reaction mixture was filtered through celite and concentrated to furnish the crude titled compound which was purified by preparative HPLC (22 mg).

Following examples were prepared by using the analogous procedures described for examples 40-41.

| Example No. | Structure/IUPAC name | Spectral data |
|---|---|---|
| 42 | 7-[2-Chloro-5-((2S,3R,4R,5S,6R)-3,4,5-trihydroxy-6-hydroxymethyl-tetrahydro-pyran-2-yl)-benzyl]-4H-benzo[1,4]oxazin-3-one | $^1$H NMR (400 MHz, DMSO-D6): δ 3.09-3.26 (m, 3H), 3.43-3.46 (m, 1H), 3.66-3.71 (m, 1H), 3.92-3.97 (m, 2H), 4.00 (d, J = 9.2 Hz, 1H), 4.10-4.12 (m, 1H), 4.46 (t, J = 6.0 Hz, 1H), 4.52 (s, 2H), 4.86 (d, J = 6.0 Hz, 1H), 4.97-4.97 (m, 2H), 6.76-6.80 (m, 3H), 7.24 (dd, J = 8.0 Hz, 1.6 Hz, 1H), 7.34 (d, J = 1.6 Hz, 1H), 7.38 (d, J = 8.0 Hz, 1H), 10.64 (s, 1H). MS (ES) m/z 436.0 (M + 1). |
| 43 | 7-[2-Methoxy-5-((2S,3R,4R,5S,6R)-3,4,5-trihydroxy-6-hydroxymethyl-tetrahydro-pyran-2-yl)-benzyl]-4H-benzo[1,4]oxazin-3-one | $^1$H NMR (400 MHz, CD$_3$OD): δ 3.30-3.44 (m, 5H), 3.67 (dd, 1H), 3.79 (s, 3H), 3.80-3.86 (m, 2H), 4.04 (d, J = 9.0 Hz, 1H), 4.49 (s, 2H), 6.73-6.90 (m, 3H), 6.91 (d, J = 8.0 Hz, 1H), 7.18 (s, 1H), 7.25 (dd, J = 8.31, 1.7 Hz, 1H) MS (ES) m/z 432.1 (M + 1) |
| 44 | (2S,3R,4R,5S,6R)-2-[4-chloro-3-(spiro[chromane-2,1'-cyclobutane]-6-ylmethyl)phenyl]-6-(hydroxymethyl)tetrahydropyran-3,4,5-triol | $^1$H NMR (400 MHz, DMSO-D6): δ 1.88 (t, J = 6.4 Hz, 2H), 1.99-2.05 (m, 2H), 2.09-2.13 (m, 2H), 2.70 (t, J = 6.8 Hz, 2H), 3.11-3.27 (m, 5H), 3.39-3.47 (m, 2H), 3.68-3.71 (m, 1H), 3.88-3.97 (m, 2H), 3.99 (d, J = 9.2 Hz, 1H), 4.46 (t, J = 5.6 Hz, 1H), 4.85 (d, J = 6.0 Hz, 1H), 4.96-4.98 (m, 2H), 6.63 (d, J = 8.8 Hz, 1H), 6.86-6.88 (m, 2H), 7.23 (dd, J = 8.4 Hz, 2.0 Hz, 1H), 7.32 (d, J = 2.0 Hz, 1H), 7.38 (d, J = 8.0 Hz, 1H), MS (ES) m/z 461.0 (M + 1) |

Example 45-46

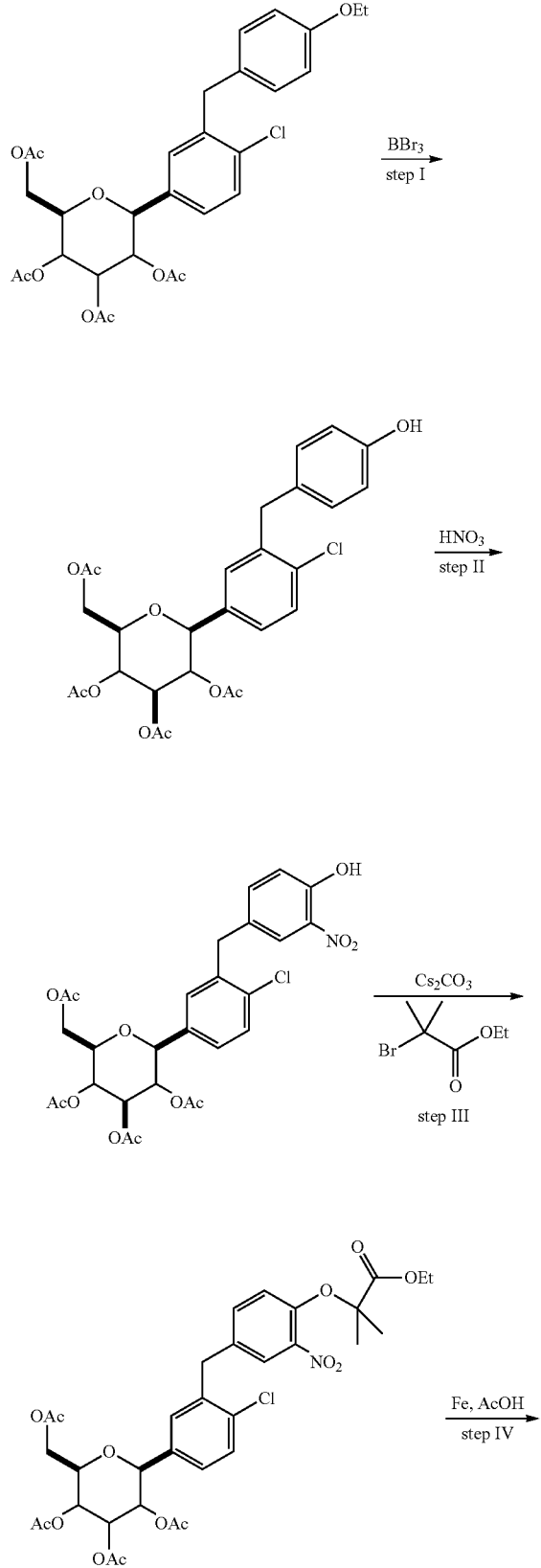

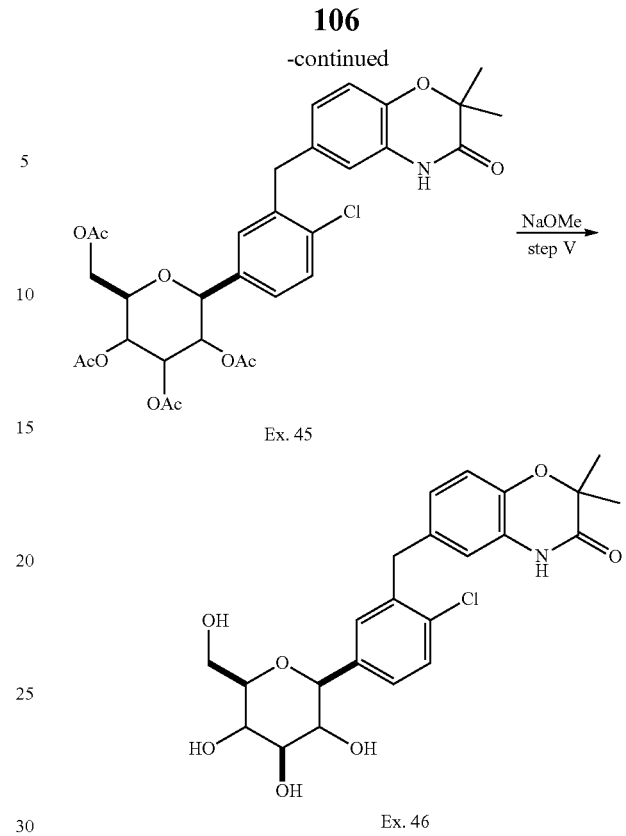

Step I:

To a stirred solution of acetic acid (2R,3R,4R,5S,6S)-3,4,5-triacetoxy-6-[4-chloro-3-(4-ethoxy-benzyl)-phenyl]-tetrahydro-pyran-2-ylmethyl ester (4.0 g, 6.93 mmol) prepared using the procedures described in *J. Med. Chem.* 2008, 51(5), 1145-49, in dichloromethane (40 mL) was added 1 molar solution of $BBr_3$ (34.6 mL, 34.6 mmol) at −78° C. under nitrogen atmosphere. Reaction was stirred at −78° C. for 1.5 h and −30° C. for 1 h. Reaction mixture was poured over ice and neutralized with sat. $NaHCO_3$ (20 mL), extracted with dichloromethane, concentrated and purified by silica gel column chromatography to furnish acetic acid (2R,3R,4R,5S,6S)-3,4,5-triacetoxy-6-[4-chloro-3-(4-hydroxy-benzyl)-phenyl]-tetrahydro-pyran-2-ylmethyl ester (2.9 g).

Step II:

To a stirred solution of compound prepared in step I (2 g, 3.64 mmol) in dichloroethane (20 mL) was added TBAB (117 mg, 0.364 mmol), 6% aqueous nitric acid (20 mmol) at 0-5° C. and stirred at room temperature for 4 h. Organic layer was separated, washed with water and brine and concentrated to furnish crude acetic acid (2R,3R,4R,5S,6S)-3,4,5-triacetoxy-6-[4-chloro-3-(4-hydroxy-3-nitro-benzyl)-phenyl]-tetrahydro-pyran-2-ylmethyl ester which was further purified by column chromatography (1.5 g)

Step III:

To a stirred solution of compound prepared in step 11 (0.70 g, 1.178 mmol) in anhydrous acetonitrile (10 mL) was added anhydrous $Cs_2CO_3$ (1.5 g, 4.71 mmol) and 2-bromo-2-methyl-propionic acid ethyl ester (0.6 mL, 5.89 mmol). Reaction was heated to reflux under nitrogen atmosphere for 15 h. Additional amount of 2-bromo-2-methyl-propionic acid ethyl ester (0.6 mL, 5.89 mmol) was added at room temperature and heating continued for 15 h. Reaction mixture was filtered, residue was washed with anhydrous acetonitrile and concentrated to obtain crude product, which contains varying amounts of products resulting from partial hydrolyses of acetates. The crude product was reacetylated by using acetic anhydride, pyridine and DMAP in dichloromethane. Reaction was quenched with aq. ammonium chloride, extracted with ethyl acetate (2×20 mL), washed with dil HCl, water, dried over sodium sulfate, concentrated and purified by column chromatography furnished 2-{4-[2-Chloro-5-((2S,3S,4R,5R,6R)-3,4,5-triacetoxy-6-acetoxymethyl-tetrahydro-pyran-2-yl)-benzyl]-2-nitro-phenoxy}-2-methyl-propionic acid ethyl ester (515 mg).

Example 45: [(2R,3R,4R,5S,6S)-3,4,5-triacetoxy-6-[4-chloro-3-[(2,2-dimethyl-3-oxo-4H-1,4-benzoxazin-6-yl)methyl]phenyl]tetrahydropyran-2-yl] methyl acetate Step IV:
To a stirred solution of compound prepared in step III (515 mg, 0.73 mmol) in glacial acetic acid (8 mL) was added iron powder (400 mg, 7.1 mmol) and stirred at 60° C. overnight. Reaction mixture was cooled to room temperature, diluted with EtOAc (15 mL) and filtered through celite. Filtrate was concentrated and purified by column chromatography to furnish [(2R,3R,4R,5S,6S)-3,4,5-triacetoxy-6-[4-chloro-3-[(2,2-dimethyl-3-oxo-4H-1,4-benzoxazin-6-yl)methyl]phenyl]tetrahydropyran-2-yl]methyl acetate (365 mg)

Example 46: 6-[2-Chloro-5-((2S,3R,4R,5S,6R)-3,4,5-trihydroxy-6-hydroxymethyl-tetrahydro-pyran-2-yl)-benzyl]-2,2-dimethyl-4H-benzo[1,4]oxazin-3-one Step V:
To a stirred solution of compound prepared in step IV (141 mg, 0.22 mmol) in methanol (6 mL) was added NaOMe (70 mg, 1.29 mmol) and stirred at room temperature for 3 h. The solvent was evaporated and the crude product was purified by silica gel column chromatography to obtain the title compound (50 mg)
$^1$H NMR (400 MHz, CD$_3$OD): δ 1.42 (s, 6H), 3.27-2.49 (m, 4H), 3.63-3.73 (m, 1H), 3.86-3.92 (m, 1H), 4.04 (d, J=5.2 Hz, 2H), 4.09-4.14 (m, 1H), 6.70-6.74 (m, 1H), 6.81-6.85 (m, 2H), 7.28-7.33 (m, 1H), 7.35-7.40 (m, 2H)
MS (ES) m/z 464.0 (M+1)
Following example was prepared by using the analogous procedures described for examples 45-46.

Example 48-49

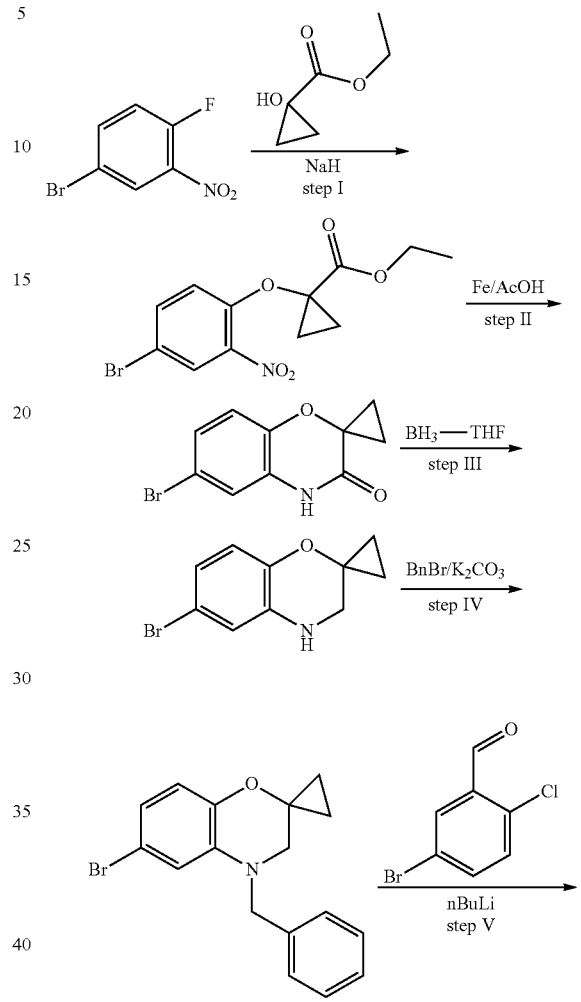

| Example No. | Structure/IUPAC name | Spectral data |
|---|---|---|
| 47 | 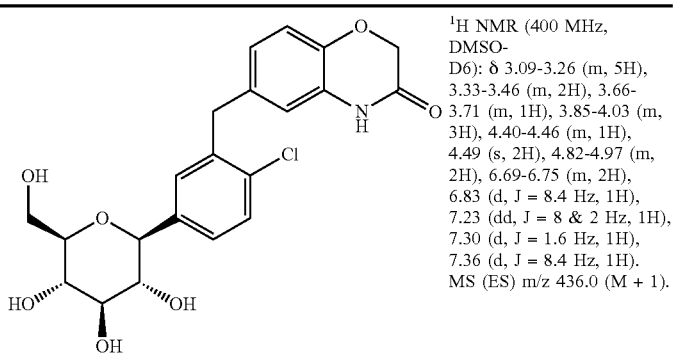<br>6-(2-chloro-5-((2S,3R,4R,5S,6R)-3,4,5-trihydroxy-6-(hydroxymethyl)tetrahydro-2H-pyran-2-yl)benzyl)-2H-benzo[b][1,4]oxazin-3(4H)-one | $^1$H NMR (400 MHz, DMSO-D6): δ 3.09-3.26 (m, 5H), 3.33-3.46 (m, 2H), 3.66-3.71 (m, 1H), 3.85-4.03 (m, 3H), 4.40-4.46 (m, 1H), 4.49 (s, 2H), 4.82-4.97 (m, 2H), 6.69-6.75 (m, 2H), 6.83 (d, J = 8.4 Hz, 1H), 7.23 (dd, J = 8 & 2 Hz, 1H), 7.30 (d, J = 1.6 Hz, 1H), 7.36 (d, J = 8.4 Hz, 1H). MS (ES) m/z 436.0 (M + 1). |

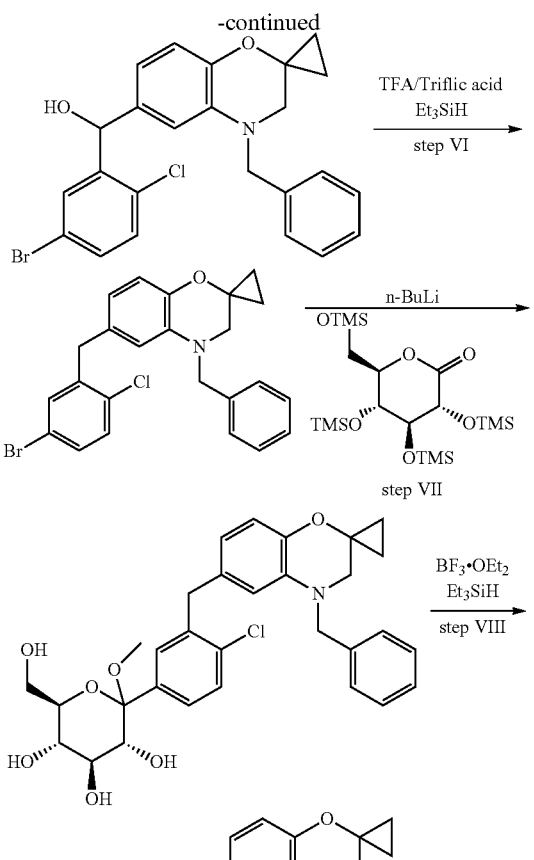

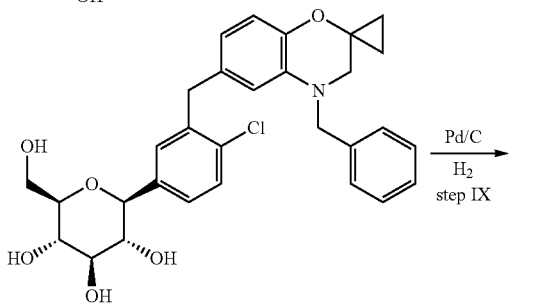

dried over anhydrous sodium sulfate, concentrated and purified by silica gel column chromatography to give 1-(4-bromo-2-nitro-phenoxy)-cyclopropanecarboxylic acid ethyl ester (3.51 g).

$^1$H NMR (400 MHz, CDCl$_3$): δ 1.20 (t, J=6.8 Hz, 3H), 1.95-1.42 (m, 2H), 1.65-1.69 (m, 2H), 4.19 (q, J=6.8 Hz, 2H), 7.05 (d, J=8.8 Hz, 1H), 7.58 (dd, J=8.8, 2.8 Hz, 1H), 7.96 (d, J=2.4 Hz, 1H).

MS (ES) m/z 329.9 (M+1).

Step II.

To a stirred solution of 1-(4-bromo-2-nitro-phenoxy)-cyclopropanecarboxylic acid ethyl ester (3.5 g, 10.6 mmol) in glacial acetic acid (40 mL) was added iron powder (5.9 g, 106.1 mmol) at room temperature and the reaction mixture was heated at 60° C. for 3 h. The mixture was cooled to room temperature, diluted with ethyl acetate, and filtered through celite bed. The filtrate was concentrated, and the resulting residue was taken in ethyl acetate and washed with water and saturated sodium bicarbonate solution, then the organic layer was dried over sodium sulfate, concentrated and the resulting residue was purified by silica gel column chromatography to furnish 6-bromospiro[4H-1,4-benzoxazine-2,1'-cyclopropane]-3-one (2.51 g).

$^1$H NMR (400 MHz, DMSO-d$_6$): δ 1.14-1.25 (m, 4H), 6.82 (d, J=8.4 Hz, 1H), 7.03-7.06 (m, 2H), 10.86 (s, 1H).

MS (ES) m/z 256.2 (M+1).

Step III.

To a stirred solution of 6-bromospiro[4H-1,4-benzoxazine-2,1'-cyclopropane]-3-one (2.6 g, 10.2 mmol) in THF (20 mL) was added 1 M solution of borane-tetrahydrofuran complex in THF (51.0 mL, 51.2 mmol). After refluxing for 6 h, the reaction mixture was cooled to room temperature and quenched by the addition of methanol. Volatiles were evaporated under reduced pressure, and the resulting residue was taken up in ethyl actate and washed with saturated aq. sodium bicarbonate solution, water, and brine. The organic layer was dried over sodium sulfate, concentrated, and the resulting residue was purified by silica gel column chromatography to furnish 6-bromospiro[3,4-dihydro-1,4-benzoxazine-2,1'-cyclopropane] (2.3 g).

$^1$H NMR (400 MHz, CDCl$_3$): δ 0.68-0.71 (m, 2H), 1.02-1.06 (m, 2H), 3.31 (s, 2H), 3.87 (bs, 1H), 6.57 (d, J=8.8 Hz, 1H), 6.72 (dd, J=8.4, 2.4 Hz, 1H), 6.77 (d, J=2.4 Hz, 1H).

MS (ES) m/z 240.1 (M+1).

Step IV.

To a stirred solution of 6-bromospiro[3,4-dihydro-1,4-benzoxazine-2,1'-cyclopropane] (3.11 g, 12.9 mmol) in DMF (20 mL) was added potassium carbonate (3.6 g, 26.0 mmol) and benzyl bromide (1.61 mL, 13.6 mmol). The reaction mixture was heated at 60° C. for 6 h then cooled to room temperature and quenched by the addition of water. The reaction mixture was extracted with ethylacetate (2×50 mL) and the combined organic layers were washed with water (20 mL) and brine (20 mL), then dried over sodium sulfate, filtered and concentrated. The crude product was purified by silica gel column chromatography to furnish 4-benzyl-6-bromo-spiro[3H-1,4-benzoxazine-2,1'-cyclopropane] (1.13 g).

$^1$H NMR (400 MHz, CDCl$_3$): δ 0.62-0.65 (m, 2H), 1.02-1.05 (m, 2H), 3.26 (s, 2H), 4.44 (s, 2H), 6.59 (d, J=8.4 Hz, 1H), 6.69 (dd, J=8.4, 2.4 Hz, 1H), 6.79 (d, J=2.0 Hz, 1H), 7.27-7.36 (m, 5H).

MS (ES) m/z 330.0 (M+1).

Step V.

To a stirred solution of 4-benzyl-6-bromo-spiro[3H-1,4-benzoxazine-2,1'-cyclopropane] (1.12 g, 3.4 mmol) in THF Step I.

To a stirred solution of ethyl-1-hydroxycyclopropane carboxylate (2.93 g, 20.5 mmol) in THF (50 mL) was added sodium hydride (60% in mineral oil, 981 mg, 24.5 mmol) under argon atmosphere. After 10 min, 15-crown-5 (0.2 mL) followed by 4-bromo-2-nitro-fluorophenol (4.5 g, 20.5 mmol) were added. The reaction mixture was stirred at room temperature overnight then quenched by the addition of methanol (1.5 mL) and diluted with ethyl acetate. The mixture was washed with brine, and the organic layer was (10 mL) was added 1.6 M solution of n-BuLi in hexanes (2.12 mL, 3.4 mmol) at −78° C. The reaction mixture was stirred for 30 min, and then transferred to a stirred solution of 5-bromo-2-chlorobenzaldehyde (745 mg, 3.4 mmol) in THF (10 mL) at −78° C. After stirring for 1 h, the reaction was quenched by the addition of saturated ammonium chloride solution and extracted with ethyl acetate. The ethyl acetate layer was washed with water, brine, dried over sodium sulphate, and concentrated. The resulting residue was purified by silica gel column chromatography to furnish (4-benzylspiro[3H-1,4-benzoxazine-2,1'-cyclopropane]-6-yl)-(5-bromo-2-chloro-phenyl)methanol (790 mg).

MS (ES) m/z 470.0 (M+1).

Step VI.

To an ice cold solution of (4-benzylspiro[3H-1,4-benzoxazine-2,1'-cyclopropane]-6-yl)-(5-bromo-2-chloro-phenyl)methanol (780 mg, 1.7 mmol) in trifluoroacetic acid (4 mL) was added triethylsilane (1.32 mL, 8.3 mmol) followed by triflic acid (0.15 mL, 1.7 mmol). After heating the mixture for 15 min at 50° C., the reaction was cooled to room temperature. Trifluoroacetic acid was evaporated under reduced pressure, and the resulting residue was taken in saturated aq. sodium bicarbonate solution and extracted with ethyl acetate. The organic layer was washed with water, brine, dried over sodium sulfate, and concentrated. The resulting residue was purified by silica gel column chromatography to furnish 4-benzyl-6-[(5-bromo-2-chloro-phenyl)methyl]spiro[3H-1,4-benzoxazine-2,1'-cyclopropane] (715 mg).

$^1$H NMR (400 MHz, CDCl$_3$): δ 0.64-0.67 (m, 2H), 1.04-1.07 (m, 2H), 3.28 (s, 2H), 3.88 (s, 2H), 4.42 (s, 2H), 6.42 (d, J=8.0 Hz, 1H), 6.51 (s, 1H), 6.68 (d, J=8.0 Hz, 1H), 7.17-7.35 (m, 8H).

MS (ES) m/z 448.0 (M+1).

Step VII.

To a stirred solution of 4-benzyl-6-[(5-bromo-2-chloro-phenyl)methyl]spiro[3H-1,4-benzoxazine-2,1'-cyclopropane] (710 mg, 1.6 mmol) in THF-toluene (20 mL of 1:2 mixture) was added 1.6 M solution of n-BuLi in hexanes (1.6 mL, 1.6 mmol) at −78° C. The reaction mixture was stirred for 30 min, and then transferred to a stirred solution of 2,3,4,6-tetrakis-O-(trimethylsilyl)-D-glucopyranone (730 mg, 1.6 mmol) in toluene (15 mL) at −78° C. After stirring for 40 min, 0.6 N methanesulfonic acid in methanol (7 mL) was added and stirred for 20 h at room temperature. The reaction was quenched by the addition of saturated aq. sodium bicarbonate solution (8 mL) then extracted with ethyl acetate (3×10 mL). The organic layer was dried over sodium sulphate and concentrated. The resulting residue was purified by silica gel column chromatography to furnish (3R,4S,5S,6R)-2-[3-[(4-benzylspiro[3H-1,4-benzoxazine-2,1'-cyclopropane]-6-yl)methyl]-4-chloro-phenyl]-6-(hydroxymethyl)-2-methoxy-tetrahydropyran-3,4,5-triol (350 mg).

$^1$H NMR (400 MHz, CD$_3$OD): δ 0.67-0.66 (m, 2H), 0.87-0.92 (m, 2H), 3.00 (s, 3H), 306 (d, J=9.6 Hz, 1H), 3.29 (s, 2H), 3.38-3.43 (m, 1H), 3.53-3.57 (m, 1H), 3.71-3.98 (m, 5H), 4.38 (ABq, J=16.0, 4.0 Hz, 2H), 6.38 (dd, J=8.4, 2.0 Hz, 1H), 6.52 (d, J=8.0 Hz, 1H), 6.55 (d, J=1.6 Hz, 1H), 7.20-7.31 (m, 6H), 7.41 (dd, J=8.8, 2.0 Hz, 1H), 7.50 (d, J=2.4 Hz, 1H).

MS (ES) m/z 558.2 (M+1).

Example 48: (2S,3R,4R,5S,6R)-2-[3-[(4-benzylspiro [3H-1,4-benzoxazine-2,1'-cyclopropane]-6-yl) methyl]-4-chloro-phenyl]-6-(hydroxymethyl)tetrahydropyran-3,4,5-triol Step VIII.

To a stirred solution of (3R,4S,5S,6R)-2-[3-[(4-benzylspiro[3H-1,4-benzoxazine-2,1'-cyclopropane]-6-yl)methyl]-4-chloro-phenyl]-6-(hydroxymethyl)-2-methoxy-tetrahydropyran-3,4,5-triol (340 mg, 0.6 mmol) in acetonitrile-dichloromethane (6 mL, 1:1 mixture) was added triethylsilane (0.4 mL, 2.4 mmol) and boron trifluoride diethyletharate complex (0.15 mL, 1.2 mmol) at −5° C. After stirring for 4 h at 0° C., the reaction was quenched with saturated aq. sodium bicarbonate solution (5 mL). The volatiles were evaporated under reduced pressure, and the resulting mixture was extracted with ethyl acetate (3×10 mL). The ethyl acetate layers were combined and washed with brine (10 mL), dried over sodium sulphate, and concentrated. The resulting residue was purified by silica gel column chromatography to furnish (2S,3R,4R,5S,6R)-2-[3-[(4-benzylspiro[3H-1,4-benzoxazine-2,1'-cyclopropane]-6-yl)methyl]-4-chloro-phenyl]-6-(hydroxymethyl)tetrahydropyran-3,4,5-triol (300 mg).

MS (ES) m/z 538.0 (M+1).

Example 49: (2S,3R,4R,5S,6R)-2-[4-Chloro-3-(spiro[3,4-dihydro-1,4-benzoxazine-2,1'-cyclopropane]-6-ylmethyl)phenyl]-6-(hydroxymethyl)tetrahydropyran-3,4,5-triol Step IX.

To a solution of (2S,3R,4R,5S,6R)-2-[3-[(4-benzylspiro [3H-1,4-benzoxazine-2,1'-cyclopropane]-6-yl) methyl]-4-chloro-phenyl]-6-(hydroxymethyl)tetrahydropyran-3,4,5-triol (300 mg) in methanol (3 mL), was added ethyl acetate (0.5 mL), 10% palladium on charcoal (40 mg), and 0.3 mL conc. HCl. The reaction mixture was stirred under hydrogen balloon pressure for 2 h then filtered through a celite bed which was washed with methanol, and the resulting filtrate was concentrated to a residue which was purified by preparative HPLC to furnish (2S,3R,4R,5S,6R)-2-[4-chloro-3-(spiro[3,4-dihydro-1,4-benzoxazine-2,1'-cyclopropane]-6-ylmethyl)phenyl]-6-(hydroxymethyl)tetrahydropyran-3,4,5-triol (56 mg).

$^1$H NMR (400 MHz, CD$_3$OD): δ 0.65-0.68 (m, 2H), 0.89-0.92 (m, 2H), 3.20 (s, 2H), 3.28-3.46 (m, 4H), 3.68 (dd, J=12.0, 5.6 Hz, 1H), 3.85-3.99 (m, 3H), 4.07 (d, J=9.6 Hz, 1H), 6.44 (dd, J=8.0, 2.0 Hz, 1H), 6.50-6.52 (m, 2H), 7.25 (dd, J=8.0, 2.0 Hz, 1H), 7.31-7.34 (m, 2H).

MS (ES) m/z 448.0 (M+1).

Example 50-51

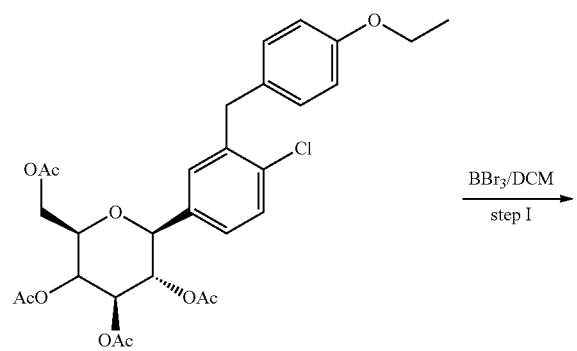

-continued

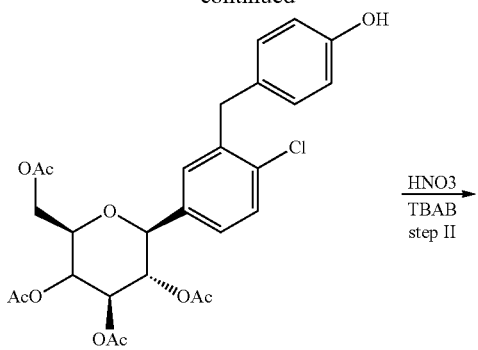

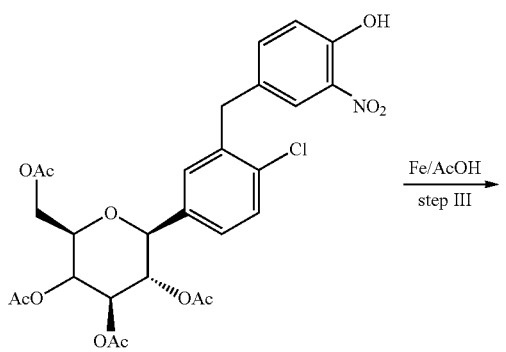

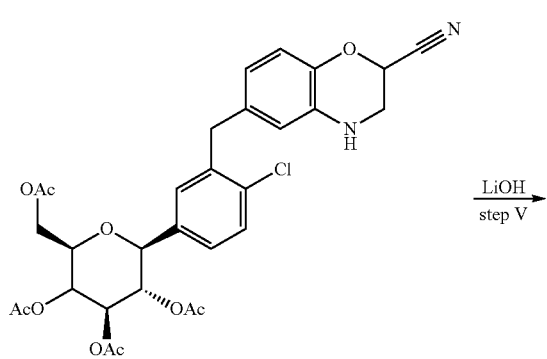
Ex. 50

-continued

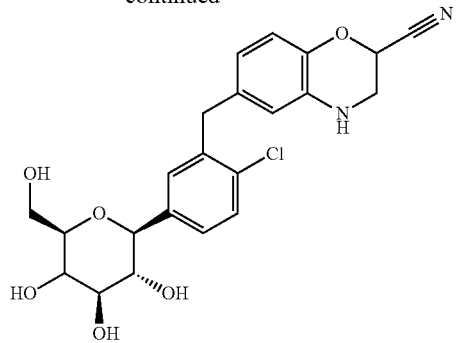
Ex. 51

Step I.
To a stirred solution of acetic acid (2R,3R,4R,5S,6S)-3,4,5-triacetoxy-6-[4-chloro-3-(4-ethoxy-benzyl)-phenyl]-tetrahydro-pyran-2-ylmethyl ester (3.0 g, 5.2 mmol, prepared using the procedures described in *J. Med. Chem.* 2008, 51(5), 1145-49) in dichloromethane (30 mL) was added boron tribromide solution (1.0 M in DCM, 26.0 mL, 26.0 mmol) at −78° C. After stirring at −15° C. for 1 h, the reaction mixture was poured onto an ice-cold saturated aqueous sodium bicarbonate solution. The mixture was extracted with dichloromethane (2×50 mL), and the combined organic layers were washed with water (20 mL) and brine (20 mL), then dried over sodium sulfate and concentrated to a residue which was purified by silica gel column chromatography to furnished (2R,3R,4R,5S,6S)-3,4,5-triacetoxy-6-[4-chloro-3-(4-hydroxy-benzyl)-phenyl]-tetrahydro-pyran-2-ylmethyl ester (2.1 g).
MS (ES) m/z 549.3 (M+1).

Step II.
To a stirred solution of (2R,3R,4R,5S,6S)-3,4,5-triacetoxy-6-[4-chloro-3-(4-hydroxy-benzyl)-phenyl]-tetrahydro-pyran-2-ylmethyl ester (5.4 g) in ethylenedichloride (55 mL) was added 6% $HNO_3$ (22.2 mL) and tetra-butyl ammonium bromide (324 mg).
The reaction mixture was heated at 50° C. for 15 min. then cooled and diluted with dichloromethane. The mixture was washed with water, saturated aqueous sodium bicarbonate solution, brine, and the organic layer was dried over anhydrous sodium sulfate then concentrated. The resulting residue was purified by silica gel column chromatography to furnish acetic acid (2R,3R,4R,5S,6S)-3,4,5-triacetoxy-6-[4-chloro-3-(4-hydroxy-3-nitro-benzyl)-phenyl]-tetrahydro-pyran-2-ylmethyl ester (4.2 g)
MS (ES) m/z 593.8 (M+1).

Step III.
To a stirred solution of acetic acid (2R,3R,4R,5S,6S)-3,4,5-triacetoxy-6-[4-chloro-3-(4-hydroxy-3-nitro-benzyl)-phenyl]-tetrahydro-pyran-2-ylmethyl ester (1.71 g, 2.9 mmol) in glacial acetic acid (15 mL) was added iron powder (3.22 g, 57.7 mmol). After stirring at 60° C. for 15 min, the reaction mixture was filtered through a celite bed. The filtrate was concentrated under reduced pressure, and the resulting residue was taken up in ethyl acetate and the solution was washed with water, saturated aqueous sodium bicarbonate solution, and brine. The organic layer was dried over anhydrous sodium sulfate and concentrated to a residue which was purified by silica gel column chromatography to furnish acetic acid (2R,3R,4R,5S,6S)-3,4,5-triacetoxy-6-[3-(3-amino-4-hydroxy-benzyl)-4-chloro-phenyl]-tetrahydro-pyran-2-ylmethyl ester (1.3 g)
MS (ES) m/z 563.9 (M+1).

Example 50: Acetic acid (2R,3R,4R,5S,6S)-3,4,5-triacetoxy-6-[4-chloro-3-(2-cyano-3,4-dihydro-2H-benzo[1,4]oxazin-6-ylmethyl)-phenyl]-tetrahydro-pyran-2-ylmethyl ester Step IV.

To a stirred solution of acetic acid (2R,3R,4R,5S,6S)-3,4,5-triacetoxy-6-[3-(3-amino-4-hydroxy-benzyl)-4-chloro-phenyl]-tetrahydro-pyran-2-ylmethyl ester (1.8 g, 3.2 mmol) in acetonitrile (15 mL) was added 2-chloroacrylonitrile (0.35 mL, 4.5 mmol) and potassium carbonate (882 mg, 6.4 mmol). After the reaction was refluxed overnight, the mixture was filtered through a celite bed. The filtrate was concentrated and purified by silica gel column chromatography to furnish acetic acid (2R,3R,4R,5S,6S)-3,4,5-triacetoxy-6-[4-chloro-3-(2-cyano-3,4-dihydro-2H-benzo[1,4]oxazin-6-ylmethyl)-phenyl]-tetrahydro-pyran-2-ylmethyl ester (440 mg).

MS (ES) m/z 615.2 (M+1).

Example 51: 6-[2-Chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carbonitrile Step V.

To a stirred solution of acetic acid (2R,3R,4R,5S,6S)-3,4,5-triacetoxy-6-[4-chloro-3-(2-cyano-3,4-dihydro-2H-benzo[1,4]oxazin-6-ylmethyl)-phenyl]-tetrahydro-pyran-2-ylmethyl ester (430 mg) in THF:Methanol:water (2:1:1 mixture, 4 mL) was added lithium hydroxide (20 mg). After stirring at room temperature overnight, the reaction mixture was concentrated. The resulting residue was taken up in 50% methanol in ethyl acetate then filtered through celite bed. The filtrate was concentrated, and the residue was purified by preparative HPLC to furnish 6-[2-chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carbonitrile (35 mg).

$^1$H NMR (400 MHz, CD$_3$OD): δ 3.26-3.50 (m, 6H), 3.68 (dd, J=12.0 Hz, 4.8 Hz, 1H), 3.85-3.97 (m, 3H), 4.08 (d, J=9.2 Hz, 1H), 5.25 (t, J=2.8 Hz, 1H), 6.48-6.51 (m, 2H), 6.68 (d, J=8.0 Hz, 1H), 7.26 (dd, J=8.4 Hz, 2.4 Hz, 1H), 7.32-7.34 (m, 2H).

MS (ES) m/z 447.1 (M+1).

Examples 52-53

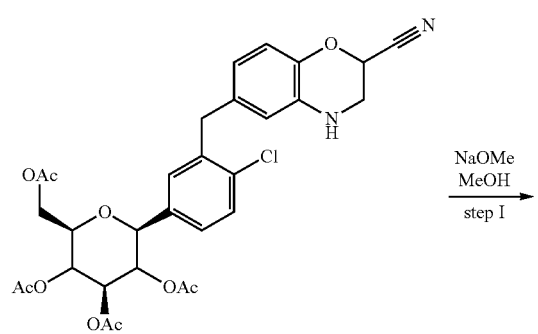

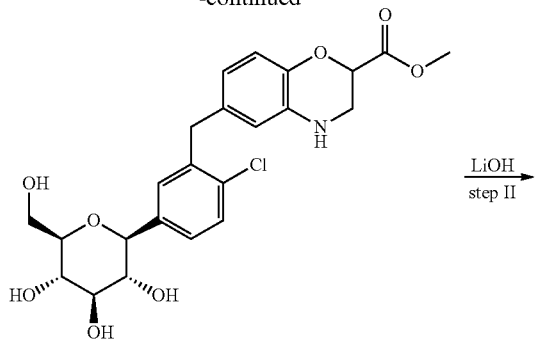

Ex. 52

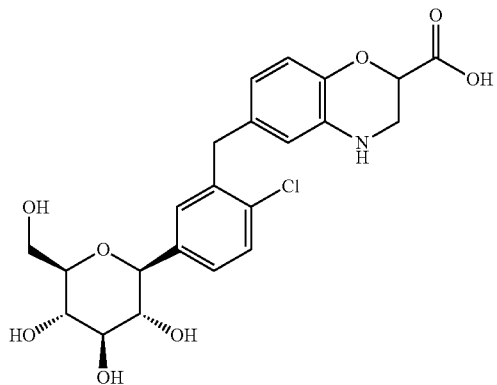

Ex. 53

Example 52: 6-[2-chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carboxylic acid methyl ester Step I.

To a stirred solution of acetic acid (2R,3R,4R,5S,6S)-3,4,5-triacetoxy-6-[4-chloro-3-(2-cyano-3,4-dihydro-2H-benzo[1,4]oxazin-6-ylmethyl)-phenyl]-tetrahydro-pyran-2-ylmethyl ester (180 mg) in methanol (2 mL) was added sodium methoxide (20 mg). After stirring at room temperature overnight, the reaction mixture was concentrated to furnish 6-[2-chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carboxylic acid methyl ester.

The resulting crude material was taken for the further conversion (195 mg).

MS (ES) m/z 480.1 (M+1).

Example 53: 6-[2-Chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carboxylic acid Step II.

To a stirred solution of 6-[2-chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carboxylic acid methyl ester (190 mg) in THF:Methanol:water (1:1:1 mixture, 1.5 mL) was added lithium hydroxide (17 mg). After stirring at room temperature overnight, the reaction mixture was concentrated, and the resulting residue was taken up in 50% methanol in ethyl acetate. The solution was filtered through a celite bed, and the filtrate was concentrated to a residue which was purified by preparative HPLC to furnish 6-[2-chloro-5-((2S,3R,4R,5S,6R)-3,4,5-trihydroxy-6-hydroxymethyl-tetrahydro-pyran-2-yl)-benzyl]-3,4-dihydro-2H-benzo[1,4]oxazine-2-carboxylic acid (23 mg).

$^1$H NMR (400 MHz, CD$_3$OD): δ 3.19-3.44 (m, 5H), 3.56 (dd, J=11.6 Hz, 2.8 Hz, 1H), 3.68 (dd, J=12.0 Hz, 5.2 Hz, 1H), 3.84-3.97 (m, 3H), 4.07 (d, J=9.2 Hz, 1H), 4.33 (dd, J=8.0, 2.4 Hz, 1H), 6.42-6.45 (m, 2H), 6.71 (d, J=8.0 Hz, 1H), 7.24 (dd, J=8.4 Hz, 2.4 Hz, 1H), 7.29-7.32 (m, 2H).

MS (ES) m/z 466.0 (M+1).

Examples 54-56

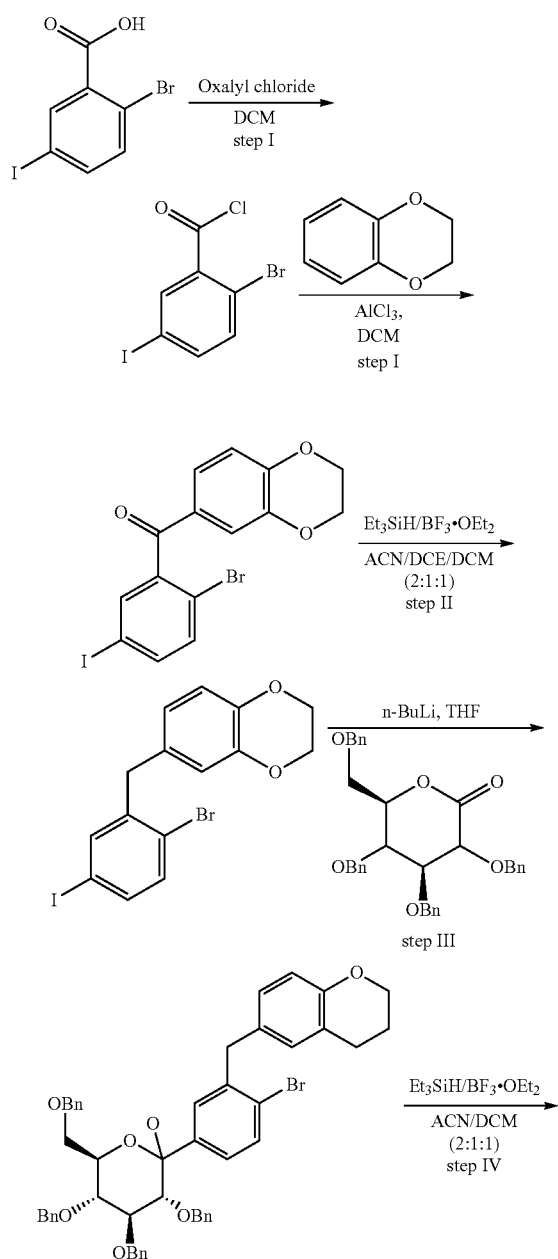

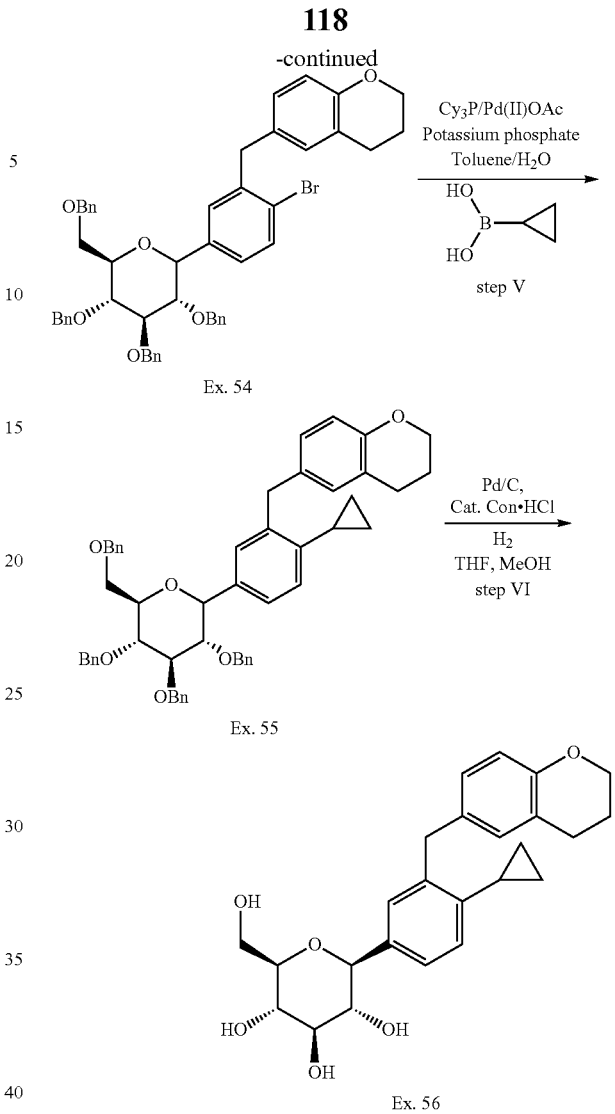

Step I.

To a stirred solution of 2-bromo-5-iodobenzoic acid (1.0 g, 3.06 mmol) in DCM (5 mL) was added DMF (0.2 mL) and oxalyl chloride (0.44 mL, 4.59 mmol) at 0° C. After complete addition, the reaction mixture was stirred at room temperature for 3 h. The volatiles were evaporated under reduced pressure, and the crude product was dissolved in DCM (4 mL) and added to chroman (488 mg, 3.67 mmol) which had been cooled to 0° C. To this mixture was added aluminum chloride (488 mg, 3.67 mmol) in portions. After stirring for 4 h, the reaction was quenched by pouring it into crushed ice. This was extracted with dichloromethane (50 mL×2). The dichloromethane layers were combined and washed with water (20 mL), saturated aqueous sodium bicarbonate solution (20 mL×2), and brine (20 mL), then dried over sodium sulfate, and concentrated. The crude product was purified by column chromatography to furnish (2-bromo-5-iodo-phenyl)-chroman-6-yl-methanone (1.2 g).

Step II.

To a stirred solution of (2-bromo-5-iodo-phenyl)-chroman-6-yl-methanone (2.0 g, 4.51 mmol) in acetonitrile:dichloromethane (2:1 mixture, 9 mL) was added triethylsilane (2.52 mL, 15.78 mmol) and boron trifluoride diethyl etherate complex (1.11 mL, 9.02 mmol) at 0° C. After stirring overnight at room temperature, reaction was quenched by the addition of saturated aqueous sodium bicarbonate solution. Volatiles were evaporated under reduced pressure. The aqueous layer was extracted with ethyl acetate (2×20 mL). Ethyl acetate layer was washed with water, brine, dried over sodium sulfate, concentrated and purified by silica gel column chromatography to furnish 6-(2-bromo-5-iodo-benzyl)-chroman (1.5 g).

$^1$H NMR (400 MHz, CDCl$_3$): δ 2.03 (m, 2H), 2.77 (t, J=6.4 Hz, 2H), 3.93 (s, 2H), 4.18 (t, J=5.2 Hz, 2H), 6.73 (d, J=8.4 Hz, 1H), 6.83 (s, 1H), 6.89 (dd, J=8.4 Hz, 1.6 Hz, 1H), 7.28 (s, 1H), 7.39 (dd, J=8.4 Hz, 2.0 Hz, 1H), 7.44 (d, J=2.0 Hz, 1H).

Step III.

To a stirred solution of 6-(2-bromo-5-iodo-benzyl)-chroman (1.0 g, 2.33 mmol) in dry THF (6 mL) was added n-BuLi (1.6 M in hexane, 1.45 mL, 2.33 mmol) at −78° C. After stirring for 45 min, the reaction mixture was transferred to a cooled solution of 2,3,4,6-tetrakis-O-(benzyl)-D-glucopyranone (1.66 g, 2.56 mmol) in THF (6 mL) at −78° C. After stirring for 1 h, a solution of methane sulfonic acid (0.3 mL) in methanol (6 mL) was added, and the reaction was allowed to attain room temperature. After stirring overnight, the reaction was quenched by the addition of a saturated sodium bicarbonate solution (10 mL), and the resulting mixture was extracted with ethyl acetate (50 mL×3). The organic layers were combined and dried over sodium sulfate, concentrated and purified by silica gel column chromatography to furnish 6-[2-bromo-5-((3R,4S,5R,6R)-3,4,5-tris-benzyloxy-6-benzyloxymethyl-2-methoxy-tetrahydro-pyran-2-yl)-benzyl]-chroman (900 mg).

Example 54: 6-[2-bromo-5-((3S,4R,5R,6R)-3,4,5-tris-benzyloxy-6-benzyloxymethyl-tetrahydro-pyran-2-yl)-benzyl]-chroman Step IV.

To a stirred solution of 6-[2-bromo-5-((3R,4S,5R,6R)-3,4,5-tris-benzyloxy-6-benzyloxymethyl-2-methoxy-tetrahydro-pyran-2-yl)-benzyl]-chroman (900 mg, 1.05 mmol) in acetonitrile:dichloromethane (1:1 mixture, 6 mL) was added triethylsilane (0.34 mL, 2.1 mmol) and boron trifluoride diethyletharate complex (0.19 mL, 1.58 mmol), at □0° C. After stirring for 2 h, the reaction was quenched with saturated aqueous sodium bicarbonate solution. The volatiles were evaporated under reduced pressure; the resulting mixture was extracted with ethyl acetate (2×10 mL). The organic layers were combined and dried over sodium sulfate then concentrated to a residue which was purified by silica gel column chromatography to furnish 6-[2-bromo-5-((3S,4R,5R,6R)-3,4,5-tris-benzyloxy-6-benzyloxymethyl-tetrahydro-pyran-2-yl)-benzyl]-chroman (600 mg).

Example 55: 6-[2-cyclopropyl-5-((3S,4R,5R,6R)-3,4,5-tris-benzyloxy-6-benzyloxymethyl-tetrahydro-pyran-2-yl)-benzyl]-chroman Step V.

To a stirred solution of 6-[2-bromo-5-((3S,4R,5R,6R)-3,4,5-tris-benzyloxy-6-benzyloxymethyl-tetrahydro-pyran-2-yl)-benzyl]-chroman (300 mg, 0.363 mmol) in toluene (1.6 mL) was added tricyclohexylphosphine (10 mg), potassium phosphate (346 mg, 1.63 mmol), water (81 µl), cyclopropylboronic acid (93 mg, 1.09 mmol). The reaction mixture was degassed for 45 min then palladium (II) acetate (4 mg) was added. After heating overnight at 100° C., the reaction mixture was cooled to room temperature and was filtered through celite. The celite was washed with an additional ethyl acetate (30 mL) and the organic layer of the filtrate was separated and washed with water (20 mL) followed by brine (20 mL), then dried over sodium sulfate and concentrated to give crude product which was further purified by column chromatography to furnish 6-[2-cyclopropyl-5-((3S,4R,5R,6R)-3,4,5-tris-benzyloxy-6-benzyloxymethyl-tetrahydro-pyran-2-yl)-benzyl]-chroman (250 mg).

Example 56: (2S,3R,4R,5S,6R)-2-(3-Chroman-6-ylmethyl-4-cyclopropyl-phenyl)-6-hydroxymethyl-tetrahydro-pyran-3,4,5-triol Step VI.

To a stirred solution of 6-[2-cyclopropyl-5-((3S,4R,5R,6R)-3,4,5-tris-benzyloxy-6-benzyloxymethyl-tetrahydro-pyran-2-yl)-benzyl]-chroman (650 mg) in THF (5 mL) was added 10% palladium charcoal activated (dry) (100 mg), methanol (5 mL), and conc. HCl (0.2 mL). The reaction mixture was stirred under hydrogen atmosphere (bladder pressure) overnight then filtered through a celite bed. The filtrate was concentrated and purified by preparative HPLC to furnish (2S,3R,4R,5S,6R)-2-(3-chroman-6-ylmethyl-4-cyclopropyl-phenyl)-6-hydroxymethyl-tetrahydro-pyran-3,4,5-triol (63 mg).

$^1$H NMR (400 MHz, CD$_3$OD): δ 0.52-0.56 (m, 2H), 0.81-0.89 (m, 2H), 1.80-1.85 (m, 1H), 1.90-1.96 (m, 2H), 2.69 (t, J=6.0 Hz, 2H), 3.29-3.47 (m, 3H), 3.67 (dd, J=12.0 Hz, 5.0 Hz, 1H), 3.87 (dd, J=12.0 Hz, 1.6 Hz, 1H), 4.07 (d, J=8.8 Hz, 2H), 4.11-4.09 (m, 4H), 6.58 (d, J=8.0 Hz, 1H), 6.80-6.84 (m, 2H), 6.96 (d, J=8.0 Hz, 1H), 7.10-7.22 (m, 2H).

MS (ES) m/z 444.1 (M+18).

Examples 57-58

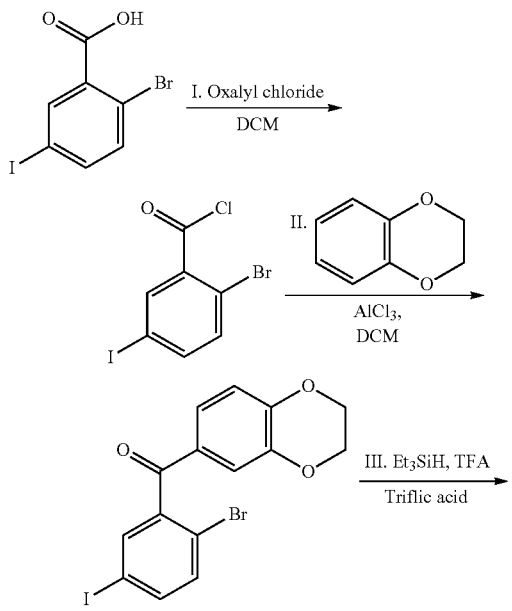

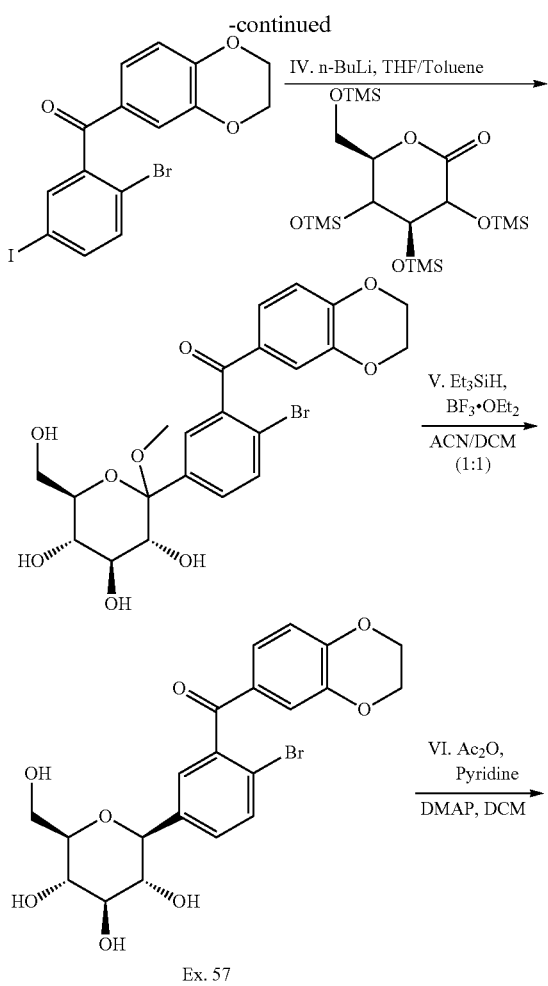

Ex. 57

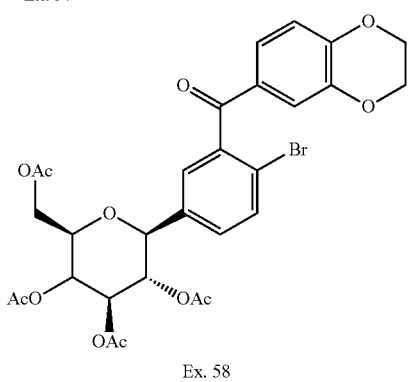

Ex. 58

Step I:
To a stirred solution of 2-bromo-5-iodobenzoic acid (25.0 g, 76.48 mmol) in dichloromethane (200 mL) was added oxalylchloride (10.3 mL, 114.74 mmol) at 0° C. followed by DMF (0.9 mL). After complete addition, the reaction mixture was stirred at room temperature for 3 h. Volatiles were evaporated under reduced pressure to furnish 2-bromo-5-iodo-benzoyl chloride (26.4 g). The crude product was used for the next step immediately.

Step II:
To a stirred solution of 2-bromo-5-iodo-benzoyl chloride (26.4 g, 76.56 mmol) in dichloromethane (250 mL) was added benzo(1,4)-dioxane (10.41 g, 76.26 mmol) at 0° C. To this reaction mixture, AlCl$_3$ (40.78 g, 305.47 mmol) was added in portions. After stirring overnight at room temperature, the reaction mixture was poured into crushed ice. The resulting mixture was extracted with dichloromethane (500 mL×2). The dichloromethane layers were combined and washed with water (200 mL), saturated aqueous sodium bicarbonate solution (200 mL×2), and brine (200 mL), then dried over sodium sulfate and concentrated. The solid product was triturated with hexanes, and the triturated product was dried under vacuum to furnish (2-bromo-5-iodo-phenyl)-(2,3-dihydro-benzo[1,4]dioxin-6-yl)-methanone (30 g).
$^1$H NMR (400 MHz, DMSO-D$_6$): δ 4.29-4.37 (m, 4H), 7.02 (d, J=8.4 Hz, 1H), 7.16 (d, J=2.4 Hz, 1H), 7.18-7.19 (m, 1H), 7.53 (d, J=8.4 Hz, 1H), 7.77-7.81 (m, 1H), 7.82 (d, J=2.0 Hz, 1H).

Step III:
To a stirred solution of (2-bromo-5-iodo-phenyl)-(2,3-dihydro-benzo[1,4]dioxin-6-yl)-methanone (30.0 g, 67.4 mmol) in trifluoroacetic acid (100 mL) was added triethylsilane (86.2 mL, 539.3 mmol) followed by triflic acid (6.0 mL, 67.42 mmol) at room temperature. After stirring for 25 min at room temperature, volatiles were evaporated under reduced pressure. The resulting residue was taken up in ethyl acetate and washed with saturated aqueous sodium bicarbonate solution (200 mL×2), water (200 mL), and brine (200 mL), then dried over sodium sulfate, concentrated and purified by silica gel column chromatography to furnish 6-(2-bromo-5-iodo-benzyl)-2,3-dihydro-benzo[1,4]dioxine (26.5 g).
$^1$H NMR (400 MHz, DMSO-D$_6$): δ 3.90 (s, 4H), 4.2 (s, 2H), 6.65 (dd, J=8.4 Hz, J=2.0 Hz, 1H), 6.68 (d, J=2.0 Hz, 1H), 6.77 (d, J=8.4 Hz, 1H), 7.39 (d, J=8.4 Hz, 1H), 7.50 (dd, J=8.4 Hz, J=2.4 Hz 1H), 7.67 (d, J=2.8 Hz, 1H).

Step IV:
To a stirred solution of 6-(2-bromo-5-iodo-benzyl)-2,3-dihydro-benzo[1,4]dioxine (26.5 g, 61.47 mmol) in THF:toluene 2:1 (300 mL) was added 1.6 M solution of n-BuLi in hexanes (42.3 mL, 67.62 mmol) at −78° C. The reaction mixture was stirred for 1 h, and then transferred to a stirred solution of 2,3,4,6-tetrakis-O-(trimethylsilyl)-D-glucopyranone (28.69 g, 61.47 mmol) in toluene (100 mL) at ~78° C. After stirring for 1 h, 0.6 N methanesulfonic acid in methanol (265 mL) was added dropwise and stirred the reaction mixture for 16 h at room temperature. Reaction was quenched by the addition of aq. NaHCO$_3$ solution (~75 mL) and extracted with ethyl acetate (250 mL×3), dried over sodium sulfate, concentrated and purified by silica gel column chromatography to furnish (3R,4S,5S,6R)-2-[4-Bromo-3-(2,3-dihydro-benzo[1,4]dioxin-6-ylmethyl)-phenyl]-6-hydroxymethyl-2-methoxy-tetrahydro-pyran-3,4,5-triol (28.4 g)

Example 57: [(2R,3R,4R,5S,6S)-3,4,5-triacetoxy-6-[4-bromo-3-(2,3-dihydro-1,4-benzodioxin-6-ylmethyl)phenyl]tetrahydropyran-2-yl]methyl acetate Step V:
To a stirred solution of (3R,4S,5S,6R)-2-[4-bromo-3-(2, 3-dihydro-benzo[1,4]dioxin-6-ylmethyl)-phenyl]-6-hydroxymethyl-2-methoxy-tetrahydro-pyran-3,4,5-triol (28.4 g, 57.1 mmol) in acetonitrile-dichloromethane 1:1 (250 mL) was added triethylsilane (36.5 mL, 228.4 mmol) and boron trifluoride diethyletharate complex (14.1 mL, 114.2 mmol) at Q 10° C. After stirring for 4 h at 10° C., the reaction was quenched with saturated aqueous sodium bicarbonate (~100 mL). The organic layer was separated, and the aqueous layer was extracted with ethyl acetate (3×150 mL). The organic layers were combined and dried over sodium sulfate, concentrated to furnish (3R,4R,5S,6R)-2-[4-bromo-3-(2,3-di-hydro-benzo[1,4]dioxin-6-ylmethyl)-phenyl]-6-hydroxymethyl-tetrahydro-pyran-3,4,5-triol (28.4 g). Crude product was used for next reaction without purification.

Example 58: [(2R,3R,4R,5S,6S)-3,4,5-triacetoxy-6-[4-bromo-3-(2,3-dihydro-1,4-benzodioxin-6-ylmethyl)phenyl]tetrahydropyran-2-yl] methyl acetate Step V:

To a stirred solution of (3R,4R,5S,6R)-2-[4-Bromo-3-(2,3-dihydro-benzo[1,4]dioxin-6-ylmethyl)-phenyl]-6-hydroxymethyl-tetrahydro-pyran-3,4,5-triol (28.4 g, 60.81 mmol) in dichloromethane (300 mL) was added pyridine (40 mL, 486.5 mmol), acetic anhydride (50 mL, 486.5 mmol) and DMAP (740 mg, 6.08 mmol) at room temperature. After stirring for 2 h, volatiles were evaporated under reduced pressure. The resulting residue was taken up in ethyl acetate (500 ml) and washed with 1N HCl (200 mL×2) followed by brine (200 ml), then dried over sodium sulfate and concentrated. The resulting crude compound was dissolved in ethanol (320 mL) at 65° C. and allowed to cool to room temperature while stirring. Light yellow solid formed was filtered and washed with cold ethanol (150 mL) followed by hexane (200 mL) to get acetic acid (2R,3R,4R,5S)-3,4,5-triacetoxy-6-[4-bromo-3-(2,3-dihydro-benzo[1,4]dioxin-6-ylmethyl)-phenyl]-tetrahydro-pyran-2-ylmethyl ester powder (22.5 g, purity 98%).

Examples 59-60

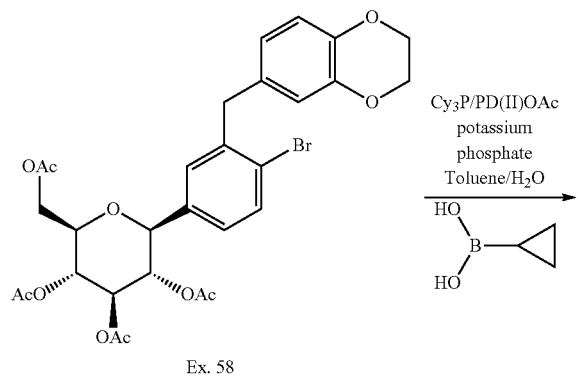

Ex. 58

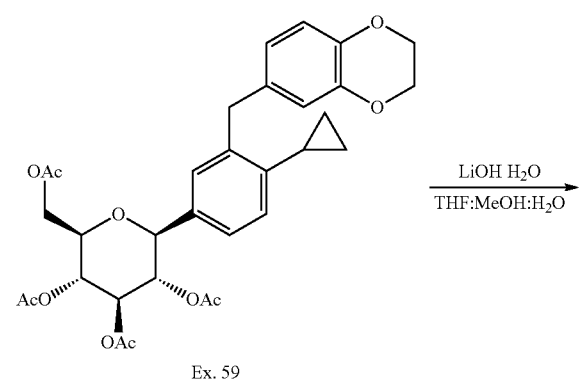

Ex. 59

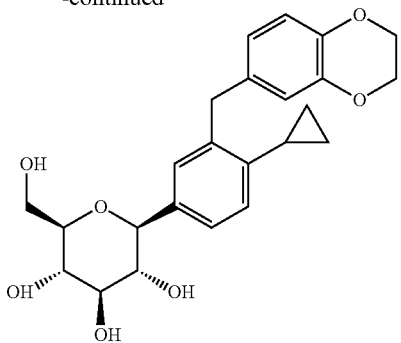

Ex. 60

Example 59: Acetic acid (2R,3R,4R,5S)-3,4,5-triacetoxy-6-[4-cyclopropyl-3-(2,3-dihydro-benzo[1,4]dioxin-6-ylmethyl)-phenyl]-tetrahydro-pyran-2-ylmethyl ester Step I:

To a stirred solution of acetic acid (2R,3R,4R,5S)-3,4,5-triacetoxy-6-[4-bromo-3-(2,3-dihydro-benzo[1,4]dioxin-6-ylmethyl)-phenyl]-tetrahydro-pyran-2-ylmethyl ester (10.0 g, 15.74 mmol) in toluene (100 mL) was added tricyclohexylphosphine (1.76 g, 6.29 mmol), a solution of potassium phosphate tribasic (13.3 g, 62.9 mmol) in water (15 mL), and cyclopropylboronic acid (4.06 g, 47.2 mmol). The reaction mixture was degassed for 45 min then palladium (II) acetate (529 mg, 2.3 mmol) was added. The reaction mixture was stirred at 90° C. overnight then cooled to room temperature and filtered through celite, and the celite was washed with ethyl acetate (200 mL). The organic layer of the filtrate was separated and washed with water (100 mL) followed by brine (100 mL), then dried over sodium sulfate and concentrated to give crude product which was further purified by column chromatography to furnish acetic acid (2R,3R,4R,5S)-3,4,5-triacetoxy-6-[4-cyclopropyl-3-(2,3-dihydro-benzo[1,4]dioxin-6-ylmethyl)-phenyl]-tetrahydro-pyran-2-ylmethyl ester (7.25 g, purity 98%) and this was recrystallized by absolute ethanol to give white solid (5.25 g, purity >99%).

$^1$H NMR (400 MHz, CDCl$_3$): δ 0.57-0.62 (m, 2H), 0.84-0.86 (m, 2H), 1.76 (s, 3H), 1.77-1.80 (m, 1H), 1.99 (s, 3H), 2.05 (s, 3H), 2.08 (s, 3H), 3.78-3.82 (m, 1H), 3.99-4.10 (ABq, J=15.6 Hz, 2H), 4.14 (dd, J=12.4 Hz, 2.4 Hz, 1H), 4.22 (s, 4H), 4.26 (d, J=12.4 Hz, 4.8 Hz, 1H), 4.33 (d, J=9.6 Hz, 1H), 5.14 (t, J=9.2 Hz, 1H), 5.22 (t, J=9.2 Hz, 1H), 5.30 (t, J=9.2 Hz, 1H), 6.57-6.59 (m, 2H), 6.76 (dd, J=7.2 Hz, 2.0 Hz, 1H), 6.98 (d, J=8.4 Hz, 1H), 7.02 (d, J=1.6 Hz, 1H), 7.17 (dd, J=8.0 Hz, 1.6 Hz, 1H).

MS (ES) m/z 597.3 (M+1).

Example 60: (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol Step II:

To a stirred solution of acetic acid (2R,3R,4R,5S)-3,4,5-triacetoxy-6-[4-cyclopropyl-3-(2,3-dihydro-benzo[1,4]dioxin-6-ylmethyl)-phenyl]-tetrahydro-pyran-2-ylmethyl ester (10.5 g, 17.61 mmol) in methanol:THF:water 3:2:1 (120 mL) was added lithium hydroxide (813 mg, 19.37 mmol). After stirring for 2 h at room temperature, the volatiles were evaporated under reduced pressure. The resulting residue was taken up in ethyl acetate (150 mL) and washed with brine (75 mL), brine containing 10 mL of 5% aqueous KHSO$_4$ (75 mL), and brine (20 mL) again, then dried over sodium sulfate and concentrated to furnish (2S,3R,4R,5S,6R)-2-[4-cyclopropyl-3-(2,3-dihydro-benzo[1,4]dioxin-6-ylmethyl)-phenyl]-6-hydroxymethyl-tetrahydro-pyran-3,4,5-triol (7.25 g)

$^1$H NMR (400 MHz, CD$_3$OD): δ 0.53-0.56 (m, 2H), 0.81-0.86 (m, 2H), 1.80-1.82 (m, 1H), 3.34-3.45 (m, 4H), 3.67 (dd, J=12.0, 5.2 Hz, 1H), 3.86 (d, J=11.6 Hz, 1H), 3.99-4.09 (m, 3H), 4.17 (s, 4H), 6.58-6.62 (m, 2H), 6.68 (d, J=8.0 Hz, 1H), 6.96 (d, J=7.6 Hz, 1H), 7.19 (m, 2H). MS (ES) m/z 446.2 (M+18).

Example 61-62

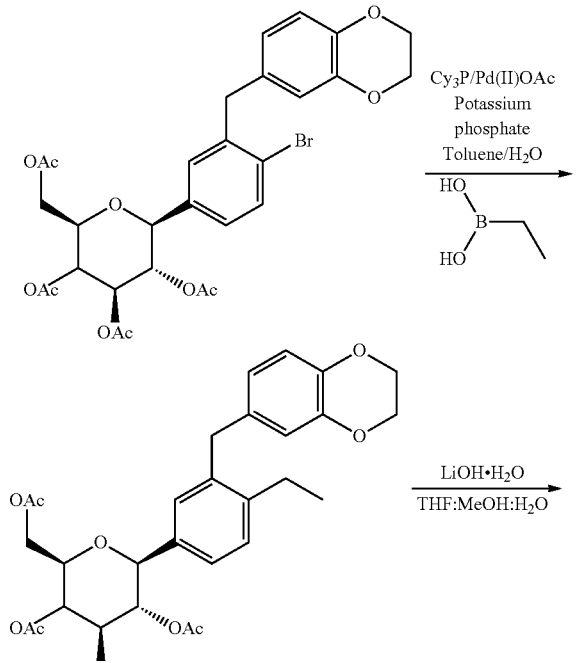

Example 61: Acetic acid (2R,3R,4R,5S)-3,4,5-triacetoxy-6-[3-(2,3-dihydro-benzo[1,4]dioxin-6-ylmethyl)-4-ethyl-phenyl]-tetrahydro-pyran-2-ylmethyl ester Step I:
To a stirred solution of acetic acid (2R,3R,4R,5S)-3,4,5-triacetoxy-6-[4-bromo-3-(2,3-dihydro-benzo[1,4]dioxin-6-ylmethyl)-phenyl]-tetrahydro-pyran-2-ylmethyl ester (10.0 g, 15.74 mmol) in toluene (200 mL) was added tricyclohexylphosphine (1.76 g, 6.29 mmol), a solution of potassium phosphate tribasic (13.3 g, 62.9 mmol) in water (15 mL), and ethylboronic acid (3.4 g, 47.2 mmol). The reaction mixture was degassed for 45 min then palladium (II) acetate (529 mg, 2.3 mmol) was added. After refluxing overnight, the reaction mixture was cooled to room temperature, and water was added. The resulting mixture was extracted with ethyl acetate, (2×200 mL), washed with water and brine, then dried over sodium sulfate, concentrated and purified by column chromatography to furnish acetic acid (2R,3R,4R,5S)-3,4,5-triacetoxy-6-[3-(2,3-dihydro-benzo[1,4]dioxin-6-ylmethyl)-4-ethyl-phenyl]-tetrahydro-pyran-2-ylmethyl ester (5.4 g).

Example 62: (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol Step II:
To a stirred solution of acetic acid (2R,3R,4R,5S)-3,4,5-triacetoxy-6-[3-(2,3-dihydro-benzo[1,4]dioxin-6-ylmethyl)-4-ethyl-phenyl]-tetrahydro-pyran-2-ylmethyl ester (9.3 g, 15.9 mmol) in methanol:THF:water 3:2:1 (170 mL) was added lithium hydroxide (764 mg, 19.1 mmol). After stirring for 2 h at room temperature, the volatiles were evaporated under reduced pressure. The resulting residue was taken up in ethyl acetate (150 mL) and washed with brine (75 mL), brine containing 5 mL of 5% aqueous KHSO$_4$ (75 mL), and brine (20 mL) again, then dried over sodium sulfate and concentrated to furnish (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol (6.5 g)

$^1$H NMR (400 MHz, CD$_3$OD): δ 1.07 (t, J=7.6 Hz, 3H), 2.57 (q, J=7.6 Hz, 2H), 3.34-3.50 (m, 4H), 3.68 (dd, J=12.0, 5.6 Hz, 1H), 3.85-3.91 (m, 3H), 4.08 (d, J=9.6 Hz, 1H), 4.17 (s, 4H), 6.53-6.58 (m, 2H), 6.68 (d, J=8.4 Hz, 1H), 7.15-7.25 (m, 3H).

MS (ES) m/z 434.2 (M+18).

Examples 63-65

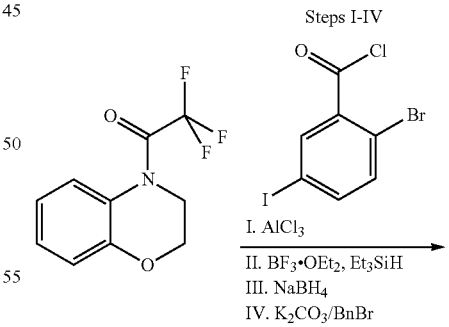

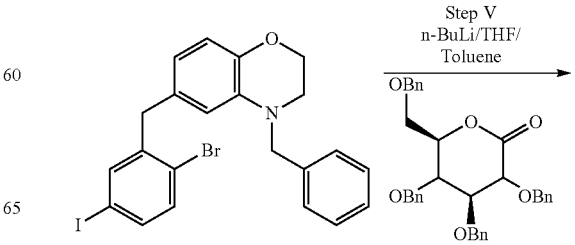

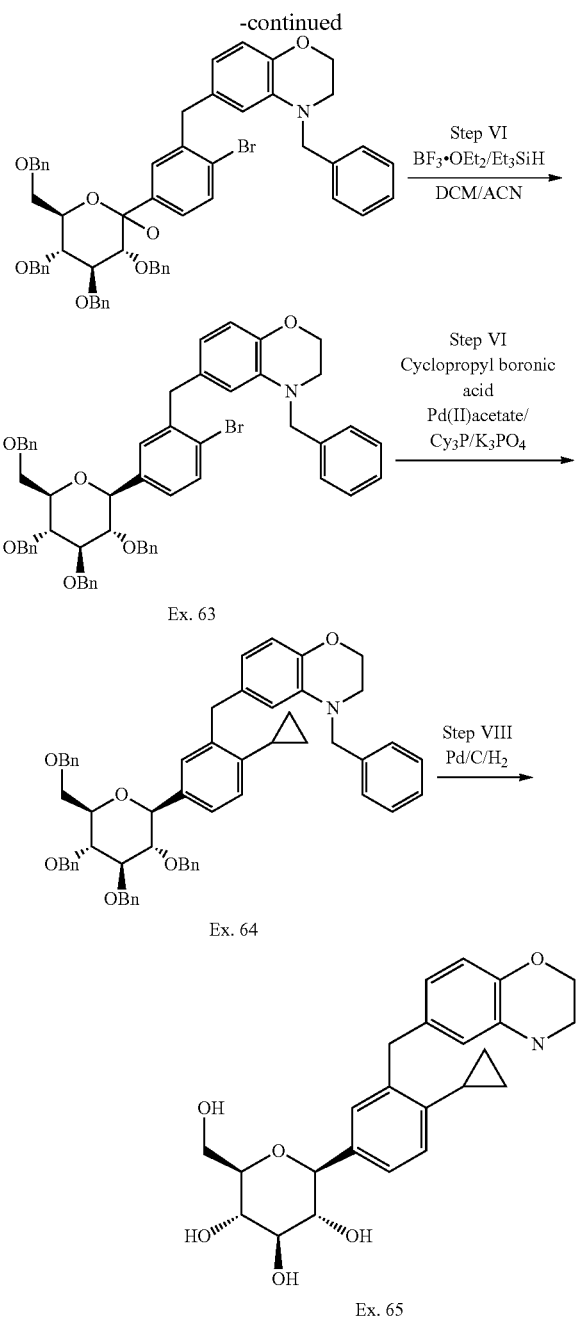

Ex. 63

Ex. 64

Ex. 65

Step I.

To a stirred solution of 1-(2,3-dihydro-benzo[1,4]oxazin-4-yl)-2,2,2-trifluoro-ethanone (9.2 g, 39.77 mmol) in dichloromethane (70 mL) was added 5-iodo-2-bromobenzoyl chloride (13.7 g, 39.77 mmol) in dichloromethane (30 mL) at 0° C. followed by addition of AlCl$_3$ (13.3 g, 99.41 mmol). After 3 h, the reaction mixture was brought to room temperature and stirred overnight. The reaction was quenched by pouring it over crushed ice and the resultanting mixture was extracted with dichloromethane (100×2 mL). The organic layers were combined and washed with aq. sodium bicarbonate (20 mL) and water (20 mL) then concentrated to furnish 6-(2-bromo-5-iodo-benzoyl)-4-(2,2,2-trifluoro-acetyl)-4H-benzo[1,4]oxazin-3-one (16.1 g).

MS (ES) m/z: 539.7 [M($^{79}$Br)+1], 541.7 [M($^{81}$Br)+1]

Step II.

To a stirred solution of 6-(2-bromo-5-iodo-benzoyl)-4-(2,2,2-trifluoro-acetyl)-4H-benzo[1,4]oxazin-3-one (16.0 g, 29.252 mmol) in 1,2-dichloroethane/MeCN (1:2 mixture, 60 mL) was added triethylsilane (9.9 mL, 62.43 mmol) and borontrifluoride diethyletherate complex (4.9 mL, 38.51 mmol) simultaneously at −10° C. After stirring overnight at room temperature, the reaction was heated at 50° C. for 3 h. The reaction was quenched by the addition of aq. sodium bicarbonate (50 mL). Volatiles were evaporated under reduced pressure, and the resulting residue was extracted with ethyl acetate (2×100 mL). The organic layers were combined and washed with water and brine, then dried over sodium sulfate and concentrated to a residue which was purified by silica gel column chromatography to furnish 1-[6-(2-bromo-5-iodo-benzyl)-2,3-dihydro-benzo[1,4]oxazin-4-yl]-2,2,2-trifluoro-ethanone (12.1 g).

MS (ES) m/z 544.7 (M+18).

Step III.

To a stirred solution of 1-[6-(2-bromo-5-iodo-benzyl)-2,3-dihydro-benzo[1,4]oxazin-4-yl]-2,2,2-trifluoro-ethanone (12.0 g, 22.81 mmol) in methanol (100 mL) and THF (20 mL) was added sodium borohydride (1.73 g, 45.62 mmol) portion wise and the reaction mixture was stirred at room temperature for 1 h. The excess of sodium borohydride was quenched by adding 1N HCl. Methanol was evaporated and the residue was partitioned between dichloromethane and water. The organic layer was washed with water, and brine, then concentrated to furnish the crude product which was purified by silica gel column chromatography to provide 6-(2-bromo-5-iodo-benzyl)-3,4-dihydro-2H-benzo[1,4]oxazine (9.45 g).

MS (ES) m/z: 429.8 [M($^{79}$Br)+1], 431.8 [M($^{81}$Br)+1]

Step IV.

To a stirred solution of 6-(2-bromo-5-iodo-benzyl)-3,4-dihydro-2H-benzo[1,4]oxazine (9.4 g, 21.86 mmol) in DMF (50 mL) was added potassium carbonate (6.04 g, 43.71 mmol), benzyl bromide (3.2 mL, 26.23 mmol) and the mixture was heated to 50° C. overnight. The reaction mixture was cooled to room temperature, quenched by the addition of water (100 mL), then extracted with ethyl acetate (3×50 mL). The organic layers were combined then washed with water (50 mL), brine (50 mL), dried over sodium sulfate, and concentrated to a residue which was purified by silica gel column chromatoghraphy to furnish 4-benzyl-6-(2-bromo-5-iodo-benzyl)-3,4-dihydro-2H-benzo[1,4]oxazine (10.5 g).

MS (ES) m/z: 519.8 [M($^{79}$Br)+1], 521.8 [M($^{81}$Br)+1]

Step V.

To a stirred solution of 4-benzyl-6-(2-bromo-5-iodo-benzyl)-3,4-dihydro-2H-benzo[1,4]oxazine (2.0 g, 3.85 mmol) in THF (20 mL) was added n-Butyl lithium (2.4 mL, 3.85 mmol) at −78° C. and the mixture was stirred for 1 h. This was transferred to a solution of 2,3,4,6-tetrakis-O-(benzyl)-D-glucopyranone (2.07 g, 3.85 mmol) in THF (18 mL) at −78° C. After stirring for 1 h, the reaction was quenched with Sat. ammonium chloride (20 mL), and the resulting mixture was extracted with ethyl acetate (2×20 mL), washed with water and brine, then dried over sodium sulfate, concentrated and purified by silica gel column chromatography to furnish (3R,4S,5R,6R)-2-[3-(4-benzyl-3,4-dihydro-2H-benzo[1,4]oxazin-6-ylmethyl)-4-bromo-phenyl]-3,4,5-tris-benzyloxy-6-benzyloxymethyl-tetrahydro-pyran-2-ol (1.62 g).

MS (ES) m/z: 931.9 [M($^{79}$Br)+1], 934.0 [M($^{81}$Br)+1]

Example 63: 4-Benzyl-6-[2-bromo-5-((2S,3S,4R, 5R,6R)-3,4,5-tris-benzyloxy-6-benzyloxymethyl-tetrahydro-pyran-2-yl)-benzyl]-3,4-dihydro-2H-benzo[1,4]oxazine Step VI.

To a stirred solution of (3R,4S,5R,6R)-2-[3-(4-benzyl-3,4-dihydro-2H-benzo[1,4]oxazin-6-ylmethyl)-4-bromo-phenyl]-3,4,5-tris-benzyloxy-6-benzyloxymethyl-tetrahydro-pyran-2-ol (1.60 g, 1.72 mmol) in acetonitrile-dichloromethane mixture (3:1 mixture, 7 mL) was added triethylsilane (0.82 mL, 5.15 mmol) followed by boron trifluoride diethyletharate complex (0.42 mL, 3.43 mmol) at Q-30° C. After stirring for 2 h at 0° C., the reaction was quenched with aq. sodium bicarbonate (4 mL). The volatiles were evaporated under reduced pressure, and the resulting mixture was extracted with dichloromethane (2×20 mL). The organic layers were combined and washed with brine (3 mL), dried over sodium sulfate, then concentrated to a residue which was purified by column chromatography to furnish 4-benzyl-6-[2-bromo-5-((2S,3S,4R,5R,6R)-3,4,5-tris-benzyloxy-6-benzyloxymethyl-tetrahydro-pyran-2-yl)-benzyl]-3,4-dihydro-2H-benzo[1,4]oxazine (1.10 g).

MS (ES) m/z: 917.1 [M($^{79}$Br)+1], 919.1 [M($^{81}$Br)+1]

Example 64: 4-Benzyl-6-[2-cyclopropyl-5-((2S,3S, 4R,5R,6R)-3,4,5-tris-benzyloxy-6-benzyloxymethyl-tetrahydro-pyran-2-yl)-benzyl]-3,4-dihydro-2H-benzo[1,4]oxazine Step VII.

To a stirred solution of 4-benzyl-6-[2-bromo-5-((2S,3S,4R,5R,6R)-3,4,5-tris-benzyloxy-6-benzyloxymethyl-tetrahydro-pyran-2-yl)-benzyl]-3,4-dihydro-2H-benzo[1,4]oxazine (0.35 g, 0.38 mmol) in toluene:water (10:1 mixture, 10 mL) was added cyclopropylboronic acid (49.2 mg, 0.5731 mmol) tricyclohexylphosphine (26.7 mg, 0.0955 mmol), and potassium phosphate (0.28 g, 1.34 mmol). The reaction mixture was degassed for 45 min then palladium (II) acetate (8.5 mg, 0.03821 mmol) was added. After heating overnight at 100° C., the reaction mixture was cooled to room temperature and water (20 mL) was added. The resulting mixture was extracted with ethyl acetate (2×25 mL), washed with water and brine, then dried over sodium sulfate, concentrated and purified by column chromatography to furnish 4-benzyl-6-[2-cyclopropyl-5-((2S,3S,4R,5R,6R)-3,4,5-tris-benzyloxy-6-benzyloxymethyl-tetrahydro-pyran-2-yl)-benzyl]-3,4-dihydro-2H-benzo[1,4]oxazine (317 mg). The product was taken up for the next step without characterization.

Example 65: (2S,3R,4R,5S,6R)-2-[4-Cyclopropyl-3-(3,4-dihydro-2H-benzo[1,4]oxazin-6-ylmethyl)-phenyl]-6-hydroxymethyl-tetrahydro-pyran-3,4,5-triol Step VIII.

To a solution of 4-benzyl-6-[2-cyclopropyl-5-((2S,3S,4R,5R,6R)-3,4,5-tris-benzyloxy-6-benzyloxymethyl-tetrahydro-pyran-2-yl)-benzyl]-3,4-dihydro-2H-benzo[1,4]oxazine (0.42 g, 0.4783 mmol) in THF (4.7 mL) was added 10% palladium on charcoal (80 mg), 0.1 mL conc. HCl followed by methanol (4.7 mL) and the mixture was stirred under hydrogen atmosphere for 18 h. The reaction mixture was filtered through a celite bed, washed with methanol and concentrated. The resulting residue was purified by preparative HPLC to furnish (2S,3R,4R,5S,6R)-2-[4-cyclopropyl-3-(3,4-dihydro-2H-benzo[1,4]oxazin-6-ylmethyl)-phenyl]-6-hydroxymethyl-tetrahydro-pyran-3,4,5-triol (34 mg).

$^1$H NMR (400 MHz, CD$_3$OD): δ 0.53-0.57 (m, 2H), 0.82-0.86 (m, 2H), 1.81-1.88 (m, 1H), 3.27 (t, J=11.0 Hz, 2H), 3.43-3.47 (m, 3H), 3.68 (dd, J=12.0 Hz, 5.6 Hz, 1H), 3.86 (d, J=11.6 Hz, 1H), 3.99 (Abq, J=15.6 Hz, 2H), 4.08 (d, J=9.2 Hz, 1H), 4.13 (t, J=11.0 Hz, 2H), 6.39-6.41 (m, 2H), 6.54 (d, J=8.0 Hz, 1H), 6.95 (d, J=8.4 Hz, 1H), 7.17-7.21 (m, 2H).

MS (ES) m/z 428.1 (M+1).

Following example was prepared by using the procedures described for examples 63-65.

| Example No. | Structure/IUPAC name | Spectral data |
|---|---|---|
| 66 | 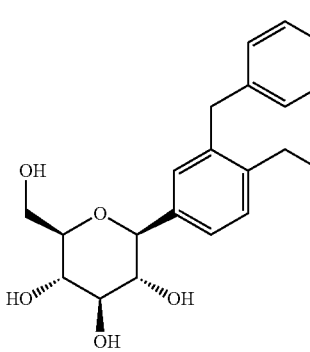<br>(2S,3R,4R,5S,6R)-2-[3-(3,4-Dihydro-2H-benzo[1,4]oxazin-6-ylmethyl)-4-ethyl-phenyl]-6-hydroxymethyl-tetrahydro-pyran-3,4,5-triol | $^1$H NMR (400 MHz, CD$_3$OD): δ 1.07 (t, J = 7.6 Hz, 3H), 2.58 (q, J = 7.6 Hz, 2H), 3.26-3.48 (m, 6H), 3.66-3.70 (m, 1H), 3.80-3.89 (m, 3H), 4.07 (d, J = 9.2 Hz, 1H), 4.13 (t, J = 4.4 Hz, 2H), 6.34-6.37 (m, 2H), 6.54 (dd, J = 7.6, 0.8 Hz, 1H), 7.14 (d, J = 7.8 Hz, 1H), 7.18 (d, J = 1.6 Hz, 1H), 7.22 (dd, J = 7.6, 1.6 Hz, 1H)<br>MS (ES) m/z 416.4 (M + 1). |

| Example No. | Structure/IUPAC name | Spectral data |
|---|---|---|
| 67 | (2S,3R,4R,5S,6R)-2-[2-(3,4-Dihydro-2H-benzo[1,4]oxazin-6-ylmethyl)-4'-methyl-biphenyl-4-yl]-6-hydroxymethyl-tetrahydro-pyran-3,4,5-triol | $^1$H NMR (400 MHz, CD$_3$OD): δ 2.36 (s, 3H), 3.26 (t, J = 4.4 Hz, 2H), 3.37-3.45 (m, 5H), 3.65-3.80 (m, 3H), 3.88 (d, J = 11.4 Hz, 1H), 4.12 (t, J = 4.4 Hz, 2H), 6.18 (dd, J = 8.1 Hz, 1.7 Hz, 1H), 6.25 (s, 1H), 6.48 (d, J = 8.1 Hz, 1H), 7.07 (d, J = 8.0 Hz, 2H), 7.16 (d, J = 7.8 Hz, 3H), 7.28-7.32 (m, 2H).<br>MS (ES) m/z 4478.2 (M + 1). |

Ex. 68  Ex. 69

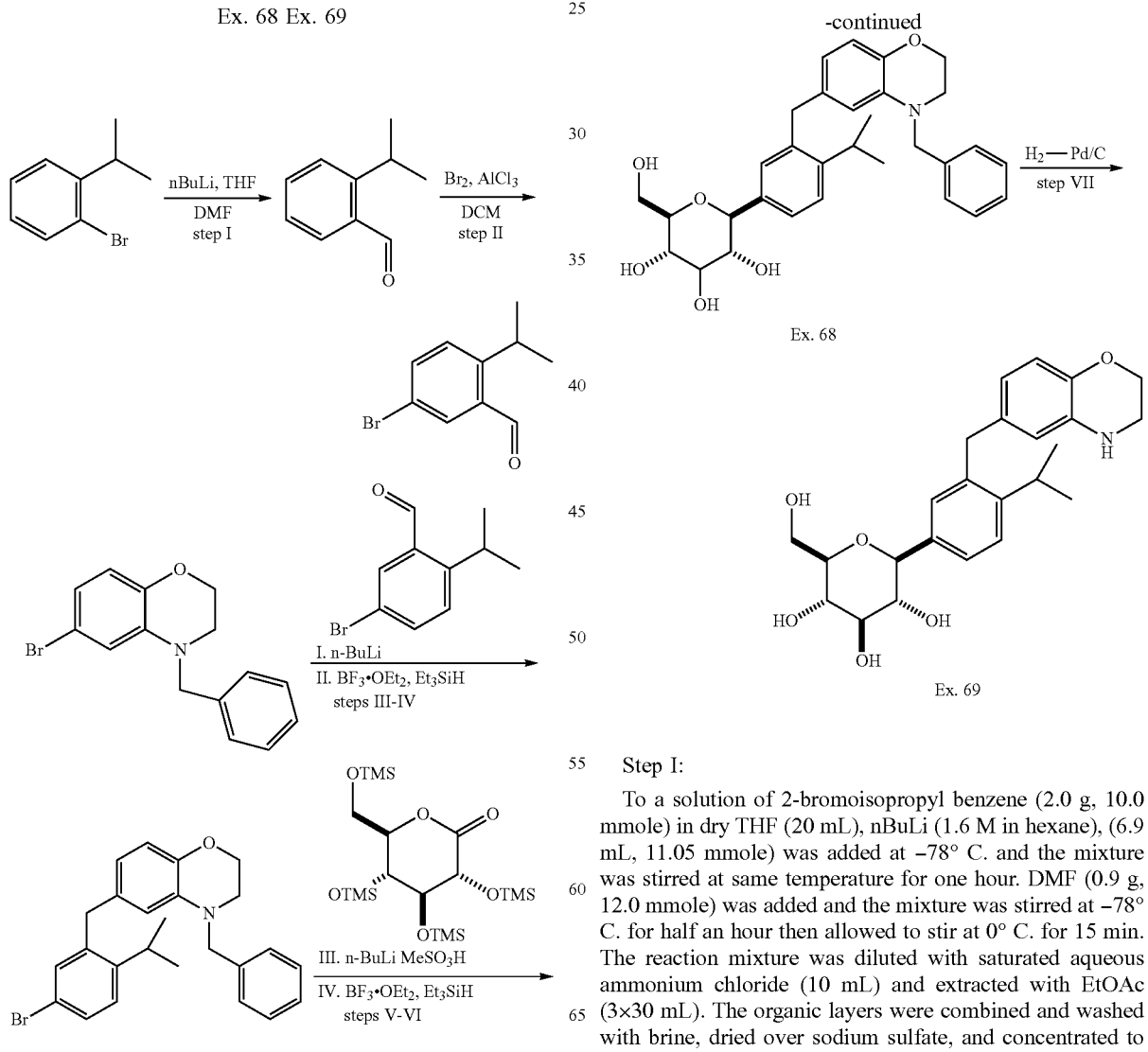

Ex. 68

Ex. 69

Step I:

To a solution of 2-bromoisopropyl benzene (2.0 g, 10.0 mmole) in dry THF (20 mL), nBuLi (1.6 M in hexane), (6.9 mL, 11.05 mmole) was added at −78° C. and the mixture was stirred at same temperature for one hour. DMF (0.9 g, 12.0 mmole) was added and the mixture was stirred at −78° C. for half an hour then allowed to stir at 0° C. for 15 min. The reaction mixture was diluted with saturated aqueous ammonium chloride (10 mL) and extracted with EtOAc (3×30 mL). The organic layers were combined and washed with brine, dried over sodium sulfate, and concentrated to yield 2-isopropyl benzaldehyde (1.4 g).

Step II:

A solution of 2-isopropyl benzaldehyde (1.5 g, 10.13 mmole) in DCM (10 mL) was added to a solution of AlCl$_3$ (2.6 g, 20.26 mmole) in DCM (10 mL) at 0° C. followed by addition of a dilute solution of Br$_2$ (0.67 mL, 13.1 mmole in 20 mL DCM) to the reaction mixture. The solution was stirred at 0° C. for 6 hours then stirred overnight at room temperature. The reaction mixture was basified using saturated aqueous sodium bicarbonate and extracted with DCM (30×2 mL). The organic layers were combined and the crude product was obtained by evaporation of the solvent. The crude product was purified by column chromatography using 1% EtOAc in Hexane to yield 5-bromo-2-isopropyl-benzaldehyde (800 mg).

Step III:

To a solution of 4-Benzyl-6-bromo-3,4-dihydro-2H-benzo[1,4]oxazine (1.5 g, 4.93 mmol) in THF (20 mL) was added 1.6 M n-butyl lithium in hexanes (3.0 mL, 74.93 mmol) at −78° C. The reaction was stirred for 30 min. then transferred to a stirred solution of 5-bromo-2-isopropylbenzaldehyde (1.12 g, 4.93 mmol) in THF (15 mL) at −78° C. After stirring for 30 min, the reaction was quenched by the addition of saturated aqueous solution of ammonium chloride. The resulting mixture was extracted with ethyl acetate (3×30 mL), and the combined organic layers were washed with water (25 mL) and brine (25 mL), then dried over sodium sulfate, concentrated and purified using neutral alumina column chromatography to give (4-Benzyl-3,4-dihydro-2H-benzo[1,4]oxazin-6-yl)-(5-bromo-2-isopropyl-phenyl)-methanol (1.3 g).

Step IV.

To an ice cold solution of (4-Benzyl-3,4-dihydro-2H-benzo[1,4]oxazin-6-yl)-(5-bromo-2-isopropyl-phenyl)-methanol (1.3 g, 2.87 mmol) in dichloromethane (25 mL) was added Et$_3$SiH (4.8 mL, 5.70 mmol) followed by BF$_3$.OEt$_2$ (0.74 mL, 5.7 mmol). The reaction mixture was stirred at room temperature overnight then quenched by the addition of aq. NaHCO$_3$. The reaction mixture was extracted with ethyl acetate (3×30 mL), and the combined organic layers were washed with brine (30 mL) and dried over sodium sulfate. Crude product obtained after evaporation of the solvent was purified by silica gel column chromatography to furnish 4-Benzyl-6-(5-bromo-2-isopropyl-benzyl)-3,4-dihydro-2H-benzo[1,4]oxazine (1.0 g).

Step V:

To a stirred solution of 4-Benzyl-6-(5-bromo-2-isopropyl-benzyl)-3,4-dihydro-2H-benzo[1,4]oxazine (1.0 g, 2.29 mmol) in THF-toluene (15 mL of 1:2 mixture) was added 1.6 M solution of n-BuLi in hexanes (1.40 mL, 1.40 mmol) at −78° C. The reaction mixture was stirred for 30 min. then transferred to a stirred solution of 2,3,4,6-tetrakis-O-(trimethylsilyl)-D-glucopyranone (1.0 g, 2.29 mmol) in toluene (10 mL) at −78° C. After stirring for 40 min., 0.6 N methanesulfonic acid in methanol (10 mL) was added and the reaction was stirred for 20 h at room temperature then quenched by the addition of aq. saturated NaHCO$_3$ (10 mL). The resulting mixture was extracted with ethyl acetate (3×20 mL), and the organic layers were combined and dried over sodium sulphate, and concentrated to a residue which was purified by silica gel column chromatography to furnish (3R,4S,5S,6R)-2-[3-(4-Benzyl-3,4-dihydro-2H-benzo[1,4]oxazin-6-ylmethyl)-4-isopropyl-phenyl]-6-hydroxymethyl-2-methoxy-tetrahydro-pyran-3,4,5-triol (600 mg).

Example 68: (2S,3R,4R,5S,6R)-2-[3-(4-Benzyl-3,4-dihydro-2H-benzo[1,4]oxazin-6-ylmethyl)-4-isopropyl-phenyl]-6-hydroxymethyl-tetrahydro-pyran-3,4,5-triol Step VI:

To a stirred solution of (3R,4S,5S,6R)-2-[3-(4-Benzyl-3,4-dihydro-2H-benzo[1,4]oxazin-6-ylmethyl)-4-isopropyl-phenyl]-6-hydroxymethyl-2-methoxy-tetrahydro-pyran-3,4,5-triol (600 mg, 1.09 mmol) in acetonitrile-dichloroethane mixture (1:1 mixture, 10 mL) was added triethylsilane (0.7 mL, 4.4 mmol) and boron trifluoride diethyletharate complex (0.27 mL, 2.18 mmol) at −20° C. After stirring for 4 h at 0° C., the reaction was quenched with aq. saturated NaHCO$_3$ solution (8 mL). The volatiles were evaporated under reduced pressure; the resulting mixture was extracted with ethyl acetate (3×20 mL). The organic layers were combined and washed with brine (5 mL), dried over sodium sulphate, concentrated to a residue which was purified by column chromatography to furnish (2S,3R,4R,5S,6R)-2-[3-(4-Benzyl-3,4-dihydro-2H-benzo[1,4]oxazin-6-ylmethyl)-4-isopropyl-phenyl]-6-hydroxymethyl-tetrahydro-pyran-3,4,5-triol (520 mg).

Example 69: (2S,3R,4R,5S,6R)-2-[3-(3,4-Dihydro-2H-benzo[1,4]oxazin-6-ylmethyl)-4-isopropyl-phenyl]-6-hydroxymethyl-tetrahydro-pyran-3,4,5-triol Step VII:

To a solution (2S,3R,4R,5S,6R)-2-[3-(4-benzyl-3,4-dihydro-2H-benzo[1,4]oxazin-6-ylmethyl)-4-isopropyl-phenyl]-6-hydroxymethyl-tetrahydro-pyran-3,4,5-triol (520 mg, 1.0 mmol) in methanol (5 mL) was added 10% palladium on charcoal (150 mg), 0.05 mL conc. HCl and the mixture was stirred under hydrogen balloon pressure for 18 h. The reaction mixture was filtered through a celite bed, and the celite was washed with methanol. The resulting filtrate was concentrated to a residue which was purified by preparative HPLC to furnish (2S,3R,4R,5S,6R)-2-[3-(3,4-Dihydro-2H-benzo[1,4]oxazin-6-ylmethyl)-4-isopropyl-phenyl]-6-hydroxymethyl-tetrahydro-pyran-3,4,5-triol (70 mg).

$^1$H NMR (400 MHz, CD$_3$OD): δ 1.06 (s, 3H), 1.08 (s, 3H), 3.10-3.180 (m, 1H), 3.26-3.30 (m, 2H), 3.34-3.48 (m, 4H), 3.66-3.70 (m, 1H), 3.83-3.89 (m, 3H), 4.07 (d, J=9.20 Hz, 1H), 4.11-4.13 (m, 2H), 6.32 (dd, J=2.4 Hz, J=8.4 Hz, 1H), 6.36 (d, J=1.6 Hz, 1H), 6.53 (d, J=8.4 Hz, 1H), 7.18 (s, 1H), 7.24-7.28 (m, 2H). MS (ES) m/z 430.3 (M+1).

Examples 70-71

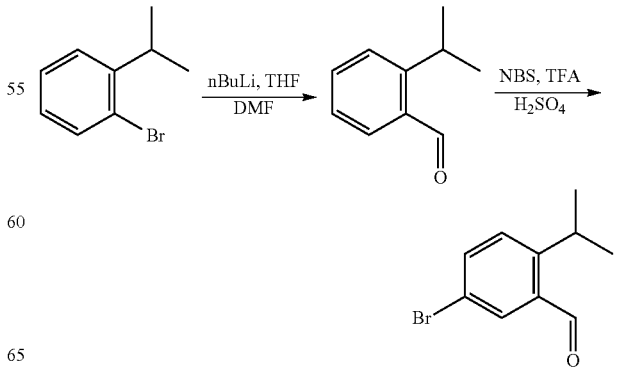

Step I:

To a solution of 2-bromoisopropyl benzene (2.0 g, 10.0 mmole) in dry THF (20 mL), nBuLi (1.6 M in hexanes) (6.9 mL, 11.05 mmole) was added at −78° C. and the mixture was stirred at same temperature for one hour. DMF (0.9 g, 12.0 mmole) was added and the mixture was stirred at −78° C. for an additional half an hour, then allowed to stir at 0° C. for 15 min. The reaction mixture was diluted with saturated aqueous ammonium chloride (10 mL) and extracted with ethyl acetate (3×30 mL). The combined organic layers were washed with brine and dried over sodium sulfate. The solvent was evaporated to yield 2-isopropyl benzaldehyde (1.4 g).

Step II:

To a solution of trifluoroacetic acid (50 ml) and 2-isopropylbenzaldehyde (2.0 g, 13.5 mmol) was added conc. sulphuric acid (98%) (10 ml) at room temperature, followed by N-bromosuccinamide (NBS, 3.6 g 20.2 mmol) in portions. After 2 hrs, the mixture was poured into ice water and extracted with dichloromethane (3×30 mL). The organic layers were combined and neutralized with saturated aqueous sodium bicarbonate, washed with brine (30 mL), dried over sodium sulfate and concentrated. The resulting residue was purified by column chromatography to furnish 5-bromo-2-isopropylbenzaldehyde (1.80 g).

$^1$H NMR (400 MHz, CDCl$_3$): δ 1.30 (d, J=6.8 Hz, 6H), 3.84-3.91 (m, 1H), 7.33 (d, J=8.4 Hz, 1H), 7.65 (dd, J=2.0, J=8.4 Hz, 1H), 7.93 (d, J=2.0 Hz, 1H), 10.3 (s, 1H).

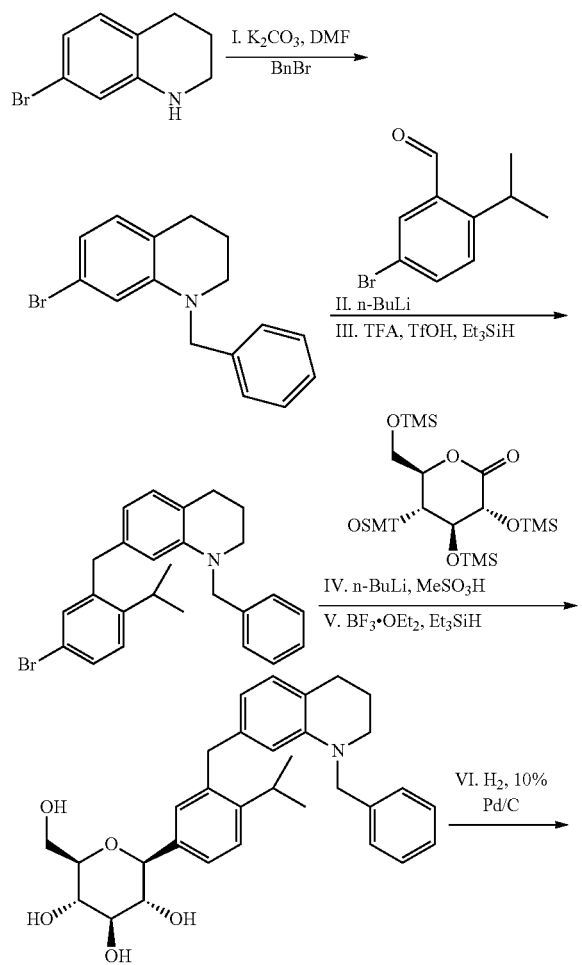

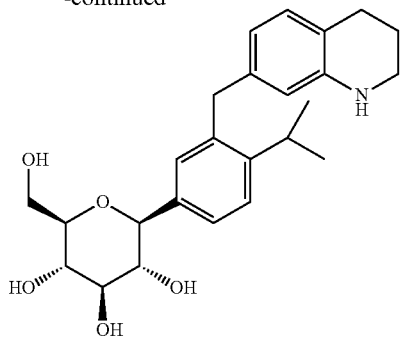

Step I:

To a stirred solution of 7-bromo-1,2,3,4-tetrahydroquinoline (7.0 g, 33.0 mmol) in DMF (50 mL) was added potassium carbonate (13.6 g, 99.0 mmol), and benzyl bromide (4.33 mL, 36.3 mmol), and the mixture was heated to 60° C. for 12 h, then cooled to room temperature and quenched by the addition of ice-cold water (150 mL). The resulting mixture was extracted with ethyl acetate (3×50 mL), and the organic layers were combined and washed with water (50 mL) and brine (50 mL), then dried over sodium sulfate, concentrated and purified by silica gel column chromatography to furnish 1-benzyl-7-bromo-1,2,3,4-tetrahydro-quinoline (7.1 g).

Step II:

To a solution of 1-benzyl-7-bromo-1,2,3,4-tetrahydroquinoline (2.50 g, 8.27 mmol) in THF (20 mL) was added 1.6 M n-butyl lithium in hexanes (5.14 mL, 8.27 mmol) at −78° C. The mixture was stirred for 45 min. then transferred to a stirred solution of 5-bromo-2-isopropylbenzaldehyde (1.87 g, 8.27 mmol) in THF (15 mL) at −78° C. After stirring for 30 min, the reaction was quenched by the addition of saturated aqueous solution of ammonium chloride, and the resulting mixture was extracted with ethyl acetate (3×30 mL). The organic layers were combined and washed with water (25 mL) and brine (25 mL), then dried over sodium sulfate, concentrated and purified using neutral alumina column chromatography to furnish (1-benzyl-1,2,3,4-tetrahydro-quinolin-7-yl)-(5-bromo-2-isopropyl-phenyl)-methanol (2.64 g).

$^1$H NMR (400 MHz, CDCl$_3$): δ 0.85 (d, J=7.2 Hz, 3H), 1.11 (d, J=6.8 Hz, 3H), 1.97-2.03 (m, 2H), 2.78 (t, J=6.4 Hz, 2H), 2.92-2.99 (m, 1H), 3.40 (t, J=5.6 Hz, 2H), 4.40 (s, 2H), 5.85 (d, J=3.2 Hz, 1H), 6.36 (s, 1H), 6.47 (d, J=1.2 Hz, 1H), 6.91 (d, J=7.6 Hz, 1H), 7.04 (d, J=8.0 Hz, 1H), 7.14-7.34 (m, 7H), 7.62 (d, J=2.0 Hz, 1H).

MS (ES) m/z 452 (M+2).

Step III:

To a solution of (1-benzyl-1,2,3,4-tetrahydro-quinolin-7-yl)-(5-bromo-2-isopropyl-phenyl)-methanol (2.61 g, 5.79 mmol) in TFA (7.0 mL), Et$_3$SiH (4.63 mL, 28.95 mmol) was added followed by triflic acid (1.0 mL, 11.5 mmol) at room temperature. The reaction mixture was stirred at room temperature for 30 min. The reaction was evaporated to dryness and neutralized by adding saturated aqueous NaHCO$_3$ (15 mL). The resulting mixture was extraction with dichloromethane (3×30 mL). Crude product obtained after evaporation solvent was purified by using neutral alumina column chromatography to furnish 1-benzyl-7-(5-bromo-2-isopropyl-benzyl)-1,2,3,4-tetrahydro-quinoline (1.80 g).

$^1$H NMR (400 MHz, CDCl$_3$): δ 1.05 (d, J=7.2 Hz, 6H), 1.96-2.02 (m, 2H), 2.76 (t, J=6.0 Hz, 2H), 2.98-3.04 (m,

1H), 3.35 (t, J=5.6 Hz, 2H), 3.80 (s, 2H), 4.37 (s, 2H), 6.19 (s, 1H), 6.27 (d, J=7.6 Hz, 1H), 6.85 (d, J=7.6 Hz, 1H), 7.07 (d, J=8.80 Hz, 1H), 7.14-7.29 (m, 7H).

MS (ES) m/z 436 (M+2).

Step IV:

To a stirred solution of 1-benzyl-7-(5-bromo-2-isopropyl-benzyl)-1,2,3,4-tetrahydro-quinoline (1.50 g, 3.45 mmol) in THF-toluene 1:2 (15 mL) was added 1.6 M solution of n-BuLi in hexanes (2.16 mL, 3.45 mmol) at −78° C. The reaction mixture was stirred for 45 min., and then transferred to a stirred solution of 2,3,4,6-tetrakis-O-(trimethylsilyl)-D-glucopyranone (1.60 g, 3.45 mmol) in toluene (10 mL) at −78° C. After stirring for 45 min., 0.6 N methanesulfonic acid in methanol (15 mL) was added and the mixture was stirred for 20 h at room temperature. The reaction was quenched by addition of aq. saturated NaHCO₃ (10 mL) and the resulting mixture was extracted with ethyl acetate (3×20 mL). The organic layers were combined and dried over sodium sulphate, concentrated and purified by silica gel column chromatography to furnish (2S,3R,4S,5S,6R)-2-[3-(1-Benzyl-1,2,3,4-tetrahydro-quinolin-7-ylmethyl)-4-isopropyl-phenyl]-6-hydroxymethyl-2-methoxy-tetrahydro-pyran-3,4,5-triol (1.27 g).

Example 70: (2S,3R,4R,5S,6R)-2-[3-(1-Benzyl-1,2,3,4-tetrahydro-quinolin-7-ylmethyl)-4-isopropyl-phenyl]-6-hydroxymethyl-tetrahydro-pyran-3,4,5-triol Step V:

To a stirred solution of (2S,3R,4S,5S,6R)-2-[3-(1-benzyl-1,2,3,4-tetrahydro-quinolin-7-ylmethyl)-4-isopropyl-phenyl]-6-hydroxymethyl-2-methoxy-tetrahydro-pyran-3,4,5-triol (1.20 g, 2.19 mmol) in acetonitrile-dichloroethane 1:1 (20 mL) was added triethylsilane (1.39 mL, 8.76 mmol) at room temperature, then the reaction mixture cooled to −50 to −60° C. and boron trifluoride diethyletharate complex (0.55 mL, 4.38 mmol) was added dropwise, and the reaction mixture was stirred at same temperature and allowed to stir at below −30° C. for 2 hours and at −20° C. for 1 hour and then below 0° C. for 1 hour. The reaction was quenched with aq. saturated NaHCO₃ solution (20 mL). The volatiles were evaporated under reduced pressure, and the resulting mixture was extracted with ethyl acetate (3×20 mL). The organic layers were combined and washed with brine (5 mL), dried over sodium sulphate, and concentrated to furnish (2S,3R,4R,5S,6R)-2-[3-(1-Benzyl-1,2,3,4-tetrahydro-quinolin-7-ylmethyl)-4-isopropyl-phenyl]-6-hydroxymethyl-tetrahydro-pyran-3,4,5-triol (1.0 g). Crude product was used for next step without purification.

Example 71: (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol Step-VI:

To a solution (2S,3R,4R,5S,6R)-2-[3-(1-benzyl-1,2,3,4-tetrahydro-quinolin-7-ylmethyl)-4-isopropyl-phenyl]-6-hydroxymethyl-tetrahydro-pyran-3,4,5-triol (1.0 g, 1.0 mmol) in methanol (20 mL) was added 10% dry palladium on charcoal (200 mg) and conc. HCl (0.2 mL), and the mixture was stirred under hydrogen balloon pressure for 18 h. The reaction mixture was filtered through a celite bed which was washed with methanol and the filtrate was concentrated. The resulting residue was purified by preparative HPLC to furnish (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol (320 mg).

¹H NMR (400 MHz, CD₃OD): δ 1.07 (s, 3H), 1.08 (s, 3H), 1.84-1.88 (m, 2H), 2.67 (t, J=6.4 Hz, 2H), 3.17 (t, J=5.6 Hz, 3H), 3.37-3.46 (m, 5H), 3.65-3.70 (m, 1H), 3.83-3.88 (m, 2H), 4.08 (d, J=9.2 HZ, 1H), 6.26 (s, 1H), 6.32 (d, J=8.0 Hz, 1H), 6.74 (d, J=7.60 Hz, 1H), 7.19 (s, 1H), 7.22-7.26 (m, 2H).

MS (ES) m/z 428.1 (M+1).

Following example was prepared by using the procedures described for examples 70-71.

| Example No. | Structure/IUPAC name | Spectral data |
|---|---|---|
| 72 | 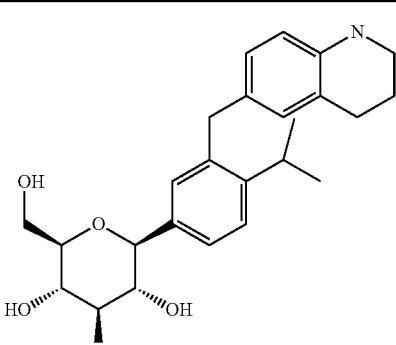<br>(2R,3S,4R,5R,6S)-2-Hydroxymethyl-6-[4-isopropyl-3-(1,2,3,4-tetrahydro-quinolin-6-ylmethyl)-phenyl]-tetrahydro-pyran-3,4,5-triol. | ¹H NMR (400 MHz, CD₃OD): δ 1.06 (s, 3H), 1.07 (s, 3H), 1.82-1.88 (m, 2H), 2.65 (t, J = 6.8 Hz, 2H), 3.12 (m, 1H), 3.16 (t, J = 10.20 Hz, 2H), 3.38-3.46 (m, 4H), 3.66 (dd, J = 4.4 Hz, J = 12.0 Hz, 1H), 3.84-3.88 (m, 3H), 4.08 (d, J = 9.2 HZ, 1H), 6.43 (d, J = 8.0 Hz, 1H), 6.63-6.70 (m, 2H), 7.18 (s, 1H), 7.24-7.26 (m, 2H). MS (ES) m/z 428.1 (M + 1). |

The below list of examples, but not limited to these, can also be synthesized following the general synthesis described herein above:

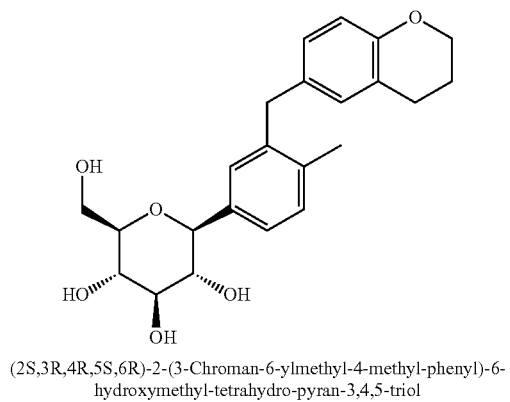

(2S,3R,4R,5S,6R)-2-(3-Chroman-6-ylmethyl-4-methyl-phenyl)-6-hydroxymethyl-tetrahydro-pyran-3,4,5-triol

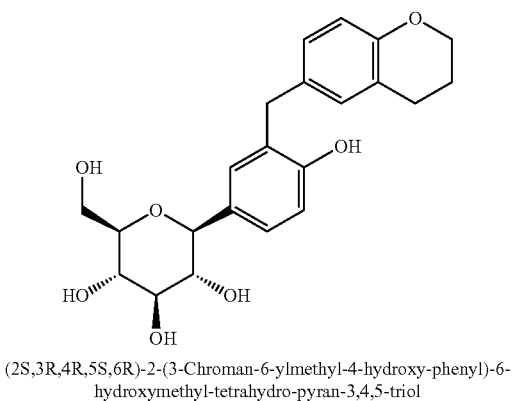

(2S,3R,4R,5S,6R)-2-(3-Chroman-6-ylmethyl-4-hydroxy-phenyl)-6-hydroxymethyl-tetrahydro-pyran-3,4,5-triol

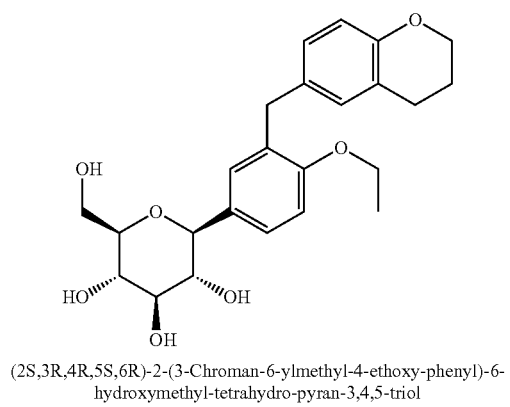

(2S,3R,4R,5S,6R)-2-(3-Chroman-6-ylmethyl-4-ethoxy-phenyl)-6-hydroxymethyl-tetrahydro-pyran-3,4,5-triol

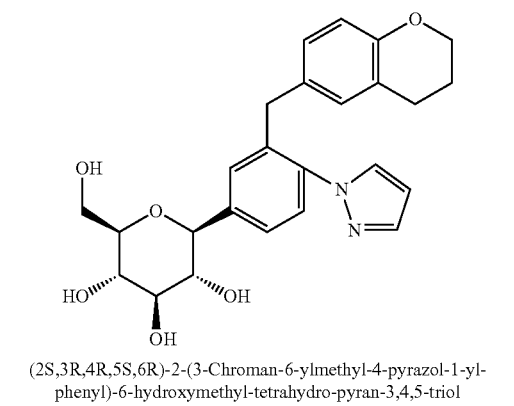

(2S,3R,4R,5S,6R)-2-(3-Chroman-6-ylmethyl-4-pyrazol-1-yl-phenyl)-6-hydroxymethyl-tetrahydro-pyran-3,4,5-triol

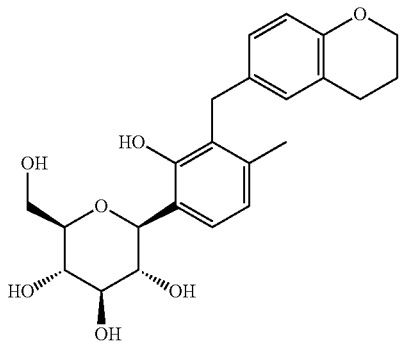

(2S,3R,4R,5S,6R)-2-(3-Chroman-6-ylmethyl-2-hydroxy-4-methyl-phenyl)-6-hydroxymethyl-tetrahydro-pyran-3,4,5-triol

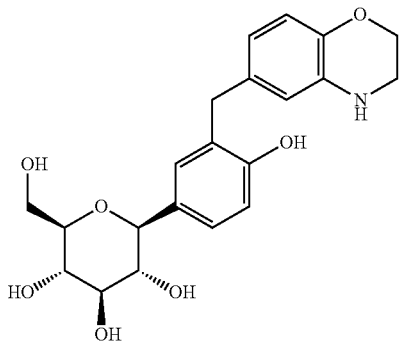 [SMILES: CCc1ccc([C@@H]2O[C@H](CO)[C@@H](O)[C@H](O)[C@H]2O)cc1Cc1ccc2c(c1)NCCO2]

(2S,3R,4R,5S,6R)-2-[3-(3,4-Dihydro-2H-benzo[1,4]oxazin-6-ylmethyl)-4-hydroxy-phenyl]-6-hydroxymethyl-tetrahydro-pyran-3,4,5-triol

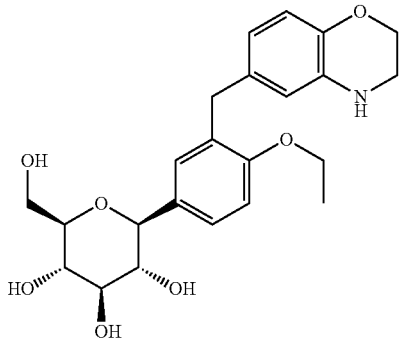

(2S,3R,4R,5S,6R)-2-[3-(3,4-Dihydro-2H-benzo[1,4]oxazin-6-ylmethyl)-4-ethoxy-phenyl]-6-hydroxymethyl-tetrahydro-pyran-3,4,5-triol

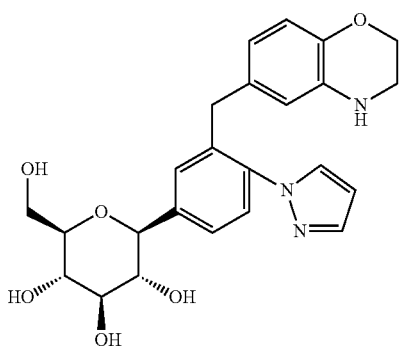

(2S,3R,4R,5S,6R)-2-[3-(3,4-Dihydro-2H-benzo[1,4]oxazin-6-ylmethyl)-4-pyrazol-1-yl-phenyl]-6-hydroxymethyl-tetrahydro-pyran-3,4,5-triol

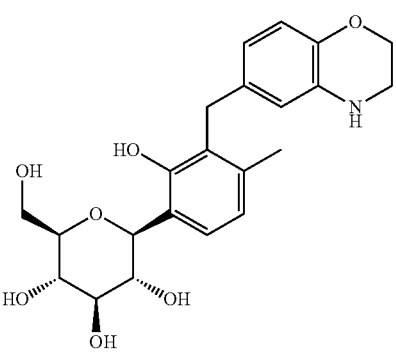

2S,3R,4R,5S,6R)-2-[3-(3,4-Dihydro-2H-benzo[1,4]oxazin-6-ylmethyl)-2-hydroxy-4-methyl-phenyl]-6-hydroxymethyl-tetrahydro-pyran-3,4,5-triol

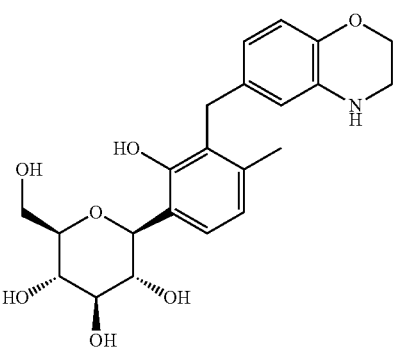

(2S,3R,4R,5S,6R)-2-[3-(3,4-Dihydro-2H-benzo[1,4]oxazin-6-ylmethyl)-2-hydroxy-4-methyl-phenyl]-6-hydroxymethyl-tetrahydro-pyran-3,4,5-triol

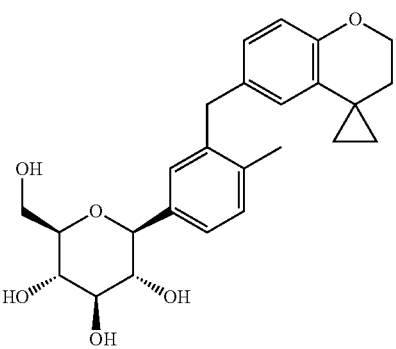

(2R,3S,4R,5S,6S)-2-(hyroxymethyl)-6-[4-methyl-3-(spiro[chromane-4-1'-cyclopropane]-6-ylmethyl)phenyl]tetrahydropyran-3,4,5-triol

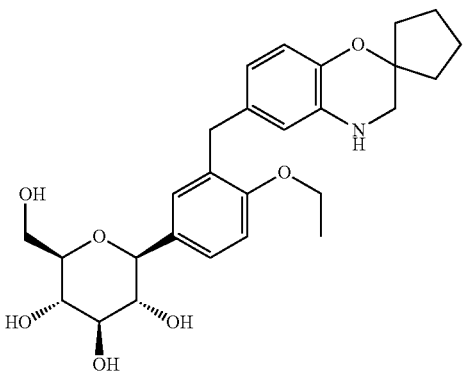

(2S,3R,4R,5S,6R)-2-[4-ethoxy-3-(spiro[3,4-dihydro-1,4-benzoxazine-2,1'-cyclopentane]-6-ylmethyl)phenyl]-6-(hydroxymethyl)tetrahydropyran-3,4,5-triol

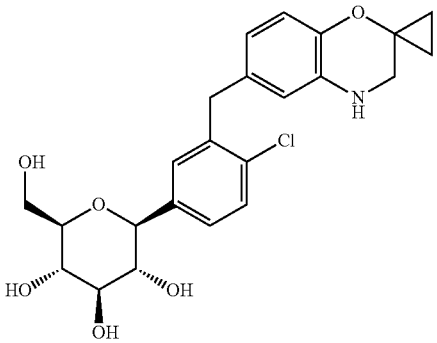

(2S,3R,4R,5S,6R)-2-[4-chloro-3-(spiro[3,4-dihydro-1,4-benzoxazine-2,1'-cyclopropane]-6-ylmethyl)phenyl]-6-(hydroxymethyl)tetrahydropyran-3,4,5-triol

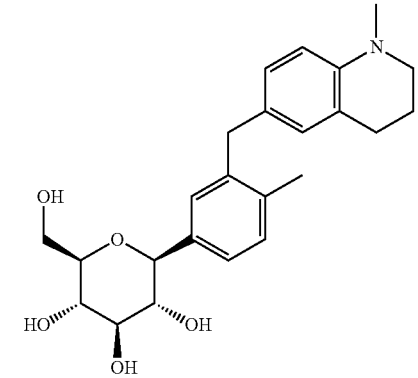

(2R,3S,4R,5R,6S)-2-Hydroxymethyl-6-[4-methyl-3-(1-methyl-1,2,3,4-tetrahydro-quinolin-6-ylmethyl)-phenyl]-tetrahydro-pyran-3,4,5-triol

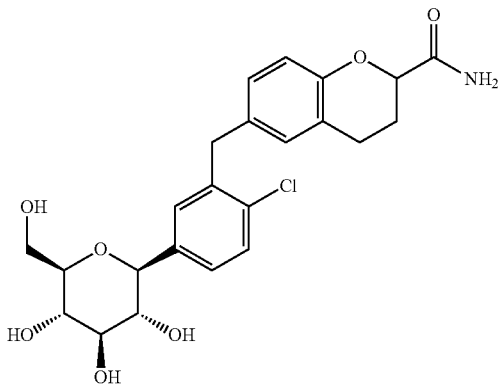

6-[2-Chloro-5-((2S,3R,4R,5S,6R)-3,4,5-trihydroxy-6-hydroxymethyl-tetrahydro-pyran-2-yl)-benzyl]-chroman-2-carboxylic acid amide

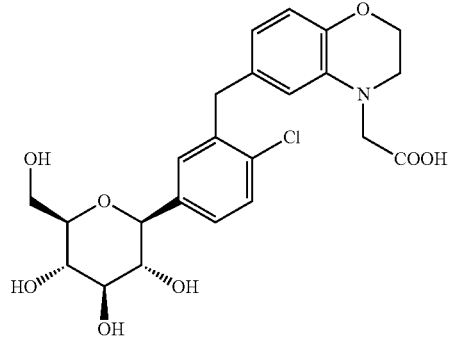

{6-[2-Chloro-5-((2S,3R,4R,5S,6R)-3,4,5-trihydroxy-6-hydroxymethyl-tetrahydro-pyran-2-yl)-benzyl]-2,3-dihydro-benzo[1,4]oxazin-4-yl}-acetic acid

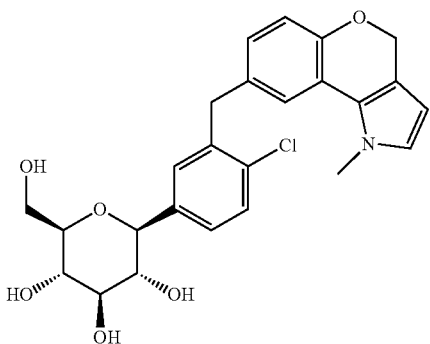

(2S,3R,4R,5S,6R)-2-[4-Chloro-3-(1-methyl-1,4-dihydro-chromeno[4,3-b]pyrrol-8-ylmethyl)-phenyl]-6-hydroxymethyl-tetrahydro-pyran-3,4,5-triol

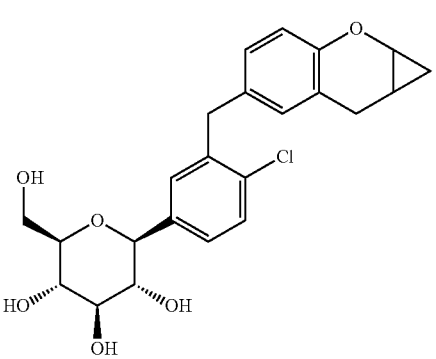

(2S,3R,4R,5S,6R)-2-[4-Chloro-3-(1,1a,2,7a-tetrahydro-7-oxa-cyclopropa[b]naphthalen-4-ylmethyl)-phenyl]-6-hydroxymethyl-tetrahydro-pyran-3,4,5-triol

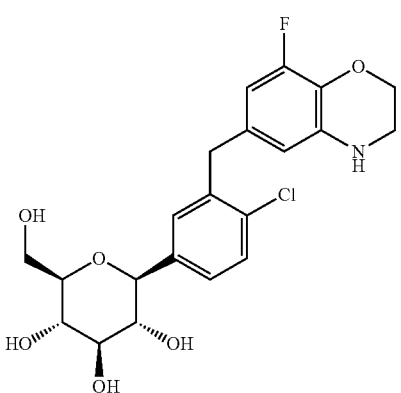

(2S,3R,4R,5S,6R)-2-[4-Chloro-3-(8-fluoro-3,4-dihydro-2H-benzo[1,4]oxazin-6-ylmethyl)-phenyl]-6-hydroxymethyl-tetrahydro-pyran-3,4,5-triol

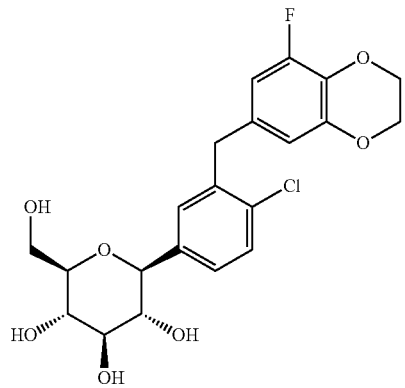

(2S,3R,4R,5S,6R)-2-[4-Chloro-3-(8-fluoro-2,3-dihydro-benzo[1,4]dioxin-6-ylmethyl-phenyl]-6-hydroxymethyl-tetrahydro-pyran-3,4,5-triol

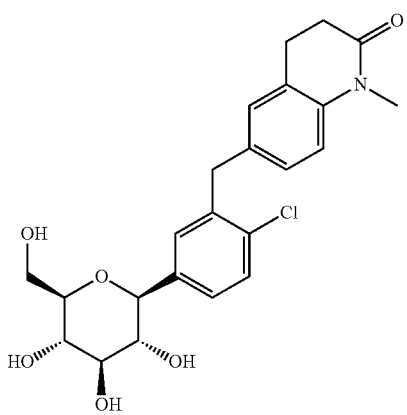

6-[2-Chloro-5-((2S,3R,4R,5S,6R)-3,4,5-trihydroxy-6-hydroxymethyl-tetrahydro-pyran-2-yl)benzyl]-1-methyl-3,4-dihydro-1H-quinolin-2-one

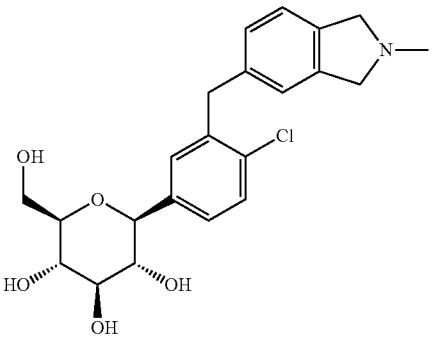

(2S,3R,4R,5S,6R)-2-[4-Chloro-3-(2-methyl-2,3-dihydro-1H-isoindol-5-ylmethyl-phenyl]-6-hydroxymethyl-tetrahydro-pyran-3,4,5-triol

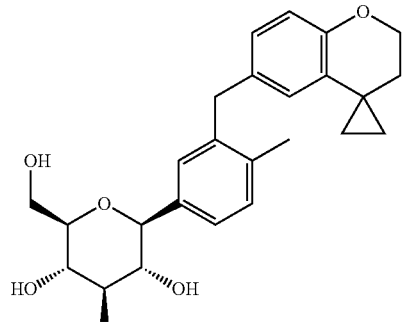

(2S,3R,4R,5S,6R)-2-[4-chloro-3-(spiro[cyclopropane-1,4'-isochromane]-7'-ylmethyl)phenyl]-6-(hydroxymethyl)tetrahydropyran-3,4,5-triol -continued

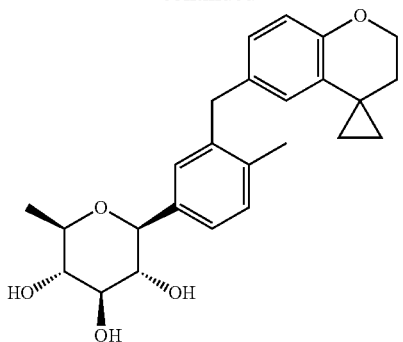

(2R,3S,4S,5R,6S)-2-methyl-6-[4-methyl-3-(spiro[chromane-4,1'-cycloproane-6-ylmethyl)phenyl]tetrahydropyran-3,4,5-triol

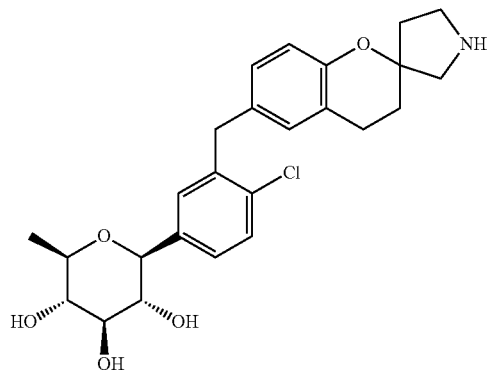

(2S,3R,4S,5S,6R)-2-[4-chloro-3-(spiro[chromane-2,3'-pyrrolidine]-6-ylmethyl)phenyl]-6-methyl-tetrahydropyran-3,4,5-triol

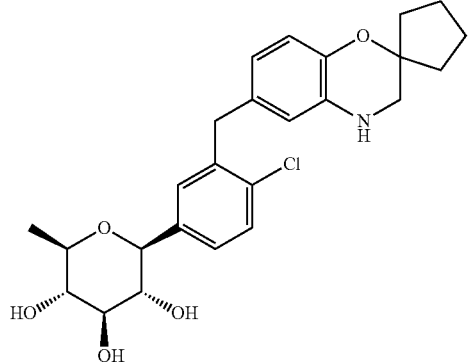

(2S,3R,4S,5S,6R)-2-[4-chloro-3-(spiro[3,4-dihydro-1,4-benzoxazine-2,1'-cyclopentane]-6-ylmethyl)phenyl]-6-methyl-tetrahydropyran-3,4,5-triol

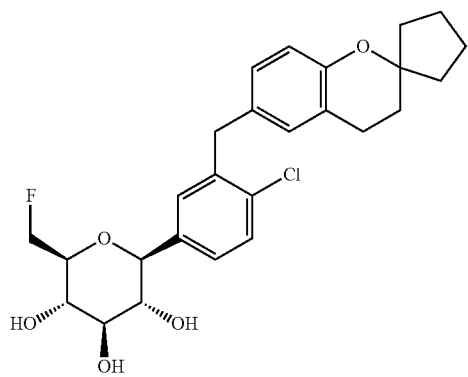

(2S,3R,4R,5S,6S)-2-[4-chloro-3-(spiro[3,4-dihydro-1,4-benzoxanine-2,1'-cyclopentane]-6-ylmethyl)phenyl]-6-(fluoromethyl)tetrahydropyran-3,4,5-triol -continued

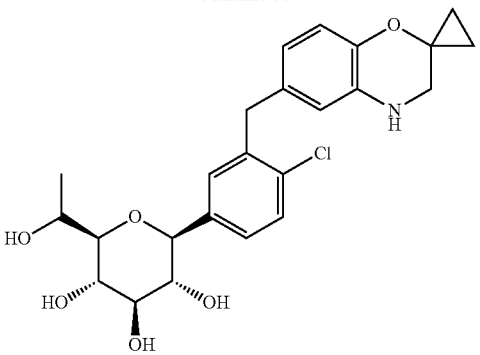

(2S,3R,4R,5S,6R)-2-[4-chloro-3-(spiro[3,4-dihydro-1,4-benzoxazine-2,1'-cyclopropane]-6-ylmethyl)phenyl]-6-(1-hydroxyethyl)tetrahydropyran-3,4,5-triol

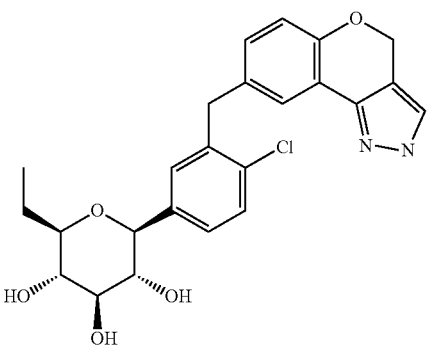

(2S,3R,4S,5S,6R)-2-[4-chloro-3-(2,4-dihydrochromeno[4,3-c]pyrazol-8-ylmethyl)phenyl]-6-ethyl-tetrahydropyran-3,4,5-triol

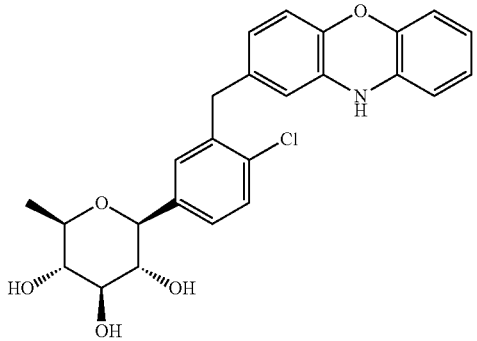

(2S,3R,4S,5S,6R)-2-[4-chloro-3-(10H-phenoxazin-2-ylmethyl)phenyl]-6-methyl-tetrahydropyran-3,4,5-triol

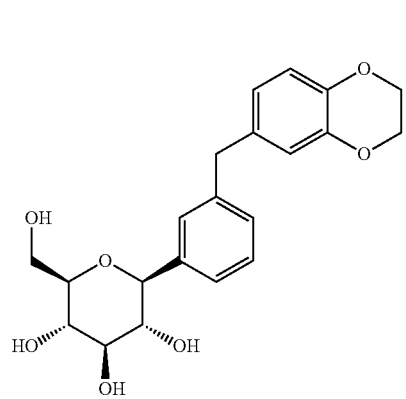

(2S,3R,4R,5S,6R)-2-[3-(2,3-dihydro-1,4-benzodioxin-6-ylmethyl)-4-isopropyl-phenyl]-6-(hydroxymethyl)tetrahydropyran-3,4,5-triol -continued

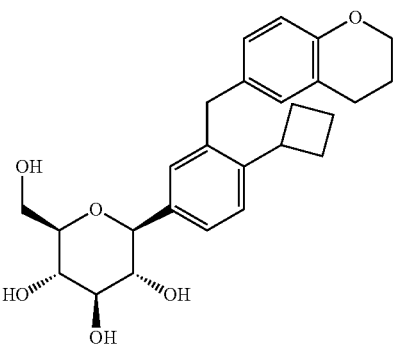

(2S,3R,4R,5S,6R)-2-[3-(chroman-6-ylmethyl)-4-cyclobutyl-phenyl]-6-(hydroxymethyl)tetrahydropyran-3,4,5-triol

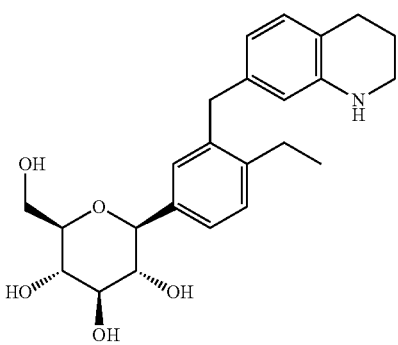

(2S,3R,4R,5S,6R)-2-[4-ethyl-3-(1,2,3,4-tetrahydroquinolin-7-ylmethyl)phenyl]-6-(hydroxymethyl)tetrahydropyran-3,4,5-triol

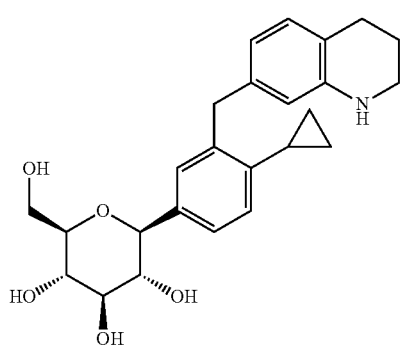

(2S,3R,4R,5S,6R)-2-[4-cyclopropyl-3-(1,2,3,4-tetrahydroquinolin-7-ylmethyl)phenyl]-6-(hydroxymethyl)tetrahydropyran-3,4,5-triol

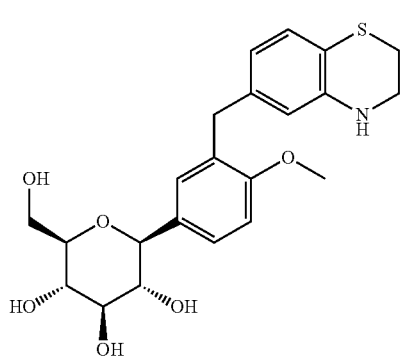

(2S,3R,4R,5S,6R)-2-[3-(3,4-dihydro-2H-1,4-benzothiazin-6-ylmethyl)-4-methoxy-phenyl]-6-(hydroxymethyl)tetrahydropyran-3,4,5-triol -continued

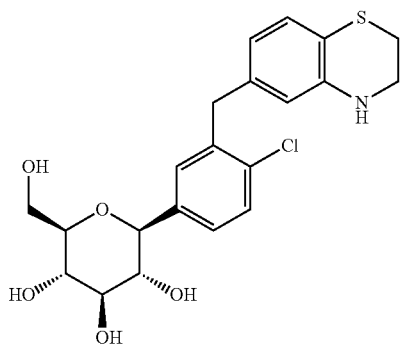

(2S,3R,4R,5S,6R)-2-[4-chloro-3-(3,4-dihydro-2H-1,4-benzothiazin-6-ylmethyl)phenyl]-6-(hydroxymethyl)tetrahydropyran-3,4,5-triol

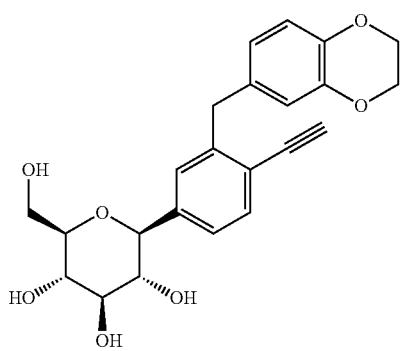

(2S,3R,4R,5S,6R)-2-[3-(2,3-dihydro-1,4-benzodioxin-6-ylmethyl)-4-ethynyl-phenyl]-6-(hydroxymethyl)tetrahydropyran-3,4,5-triol

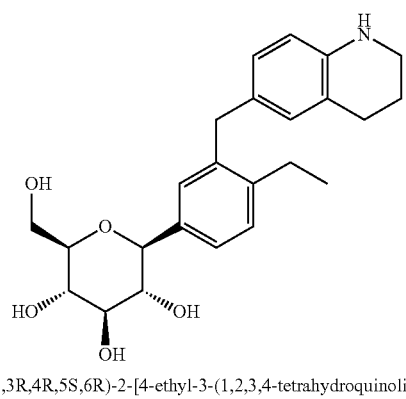

(2S,3R,4R,5S,6R)-2-[4-ethyl-3-(1,2,3,4-tetrahydroquinolin-6-ylmethyl)phenyl]-6-(hydroxymethyl)tetrahydropyran-3,4,5-triol

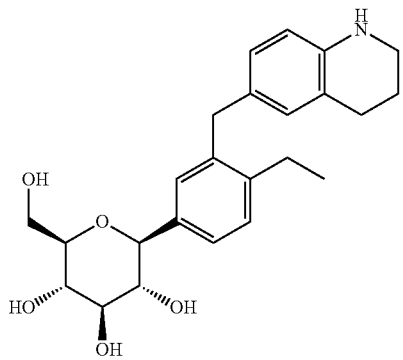

(2S,3R,4R,5S,6R)-2-[4-ethyl-3-(1,2,3,4-tetrahydroquinolin-6-ylmethyl)phenyl]-6-(hydroxymethyl)tetrahydropyran-3,4,5-triol

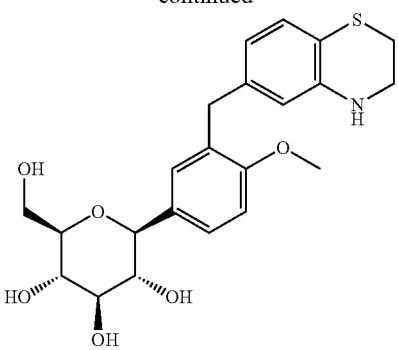

(2S,3R,4R,5S,6R)-2-[3-(3,4-dihydro-2H-1,4-benzothiazin-6-ylmethyl)-4-methoxy-phenyl]-6-(hydroxymethyl)tetrahydropyran-3,4,5-triol

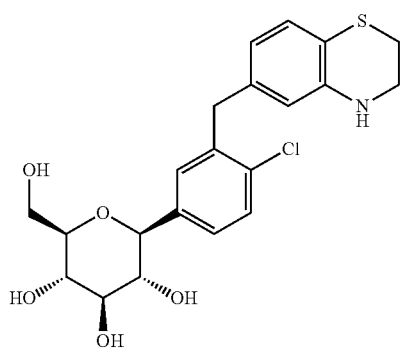

(2S,3R,4R,5S,6R)-2-[4-chloro-3-(3,4-dihydro-2H-1,4-benzothiazin-6-ylmethyl)phenyl]-6-(hydroxymethyl)tetrahydropyran-3,4,5-triol

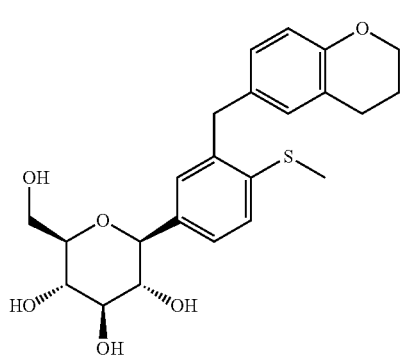

(2S,3R,4R,5S,6R)-2-[3-(chroman-6-ylmethyl)-4-methylsulfanyl-phenyl]-6-(hydroxymethyl)tetrahydropyran-3,4,5-triol

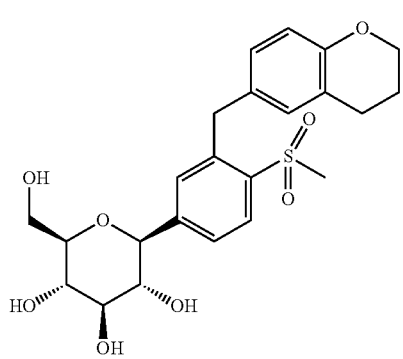

(2S,3R,4R,5S,6R)-2-[3-(chroman-6-ylmethyl)-4-methylsulfonyl-phenyl]-6-(hydroxymethyl)tetrahydropyran-3,4,5-triol

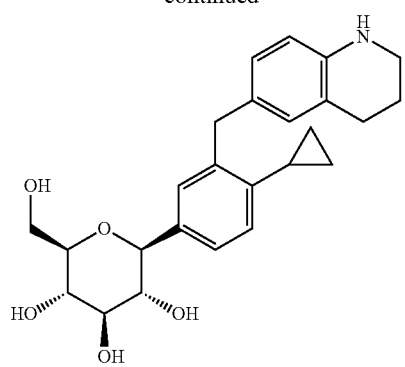

(2S,3R,4R,5S,6R)-2-[4-cyclopropyl-3-(1,2,3,4-tetrahydroquinolin-6-ylmethyl)phenyl]-6-(hydroxymethyl)tetrahydropyran-3,4,5-triol

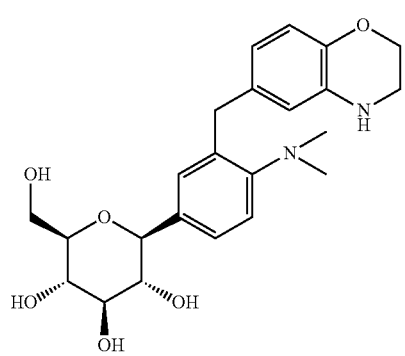

(2S,3R,4R,5S,6R)-2-[3-(3,4-dihydro-2H-1,4-benzoxazin-6-ylmethyl)-4-dimethylamino-phenyl]-6-(hydroxymethyl)tetrahydropyran-3,4,5-triol

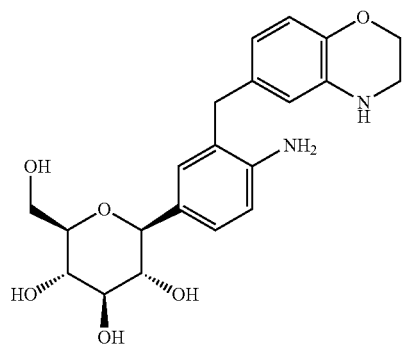

(2S,3R,4R,5S,6R)-2-[4-amino-3-(3,4-dihydro-2H-1,4-benzoxazin-6-ylmethyl)phenyl]-6-(hydroxymethyl)tetrahydropyran-3,4,5-triol

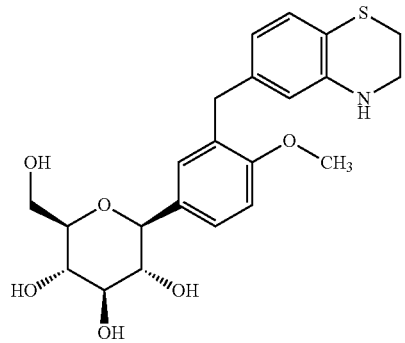

(2S,3R,4R,5S,6R)-2-[3-(3,4-dihydro-2H-1,4-benzothiazin-6-ylmethyl)-4-methoxy-phenyl]-6-(hydroxymethyl)tetrahydropyran-3,4,5-triol

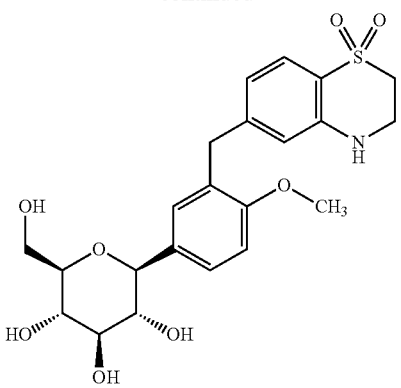

(2S,3R,4R,5S,6R)-2-[3-[(1,1-dioxo-3,4-dihydro-2H-benzo[b][1,4]thiazin-6-yl)methyl]-4-methoxy-phenyl]-6-(hydroxymethyl)tetrahydropyran-3,4,5-triol

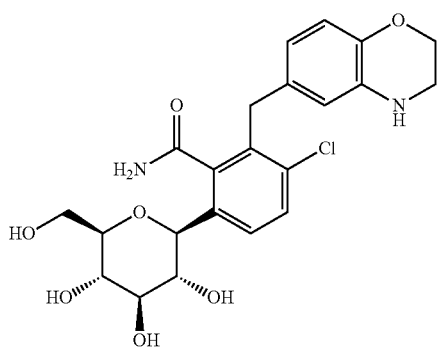

3-chloro-2-(3,4-dihydro-2H-1,4-benzoxazin-6-ylmethyl)-6-[(2S,3R,4R,5S,6R)-3,4,5-trihydroxy-6-(hydroxymethyl)tetrahydropyran-2-yl]benzamide

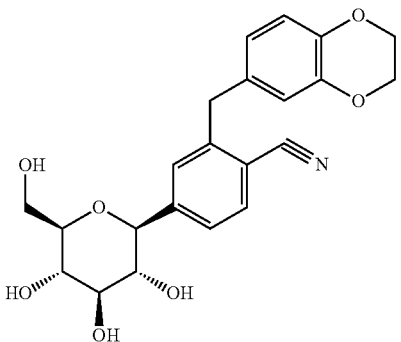

2-(2,3-dihydro-1,4-benzodioxin-7-ylmethyl)-4-[(2S,3R,4R,5S,6R)-3,4,5-trihydroxy-6-(hydroxymethyl)tetrahydropyran-2-yl]benzonitrile

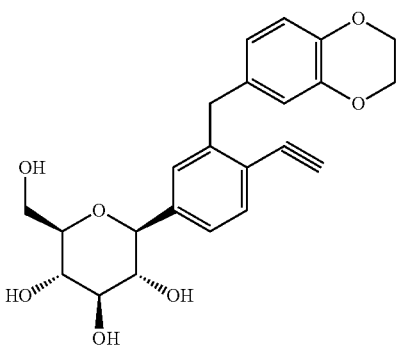

(2S,3R,4R,5S,6R)-2-[3-(2,3-dihydro-1,4-benzodioxin-7-ylmethyl)-4-ethynyl-phenyl]-6-(hydroxymethyl)tetrahydropyran-3,4,5-triol

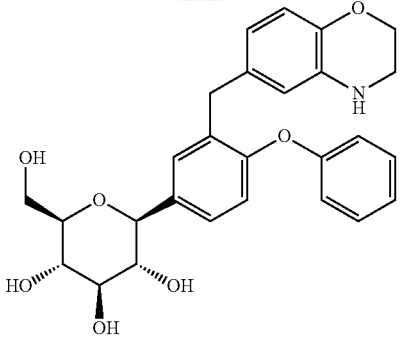

(2S,3R,4R,5S,6R)-2-[3-(3,4-dihydro-2H-1,4-benzoxazin-6-ylmethyl)-4-phenoxy-phenyl]-6-(hydroxymethyl)tetrahydropyran-3,4,5-triol

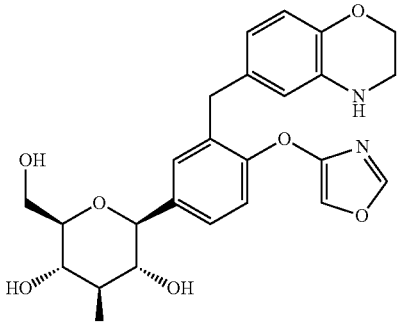

(2S,3R,4R,5S,6R)-2-[3-(3,4-dihydro-2H-1,4-benzoxazin-6-ylmethyl)-4-oxazol-4-yloxy-phenyl]-6-(hydroxymethyl)tetrahydropyran-3,4,5-triol

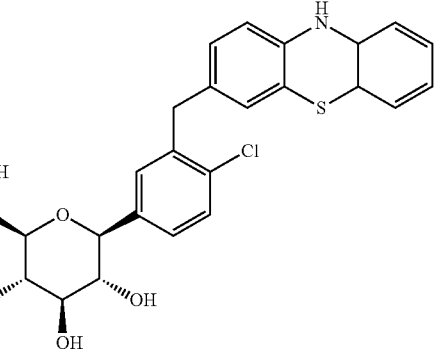

(1R,2R,3S,4S,6R)-4-[3-(9a,10-dihydro-5aH-phenothiazin-3-ylmethyl)-4-chloro-phenyl]-6-(hydroxymethyl)cyclohexane-1,2,3-triol The inhibitory effect on the sodium-dependent glucose co-transporter SGLT, SGLT1 and SGLT2, of compounds of formula I may be demonstrated using the following test procedures.

The ability of the substances to inhibit the SGLT-2 activity may be demonstrated in a test set-up in which a CHO-K1 cell line (ATCC No. CCL 6 1) or alternatively an HEK293 cell line (ATCC No. CRL-1573) is stably transfected with an expression vector pZeoSV (Invitrogen, EMBL accession number L36849) which contains the cDNA for the coding sequence of the human sodium glucose co-transporter 2 (Genbank Acc. No. NM_003041) (CHO-hSGLT2 or HEK-hSGLT2). These cell lines transport 14 C-labelled alpha-methyl-glucopyranoside (14 C-AMG, Amersham) into the interior of the cell in sodium-dependent manner.

The SGLT-2 assay is carried out as follows: CHO-hSGLT2 cells are cultivated in Ham's F12 Medium (BioWhittaker) with 10% foetal calf serum and 250 µg/mL zeocin (Invitrogen), and HEK293-hSGLT2 cells are cultivated in DMEM medium with 10% foetal calf serum and 250 µg/mL zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% CO2. The cells are washed twice with 250 µl of assay buffer (Hanks Balanced Salt Solution, 137 mM NaCl, 5.4 mM KCl, 2.8 mM CaCl2, 1.2 mM MgSO4 and 10 mM HEPES (pH 7.4), 50 µg/mL of gentamycin). 250 µl of assay buffer and 5 µl of test compound are then added to each well and the plate is incubated for a further 15 minutes in the incubator. 5 µl of 10% DMSO are used as the negative control. The reaction is started by adding 5 µl of 14 C-AMG (0.05 µCi) to each well. After 2 hours' incubation at 37° C., 5% CO2, the cells are washed again with 250 µl of PBS (200 C) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the 14 C-AMG absorbed is measured in a Topcount (Packard) using a 14 C scintillation program.

To determine the selectivity with respect to human SGLT1 an analogous test is set up in which the cDNA for hSGLTI (Genbank Ace. No. NM000343) instead of hSGLT2 cDNA is expressed in CHO-K1 or HEK293 cells.

The compounds according to the invention may for example have EC50 values below 1000 nM, particularly below 100 nM, most preferably below 10 nM. The title compounds of the above Examples were evaluated in the above described assay and the results of which are collated in Table 1.

TABLE 1

| Example Number | SGLT2 $IC_{50}$ nM (n = 1-4) | SGLT1 $IC_{50}$ nM (n = 1-4) |
|---|---|---|
| 1 | 2.7 | 655 |
| 2 | 11.1 | 2500 |
| 3 | 16 | — |
| 4 | 65 | — |
| 8 | 0.25 | 725 |
| 9 | 7.2 | — |
| 10 | 18 | — |
| 11 | 1.4 | — |
| 14 | 5.5 | 800 |
| 15 | 0.2 | 650 |
| 16 | 0.15 | 750 |
| 17 | 0.8 | 480 |
| 20 | 0.55 | >3700 |
| 21 | 0.2 | 1100 |
| 22 | 0.4 | — |
| 24 | 1.3 | 31000 |
| 25 | 1.5 | 40 |
| 28 | 0.33 | 1000 |
| 29 | 84.5 | 7000 |
| 31 | 1.2 | 404 |
| 33 | 11 | 157 |
| 35 | 9.5 | 1100 |
| 36 | 28 | — |
| 38 | 14.4 | — |
| 41 | 16.2 | 1620 |
| 42 | 0.35 | 105 |
| 43 | 3.9 | 59 |
| 46 | 14 | >3900 |
| 47 | 16.5 | >3200 |
| 60 | 2.2 | 9 |
| 62 | 0.5 | 22 |
| 65 | 2.7 | 170 |
| 66 | 0.9 | 100 |
| 69 | 1.2 | 37 |
| 71 | 1.5 | 19 |

It can be seen that the compounds of the invention are useful as inhibitors of SGLT and therefore useful in the treatment of diseases and conditions mediated by SGLT such as the metabolic disorders disclosed herein.

Co-Crystal of the Compounds of the Invention

Method 1: 1:1 Co-Crystals of Compounds of the Invention with L-Proline

Proline co-crystals were prepared from Examples 8, 60, 62 and 71, by the following method. The procedure given below pertains to the preparation of about 543 mg of the co-crystals for Examples 73-76.

Example 8, 60, 62 or 71 (about 4.28 mg) and L-proline (1.15 g) were taken in 1:1 molar ratio in 10 ml of ethanol in a 25 ml round bottom flask and refluxed for one hour at 90° C. The ethanol was then removed under vacuum (using rotatory vacuum evaporator) to yield a gummy paste. This gummy paste was stirred in 20 ml of hexane at room temperature for 5 hrs (for Examples 60 and 62), overnight for Example 8 and 2 days for Example 71. The hexane was then decanted to yield a free flowing solid. Characterization data for co-crystals prepared by this method is shown in Examples 73-76.

Powder x-ray diffraction patterns for Examples 73-76 were measured using the following conditions:
Scanning Axis: Gonio
Start Position (° 2Th.): 2.5167
End Position (° 2Th.): 49.9707
Step Size (° 2Th.): 0.0330
Scan Step Time (sec): 10.1600
Scan Type: Continuous
PSD Mode: Scanning
PSD Length (° 2Th.): 2.12
Offset (2Th.): 0.0000
Divergence Slit Type: Automatic
Irradiated Length (mm): 10.00
Specimen Length (mm): 10.00
Measurement Temperature (° C.): 25.00
Anode Material: Cu
K-Alpha1 (Å): 1.54060
K-Alpha2 (Å): 1.54443
K-Beta (Å): 1.39225
K-A2/K-A1 Ratio: 0.50000
Generator Settings: 40 mA, 45 kV
Goniometer Radius (mm): 240.00
Dist. Focus-Diverg. Slit (mm): 100.00
Incident Beam Monochromator: No
Spinning: Yes Example 73: 1:1 Proline Co-crystal with (2S,3R, 4R,5S,6R)-2-[4-Chloro-3-(3,4-dihydro-2H-benzo[1, 4]oxazin-6-ylmethyl)-phenyl]-6-hydroxymethyl-tetrahydro-pyran-3,4,5-triol (2S,3R,4R,5S,6R)-2-[4-Chloro-3-(3,4-dihydro-2H-benzo[1,4]oxazin-6-ylmethyl)-phenyl]-6-hydroxymethyl-tetrahydro-pyran-3,4,5-triol (Example 8) was completely amorphous initially but formed a crystalline complex with proline. This was confirmed by powder X-ray diffraction (PXRD) analysis. The stiochiometry of Example 8 and L-proline in the co-crystal prepared by the above method was found to be 1:1 by NMR spectroscopy & HPLC. Characterization data for co-crystals of Example 8 and proline prepared by method 1 is shown in Table 1. Relative intensities of the most prominent powder x-ray diffraction peaks for co-crystals of Example 8 and proline are shown in Table 1A.

TABLE 1

|  | Example 8 | Proline | 1:1 Co-crystal of Example 8 and proline |
|---|---|---|---|
| IR (cm−1) | 3337, 2875, 1613, 1594, 1513, 1478, 1352, 1315, 1289, 1211, 1083, 1039, 886, 819 | 3053, 2983, 2777, 2369, 1617, 1560, 1449, 1405, 1377, 1294, 1256, 1169, 1085, 1035, 983, 849 | 3585, 3208, 2914, 1622, 1591, 1513, 1480, 1457, 1406, 1369, 1317, 1291, 1214, 1127, 1075, 1034, 959, 922, 883, 836, 793 85-87 |
| MP (° C.) | 74-126 | 205 decomposes | |
| PXRD (2 θ) | amorphous | 15.14, 18.04, 19.57, 24.80, 30.57, 32.16, 39.79, 36.56, 37.65, 37.65 | 5.7, 12.9, 16.6, 17.0, 19.3, 20.6, 22.3, 23.2, 25.2, 25.7, 26.5, 27.6 |
| DSC (° C.) | Broad peak observed from 74-126 | Sharp peak observed at 205 | Three peaks were observed at 63.78, 104.34 and 155.53 |

TABLE 1A

| Angle (2-Theta) | Relative Intensity (%) |
|---|---|
| 5.7 | 28.37 |
| 12.9 | 12.28 |
| 16.6 | 16.69 |
| 17.0 | 33.15 |
| 19.3 | 100.00 |
| 20.6 | 13.03 |
| 22.3 | 13.34 |
| 23.2 | 55.29 |
| 25.2 | 25.48 |
| 25.7 | 12.95 |
| 26.5 | 20.58 |
| 27.6 | 16.72 |

TABLE 2

|  | Example 60 | Proline | 1:1 Co-crystal of Example 60 and proline |
|---|---|---|---|
| IR (cm−1) | 3349, 2930, 2875, 1589, 1506, 1458, 1429, 1360, 1284, 1258, 1203, 1124, 1086, 1068, 1020, 917, 886 | 3053, 2983, 2777, 2369, 1617, 1560, 1449, 1405, 1377, 1294, 1256, 1169, 1085, 1035, 983, 849 | 3334, 2918, 2880, 1613, 1589, 1505, 1455, 1427, 1402, 1374, 1310, 1279, 1262, 1199, 1165, 1124, 1083, 1068, 1041, 1019, 954 |
| MP (° C.) | 75-118 | 205 decomposes | 148-158 |
| PXRD (2 θ) | amorphous | 15.14, 18.04, 19.57, 24.80, 30.57, 32.16, 39.79, 36.56, 37.65, 37.65 | 4.07, 15.41, 15.80, 16.16, 16.68, 17.04, 17.59, 18.16, 18.67, 19.53, 19.91, 20.36, 21.47, 21.88, 22.23, 23.84, 26.98, 32.32 |
| DSC (° C.) | Broad peak observed from 75-118 | Sharp peak observed at 205 | Sharp peak observed at 150.58 |

TABLE 2A

| Angle (2-Theta) | Relative Intensity (%) |
|---|---|
| 4.07 | 25.22 |
| 15.41 | 19.85 |
| 15.80 | 44.90 |
| 16.16 | 87.61 |
| 16.68 | 100.00 |
| 17.04 | 36.50 |
| 17.59 | 81.41 |
| 18.16 | 51.31 |
| 18.67 | 36.27 |
| 19.53 | 32.80 |
| 19.91 | 76.22 |
| 20.36 | 52.35 |
| 21.47 | 34.08 |
| 21.88 | 48.13 |
| 22.23 | 27.34 |
| 23.84 | 25.74 |
| 26.98 | 19.61 |
| 32.32 | 15.11 |

Example 74: 1:1 Proline Co-crystal with (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol (2S,3R,4R,5S,6R)-2-[4-Cyclopropyl-3-(2,3-dihydro-benzo[1,4]dioxin-6-ylmethyl)-phenyl]-6-hydroxymethyl-tetrahydro-pyran-3,4,5-triol (Example 60) was completely amorphous initially but formed a crystalline complex with proline. This was confirmed by powder X-ray diffraction (PXRD) analysis. The stiochiometry of Example 60 and L-proline in the co-crystal prepared by method 1 was found to be 1:1 by NMR spectroscopy & HPLC. Characterization data for co-crystals of Example 60 and proline prepared by the above method is shown in Table 2. Relative intensities of the most prominent powder x-ray diffraction peaks for co-crystals of Example 60 and proline are shown in Table 2A.

Example 75: 1:1 Proline Co-crystal with (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol (Example 62) was completely amorphous initially but formed a crystalline complex with proline. This was confirmed by powder X-ray diffraction (PXRD) analysis. The stiochiometry of Example 62 and L-proline in the co-crystal prepared by method 1 was found to be 1:1 by NMR spectroscopy & HPLC. Characterization data for co-crystals of Example 62 and proline prepared by method 1 is shown in Table 3. Relative intensities of the most prominent powder x-ray diffraction peaks for co-crystals of Example 62 and proline are shown in Table 3A.

TABLE 3

| | Example 62 | Proline | 1:1 Co-crystal of Example 62 and proline |
|---|---|---|---|
| IR (cm−1) | 3340, 2966, 2931, 2874, 1589, 1506, 1456, 1429, 1358, 1285, 1258, 1202, 1124, 1085, 1068, 955, 917, 885, 833 | 3053, 2983, 2777, 2369, 1617, 1560, 1449, 1405, 1377, 1294, 1256, 1169, 1085, 1035, 983, 849 | 3316, 3198, 2965, 2913, 2873, 2679, 1605, 1505, 1455, 1427, 1409, 1358, 1311, 1286, 1257, 1201, 1127, 1085, 1069, 1018, 1004, 918, 884 |
| MP (° C.) | 76-123 | 205 decomposes | 146-151 |
| PXRD (2 θ) | amorphous | 15.14, 18.04, 19.57, 24.80, 30.57, 32.16, 39.79, 36.56, 37.65, 37.65 | 3.70, 9.68, 11.07, 14.26, 14.80, 15.40, 16.12, 16.59, 17.31, 17.98, 18.36, 18.88, 20.42, 21.18, 22.50, 23.78, 24.56, 25.79, 27.46, 31.97, 32.46 |
| DSC (° C.) | Broad peak observed from 75-118 | Sharp peak observed at 205 | Two peaks were observed at 152.15 and 163.81 |

TABLE 3A

| Angle (2-Theta) | Relative Intensity (%) |
|---|---|
| 3.70 | 15.78 |
| 9.68 | 10.68 |
| 11.07 | 21.21 |
| 14.26 | 14.81 |
| 14.80 | 22.97 |
| 15.40 | 4.98 |
| 16.12 | 8.45 |
| 16.59 | 18.78 |
| 17.31 | 100.0 |
| 17.60 | 20.35 |
| 17.98 | 47.20 |
| 18.36 | 25.18 |
| 18.88 | 36.33 |
| 20.42 | 69.29 |
| 21.18 | 27.94 |
| 22.50 | 12.25 |
| 23.78 | 33.08 |
| 24.56 | 6.92 |
| 25.79 | 21.69 |
| 27.46 | 8.90 |
| 31.97 | 7.65 |
| 32.46 | 5.98 |

Example 76: 1:1 Proline Co-crystal with (2R,3S, 4R,5R,6S)-2-Hydroxymethyl-6-[4-isopropyl-3-(1,2, 3,4-tetrahydro-quinolin-7-ylmethyl)-phenyl]-tetrahydro-pyran-3,4,5-triol (2R,3S,4R,5R,6S)-2-Hydroxymethyl-6-[4-isopropyl-3-(1,2,3,4-tetrahydro-quinolin-7-ylmethyl)-phenyl]-tetrahydro-pyran-3,4,5-triol (Example 71) was completely amorphous initially but formed a crystalline complex with proline. This was confirmed by powder X-ray diffraction (PXRD) analysis. The stiochiometry of Example 71 and L-proline in the co-crystal prepared by method 1 was found to be 1:1 by NMR spectroscopy & HPLC. Characterization data for co-crystals of Example 71 and proline prepared by method 1 is shown in Table 4.

TABLE 4

| | Example 71 | Proline | 1:1 Co-crystal of Example 71 and proline |
|---|---|---|---|
| IR (cm−1) | 3318, 2959, 2928, 1659, 1614, 1578, 1498, 1464, 1446, 1361, 1313, 1180, 1084, 1010, 886, 832, 786 | 3053, 2983, 2777, 2369, 1617, 1560, 1449, 1405, 1377, 1294, 1256, 1169, 1085, 1035, 983, 849 | 3311, 2959, 2926, 1613, 1579, 1499, 1406, 1361, 1314, 1170, 1084, 1045, 1010, 833, 785 |
| PXRD (2 θ) | Amorphous | 15.14, 18.04, 19.57, 24.80, 30.57, 32.16, 39.79, 36.56 37.65, 37.65 | 5.7, 8.8, 16.4, 19.1, 2.3, 23.6, 24.5 |
| MP (° C.) | 76-120 | 205 decomposes | 145-148 |
| DSC (° C.) | Broad peak observed at 76-120 | Sharp peak observed at 205 | Two peaks observed at 156.29 and 158.38 |

Example 77: 1:1 Proline Co-crystal with (2S,3R, 4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol Method 2: 1:1 Co-Crystals of Example 62 with L-Proline (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol (Example 62, 1500 mg, 3.6 mmol), L-proline (415 mg, 3.6 mmol) and ethanol (23 mL) were added to a 50 mL 3-neck round bottom flask equipped with nitrogen purging, magnetic stirring bar, thermometer pocket & calcium chloride guard tube and the mixture was stirred at 25-30° C. for 30 min., then heat to reflux. A clear solution was observed which was refluxed for 30 min., then slowly cool to 25-30° C. causing percipitation. Di-isopropyl ether (DIPE, 23 mL) was added while maintaining the mixture at 25-30° C. and stirring continuously for additional one to two hours at the same temperature. The precipitate was collected by filtration using vacuum (Nitrogen atmosphere), and the filter cake was washed with ethanol-DIPE mixture (1:1 v/v, 10 ml) followed by DIPE (23 mL). The product was vacuum dried at 65-70° C. for 5-6 hrs. A melting point 136° C. (ΔH 53 J/g) was observed by differential scanning calorimetry (DSC) and is shown in FIG. 1. A powder X-ray diffraction (PXRD) spectrum is shown in FIG. 2.

Figure 3:
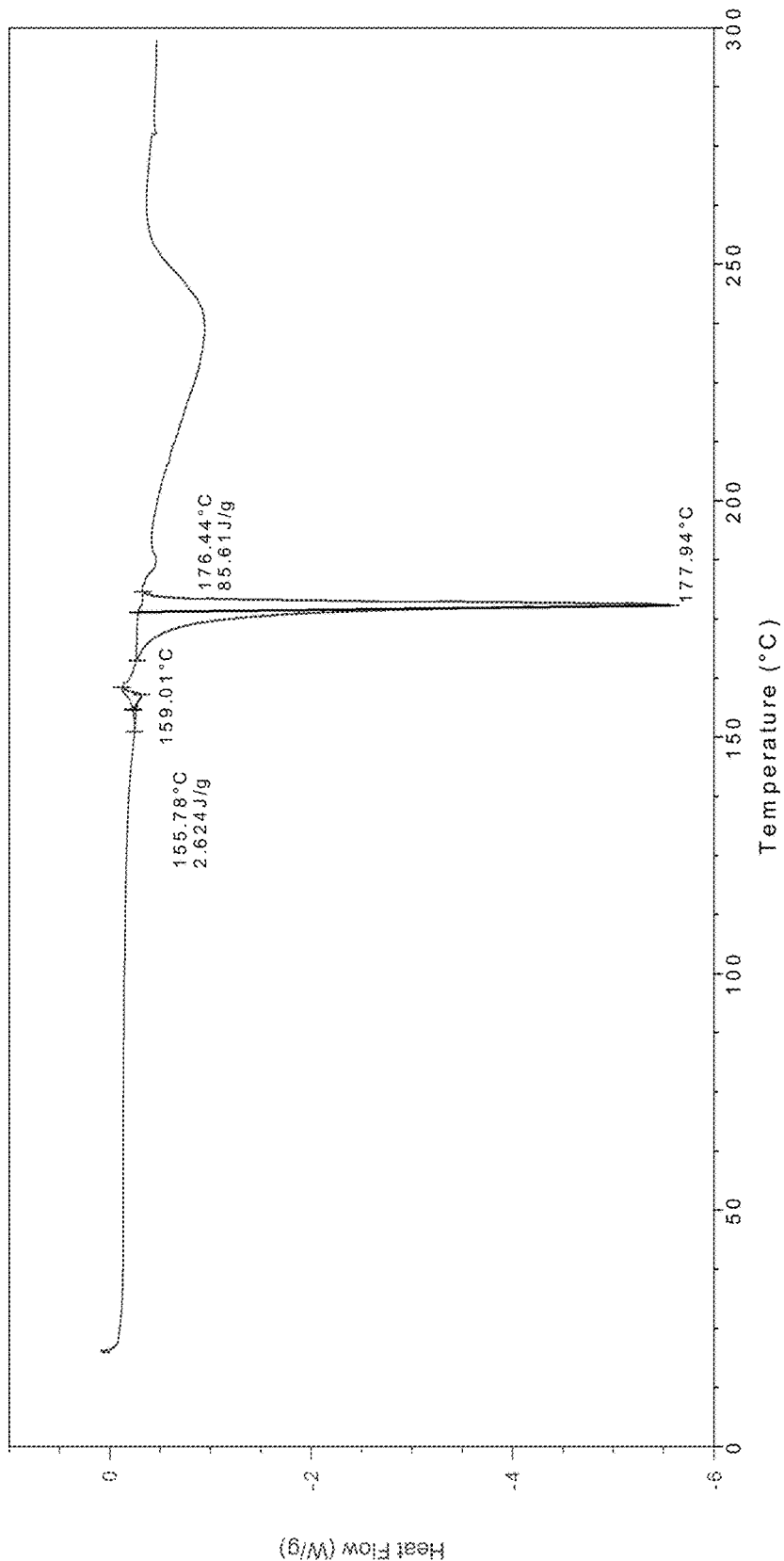
FIG. 3 is a differential scanning calorimetry thermogram of a 2:1 L-proline co-crystal of (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol prepared by method 3.

Example 78: 2:1 Proline Co-crystal with (2S,3R, 4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol Method 3: 1:2 Co-Crystals of Example 62 with L-Proline (2S,3R,4R,5S,6R)-2-[3-(2,3-Dihydro-benzo[1,4]dioxin-6-ylmethyl)-4-ethyl-phenyl]-6-hydroxymethyl-tetrahydro-pyran-3,4,5-triol (Example 62, 1 kg) was added to 15 L of ethanol with agitation while maintaining the mixture at 20-25° C. The mixture was stirred for 10 min at 20-25° C., then L-proline (537 gm) was added while maintaining the mixture at 20-25° C. The mixture was stirred at this temperature for 30 min., then heated to reflux and refluxed for 30 min. The mixture was slowly cooled to 25-30° C. then stirred for 1 hr. DIPE (15 L) was added while maintaining the temperature at 25-30° C. and the mixture was stirred at this temperature for 1 hr. The precipitated product was collected by filtration and the product was washed with DIPE (5 L). The product was air dried at 65-70° C. to yield 1.22 kg (79%) of a 1:2 co-crystal of Example 62: L-proline. A melting point 176° C. (ΔH 85 J/g) was observed by differential scanning calorimetry (DSC) and is shown in FIG. 3. A powder X-ray diffraction (PXRD) spectrum is shown in FIG. 4. Relative intensities of the most prominent powder x-ray diffraction peaks for the 1:2 co-crystals of Example 62 and proline are shown in Table 5.

TABLE 5

| Angle (2-Theta) | Relative Intensity (%) |
|---|---|
| 6.1 | 28.1 |
| 9.1 | 53.9 |
| 12.8 | 22.7 |
| 15.2 | 34.4 |
| 16.5 | 28.3 |
| 17.8 | 100.0 |
| 18.9 | 39.0 |
| 20.9 | 39.5 |
| 28.4 | 20.4 |
| — | — |

It will be understood that the invention has been described by way of example only and modifications may be made whilst remaining within the scope and spirit of the invention.

We claim:

1. A method of treating obesity, comprising administering to a mammal in need thereof a therapeutically effective amount of the compound:

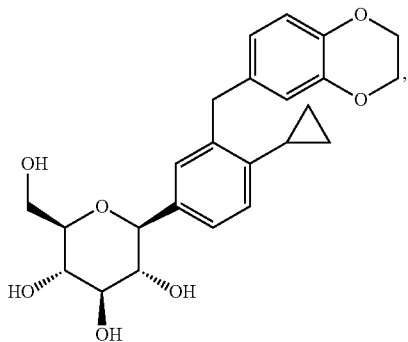 [SMILES: OC[C@H]1O[C@@H](c2ccc(C3CC3)c(Cc3ccc4c(c3)OCCO4)c2)[C@H](O)[C@@H](O)[C@@H]1O]

or a pharmaceutically acceptable salt thereof.

2. A method of treating obesity, comprising administering to a mammal in need thereof a therapeutically effective amount of the compound:

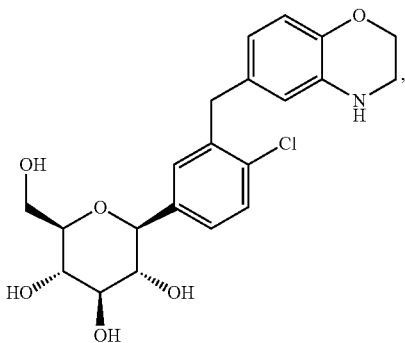 [SMILES: OC[C@H]1O[C@@H](c2ccc(Cl)c(Cc3ccc4c(c3)NCCO4)c2)[C@H](O)[C@@H](O)[C@@H]1O]

or a pharmaceutically acceptable salt thereof.

3. A method of treating obesity, comprising administering to a mammal in need thereof a therapeutically effective amount of the compound:

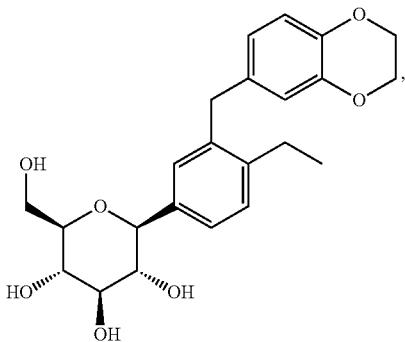 [SMILES: CCc1ccc([C@@H]2O[C@H](CO)[C@@H](O)[C@H](O)[C@H]2O)cc1Cc1ccc2c(c1)OCCO2]

or a pharmaceutically acceptable salt thereof.

4. A method of treating obesity, comprising administering to a mammal in need thereof a therapeutically effective amount of the compound:

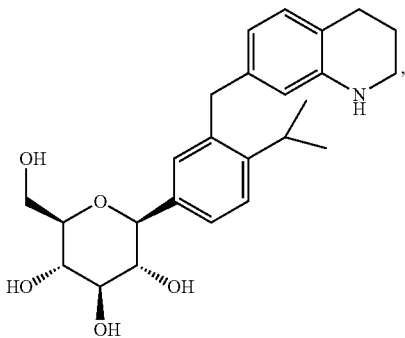 [SMILES: CC(C)c1ccc([C@@H]2O[C@H](CO)[C@@H](O)[C@H](O)[C@H]2O)cc1Cc1ccc2c(c1)NCCC2]

or a pharmaceutically acceptable salt thereof.

* * * * *